(12) United States Patent
Inoue et al.

(10) Patent No.: US 7,879,844 B2
(45) Date of Patent: Feb. 1, 2011

(54) HETEROCYCLIC JANUS KINASE 3 INHIBITORS

(75) Inventors: Takayuki Inoue, Chuo-ku (JP); Akira Tanaka, Chuo-ku (JP); Kazuo Nakai, Chuo-ku (JP); Hiroshi Sasaki, Chuo-ku (JP); Fumie Takahashi, Chuo-ku (JP); Shohei Shirakami, Chuo-ku (JP); Keiko Hatanaka, Chuo-ku (JP); Yutaka Nakajima, Chuo-ku (JP); Koichiro Mukoyoshi, Chuo-ku (JP); Hisao Hamaguchi, Chuo-ku (JP); Shigeki Kunikawa, Chuo-ku (JP); Yasuyuki Higashi, Chuo-ku (JP)

(73) Assignee: Astellas Pharma Inc., Tokyo (JP)

( * ) Notice: Subject to any disclaimer, the term of this patent is extended or adjusted under 35 U.S.C. 154(b) by 257 days.

(21) Appl. No.: 12/065,234

(22) PCT Filed: Dec. 25, 2006

(86) PCT No.: PCT/JP2006/326327

§ 371 (c)(1),
(2), (4) Date: Feb. 28, 2008

(87) PCT Pub. No.: WO2007/077949

PCT Pub. Date: Jul. 12, 2007

(65) Prior Publication Data

US 2009/0270376 A1    Oct. 29, 2009

(30) Foreign Application Priority Data

Dec. 28, 2005    (JP) ............................... 2005-378858

(51) Int. Cl.
| | |
|---|---|
| A61K 31/437 | (2006.01) |
| A61K 31/496 | (2006.01) |
| A61K 31/5377 | (2006.01) |
| A61K 31/541 | (2006.01) |
| C07D 471/04 | (2006.01) |
| C07D 471/14 | (2006.01) |
| A61P 37/00 | (2006.01) |
| A61P 25/28 | (2006.01) |
| A61P 35/00 | (2006.01) |

(52) U.S. Cl. ............................... 514/228.2; 514/253.04; 514/300; 514/303; 514/293; 546/113; 546/118; 546/82; 544/127; 544/58.2; 544/362

(58) Field of Classification Search ............... 514/228.2, 514/300, 253.04, 234.5, 303, 293; 546/113, 546/118, 82; 544/127, 58.2, 362
See application file for complete search history.

(56) References Cited

U.S. PATENT DOCUMENTS

| | | | |
|---|---|---|---|
| 6,335,342 B1 | 1/2002 | Longo et al. | |
| 6,486,322 B1 | 11/2002 | Longo et al. | |
| 6,579,882 B2 | 6/2003 | Stewart et al. | |
| 7,335,667 B2 | 2/2008 | Rodgers et al. | |
| 2003/0165576 A1 | 9/2003 | Fujii et al. | |
| 2003/0208066 A1 | 11/2003 | Levin et al. | |
| 2004/0198737 A1 | 10/2004 | Cox et al. | |

FOREIGN PATENT DOCUMENTS

| | | |
|---|---|---|
| CN | 101228161 A | 7/2008 |
| JP | 2006-525997 | 11/2006 |
| JP | 2006-525998 | 11/2006 |
| WO | WO 99/62908 | 12/1999 |
| WO | WO 99/65908 | 12/1999 |
| WO | WO 99/65909 | 12/1999 |
| WO | WO 01/42246 A2 | 6/2001 |
| WO | WO 02/00661 A1 | 1/2002 |
| WO | WO 02/096909 A1 | 12/2002 |
| WO | WO 03/048162 A1 | 6/2003 |
| WO | WO 2004/047843 | 6/2004 |
| WO | 2004099205 | * 11/2004 |
| WO | WO 2004/099204 A1 | 11/2004 |
| WO | WO 2004/099205 A1 | 11/2004 |
| WO | WO 2005/028475 A2 | 3/2005 |
| WO | WO 2005/051393 | 6/2005 |

(Continued)

OTHER PUBLICATIONS

Chang et al., Journal of immunology (Baltimore, Md. : 1950), (Aug. 1, 2009) vol. 183, No. 3, pp. 2183-2192.*

(Continued)

*Primary Examiner*—D. Margaret Seaman
*Assistant Examiner*—Niloofar Rahmani
(74) *Attorney, Agent, or Firm*—Oblon, Spivak, McClelland, Maier & Neustadt, L.L.P.

(57) ABSTRACT

The present invention provides a compound of formula (I) having an excellent JAK3 inhibition activity and being useful as an active ingredient of an agent for treating and/or preventing various immune diseases including autoimmune diseases inflammatory diseases, and allergic diseases. The compound according to the present invention has an inhibition activity against JAK3 and is thus useful as an active ingredient of an agent for treating or preventing diseases caused by undesirable cytokine signal transmission (e.g., rejection during organ/tissue transplantation, autoimmune diseases, multiple sclerosis, rheumatoid arthritis, psoriasis, asthma, atopic dermatitis, Alzheimer's disease, and atherosclerotic disease), or diseases caused by abnormal cytokine signal transmission (e.g., cancer and leukemia).

(I)

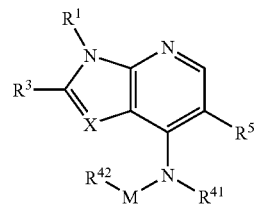

21 Claims, No Drawings

FOREIGN PATENT DOCUMENTS

| WO | WO 2005/060972 | | 7/2005 |
|---|---|---|---|
| WO | WO 2005/105146 A1 | | 11/2005 |
| WO | WO 2006/046023 A1 | | 5/2006 |
| WO | WO 2006/046024 A1 | | 5/2006 |
| WO | WO 2006/056399 A2 | | 6/2006 |
| WO | WO 2006/069080 A2 | | 6/2006 |
| WO | 2006127587 | * | 11/2006 |
| WO | WO 2006/127587 A1 | | 11/2006 |
| WO | WO 2007/002433 A1 | | 1/2007 |
| WO | WO 2007/007919 A2 | | 1/2007 |
| WO | WO 2007/077949 A1 | | 7/2007 |
| WO | WO 2008/084861 A1 | | 7/2008 |

OTHER PUBLICATIONS

U.S. Appl. No. 12/522,987, filed Jul. 13, 2009, Shirakami, et al.

U.S. Appl. No. 11/995,445, filed Jan. 11, 2008, Inoue, et al.

John J. O'Shea, et al., "Cytokine Signaling in 2002: New Surprises in the Jak/Stat Pathway", Cell, Revew, vol. 109, Apr. 2002, pp. s121-s131.

Katsutoshi Ozaki, et al., "A critical Role for IL-21 in Regulating Immunoglobulin Production", Science, vol. 298, Nov. 22, 2002, with cover page and pp. 1630-1634.

Paolo Macchi, et al., "Mutations of Jak-3 gene in patients with autosomal severe combined immune deficiency (SCID)", Letters to Nature, vol. 377, Sep. 7, 1995, pp. 65-68.

Sarah M. Russell, et al., "Mutation of Jak3 in a Patient with SCID: Essential Role of Jak3 in Lymphoid Development", Science, vol. 270, Nov. 3, 1995, pp. 797-800.

Paul S. Changelian, et al., "Prevention of Organ Allograft Rejection by a Specific Janus Kinase 3 Inhibitor", Science, vol. 302, Oct. 31, 2003, with cover page and pp. 875-878.

Elizabeth Kudlacz, et al., "The Novel JAK-3 Inhibitor CP-690550 Is a Potent Immunisuppressive Agent in Various Murine Models," American Journal of Transplantation 2004, v. 4, pp. 51-57.

T.R. Elworthy, et al., "N-Arylpiperazinyl-N-propylamino deroivatives of heteroaryl amides as functional uroselective alphal-adrenoreceptor antagonist", Journal of Medicinal Chemistry, vol. 40, No. 17, Jan. 1, 1997, pp. 2674-2687.

Chinese Office Action Issued Oct. 21, 2010 in Chinese Application No. 200680025631.2 (w/English Translation).

Decision of Rejection issued Sep. 20, 2010 in Saudi Arabian Serial No. 69267470 (corresponding to U.S. Appl. No. 12/065,234) filed Dec. 24, 2006 (w/English Translation).

European Search Report issued Oct. 14, 2010 in European Application No. 10174035.5-1211.

A.H.M. Al-Shaar, et al., "The Synthesis of Heterocycles via Additional-Elimination Reactions of 4- and 5-Aminoimidazoles", Journal of the Chemical Society, Jan. 1, 1992, pp. 2789-2811.

Singapore Office Action dated Oct. 29, 2010, issued in Singapore Patent Application No. 200804747-4, Filing Date, Dec. 25, 2006.

* cited by examiner

HETEROCYCLIC JANUS KINASE 3 INHIBITORS

The present invention relates to a novel condensed heterocyclic compound and to a medicament containing the compound as an active ingredient, and more particularly, to an immune disease treating agent.

BACKGROUND ART

Janus kinase 3 (hereafter referred to as JAK3) is a family of protein kinases. Although kinases in this family, other than JAK3, are expressed in a wide range of tissues, JAK3 is expressed locally in hematopoietic cells. This does not contradict the fact that JAK3 plays an important role in signal transmission via various receptors, such as interleukin (hereafter referred to as IL)-2, IL-4, IL-7, IL-9, IL-15, and IL-21 by noncovalent association with the common γ chain (refer to nonpatent literature 1 and nonpatent literature 2).

In XSCID (X-linked severe combined immunodeficiency) patient populations, JAK3 protein level lowers or a genetic defect is found in the common γ chain. It is indicated that this problem occurs because immunosuppression blocks JAK3-dependent signaling pathways (refer to nonpatent literature 3 and nonpatent literature 4). Animal experiments have shown that JAK3 not only plays an important role in maturation of B-lymphocytes and T-lymphocytes but also in maintaining the function of T-cells. Hence, it is expected that diseases involving proliferative abnormality of T-cells, such as rejection during organ/tissue transplantation and autoimmune diseases, can be treated by controlling immune response through this mechanism.

On the other hand, a pyrrolopyridine derivative (patent literature 1) represented by formula (A) or (B) or an imidazopyridine derivative (refer to patent literature 2) is known as a compound having JAK3 inhibition activity.

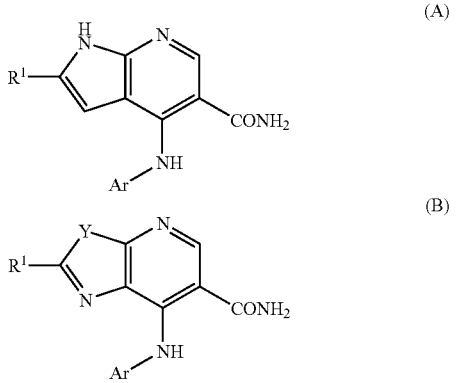

(For the symbols in the formulas, refer to the corresponding patent publications.)

Furthermore, a pyrrolopyrimidine derivative (refer to patent literature 3, patent literature 4, patent literature 5, and patent literature 6) represented by formula (C) is also known as a compound having JAK3 inhibition activity.

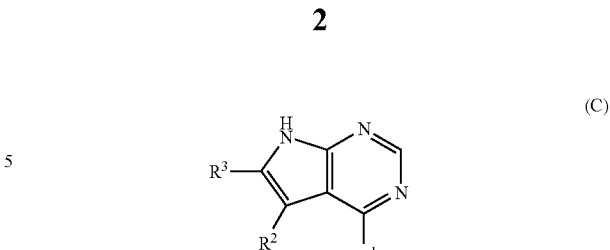

(For the symbols in the formula, refer to the corresponding patent publications.)

Still further, a pyrrolopyridine derivative (refer to patent literature 7) represented by formula (D) is also known as a compound having JAK3 inhibition activity.

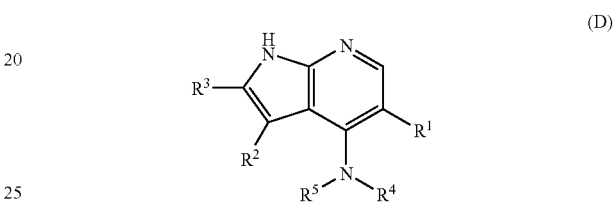

(For the symbols in the formula, refer to the corresponding patent publication.)

However, in any literature, the compound according to the present invention is not disclosed specifically.

[Nonpatent literature 1] J. J. O'shea et al, Cell, Vol. 109 (suppl.), S121, 2002
[Nonpatent literature 2] K. Ozaki et al, Science, Vol. 298, p. 1630, 2002
[Nonpatent literature 3] P. Macchi et al, Nature, Vol. 377, p. 65, 1995
[Nonpatent literature 4] S. M. Russell et al, Science, Vol. 270, p. 797, 1995
[Patent literature 1] WO 2004/099205
[Patent literature 2] WO 2004/099204
[Patent literature 3] WO 99/065908
[Patent literature 4] WO 99/065909
[Patent literature 5] WO 01/042246
[Patent literature 6] WO 02/000661
[Patent literature 7] WO 2006/069080

DISCLOSURE OF THE INVENTION

Problem to be Solved by the Invention

As a result of intensive studies with an object of providing a useful pharmaceutical composition having JAK3 inhibition activity, the inventors have found that a novel condensed heterocyclic compound has an excellent JAK3 inhibition activity, and have completed the present invention.

More specifically, the present invention provides a novel condensed heterocyclic compound represented by the following formula (I) or pharmaceutically acceptable salts thereof, and a pharmaceutical composition containing the compound, more particularly, a pharmaceutical composition serving as an agent for treating and/or preventing autoimmune diseases, inflammatory diseases, and allergic diseases.

The condensed heterocyclic compound is a condensed pyridine compound represented by the following formula (I):

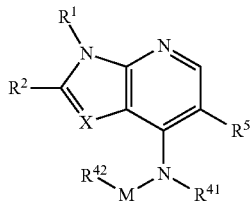

(I)

wherein

X is N or CR³,

M is (CH₂)$_m$; m is 0 or 1,

R¹ is —H or lower alkyl which may be substituted,

R² is —H or lower alkyl which may be substituted,

R³ is —H, halogen, or lower alkyl which may be substituted,

R⁴¹ is —H or heteroaryl which may be substituted,

R⁴² is a bridged ring group which may be substituted,

R⁵ is a group selected from the group consisting of halogen, cyano, acyl, acylamino, lower alkyl, lower alkenyl, —O-lower alkyl, 5- or 6-membered heterocycloalkyl, 5- or 6-membered heterocycloalkenyl, and 5-membered heteroaryl, each of which may be substituted, provided that when R⁵ is 5-membered heteroaryl, X is —CR³, or R⁴¹ and R⁵ may be linked via a specific functional group to form bivalent groups shown below:

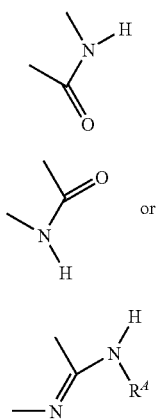

wherein R⁴ is —H or acyl which may be substituted, or pharmaceutically acceptable salts thereof.

Effect of the Invention

The compound according to the present invention has JAK3 inhibition activity and is thus useful as an active ingredient of an agent for treating and/or preventing diseases caused by undesirable cytokine signal transmission (e.g., rejection during organ/tissue transplantation, autoimmune diseases, asthma, atopic dermatitis, Alzheimer's disease, and atherosclerotic disease), or diseases caused by abnormal cytokine signal transmission (e.g., cancer and leukemia).

BEST MODES FOR CARRYING OUT THE INVENTION

The compound according to the present invention represented by the formula (I) is characterized in its chemical structure that the compound has a cross-linked amine and also has a skeleton in which 5- and 6-membered heterocycles are condensed, just as in 1H-pyrrolo[2,3-b]pyridine, 1H-imidazo[4,5-b]pyridine, or pyrazolo[1,5-a]pyrimidine, and is further characterized in pharmacology that the compound has a JAK3 inhibition activity.

The present invention is described below in detail.

The term "alkyl" in this specification is a straight or branched monovalent group.

The term "lower alkyl" in the specification is a $C_1$-$C_6$ straight or branched alkyl and may include, such as methyl, ethyl, n-propyl, isopropyl, n-butyl, isobutyl, t-butyl, n-pentyl, neopentyl, and n-hexyl, preferably methyl, ethyl, n-propyl, isopropyl, and isobutyl, and particularly preferably methyl and ethyl.

The term "lower alkenyl" in the specification is $C_2$-$C_6$ straight or branched alkenyl having a double bond at each possible site, and may include, such as ethenyl (vinyl), 1-propenyl, 2-propenyl(allyl), 1-methylethen-1-yl, 1-buten-1-yl, 2-buten-1-yl, 3-buten-1-yl, 1-methyl-1-propen-1-yl, 2-methyl-1-propen-1-yl, 1-methyl-2-propen-1-yl, and 2-methyl-2-propen-1-yl, preferably 1-methyl-2-propen-1-yl.

The term "halogen" means fluoro, chloro, bromo, and iodo, preferably fluoro.

The term "cycloalkyl" is a $C_3$-$C_8$ monovalent nonaromatic carbocyclic group, and may partially have unsaturated bonds or may be condensed with a benzene ring. However, bridged cycloc hydrocarbons are excluded. Cycloalkyl may include, such as cyclopropyl, cyclobutyl, cyclohexyl, cycloheptyl, cyclooctyl, cyclobutenyl, cyclohexenyl, cyclooctadienyl, indanyl, and tetrahydronaphthyl, preferably cyclohexyl.

The term "heterocycloalkyl" is a 5- to 6-membered nonaromatic saturated heterocycle which may have one or more identical or different hetero atoms selected from the group consisting of nitrogen atoms, oxygen atoms, and sulfur atoms which may be oxidized. Heterocycloalkyl may be partially unsaturated or may be condensed with a benzene ring. However, aza-bridged cyclic hydrocarbons are excluded. Heterocycloalkyl may include, such as aziridinyl, azetidinyl, pyrrolizinyl, piperidinyl, homopiperidinyl, morpholinyl, thiomorpholinyl, piperazinyl, tetrahydrofuranyl, tetrahydrothiophenyl, dihydrooxazolyl, tetrahydropyranyl, tetrahydrothiopyranyl, indolynyl, tetrahydroquinolyl, tetrahydroisoquinolyl, and benzoxazinyl, preferably dihydrooxazolyl, oxadiazolyl, oxadiazolanyl, and furanyl.

The term "heterocycloalkenyl" is partially substituted "heterocycloalkyl".

The term "cyclic amino" is, among groups defined in "heterocycloalkyl" a monovalent 3- to 8-membered nonaromatic cyclic amine which has at least one nitrogen atom, and may have one or more identical or different hetero atoms selected from the group consisting of nitrogen atoms, oxygen atoms, and sulfur atoms which may be oxidized, wherein at least one nitrogen atom has a bond. However, aza-bridged cyclic hydrocarbons are excluded. The "Cyclic amino" may include, such as aziridino, azetidino, pyrrolidino, piperidino, homopiperidino, morpholino, thiomorpholino, and piperazino.

The term "aryl" is an aromatic hydrocarbon group and may include, phenyl, naphthyl, and indenyl, preferably $C_6$-$C_{10}$ aryl, and more preferably phenyl.

The term "heteroaryl" is a monovalent 5- or 6-membered aromatic heterocyclic group having one or more identical or different hetero atoms selected from the group consisting of nitrogen, oxygen and sulfur atoms, and may be condensed with a benzene ring. "Heteroaryl" may include, such as pyridyl, pyrazinyl, pyrimidinyl, pyridazinyl, pyrrolyl, pyrazolyl, imidazolyl, oxazolyl, thiazolyl, thienyl, furyl, oxadiazolyl, thiadiazolyl, quinolyl, isoquinolyl, benzothiazolyl, benzoxazolyl, indolyl, indazolyl, quinoxalyl, andquinazolyl, preferably pyridazinyl, pyridyl, pyrazinyl, thiazolyl, pyrazolyl, and thioxazolyl.

The term "bridged ring group" means "bridged cyclic hydrocarbon" and "aza-bridged cyclic hydrocarbon".

The term "bridged cyclic hydrocarbon" is a saturated or unsaturated, bicyclic or polycyclic bridged hydrocarbon group having two or three $C_3$-$C_{10}$ cycloalkyl rings. Non bridged cycloalkyls are excluded. Bicyclic or polycyclic $C_4$-$C_{16}$ bridged hydrocarbon groups are particularly preferable. Bridged cyclic hydrocarbon may include, such as bicyclo[2.1.1]hexyl, bicyclo[2.2.1]heptyl, bicyclo[2.2.2]octyl, bicyclo[4.3.1]decyl, bicyclo[3.3.1]nonyl, bornyl, bornenyl, norbbrnyl, norbornenyl, 6,6-dimethylbicyclo[3.1.1]heptyl, tricyclobutyl, and adamantyl, preferably adamantyl or bicyclo[2.2.1]heptyl.

The term "aza-bridged cyclic hydrocarbon" is a saturated or unsaturated, bicyclic or polycyclic bridged hydrocarbon group in which at least one of atoms constituting a ring is a nitrogen atom. Non bridged heterocycloalkyls are excluded. Bicyclic or polycyclic $C_4$-$C_{16}$ aza-bridged hydrocarbon groups are particularly preferable. The term "aza-bridged cyclic hydrocarbon" may include, such as azanorbornyl, quinuclidinyl, isoquinuclidinyl, tropanyl, azabicyclo[3.2.1]octanyl, azabicyclo[2.2.1]heptanyl, 2-azabicyclo[3.2.1]octanyl, azabicyclo[3.2.1]octanyl, azabicyclo[3.2.2]nonanyl, azabicyclo[3.3.0]nonanyl, and azabicyclo[3.3.1]nonanyl, preferably tropanyl, 2-oxa-5-azabicyclo[2.2.1]hept-5-yl.

The term "acyl" means —C (=O)-lower alkyl, —C (=O)-cycloalkyl, —C (=O)-heterocycloalkyl, —C (=O)-aryl, —C (=O)-heteroaryl, carbamoyl, lower alkylcarbamoyl, —C (=O)—C (=O)-NH-lower alkyl, cycloalkylcarbamoyl, heterocycloalkylcarbamoyl, arylcarbamoyl, and heteroarylcarbamoyl. The term "lower alkyl," "cycloalkyl," "heterocycloalkyl," "aryl" and "heteroaryl" have the above-mentioned meanings.

X in the formula (I) is preferably CH.

$R^1$ in the formula (I) is preferably —H. $R^2$ in the formula (I) is preferably —H or $CH_3$, and more preferably —H.

$R^{41}$ in the formula (I) is preferably —H.

Furthermore, $R^{42}$ in the formula (I) is preferably adamantyl or tropanyl, each of which may be substituted with OH.

Still further, $R^5$ in the formula (I) is preferably carbamoyl which may be substituted or —C(=O)-lower alkyl which may have OH more preferably —$CONH_2$ or hydroxyacetyl. As another embodiment, $R^{41}$ and $R^5$ are bonded via a specific functional group to form a cyclic structure described above, preferably formula (I-C).

As substituents which are allowed to be used for "which may be substituted" of $R^1$, $R^2$, $R^3$, $R^{41}$, $R^{42}$ and/or $R^5$, the following groups described in items (a) to (g) are included:
(a) Halogen
(b) —OH, —O—$R^Z$, —O-phenyl, —OCO—$R^Z$, —OCONH—$R^Z$, oxo (=O)
(c) —SH, —S—$R^Z$, —S-phenyl, —S-heteroaryl, —SO—$R^Z$, —SO-phenyl, —SO-heteroaryl, —$SO_3H$, —$SO_2^Z$, —$SO_2$-phenyl, —$SO_2$-heteroaryl, sulfamoyl which may be substituted with one or two $R^Z$ groups.
(d) Amino which may be substituted with one or two $R^Z$ groups, —NHCO—$R^Z$, —NHCO-phenyl, —$NHCO_2$—$R^Z$, —$NHCONH_2$, —NHCONH—$R^Z$, —$NHSO_2$—$R^0$, —$NHSO_2$-phenyl, —$NHSO_2NH_2$, —$NO_2$, =N—O—$R^Z$;
(e) —CHO, CO—$R^Z$, —$CO_2H$, —$CO_2$—$R^Z$, carbamoyl which may be substituted with one or two $R^Z$ groups, —CO-cyclic amino, —COCO—$R^Z$, cyano;
(f) $R^Z$
(g) Phenyl which may be substituted with one or more groups selected from the substituents described in the above items (a) to (f), 5- or 6-membered heterocycloalkyl, 5- or 6-membered heteroaryl, 5- or 6-membered heterocycloaryl.

$R^Z$ in the above items (a) to (g) may include "cyano; —OH; and lower alkyl which may be substituted with one to three groups selected from the group consisting of —O-lower alkyl, —NH-lower alkyl, —CONH-lower alkyl, 5- or 6-membered heterocycloalkyl, and 5- or 6-membered heteroaryl."

The compound according to the present invention may include geometric isomers and tautomeric isomers depending on the type of constituent. In addition, the compound according to the present invention may have asymmetric carbon atoms. All of the isomers, including separated isomers and mixtures thereof, are included within the scope of the present invention. Furthermore, labeled compounds, that is, compounds obtained by substituting one or more atoms of the compound according to the present invention with radioactive or nonradioactive isotopes are also included in the scope of the present invention.

Furthermore, the pharmaceutically acceptable prodrug of the compound of the present invention is also included in the scope of the present invention. The pharmaceutically acceptable prodrug is a compound having a group that can be converted into amino group, hydroxyl group, carboxyl group, etc. through solvolysis or under physiological conditions. The groups described in Prog. Med., Vol. 5, p. 2157-2161, 1985 and "Iyakuhin No Kaihatsu (Development of Medicines)" (Hirokawa Pub. Co., 1990), Vol. 7, Molecular Design, p. 163-198 are taken as examples of groups forming such prodrugs.

The compound represented by the formula (I) may form acid or base addition salts. These salts should only be pharmaceutically acceptable salts. More specifically, the salts may include an acid addition salt with an inorganic acid (e.g., hydrochloric acid, hydrobromic acid, hydriodic acid, sulfuric acid, nitric acid, and phosphoric acid), and an acid addition salt with an organic acid (e.g., formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, and glutamic acid); a salt with an inorganic base (e.g., sodium, potassium, magnesium, calcium, and aluminum), and a salt with an organic base (e.g., methylamine, ethylamine, ethanolamine, lysine, and ornithine); an ammonium salt; and the like.

Still further, various hydrates, solvates; and crystalline polymorphic forms of the compound represented by the formula (I) and salts thereof are also included in the scope of the present invention.

Process

The compound according to the present invention can be produced using the characteristics based on the basic skeleton or the type of substituent thereof and by applying various known synthesis methods. During the production, protecting the relevant functional group with a suitable protective group or replacing the relevant functional group with a group that can be easily converted into the functional group at the stage of a starting substance or an intermediate may occasionally be effective depending on the type of the functional group in production technology. This kind of functional group may include, for example, amino group, hydroxyl group, and carboxyl group. The protective group for such a functional group may include, for example, the protective groups described in "Protective Groups in Organic Synthesis (3rd. Ed, 1999)" written by T. W. Greene and P. G. Wuts, and one of these should only be selected and used as necessary depending on reaction conditions. In this kind of method, the desired component can be obtained by introducing the protective group, by carrying out reaction and by eliminating the protective group as necessary, or by converting the group into a desired group.

In addition, the prodrug of the compound according to the present invention can be produced by introducing a specific group or by carrying out reaction using the obtained compound represented by the formula (I) at the stage of a starting substance or an intermediate, just as in the case of the above-mentioned protective group. The reaction can be carried out using methods known to those skilled in the art, such as ordinary esterification, amidation, and dehydration.

The abbreviations used in the specification are as follows:

Pr: Preparation number; Ex: Example number; Structure: chemical structure; Rf-Syn: the number of an Example to which reference was made (the number indicates that the relevant compound was produced according to a production method similar to that for producing the compound described in the Example designated by the number.); HPLC: high performance liquid chromatography; TLC: thin layer chromatography; Rf: rate of flow value; Data: NMR data and/or MS data; 1H-NMR: $^1$H-nuclear magnetic resonance; MS: mass spectrometry; (M+H)+:(M+H)$^+$; (M+Na)+:(M+Na)$^+$; (M−H)−: (M−H)$^-$.

<First Process>

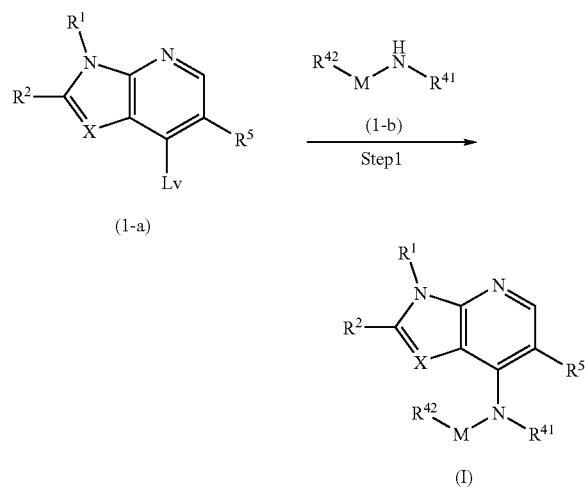

[wherein $R^1$, $R^2$, $R^{41}$, $R^{42}$, $R^5$, M and X are as defined above, and Lv is a leaving group.]

In this process, the compound represented by the formula (I-a) and having a leaving group is reacted with the amine represented by the formula (I-b) to produce the compound according to the present invention represented by the formula (I). The leaving group Lv may include halogen (e.g., chloro and bromo); sulfonyloxy (e.g., methanesulfonyloxy, ethanesulfonyloxy, benzenesulfonyloxy, p-toluenesulfonyloxy, p-nitrobenzenesulfonyloxy, and trifluorometanesulfonyloxy); etc.

In Step 1, the leaving group Lv of the compound represented by the formula (I-a) is substituted with amine. This reaction is carried out under atmospheric pressure or under pressure in the absence of a solvent or in the presence of a suitable solvent.

The solvent may include, for example, aromatic hydrocarbons (e.g., toluene and xylene); ketones (e.g., acetone and methyl ethyl ketone); ethers (e.g., diethylether, tetrahydrofuran (THF), dioxane, and diethoxyethane); alcohols (e.g., methanol (MeOH), ethanol (EtOH), 2-propanol (i-PrOH), and 1-butanol (n-BuOH)); halogenated hydrocarbons (e.g., dichloromethane, 1,2-dichloroethane, chloroform, and carbon tetrachloride); acetonitrile; aprotic solvents (e.g., dimethylformamide (DMF), 1,3-dimethyl-2-imidazolidinone, N-methylpyrrolidone (NMP), and dimethylsulfoxide (DMSO)); water; or a mixture of these. It is preferable that the reaction is carried out in the presence of a base, and the base may include, for example, alkaline carbonates (e.g., sodium carbonate and potassium carbonate); alkaline hydrogencarbonates (e.g., sodium hydrogencarbonate and potassium hydrogencarbonate); alkoxides (e.g., sodium methoxide, sodium ethoxide, and potassium t-butoxide); tertiary amines (e.g., triethylamine, tributylamine, and diisopropylethylamine); organic bases (e.g., 1,8-diazabicyclo[5.4.0]undeca-7-ene, pyridine, and lutidine) However, an excess amount of the compound (I-b) can also be used. Although the reaction temperature differs depending on the type of a starting compound and reaction conditions, the reaction can usually be carried out at a temperature approximately ranging from ambient temperature to the refluxing temperature of a solvent. The reaction can also usually be carried out in the presence of a base, such as sodium hydroxide and sodium carbonate, in an organic solvent inert to the reaction, such as N,N-dimethylformamide and N,N-dimethylacetamide, under ambient temperature to heating. In addition, the amine represented by the formula (I-b) can also be used as a salt thereof for the reaction.

Furthermore, microwave irradiation can also be carried out under heating. Still further, the reaction can also be carried out by a coupling reaction using a phosphorus reagent, such as 2-(di-t-butylphosphino)biphenyl, and a palladium catalyst, such as palladium acetate, in the presence of a base, such as cesium carbonate.

For the reaction, it is possible to use the methods described in the Preparation(s) or the Example(s) of the present specification or methods similar to those. The compound represented by the formula (I-a) can thus be produced using known methods, methods obvious to those skilled in the art, or the methods described in the reference examples or the Examples of the present specification or methods similar to those.

<Second Process>

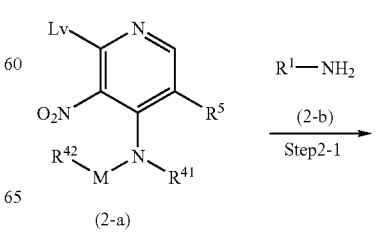

-continued

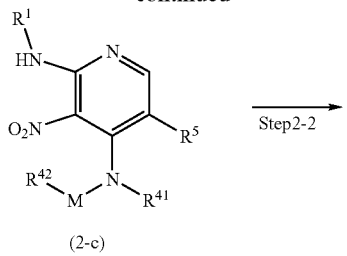

(2-c)

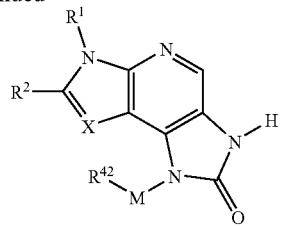

(I-3)

[wherein $R^1$, $R^2$, $R^{42}$, X, and M are as defined forgoing.]

In this process, the compound according to the present invention represented by the formula (3-a) and having a carboxyl group is used as a starting compound to produce the compound according to the present invention represented by the formula (I-3).

In Step 3, the carboxyl group of the compound represented by the formula (3-a) is reacted with an azidation agent, such as diphenylphosphoryl azide (DPPA) and sodium azide, to construct an imidazolone ring according to the so-called Curtius rearrangement reaction. It is advantageous that the reaction is carried out in the presence of a base.

Usually, triethylamine, pyridine, etc. can be used as a base, and the reaction can be carried out under ambient temperature to heating or under heating and refluxing.

<Fourth Process>

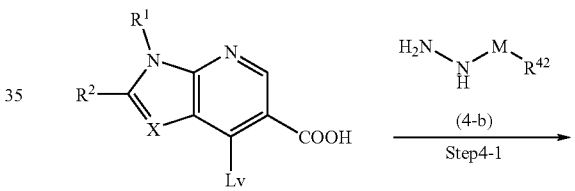

(4-a)

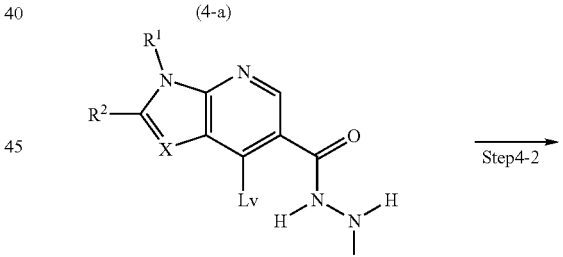

(4-c)

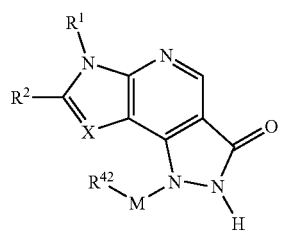

(I-4)

[wherein $R^1$, $R^2$, $R^{42}$, M, X and Lv are as defined forgoing.]

(I-2)

[wherein $R^1$, $R^2$, $R^{41}$, $R^{42}$, $R^5$, M and Lv are as defined forgoing.]

In this process, the nitropyridine compound represented by the formula (2-a) is reacted with the amine represented by the formula (2-b), and the leaving group at the second position is substituted with the amine to derive the aminonitropyridine compound represented by the formula (2-c). The derived compound is used to produce the compound according to the present invention represented by the formula (I-2).

The method used in Step 1 of the first process can be incorporated in Step 2-1. The amine represented by the formula (2-b) can also be used as a salt thereof for the reaction.

In Step 2-2 in the case that —$R^2$ is —H, an imidazole ring can be constructed by reacting an orthoformate, such as ethyl orthoformate, in the presence of an acid catalyst. It is desirable that the nitro group should be reduced before the orthoformate is used for the reaction. Furthermore, the method to be used in the case that the compound represented by the formula (I-2) wherein —$R^2$ is not —H is synthesized may include, for example, the method in which the amino group of the compound represented by the formula (2-c) is acylated in advance, the method in which tetraalkylorthocatbonate or alkylisothiocyanate is used instead of the orthoformate, and the method in which carboxylic acid or carboxylic anhydride is reacted with a strong acid, such as sulfonic acid. These actions can be carried out in a solvent inert to the reactions or in the absence of a solvent, under ambient temperature to heating or under heating and refluxing.

<Third Process>

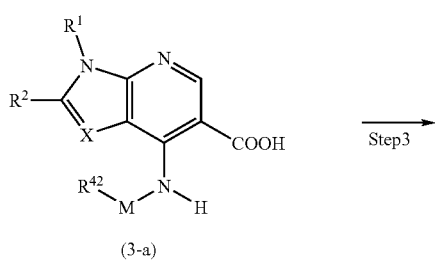

(3-a)

In this process, the carboxylic compound represented by the formula (4-a) is reacted with the hydrazine derivative represented by the formula (4-b) to obtain the hydrazide represented by the formula (4-c). From the hydrazide, the compound according to the present invention represented by the formula (I-4) is produced.

Step 4-1 can be carried out similarly to the reaction in which the compound represented by the formula (4-a) and the compound represented by the formula (4-b) are condensed by amidation. The compound (4-a) can be used as a free acid for the reaction, and the reactive derivative thereof can also be used for the reaction. The reactive derivative of the compound (4-a) may include an acid halide (e.g., acid chloride and acid bromide); an ordinary ester (e.g., methyl ester, ethyl ester, and benzyl ester); acid azide; an activated ester with N-hydroxybenzotriazole (HOBt), p-nitrophenyl, or N-hydroxysuccinimide); a symmetric acid anhydride; a mixed acid anhydride with a halocarboxylic acid alkyl ester (e.g., alkyl halide carbonate), pivaloyl halide, p-toluenesulfonic acid chloride, etc.; and a mixed acid anhydride, such as a phosphoric acid-type mixed acid anhydride obtained by reaction with diphenylphosphoryl chloride or N-methylmorpholine; etc.

When the compound (4-a) is reacted in the form of a free acid or reacted without isolating the activated ester, it is preferable to use a condensing agent, such as dicyclohexylcarbodiimide (DCC), 1,1'-carbonylbis-1H-imidazole (CDI), diphenylphosphoryl azide (DPPA), diethyphosphoryl cyanide (DEPC), and 1-ethyl-3-(3-dimethylaminopropyl) carbodiimide hydrochloride (EDCI HCl).

The reaction is carried out in an organic solvent inert to the reaction, such as halogenated hydrocarbons, aromatic hydrocarbons, ethers, esters (e.g., ethyl acetate), acetonitrile, DMF, and DMSO, under cooling, under cooling to ambient temperature, or under ambient temperature to heating, although the conditions differ depending on the reactive derivative or the condensing agent to be used.

In order to smoothly advance the reaction, it is occasionally advantageous that an excess amount of the compound (4-b) is used for the reaction or the reaction is carried out in the presence of a base, such as N-methylmorpholine, trimethylamine, triethylamine, diisopropylethylamine, N,N-dimethylaniline, pyridine, 4-(N,N-dimethylamino)pyridine, picoline, and lutidine. Pyridine can also be used as a solvent.

The method used in Step 1 of the first process can be incorporated in Step 4-2.

<Fifth Process>

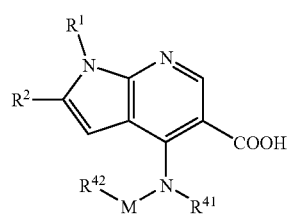

(5-a)

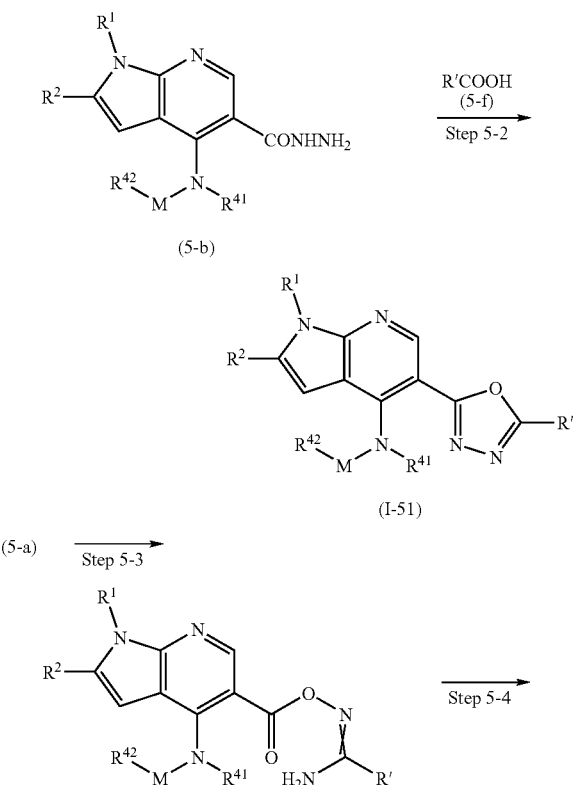

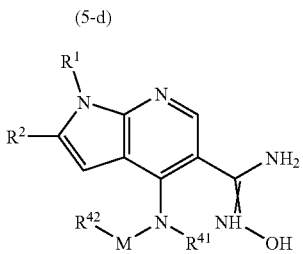

-continued (I-53)

[wherein $R^1$, $R^2$, $R^{41}$, $R^{42}$ and M are as defined above, R' is suitable substituent. The carboxylic acid represented by the formula (5-f) is a marketed product or can be prepared using a marketed product.]

In step 5-2, step 5-4 and step 5-6, a reaction for constructing an oxadiazole ring at $R^5$ is carried out.

In Step 5-1, a reaction for synthesizing an acid hydrazide from the carboxylic acid represented by the formula (5-a) is carried out. Furthermore, the intermediate represented by the formula (5-c) can also be synthesized from the carboxylic acid represented by the formula (5-a). The reaction in Step 4-1 can be incorporated in each of these reactions.

In Step 5-2, Step 5-4, and step 5-6, a reaction for constructing an oxadiazole ring is carried out under ambient temperature to heating. An organic base may be added to advance the reaction.

In Step 5-5, the aromatic nitrile compound represented by the formula (5-d) is reacted with hydroxylamine to obtain hydroxyamidine represented by the formula (5-e). The obtained hydroxyamidine is reacted with the carboxylic acid represented by the formula (5-f) to produce the compound according to the present invention represented by the formula (I-53).

In Step 5-5, the reaction with free hydroxylamine or hydroxylamine hydrochloride is carried out in the presence of a base, whereby the hydroxyamidine represented by the formula (5-e) can be produced.

The reaction can be carried out in a solvent inert to the reaction. The solvent may include, for example, alcohols (e.g., methanol (MeOH), ethanol (EtOH), and 2-propanol (iPrOH)); aromatic hydrocarbons (e.g., toluene and xylene); ethers (e.g., diethylether, tetrahydrofuran (THF), dioxane, and diethoxyethane); halogenated hydrocarbons (e.g., dichloromethane, 1,2-dichloroethane, chloroform, and carbon tetrachloride); aprotic solvents (e.g., DMF, 1,3-dimethyl-2-imidazolidinone, and DMSO); water; or a mixture of these. Usually, alcohols are used for the reaction. In the case that hydroxylamine hydrochloride is used for the reaction as, described above, it is preferable that the reaction is carried out in the presence of a base, and the base may include, for example, alkaline carbonates (e.g., sodium carbonate and potassium carbonate); alkaline hydrogencarbonates (e.g., sodium hydrogencarbonate and potassium hydrogencarbonate); alkoxides (e.g., sodium methoxide, sodium ethoxide, and potassium t-butoxide); tertiary amines (e.g., triethylamine and diisopropylethylamine); and organic bases (e.g., 1,8-diazabicyclo[5.4.0]undeca-7-ene, pyridine, and lutidine) Although the reaction temperature differs depending on the type of a starting compound and reaction conditions, the reaction can usually be carried out at a temperature approximately ranging from ambient temperature to the refluxing temperature of a solvent. The reaction can usually be carried out in the presence of a base, such as sodium carbonate, in an organic solvent inert to the reaction, such as methanol, under ambient temperature to heating.

Step 5-6 consists of two stages: acylation of hydroxyamidine and subsequent cyclization. The intermediate producing method in Step 4-1 can be incorporated in the acylation in the first stage. However, the reaction is usually carried out under ambient temperature to heating, or under heating and refluxing. The cyclization in the second stage can be carried out by isolating and purifying an acyl and by heating the acyl in an organic solvent inert to the reaction, such as ethanol and dioxane, in the presence or absence of a base. The base may include an inorganic base, such as sodium acetate, or an organic base, such as diisopropylethylamine. The reaction consisting of the two stages can be carried out by one operation by performing ordinary acylation and then by directly heating the reaction mixture or by carrying out reaction under microwave irradiation.

The solvent may include, for example, aromatics (e.g., toluene, xylene, and pyridine); ethers (e.g., diethylether, tetrahydrofuran, dioxane, and diethoxyethane); halogenated hydrocarbons (e.g., dichloromethane, 1,2-dichloroethane, chloroform, and carbon tetrachloride); acetonitrile; aprotic solvents (e.g., DMF, N,N-dimethylacetamide (DMA), 1,3-dimethyl-2-imidazolidinone, N-methylpyrrolidone (NMP), and DMSO)); water; or a mixture of these. Although the reaction temperature differs depending on the type of a starting compound and reaction conditions, the reaction can be carried out under ambient temperature to heating.

<Sixth Process>

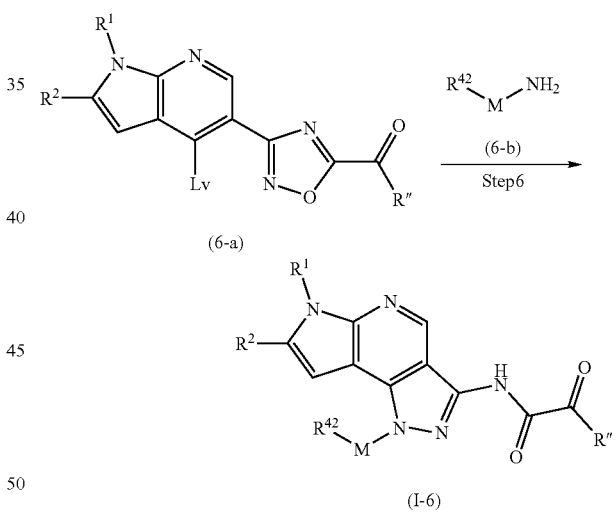

[wherein $R^1$, $R^2$, $R^{42}$, M, and Lv are as defined above; R" is suitable substituent.]

In Step 6, in the case that the compound represented by the formula (6-a) is reacted with the primary amine represented by the formula (6-b), after ipso substitution, the oxadiazole ring is opened to construct an aminopyrazolone ring. The reaction conditions described in Step 1 can be incorporated herein as the reaction conditions. The reaction can be carrying out under ambient temperature to refluxing temperature.

In addition, some of the compounds represented by the formula (I) can also be produced from the compound according to the present invention produced as described above by appropriately combining processes usually used by those skilled in the art, such as known alkylation, acylation, substitution, oxidation, reduction, hydrolysis, deprotection, halogenation, and Mannich reaction. For example, when the compound according to the present invention wherein —R$^5$ is —CO$_2$H is produced from the compound according to the present invention wherein R$^5$ is lower alkyloxycarbonyl, hydrolysis can be used referring to the method described in "Jikken Kagaku Koza (Courses in Experimental Chemistry) (5th Ed., 2003)." Moreover, when the compound according to the present invention wherein R$^5$ is halogen is produced from the compound according to the present invention wherein both R$^3$ and R$^5$ are —H, halogenation can be used referring to the method described in "Jikken Kagaku Koza (Courses in Experimental Chemistry) (5th Ed., 2003)." Still further, when the compound according to the present invention wherein R$^3$ is a lower alkyl substituted with a group selected from the group consisting of mono(lower alkyl)amino, di(lower alkyl) amino, and cyclic amino is produced from the compound according to the present invention wherein R$^3$ is —H, the Mannich reaction can be used referring to the methods described in "Jikken Kagaku Koza (Courses in Experimental Chemistry) (5th Ed., 2003)"; C. Mannich et al., Arch. Pharm., 1912, Vol. 250, p. 647; J. H. Brewster et al., Org. React., 1953, Vol. 7, p. 99; F. F. Blicke, Org. React., 1942, Vol. 1, p. 303; K. W. Merz et al., Pharmazie, 1956, Vol. 11, p. 5-05; etc.

The processes capable of being usually used by those skilled in the art are not only used for the compound according to the present invention but can also be used for intermediates formed during production. The processes can also advance to subsequent processes.

The compound produced as described above is in a free form or subjected to salt-forming processing using a conventional method and isolated and purified as a salt thereof. The isolation and purification are carried out by performing ordinary chemical operations, such as extraction, concentration, evaporation, crystallization, filtration, recrystallization, and various types of chromatography.

Various types of isomers can be isolated by utilizing the difference in physicochemical properties between the isomers using a conventional method. For example, a racemic mixture can be converted into an optically pure isomer using a general racemic resolution method, such as the method in which the racemic mixture is converted into a diastereomer salt with a general optically-active acid, such as tartaric acid, and subjected to optical resolution. Furthermore, the diastereo mixture can be separated by fractional crystallization or various types of chromatography, for example. Still further, the optically-active compound can also be produced using a suitable optically-active material.

The pharmacological activity of the compound according to the present invention was verified by carrying out the following test.

Test Example 1

JAK3 Inhibition Test

The JAK3 inhibition test was performed as described below according to the method of Okimoto et al.

(1) Preparation of Human JAK3

Purified human JAK3 kinase domain was purchased from Carna Biosciences, Inc. (Kobe, Japan). This is obtained as described below. His-tag (41 kDa) was attached to the N-terminal of the 796-1124 (C-terminal) fragment of the human JAK3 protein (accession number #NM_000215), expressed using baculovirus expression system, and then purified using Ni-NTA affinity column chromatography.

(2) Measurement of JAK3 Activity

As substrates, Biotin-Lyn-Substrate-2 (Biotin-XEQED EPEGF YFEWL EPE, X=∈-Acp (PEPTIDE INSTITUTE, INC., Osaka, Japan) and ATP were used. As an assay buffer, 15 mM Tris-HCl pH 7.5 containing 0.01% Tween 20 and 2 mM DTT was used. Normally, 20 µL of a substrate solution (an assay buffer containing 627 nM Biotin-Lyn-Substrate-2, 20 µM ATP, and 25 mM MgCl$_2$), an assay buffer containing 10 µL of a substance to be tested, and 20 µL of an enzyme solution were added to a microplate, and stirred sufficiently.

After incubation at ambient temperature for one hour, the plate was washed with a cleaning buffer (50 mM Tris-HCl pH 7.5, 150 mM NaCl, 0.02% Tween 20), and a blocking buffer (a cleaning buffer containing 0.1% bovine serum albumin) was added to the plate. After incubation at ambient temperature for 30 minutes, the blocking buffer was removed, and an HRP-PY-20 solution (obtained by diluting HRP-PY-20 solution with the blocking buffer 500 times) was added. After incubation at ambient temperature for 30 minutes, the plate was washed four times, and a TMB substrate solution (Sigma) was added to the plate. After incubation at ambient temperature for four minutes, 1M sulfuric acid was added to stop the reaction. Enzyme activity was measured as absorbance at 450 nm. The efficacy of the test compound as a JAK3 inhibitor was expressed as an IC$_{50}$ value.

The IC$_{50}$ values described below are results obtained in the test.

The results of those tests are shown in the Table 1. Table 1: JAK3 inhibitory activity of the compound of the present invention.

TABLE 1

| Ex | IC$_{50}$ (nM) |
|---|---|
| 29 | 2.3 |
| 32 | 1.9 |
| 33 | 2.1 |
| 34 | 0.17 |
| 121 | 1.1 |
| 122 | 0.43 |
| 133 | 4.4 |
| 143 | 0.69 |
| 379 | 1.2 |
| 384 | 0.28 |
| 405 | 0.65 |
| 426 | 2.3 |
| 434 | 0.86 |
| 484 | 0.31 |
| 498 | 1.3 |
| 543 | 0.33 |

It is verified that the compound according to the present invention has inhibition activity against JAK3 and is useful as an active ingredient of an agent for treating or preventing diseases caused by undesirable cytokine signal transmission (e.g., rejection during organ/tissue transplantation, autoimmune diseases, asthma, atopic dermatitis, Alzheimer's disease, and atherosclerotic disease), or diseases caused by abnormal cytokine signal transmission (e.g., cancer and leukemia).

In addition, on the basis of the JAK3 inhibition activity, the compound according to the present invention is useful for treating and/or preventing the following diseases.

The pharmaceutical composition of the present invention comprising JAK3 inhibitor such as the compound (I) is useful as a therapeutic or prophylactic agent for diseases or conditions caused by undesirable cytokine signal transduction, such as rejection reaction in organ/tissue transplantation, autoimmune diseases, asthma, atopic dermatitis, Alzheimer's disease, atherosclerosis, tumors, myelomas, and leukemia as exemplified below: rejection reactions by transplantation of organs or tissues such as the heart, kidney, liver, bone marrow, skin, cornea, lung, pancreas, islet, small intestine, limb, muscle, nerve, intervertebral disc, trachea, myoblast, cartilage, etc.; and graft-versus-host reactions following bone marrow transplantation; autoimmune diseases such as rheumatoid arthritis, systemic lupus, erythematosus, Hashimoto's thyroiditis, multiple sclerosis, myasthenia gravis, type I diabetes and complications from diabetes, etc.

Furthermore, pharmaceutical preparations of the JAK3 inhibitor, such as the compound (I), are useful for the therapy or prophylaxis of the following diseases.

Inflammatory or hyperproliferative skin diseases or cutaneous manifestations of immunologically-mediated diseases (e.g., psoriasis, atopic dermatitis, contact dermatitis; eczematoid dermatitis, seborrheic dermatitis, lichen planus, pemphigus, bullous penphigoid, epidermolysis bullosa, urticaria, angioedema, vasculitides, erythema, dermal eosinophilia, lupus erythematosus, acne, alopecia greata, etc.);

autoimmune diseases of the eye (e.g., keratoconjunctivitis, vernal conjunctivitis, uveitis associated with Behcet's disease, keratitis, herpetic keratitis, conical keratitis, corneal epithelial dystrophy, keratoleukoma, ocular premphigus, Mooren's ulcer, scleritis, Grave's opthalmopathy, Vogt-Koyanagi-Harada syndrome, keratoconjunctivitis sicca (dry eye), phlyctenule, iridocyclitis, sarcoidosis, endocrine opthalmopathy, etc.);

reversible obstructive airways diseases [asthma (e.g., bronchial asthma, allergic asthma, intrinsic asthma, extrinsic asthma, dust asthma, etc.), particularly chronic or inveterate asthma (e.g., late asthma, airway hyper-responsiveness, etc.), bronchitis, etc.]; mucosal or vascular inflammations (e.g., gastric ulcer, ischemic or thrombotic vascular injury, ischemic bowel diseases, enteritis, necrotizing enterocolitis, intestinal damages associated with thermal burns, leukotriene B4-mediated diseases, etc.);

intestinal inflammations/allergies (e.g., coeliac diseases, proctitis, eosinophilic gastroenteritis, mastocytosis, Crohn's disease, ulcerative colitis, etc.);

food-related allergic diseases with symptomatic manifestation remote from the gastrointestinal tract (e.g., migraine, rhinitis, eczema, etc.);

autoimmune diseases and inflammatory conditions (e.g., primary mucosal edema, autoimmune atrophic gastritis, premature menopause, male sterility, juvenile diabetes mellitus, pemphigus vulgaris, pemphigoid, sympathetic ophthalmitis, lens-induced uveitis, idiopathic leukopenia, active chronic hepatitis, idiopathic cirrhosis, discoid lupus erythematosus, autoimmune brchitis, arthritis (e.g., arthritis deformans, etc.), polychondritis, etc.); allergic conjunctivitis.

Therefore, the pharmaceutical composition of the present invention is useful for the therapy and prophylaxis of liver diseases [e.g., immunogenic diseases (e.g., chronic autoimmune liver diseases such as autoimmune hepatic diseases, primary biliary cirrhosis, sclerosing cholangitis, etc.), partial liver resection, acute liver necrosis (e.g., necrosis caused by toxins, viral hepatitis, shock, anoxia, etc.), hepatitis B, non-A/non-B hepatitis, hepatocirrhosis, hepatic failure (e.g., fulminant hepatitis, late-onset hepatitis, "acute-on-chronic" liver failure (acute liver failure on chronic liver diseases, etc.), etc.), etc.].

Pharmaceutical preparations of the JAK3 inhibitor, such as the compound (I), either from alone or in combination with one or more additional agents which may include but are not limited to cyclosporin A, tacrolimus, sirolimus, everolimus, micophenolate (e.g. Cellcept(R), Myfortic(R), etc.), azathioprine, brequinar, leflunomide, sphingosine-1-phosphate receptor agonist (e.g. fingolimod, KRP-203, etc.), LEA-29Y, anti-IL-2 receptor antibody (e.g. daclizumab, etc.), anti-CD3 antibody (e.g. OKT3, etc.), Anti-T cell immunogloblin (e.g. AtGam, etc.) aspirin, CD28-B7 blocking molecules (e.g. Belatacept, Abatacept, etc.), CD40-CD154 blocking molecules (e.g. Anti-CD40 antibody, etc.), protein kinase C inhibitor (e.g. AEB-071, etc.), acetaminophen, ibuprofen, naproxen, piroxicam, and anti inflammatory steroid (e.g. prednisolone or dexamethasone) may be administrated as part of the same or separate dosage forms, via the same or different routes of administration, and on the same or different administration schedules according to standard pharmaceutical practice.

The pharmaceutical composition containing one or two or more kinds of the compound represented by, the formula (I) or pharmaceutically acceptable salts thereof as an active ingredient can be prepared using carriers, excipients, and other additives usually used for pharmaceutical preparation.

Therapeutic administration can be accomplished either by oral administration via tablets, pills, capsules, granules, powders, solutions, etc., or parenteral administration via intravenous or intramascular injections, suppositories, transdermal agents, transnasal agents, inhalers, etc. The dose of the compound is determined appropriately in consideration of the symptoms, age, sex, and the like of each patient to be treated. Usually, in the case of oral administration, a daily dose of approximately 0.001 to 100 mg/kg of the compound can be administered one or two to four times per day for an adult patient. When intravenous administration is required depending on symptoms, a dose of 0.0001 to 10 mg/kg of the compound can usually be administered one to multiple times per day for an adult patient. In the case of inhalation, a dose of 0.0001 to 1 mg/kg of the compound can usually be administered one to multiple times per day for an adult patient.

The solid composition for use in the oral administration according to the present invention is used in the form of tablets, powders, granules, etc. In such a solid composition, one or more active ingredients are mixed with at least one inactive excipient, such as lactose, mannitol, glucose, hydroxypropyl cellulose, microcrystalline cellulose, starch, polyvinyl pyrrolidone, and magnesium aluminometasilicate. According to a usual method, the composition may contain inactive additives, such as a lubricant (e.g., magnesium stearate), a disintegrating agent (e.g., carboxymethyl starch sodium), and a solubilization assisting agent. If necessary, tablets or pills may be coated with sugar or a film of a gastric or enteric coating substance.

The liquid composition for oral administration contains pharmaceutically acceptable emulsions, solutions, suspensions, syrups, or elixirs, and also contains a generally used inert diluent, such as purified water or ethanol. In addition to the inert diluent, the composition may also contain auxiliary agents, such as a solubilization assisting agent, a moistening agent, and a suspending agent, as well as sweeteners, flavors, aromatics, and antiseptics.

The injections for parenteral administration contain aseptic aqueous or non-aqueous solutions, suspensions, or emulsions. The diluent for use in the aqueous solutions may include, for example, distilled water for injection use and physiological saline. The diluent for use in the non-aqueous solutions may include, for example, propylene glycol, polyethylene glycol, plant oil (e.g., olive oil), alcohol (e.g., ethanol), and polysorbate 80 (official name). Such a composition may further contain additive agents, such as a tonicity agent, an antiseptic, a moistening agent, an emulsifying agent, a dispersing agent, a stabilizing agent, and a solubilization assisting agent. These compositions are sterilized by filtration through a bacteria retaining filter, blending of a germicide, or irradiation. Furthermore, they may also be produced in the form of sterile solid compositions and dissolved or suspended in sterile water or a sterile solvent for injection use prior to their use.

The transmucosal agents, such as inhalers and transnasal agents, are used in the form of solid, liquid or semisolid and can be produced according to conventional known methods. For example, excipients (e.g., lactose and starch), pH adjusters, antiseptics, surface active agents, lubricants, stabilizers, thickeners, etc. may also be added as necessary. For administration, suitable devices for inhalation or insufflation can be used. For example, using known devices and sprayers, such as measuring inhalation devices, the compound can be administered independently or in the form of prescribed mixture powders. Furthermore, the compound combined with pharmaceutically acceptable carriers can also be administered in the form of solutions or suspensions. Dry powder inhalers and the like may be devices for single or multiple administrations, and dry powders or capsules containing powders can also be used. Still further, the devices may be in the form of a pressure aerosol spray or the like that uses a suitable ejection agent, such as chlorofluoroalkane or hydrofluoroalkane, or a suitable gas, such as carbon dioxide.

The drug for external use may include ointments, plasters, creams, jellies, patches, sprays, lotions, eye-drops, eye ointments, etc. The drug contains generally used ointment bases, lotion bases, aqueous or non-aqueous solutions, suspensions, emulsions, etc. The ointment bases or lotion bases may include, for example, polyethylene glycol, carboxyvinal polymer, white vaseline, bleached bee wax, polyoxyethylene hydrogenated castor oil, glyceryl monostearate, stearyl alcohol, cetyl alcohol, lauromacrogol, and sorbitan sesquioleate.

EXAMPLES

Although the present invention is described below specifically by way of Examples, the present invention is not limited by these Examples at all. Starting compounds being used in Examples include novel substances, and the methods for producing such starting compounds from known compounds are described by way of Preparations.

Preparation 1

The compounds in Preparations 1-1 to 1-25 shown in the following table were produced by using the corresponding starting compounds according to the method similar to that described in Example 1.

TABLE 2

| Pr | Structure |
|---|---|
| 1-1 | |
| 1-2 | 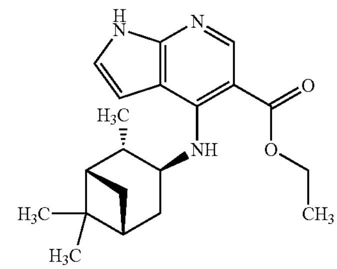 |
| 1-3 | cis/trans mix |
| 1-4 | 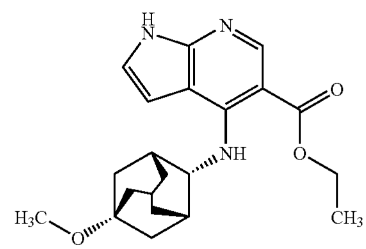 |
| 1-5 | trans |
| 1-6 | cis/trans mix |

TABLE 2-continued

| Pr | Structure |
|---|---|
| 1-7 | 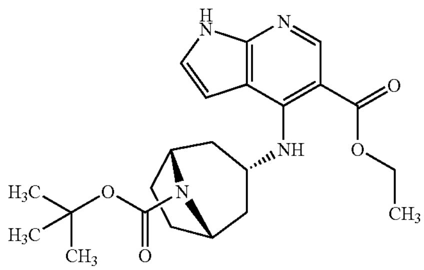 |
| 1-8 | 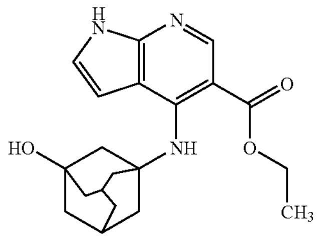 |
| 1-9 | cis/trans mix |
| 1-10 | 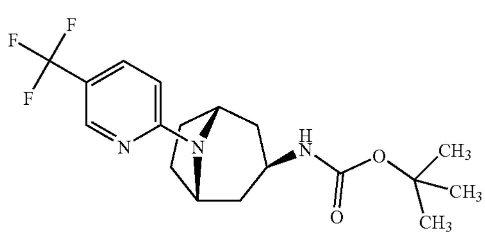 |
| 1-11 | cis or trans unknown |
| 1-12 | cis or trans unknown |
| 1-13 | |
| 1-14 | diastereomer of 1-15<br>cis or trans unknown |
| 1-15 | diastereomer of 1-14<br>cis or trans unknown |
| 1-16 | cis/trans mix |

TABLE 2-continued
| Pr | Structure |
|---|---|
| 1-17 | 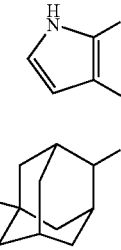<br>diastereomer of 1-18<br>cis or trans unknown |
| 1-18 | 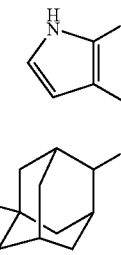<br>diastereomer of 1-17<br>cis or trans unknown |
| 1-19 | 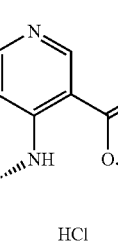<br>HCl |
| 1-20 | 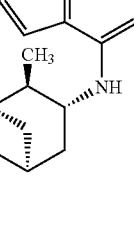 |
| 1-21 | 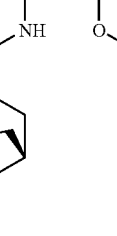 |
| 1-22 | 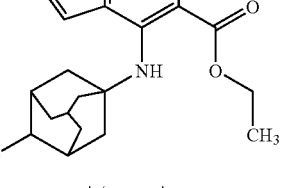<br>cis/trans mix |
| 1-23 | 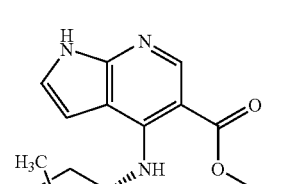 |
| 1-24 | 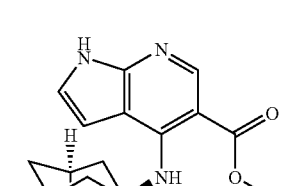 |
| 1-25 | 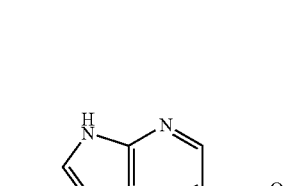 |

TABLE 3

| Pr | Data |
|---|---|
| 1-1 | MS: 342 (M + H)+ |
| 1-2 | MS: 342 (M + H)+ |
| 1-3 | MS: 460 (M + H)+ |
| 1-4 | MS: 370 (M + H)+ |
| 1-5 | MS: 370 (M + H)+ |
| 1-6 | MS: 358 (M + H)+ |
| 1-7 | 1H-NMR (400 MHz, d6-DMSO)δ: 1.32 (3H, t, J = 7.0 Hz), 1.43 (9H, s), 1.73-1.87 (2H, m), 1.90-2.08 (4H, m), 2.18-2.33 (2H, m), 4.08-4.18 (2H, m), 4.28 (2H, q, J = 7.0 Hz), 4.37-4.47 (1H, m), 6.52-6.57 (1H, m), 7.13-7.18 (1H, m), 8.56 (1H, s), 9.39 (1H, d, J = 7.6 Hz), 11.67 (1H, s). MS: 415 (M + H)+ |
| 1-8 | 1H-NMR (400 MHz, d6-DMSO)δ: 0.32 (3H, t, J = 7.1 Hz), 0.48-3.13 (14H, m), 4.26 (2H, q, J = 7.1 Hz), 4.68 (1H, s), 6.71-6.72 (1H, m), 7.23-7.24 (1H, m), 8.60 (1H, s), 9.34 (1H, s), 11.69 (1H, s). MS: 356 (M + H)+ |
| 1-9 | 1H-NMR (400 MHz, d6-DMSO)δ: 0.32 (3H, t, J = 7.1 Hz), 0.40-0.47 (2H, m), 1.95-2.17 (11H, m), 0.80-0.83 (1H, m), 4.26 (2H, q, J = 7.1 Hz), 4.73 (1H, d, J = 2.9 Hz), 6.76 (1H, dd, J = 2.4 Hz, 3.5 Hz), 7.22 (1H, dd, J = 2.6 Hz, 3.3 Hz), 8.60 (1H, s), 9.33 (1H, s), 11.68 (1H, s). MS: 356 (M + H)+ |
| 1-10 | MS: 372 (M + H)+ |
| 1-11 | MS: 471 (M + H)+ |
| 1-12 | MS: 481 (M + H)+ |
| 1-13 | MS: 405 (M + H)+ |
| 1-14 | MS: 484 (M + H)+ |
| 1-15 | MS: 484 (M + H)+ |
| 1-16 | MS: 517 (M + H)+ |
| 1-17 | MS: 445 (M + H)+ |
| 1-18 | MS: 445 (M + H)+ |
| 1-19 | MS: 300 (M + H)+ |
| 1-20 | MS: 342 (M + H)+ |
| 1-21 | MS: 354 (M + H)+ |
| 1-22 | MS: 356 (M + H)+ |
| 1-23 | MS: 342 (M + H)+ |
| 1-24 | 1H-NMR (400 MHz, d6-DMSO)δ: 1.35 (3H, t, J = 7.1 Hz), 1.68-1.77 (6H, m), 2.10-2.18 (9H, m), 4.26 (2H, q, J = 7.1 Hz), 6.75 (1H, d, J = 3.6 Hz), 7.22 (1H, d, J = 3.4 Hz), 8.60 (1H, s), 9.34 (1H, s), 11.67 (1H, s). MS: 340 (M + H)+ |
| 1-25 | 1H-NMR (400 MHz, d6-DMSO)δ: 1.32 (3H, t, J = 7.1 Hz), 1.61-2.07 (16H, m), 4.29 (2H, q, J = 7.1 Hz), 4.48 (1H, d, J = 3.5 Hz), 7.18 (1H, d, J = 3.2 Hz), 9.36 (1H, d, J = 8.0 Hz), 11.67 (1H, s). MS: 340 (M + H)+ |

Preparation 2

To glycinamide hydrochloride (34 mg) were added a solution of ethyl 3-(4-chloro-1H-pyrrolo[2,3-b]pyridin-5-yl)-1,2,4-oxadiazole-5-carboxylate (60 mg) in 1-methyl-2-pyrrolidone (0.6 ml) and 1,8-diazabicyclo[5.4.0]undec-7-ene (0.092 ml), and the mixture was stirred at 70° C. for 1 hour. After being left to cool, the reaction solution was directly purified by preparative HPLC (10 mM NH$_4$HCO$_3$+NH$_3$ (pH=9.2): CH$_3$CN=90:10 to 20:80). The active fraction was concentrated and dried to hardness to obtain 3-(4-chloro-1H-pyrrolo[2,3-b]pyridin-5-yl)-N-methyl-1,2,4-oxadiazole-5-carboxylate (23 mg) as a solid.

The compounds in Preparations 2-1 to 2-26 shown in the following table were produced using the corresponding starting compounds according to the method similar to that described in Preparation 2.

TABLE 4

| Pr | Structure |
|---|---|
| 2 | (4-chloro-1H-pyrrolo[2,3-b]pyridin-5-yl)-1,2,4-oxadiazole with C(=O)NH-Me) |
| 2-1 | (4-chloro-1H-pyrrolo[2,3-b]pyridin-5-yl)-1,2,4-oxadiazole with C(=O)-N(4-hydroxypiperidine) |

TABLE 4-continued

| Pr | Structure |
|---|---|
| 2-2 | 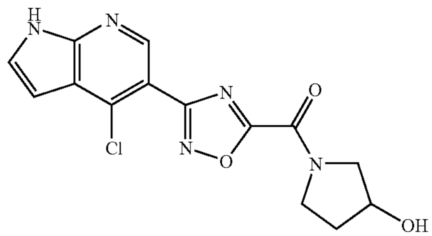 |
| 2-3 | 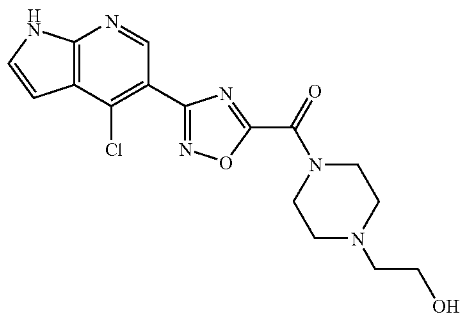 |
| 2-4 | Chiral |
| 2-5 | 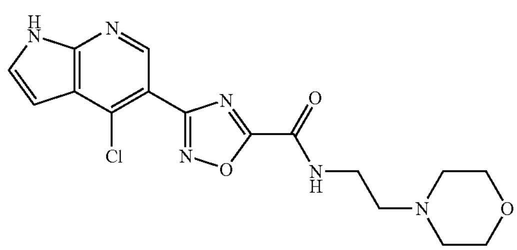 |
| 2-6 | 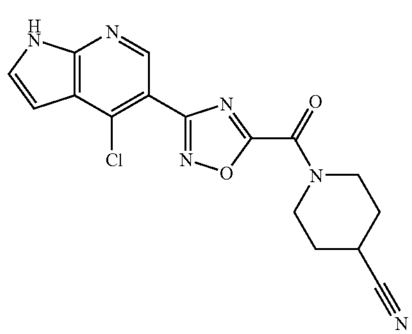 |
| 2-7 | 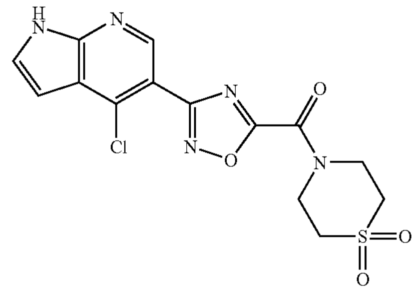 |
| 2-8 | 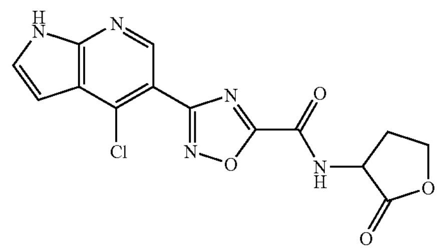 |
| 2-9 | 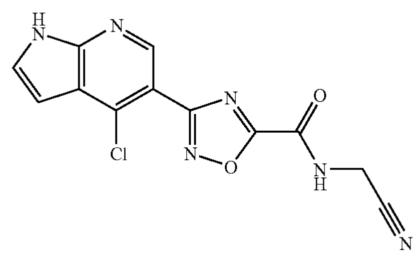 |
| 2-10 | 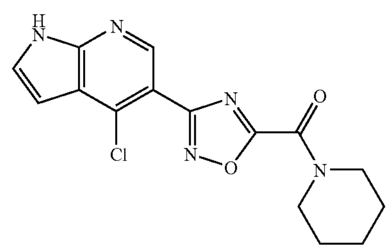 |
| 2-11 | 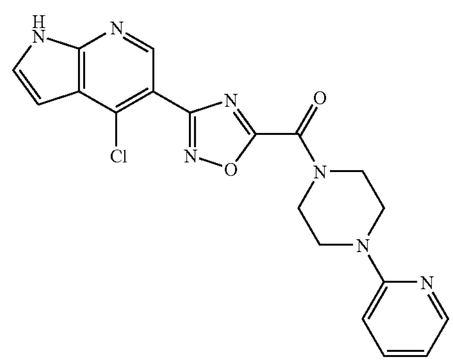 |

TABLE 4-continued

| Pr | Structure |
|---|---|
| 2-12 | 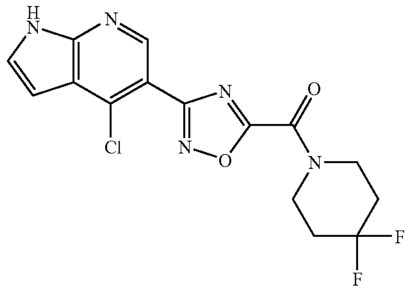 |
| 2-13 | 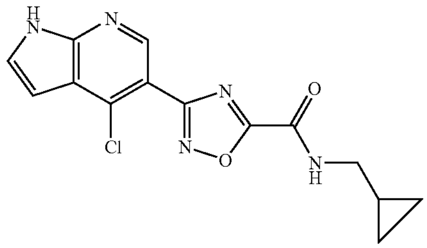 |
| 2-14 | 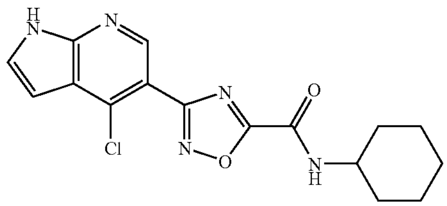 |
| 2-15 | 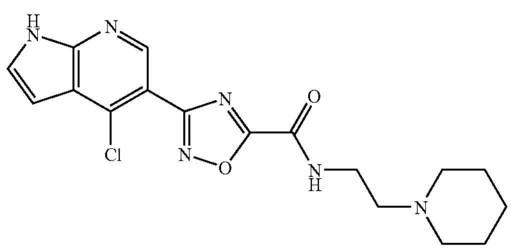 |
| 2-16 | 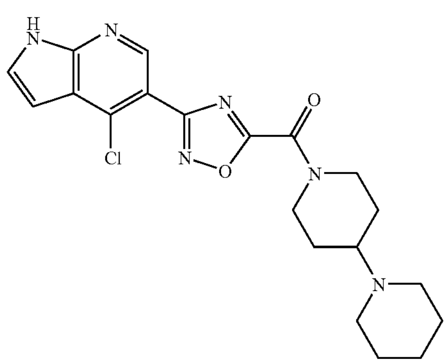 |
| 2-17 | 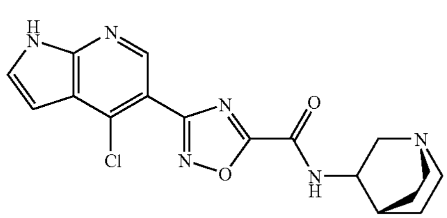 |
| 2-18 | Chiral |
| 2-19 | Chiral |
| 2-20 | 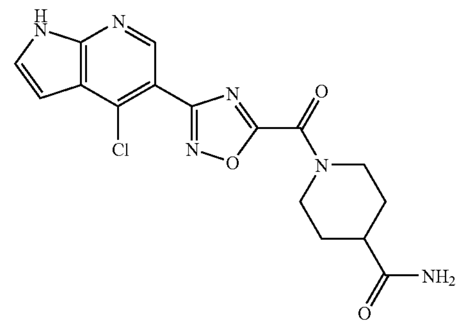 |
| 2-21 | Chiral |
| 2-22 | Chiral |
| 2-23 | Chiral |

TABLE 4-continued

| Pr | Structure |
|---|---|
| 2-24 | [Structure: 7-azaindole-Cl with oxadiazole linked to morpholine-CH2-OMe, Chiral] |
| 2-25 | [Structure: 7-azaindole-Cl with oxadiazole linked to morpholine] |
| 2-26 | [Structure: 7-azaindole-Cl with oxadiazole linked to N-methylpiperazine] |

TABLE 5

| Ex | MS data | Ex | MS data |
|---|---|---|---|
| 2 | MS: 278 (M + H)+ | 2-1 | MS: 348 (M + H)+ |
| 2-2 | MS: 334 (M + H)+ | 2-3 | MS: 377 (M + H)+ |
| 2-4 | MS: 361 (M + H)+ | 2-5 | MS: 377 (M + H)+ |
| 2-6 | MS: 357 (M + H)+ | 2-7 | MS: 382 (M + H)+ |
| 2-8 | MS: 348 (M + H)+ | 2-9 | MS: 303 (M + H)+ |
| 2-10 | MS: 332 (M + H)+ | 2-11 | MS: 410 (M + H)+ |
| 2-12 | MS: 368 (M + H)+ | 2-13 | MS: 318 (M + H)+ |
| 2-14 | MS: 346 (M + H)+ | 2-15 | MS: 375 (M + H)+ |
| 2-16 | MS: 415 (M + H)+ | 2-17 | MS: 373 (M + H)+ |
| 2-18 | MS: 322 (M + H)+ | 2-19 | MS: 322 (M + H)+ |
| 2-20 | MS: 375 (M + H)+ | 2-21 | MS: 350 (M + H)+ |
| 2-22 | MS: 334 (M + H)+ | 2-23 | MS: 378 (M + H)+ |
| 2-24 | MS: 378 (M + H)+ | 2-25 | MS: 334 (M + H)+ |
| 2-26 | MS: 347 (M + H)+ | | |

Preparation 3

Benzyl 4-chloro-1H-pyrrolo[2,3-b]pyridine-5-carboxylate (55 mg), ethyl {[(4-amino-1-adamantyl) carbonyl]amino}acetate (54 mg) and triethylamine (80 µl) were dissolved in N-methyl-2-pyrrolidone (0.55 ml) and stirred at 180° C. for 1 hour using a microwave reaction system. To the reaction solution were added ethyl acetate and water, and the mixture was extracted with ethyl acetate. The organic layer was washed with saturated brine, dried over magnesium sulfate, and evaporated under reduced pressure. The residue was purified by silica gel column chromatography (n-hexane: ethyl acetate), the obtained compound was dissolved in dioxane (1.1 ml) and methanol (1.1 ml), 10% palladium on carbon (50% wet) was added, and catalytic reduction was performed for 4 hours at ambient temperature at 1 atm. Methanol, dioxane, and 1M hydrochloric acid were added, and the precipitated solid was dissolved and filtered to remove the catalyst. The filtrate was concentrated under reduced pressure to obtain 4-({5-[(2-ethoxy-2-oxoethyl)carbamoyl]adamantan-2-yl}amino)-1H-pyrrolo[2,3-b]pyridine-5-carboxylic acid (18 mg).

TABLE 6

| Pr | Structure | Data |
|---|---|---|
| 3 | [Structure: cis/trans mix, 7-azaindole-COOH with adamantane-NH linked via NH-C(=O)-CH2-O-CH2CH3] | MS: 441(M + H) + |

Preparation 4

To a ethanol (3 ml) was added acetyl chloride carefully at 4° C. The reaction solution was stirred at 4° C. for 30 minutes. To the reaction solution were added a solution of 4-{[(2r,5s)-5-hydroxyadamantan-2-yl]amino}-1H-pyrrolo[2,3-b]pyridine-5-carbonitrile (50 mg) in chloroform (0.5 ml) and 2M hydrochloric acid/ethanol solution (0.5 ml) dropwise. The reaction solution was stirred under ambient temperature for 18 hours. The reaction solution was concentrated under reduced pressure to obtain ethyl 4-{[(2r,5s)-5-hydroxyadamantan-2-yl]amino}-1H-pyrrolo[2,3-b]pyridine-5-carboxylmidate trihydrochloride (75 mg).

TABLE 7

| Pr | Structure | Data |
|---|---|---|
| 4 | [Structure: 7-azaindole with C(=NH)-O-CH2CH3 and NH-adamantane-OH, cis, 3 HCl] | MS: 355(M − 3HCl + H) + |

Preparation 5

The compounds in Preparations 5-1 to 5-32 shown in the following table were produced using the corresponding starting compounds according to the method similar to that described in Example 3.

TABLE 8

| Pr | Structure |
|---|---|
| 5-1 | (7-azaindole-5-carboxylic acid with norbornyl-NH substituent) |
| 5-2 | (7-azaindole-5-carboxylic acid with norbornyl-NH substituent) |
| 5-3 | (7-azaindole-5-carboxylic acid with adamantyl-NH substituent) |
| 5-4 | (7-azaindole-5-carboxylic acid with dimethyl-norbornyl-NH substituent) |
| 5-5 | (7-azaindole-5-carboxylic acid with adamantyl-NH substituent) |
| 5-6 | (7-azaindole-5-carboxylic acid with adamantyl-methyl-NH substituent) |
| 5-7 | (7-azaindole-5-carboxylic acid with N-Boc-tropanyl-NH substituent) |
| 5-8 | (imidazo[4,5-b]pyridine-6-carboxylic acid with hydroxyadamantyl-NH substituent, cis) |
| 5-9 | (N-(3,4-dimethoxybenzyl)-imidazo[4,5-b]pyridine-6-carboxylic acid with hydroxyadamantyl-NH substituent, cis) |
| 5-10 | (imidazo[4,5-b]pyridine-6-carboxylic acid with methoxyadamantyl-NH substituent, trans) |

TABLE 8-continued
| Pr | Structure |
|---|---|
| 5-9 | 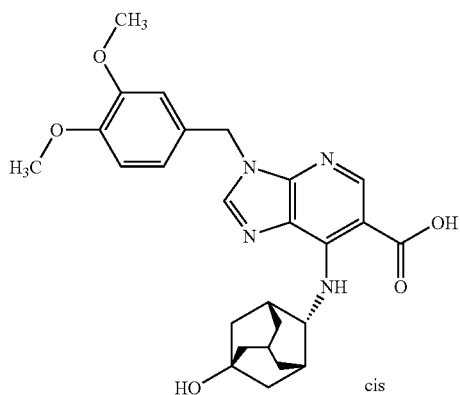 cis |
| 5-10 | 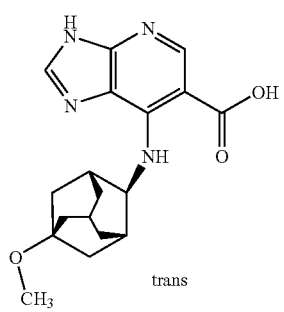 trans |
| 5-11 | 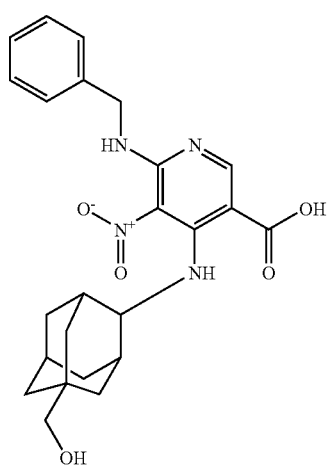 diastereomer of 5-12 cis or trans unknown |
| 5-12 | 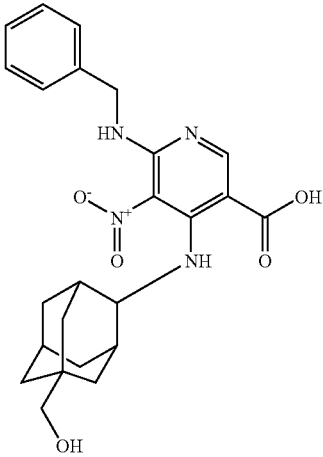 diastereomer of 5-11 cis or trans unknown |
| 5-13 | 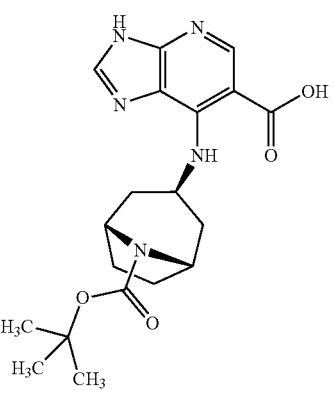 |
| 5-14 | 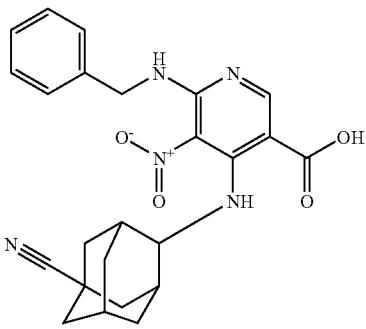 cis or trans unknown |

TABLE 8-continued

| Pr | Structure |
|---|---|
| 5-15 | (structure) |
| 5-16 | (structure) |
| 5-17 | (structure) trans |
| 5-18 | (structure) cis/trans mix |
| 5-19 | (structure) |
| 5-20 | (structure) cis/trans mix |
| 5-21 | (structure) cis |
| 5-22 | (structure) cis/trans mix |
| 5-23 | (structure) cis/trans mix |
| 5-24 | (structure) |

TABLE 8-continued

| Pr | Structure |
|---|---|
| 5-25 | (structure) |
| 5-26 | (structure) cis/trans mix |
| 5-27 | (structure) |
| 5-28 | (structure) cis |
| 5-29 | (structure) |
| 5-30 | (structure) |
| 5-31 | (structure) cis/trans mix |
| 5-32 | (structure) |

TABLE 9

| Pr | Data |
|---|---|
| 5-1 | MS: 272 (M + H)+ |
| 5-2 | MS: 272 (M + H)+ |
| 5-3 | 1H-NMR (400 MHz, d6-DMSO) δ: 1.60-2.06 (14H, m), 4.24 (1H, d, J = 7.9 Hz), 6.46 (1H, dd, J = 1.3 Hz, 3.3 Hz), 7.16 (1H, dd, J = 2.4 Hz, 3.2 Hz), 8.52 (1H, s), 9.61 (1H, s), 11.59 (1H, s), 12.33 (1H, br)MS: 312 (M + H)+ |
| 5-4 | MS: 314 (M + H)+ |
| 5-5 | 1H-NMR (400 MHz, d6-DMSO) δ: 1.67-1.75 (6H, m), 2.09-2.16 (9H, m), 6.71 (1H, s), 7.16 (1H, s), 8.56 (1H, s), 9.76 (1H, br), 11.49 (1H, s). MS: 312 (M + H)+ |
| 5-6 | MS: 326 (M + H)+ |
| 5-7 | MS: 410 (M + Na)+ |
| 5-8 | MS: 329 (M + H)+ |
| 5-9 | MS: 479 (M + H)+ |
| 5-10 | |
| 5-11 | MS: 475 (M + Na)+ |
| 5-12 | |
| 5-13 | MS: 409 (M + Na)+ |
| 5-14 | MS: 446 (M − H)− |
| 5-15 | MS: 377 (M + H)+ |
| 5-16 | MS: 209 (M − H)− |
| 5-17 | MS: 342 (M + H)+ |
| 5-18 | MS: 330 (M + H)+ |
| 5-19 | 1H-NMR (400 MHz, d6-DMSO) δ: 1.43 (9H, s), 1.70-1.88 (2H, m), 1.88-2.09 (4H, m), 2.14-2.33 (2H, m), 4.05-4.20 (2H, m), 4.34-4.46 (1H, m), 6.48-6.58 (1H, m), 7.09-7.17 (1H, m), 8.52 (1H, s), 9.67 (1H, d, J = 6.2 Hz), 11.62 (1H, s), 12.45 (1H, br). MS: 387 (M + H)+ |
| 5-20 | MS: 463 (M + Na)+ |
| 5-21 | MS: 437 (M − H)− |

TABLE 9-continued

| Pr | Data |
|---|---|
| 5-22 | MS: 371 (M + Na)+ |
| 5-23 | 1H-NMR (400 MHz, d6-DMSO) δ: 1.40-1.46 (2H, m), 1.96-2.15 (11H, m), 2.44-2.55 (1H, m), 3.82 (1H, s), 4.71 (1H, s), 6.72-6.75 (1H, m), 7.19 (1H, t, J = 2.9 Hz), 8.56 (1H, s), 9.71 (1H, br), 11.57 (1H, s). MS: 328 (M + H)+ |
| 5-24 | MS: 355 (M + Na)+ |
| 5-25 | MS: 314 (M + H)+ |
| 5-26 | MS: 437 (M − H)− |
| 5-27 | MS: 261 (M + H)+ |
| 5-28 | MS: 342 (M + H)+ |
| 5-29 | MS: 314 (M + H)+ |
| 5-30 | 1H-NMR (400 MHz, d6-DMSO) δ: 1.48-1.68 (6H, m), 1.98 (6H, s), 2.26 (2H, s), 4.66 (1H, s), 6.68 (1H, dd, J = 5.3 Hz, 11.4 Hz), 7.2 (1H, dd, J = 2.5 Hz, 3.0 Hz), 8.57 (1H, s), 9.70 (1H, br), 11.58 (1H, s). MS: 328 (M + H)+ |
| 5-31 | MS: 328 (M + H)+ |
| 5-32 | MS: 458 (M + H)+ |

Preparation 6

To a ethyl 7-[(trans-5-hydroxyadamantan-2-yl)amino]-3H-imidazo[4,5-b]pyridine-6-carboxylate (50 mg) was added 47% aqueous hydrobromic acid (0.75 ml), and the mixture was stirred at 120° C. for 1 hour using a microwave reaction system. After the reaction solution was cooled, the pH was adjusted to 5 with aqueous potassium carbonate, and the obtained solid was collected by filtration and washed with water to obtain 7-[(trans-5-bromoadamantan-2-yl)amino]-3H-imidazo[4,5-b]pyridine-6-carboxylic acid (44 mg).

The compounds in Preparations 6-1 shown in the following table were produced using the corresponding starting compounds according to the method similar to that described in Preparation 6.

TABLE 10

| Pr | Structure | Data |
|---|---|---|
| 6 | (structure) | MS: 391, 393 (M + H) + trans |
| 6-1 | (structure) | MS: 391, 393 (M + H) + cis |

Preparation 7

A mixture of ethyl 7-[(3-exo)-8-azabicyclo[3.2.1]oct-3-ylamino]-3H-imidazo[4,5-b]pyridine-6-carboxylate (400 mg), di-t-butyl dicarbonate (203 mg), tirethylamine (130 μl), dioxane (4 ml) and water (4 ml) was stirred at ambient temperature for 1 hour. The mixture was diluted with ethyl acetate (5 ml) and water (20 ml). The resulting precipitate was collected by filtration (ethyl 7-{[(3-exo)-8-(tert-butoxycarbonyl)-8-azabicyclo[3.2.1]oct-3-yl]amino}-3H-imidazo[4,5-b]pyridine-6-carboxylate, (200 mg)). The filtrate was diluted with ethyl acetate (50 ml) and extracted with ethyl acetate. The organic extracts were washed with brine, dried over sodium sulfate and concentrated. Recrystallization from ethyl acetate/n-hexane gave ethyl 7-{[(3-exo)-8-(tert-butoxycarbonyl)-8-azabicyclo[3.2.1]oct-3-yl]amino}-3H-imidazo[4,5-b]pyridine-6-carboxylate (1.00 mg) as a white solid.

The compounds in Preparations 7-1 shown in the following table were produced using the corresponding starting compounds according to the method similar to that described in Example 64.

TABLE 11

| Pr | Structure | Data |
|---|---|---|
| 7 | (structure) | MS: 416 (M + H) + |
| 7-1 | (structure) | MS: 415 (M + H) + |

Preparation 8

The compounds in Preparations 8-1 to 8-3 shown in the following table were produced using the corresponding starting compounds according to the method similar to that described in Example 44.

TABLE 12

| Pr | Structure | Data |
|---|---|---|
| 8-1 | F-adamantyl-NH-C(O)-O-CH2-phenyl, cis/trans mix | MS: 326 (M + Na) + |
| 8-2 | F-adamantyl-NH-C(O)-O-CH2-phenyl, cis | MS: 326 (M + Na) + |
| 8-3 | F-adamantyl-NH-C(O)-O-CH2-phenyl, trans | MS: 326 (M + Na) + |

Preparation 9

The compounds in Preparations 9-1 to 9-2 shown in the following table were produced using the corresponding starting compounds according to the method similar to that described in Example 10.

TABLE 13

| Pr | Structure | Data |
|---|---|---|
| 9-1 | 7-azaindole-4-Cl-3-C(O)NH-NH-C(O)-C(O)-O-CH3 | MS: 319 (M + Na) + |
| 9-2 | 7-azaindole-4-(adamantyl-OH)NH-3-CH2NH-C(O)-C(O)-O-CH2CH3, cis | MS: 424 (M − H2O + H) + |

Preparation 10

The compounds in Preparations 10-1 to 10-18 shown in the following table were produced using the corresponding starting compounds according to the method similar to that described in Example 4.

TABLE 14

| Pr | Structure |
|---|---|
| 10-1 | 2-amino-3-nitro-4-(adamantyl)NH-pyridine-5-carboxamide |
| 10-2 | 4-chloro-7-azaindole-5-C(O)NH-ethyl |
| 10-3 | 1-(3,4-dimethoxybenzyl)-7-(adamantyl-OH)NH-imidazo[4,5-b]pyridine-6-C(O)NH-CH2-(4-fluorophenyl), cis |
| 10-4 | 2-benzylamino-3-nitro-4-(adamantyl-CH2OH)NH-pyridine-5-carboxamide, diastereomer of 10-18 cis or trans unknown |

TABLE 14-continued
| Pr | Structure |
|---|---|
| 10-5 | 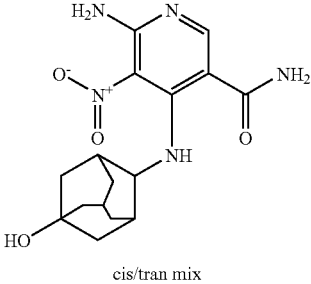 cis/tran mix |
| 10-6 | 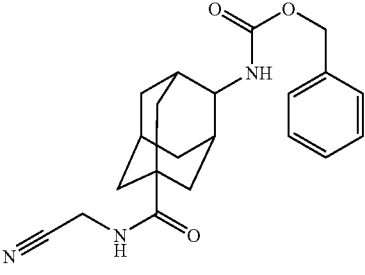 cis or trans unknown |
| 10-7 | 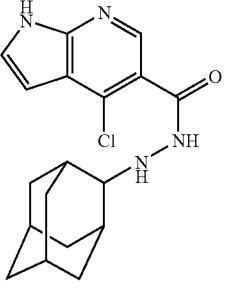 |
| 10-8 | 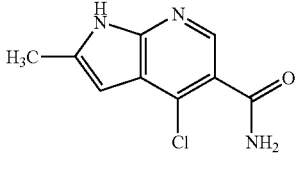 |
| 10-9 | 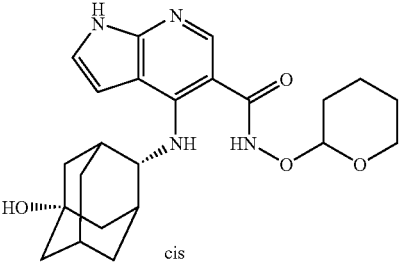 cis |
| 10-10 | 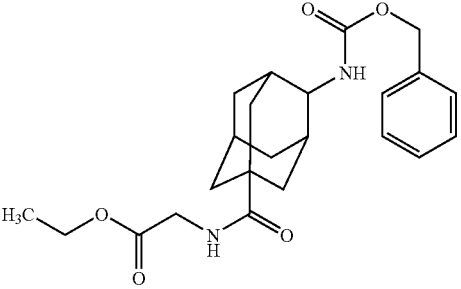 cis or trans unknown |
| 10-11 | 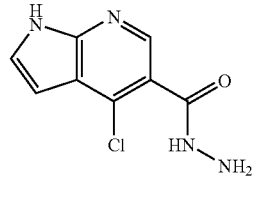 |
| 10-12 | 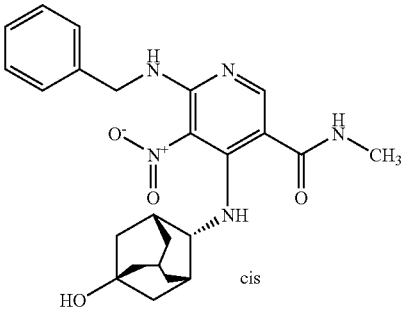 cis |
| 10-13 | 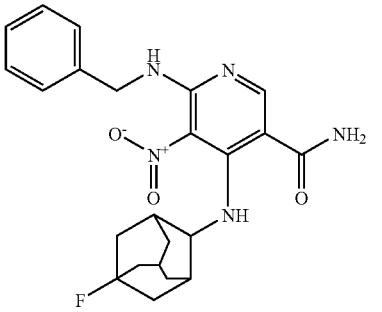 cis/trans mix |
| 10-14 | 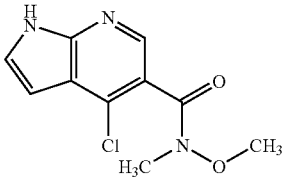 |

TABLE 14-continued

| Pr | Structure |
|---|---|
| 10-15 | (structure: benzylamino-pyridine with nitro group, carboxamide, and cyanoadamantyl-NH substituent) cis or trans unknown |
| 10-16 | (structure: 2-chlorothiazole-4-carboxamide) |
| 10-17 | (structure: 4-chloro-1H-pyrrolo[2,3-b]pyridine-5-carboxylic acid N-methylamide) |
| 10-18 | (structure: benzylamino-pyridine with nitro, carboxamide, and hydroxymethyladamantyl-NH substituent) diastereomer of 10-4 cis or trans unknown |

TABLE 15

| Pr | Data |
|---|---|
| 10-1 | MS: 332 (M + H)+ |
| 10-2 | MS: 246 (M + Na)+ |
| 10-3 | MS: 586 (M + H)+ |
| 10-4 | MS: 452 (M + H)+ |
| 10-5 | MS: 370 (M + Na)+ |
| 10-6 | MS: 368 (M + H)+ |
| 10-7 | 1H-NMR (400 MHz, d6-DMSO) δ: 1.39-1.45 (2H, m), 1.65-1.86 (8H, m), 1.94-1.97 (2H, m), 2.15-2.20 (2H, m), 3.08-3.11 (1H, m), 5.05-5.08 (1H, m), 6.55-6.57 (1H, m), 7.66-7.68 (1H, m), 8.19 (1H, s), 9.85 (1H, d, J = 6.8 Hz), 12.20 (1H, brs). MS: 367 (M + Na)+ |
| 10-8 | MS: 232 (M + Na)+ |

TABLE 15-continued

| Pr | Data |
|---|---|
| 10-9 | MS: 427 (M + H)+ |
| 10-10 | MS: 415 (M + H)+ |
| 10-11 | MS: 233 (M + Na)+ |
| 10-12 | MS: 474 (M + Na)+ |
| 10-13 | MS: 462 (M + Na)+ |
| 10-14 | MS: 262 (M + Na)+ |
| 10-15 | MS: 447 (M + H)+ |
| 10-16 | |
| 10-17 | MS: 232 (M + Na)+ |
| 10-18 | MS: 452 (M + H)+ |

Preparation 11

To a solution of 4-chloro-1H-pyrrolo[2,3-b]pyridine-5-carboxylic acid (350 mg) in N,N-dimethylformamide (4 ml) were added N,N-carbonyl diimidazole (289 mg) and glycinemethylester hydrochloride (447 mg) successively under ambient temperature. The mixture was stirred at ambient temperature for 2 hours. To the reaction solution was added water. The precipitated solid was filtered, washed with water, and dried to obtain 4-chloro-5-(1H-imidazol-1-ylcarbonyl)-1H-pyrrolo[2,3-b]pyridine (325 mg) as a white solid.

TABLE 16

| Pr | Structure | Data |
|---|---|---|
| 11 | (structure: 4-chloro-5-(1H-imidazol-1-ylcarbonyl)-1H-pyrrolo[2,3-b]pyridine) | MS: 247 (M + H) +, 245 (M − H) − |

Preparation 12

To a solution of 4-chloro-5-(1H-imidazol-1-ylcarbonyl)-1H-pyrrolo[2,3-b]pyridine(300 mg) in N,N-dimethylformamide (3 ml) were added N-ethyl-N-isopropylpropane-2-amine (0.64 ml) and glycine methylester hydrochloride (305 mg) at ambient temperature. The mixture was warmed immediately to 60° C. and stirred at 60° C. for 2 hours. After to the reaction solution was added water, the mixture was stirred for 1 hour. The precipitated solid was filtered, washed with water, and dried to obtain methyl N-[(4-chloro-1H-pyrrolo[2,3-b]pyridin-5-yl)carbonyl]glycinate (267 mg) as a white solid.

TABLE 17

| Pr | Structure | Data |
|---|---|---|
| 12 | (structure: methyl N-[(4-chloro-1H-pyrrolo[2,3-b]pyridin-5-yl)carbonyl]glycinate) | MS: 290 (M + Na) + |

Preparation 13

To a solution of benzyl rel-[(1R,2S,3S,5s)-5-hydroxyadamantan-2-yl]carbamate (1.3 g) in dichloroethane (13 ml)

were added trimethyloxonium tetrafluoroborate (1.28 g), 2,6-di-t-butyl-4-methylpyridine (2.21 g). The reaction solution was refluxed for 3 hours. The reaction solution was concentrated under reduced pressure, ethyl acetate was added, and the insoluble matter was filtered. To the filtrate was added water, and the mixture was extracted with ethyl acetate. The organic layer was washed with saturated brine, dried over anhydrous magnesium sulfate, and filtered. The filtrate was concentrated under reduced pressure. The residue was purified by silica gel column chromatography (n-hexane:ethyl acetate 19:1 to 7:3) to obtain benzyl rel-[(1R,2S,3S,5s)-5-methoxyadamantan-2-yl]carbamate (540 mg) as a colorless oily matter.

The compounds in Preparations 13-1 to 13-2 shown in the following table were produced using the corresponding starting compounds according to the method similar to that described in Preparation 13.

TABLE 18

| Pr | Structure | Data |
|---|---|---|
| 13 | (structure, trans) | MS: 338 (M + Na) + |
| 13-1 | (structure, cis) | MS: 338 (M + Na) + |
| 13-2 | (structure, cis) | MS: 352 (M + Na) + |

Preparation 14

The compounds in Preparations 14-1 to 14-6 shown in the following table were produced using the corresponding starting compounds according to the method similar to that described in Examples 12 to Examples 14.

TABLE 19

| Pr | Structure |
|---|---|
| 14-1 | (structure) |

TABLE 19-continued

| Pr | Structure |
|---|---|
| 14-2 | (structure, cis) |
| 14-3 | (structure) |
| 14-4 | (structure, cis/trans mix) |
| 14-5 | (structure) |
| 14-6 | (structure, cis) |

TABLE 20

| Pr | Data |
| --- | --- |
| 14-1 | MS: 267 (M + H)+ |
| 14-2 | MS: 414 (M + H)+ |
| 14-3 | MS: 443 (M + H)+ |
| 14-4 | MS: 467 (M + H)+ |
| 14-5 | MS: 333 (M + Na)+ |
| 14-6 | MS: 481 (M + H)+ |

Preparation 15

To a solution of (3-exo,7-endo)-7-hydroxybicyclo[3.3.1]nonan-3-carboxylic acid (700 mg) in methanol (14 ml) was added concentrated sulfuric acid (2 ml) dropwise, and the reaction solution was refluxed for 1 hour. To the reaction solution was added water, the mixture was extracted with ethyl acetate. The organic layer was washed with water, saturated aqueous sodium hydrogencarbonate, and brine, dried over magnesium sulfate, and filtered. The filtrate was concentrated under reduced pressure to obtain methyl-(3-exo,7-endo)-7-hydroxybicyclo[3.3.1]nonan-3-carboxylate (730 mg).

TABLE 21

| Pr | Structure | Data |
| --- | --- | --- |
| 15 | (structure) | MS: 221 (M + Na) + |

Preparation 16

The compounds in Preparations 16-1 to 16-3 shown in the following table were produced using the corresponding starting compounds according to the method similar to that described in Example 28.

TABLE 22

| Pr | Structure |
| --- | --- |
| 16-1 | (structure) |
| 16-2 | (structure) |
| 16-3 | (structure) |

TABLE 23

| Pr | Data |
| --- | --- |
| 16-1 | 1H-NMR (400 MHz, d6-DMSO) δ: 1.44 (9H, s), 1.77-2.39 (8H, m), 2.42 (3H, s), 4.09-4.20 (2H, m), 4.48-4.57 (1H, m), 6.61-6.66 (1H, m), 7.21-7.26 (1H, m), 8.57 (1H, s), 9.16 (1H, d, J = 7.5 Hz), 11.81 (1H, s). MS: 425 (M + H)+ |
| 16-2 | MS: 315 (M + Na)+ |
| 16-3 | MS: 425 (M + H)+ |

Preparation 17

The compound in Preparation 17 shown in the following table was produced using the corresponding starting compound according to the method similar to that described in Example 29.

TABLE 24

| Pr | Structure | Data |
| --- | --- | --- |
| 17 | (structure) | MS: 301 (M + Na) + |

Preparation 18

The compounds in Preparations 18-1 to 18-5 shown in the following table were produced using the corresponding starting compound according to the method similar to that described in Example 30.

TABLE 25

| Pr | Structure |
|---|---|
| 18-1 | 3-(4-chloro-1H-pyrrolo[2,3-b]pyridin-5-yl)-1,2,4-oxadiazole-5-carboxylic acid ethyl ester |
| 18-2 | 5-(5-(methoxymethyl)-1,2,4-oxadiazol-3-yl)-4-chloro-1H-pyrrolo[2,3-b]pyridine |
| 18-3 | trans; 4-((5-hydroxyadamantan-2-yl)amino) analog with oxadiazole ethyl ester |
| 18-4 | 5-(5-(chloromethyl)-1,2,4-oxadiazol-3-yl)-4-chloro-1H-pyrrolo[2,3-b]pyridine |
| 18-5 | cis; 4-((5-hydroxyadamantan-2-yl)amino) analog with trichloromethyl oxadiazole |

TABLE 26

| Pr | Data |
|---|---|
| 18-1 | MS: 315 (M + Na)+ |
| 18-2 | MS: 287 (M + Na)+ |
| 18-3 | MS: 424 (M + H)+ |
| 18-4 | MS: 291 (M + Na)+ |
| 18-5 | MS: 468 (M + H)+ |

Preparation 19

To a solution of 4-chloro-N'-hydroxy-1H-pyrrolo[2,3-b]pyridine-5-carboxylmidamide (100 mg) in N,N-dimethylformamide (1 ml) were added pyridine (58 µl) and 2-ethylhexyl chlorocarbonate (92 µl) at 4° C. The reaction solution was stirred at ambient temperature for 2 hours. To the reaction solution was added water. The precipitate was collected by filtration and dissolved in xylene (2 ml). The reaction solution was stirred at 160° C. for 3 hours. To the reaction solution was added water, and the precipitate was collected by filtration to obtain 3-(4-chloro-1H-pyrrolo[2,3-b]pyridin-5-yl)-1,2,4-oxadiazol-5(4H)-one (63 mg) as a white solid.

TABLE 27

| Pr | Structure | Data |
|---|---|---|
| 19 | 3-(4-chloro-1H-pyrrolo[2,3-b]pyridin-5-yl)-1,2,4-oxadiazol-5(4H)-one | MS: 235 (M − H) − |

Preparation 20

To a solution of methyl N-[(4-chloro-1H-pyrrolo[2,3-b]pyridin-5-yl)carbonyl]glycinate (167 mg) in chloroform (5 ml) was added diphosphorus pentoxide (886 mg) under ambient temperature, and the mixture was refluxed for 18 hours. The reaction solution was cooled and added to saturated aqueous sodium hydrogencarbonate. The reaction solution was extracted with ethyl acetate. The organic layer was washed with water. The organic layer was dried over magnesium sulfate and filtered. The filtrate was concentrated under reduced pressure. The residue was purified by thin-layer silica gel column chromatography (chloroform:methanol=15:1) to obtain 4-chloro-5-(5-methoxy-1,3-oxazol-2-yl)-1H-pyrrolo[2,3-b]pyridine (45 mg) as a yellowish white solid.

TABLE 28

| Pr | Structure | Data |
|---|---|---|
| 20 | 4-chloro-5-(5-methoxy-1,3-oxazol-2-yl)-1H-pyrrolo[2,3-b]pyridine | MS: 250 (M + H) + |

Preparation 21

To a solution of 4-[(5-hydroxyadamantan-2-yl)amino]-1H-pyrrolo[2,3-b]pyridine-5-carbonitrile (150 mg) in tetrahydrofuran (3 ml) was added 1.01M diisobutylaluminum hydride/toluene solution (1.93 ml) at 778° C. The reaction solution was stirred for 18 hours under ambient temperature. To the reaction solution was added 1M hydrochloric acid under ice cooling, and the mixture was stirred for 30 minutes. The mixture was extracted with chloroform and washed with water. The organic layer was dried over magnesium sulfate and filtered. The filtrate was concentrated under reduced pressure to obtain 4-[(5-hydroxyadamantan-2-yl)amino]-1H-pyrrolo[2,3-b]pyridine-5-carbaldehyde (100 mg) as a pale yellow amorphous substance.

The compound in Preparation 21-1 shown in the following table was produced using the corresponding starting compound according to the method similar to that described in Preparation 21.

TABLE 29

| Pr | Structure | Data |
|---|---|---|
| 21 | [structure: cis/trans mix] | MS: 312 (M + H) + |
| 21-1 | [structure: cis] | MS: 312 (M + H) + |

Preparation 22

To a mixture of 6-(benzylamino)-17 (5-hydroxyadamantan-2-yl)-7-nitro-1,3-dihydro-2H-imidazo[4,5-c]pyridine-2-one (68 mg) and methanol (1 ml) were added ammonium formate (197 mg) and 50% wet 10% palladium on carbon (33 mg) at ambient temperature. The mixture was refluxed for 5 hours. After the mixture was cooled, the catalyst was removed by filtration. The mothr liquid was concentrated to obtain 6,7-diamino-1-(5-hydroxyadamantan-2yl)-1,3-dihydro-2H-imidazo[4,5-c]pyridine-2-one (54 mg).

The compounds in Preparations 22-1 to 22-3 shown in the following table were produced using the corresponding starting compounds according to the method similar to that described in Preparation 22.

TABLE 30

| Pr | Structure |
|---|---|
| 22 | [structure: cis or trans unknown] |
| 22-1 | [structure: cis or trans unknown] |
| 22-2 | [structure: cis/trans mix] |
| 22-3 | [structure: cis] |

TABLE 31

| Pr | Data |
|---|---|
| 22 | MS: 316 (M + H)+ |
| 22-1 | MS: 332 (M + H)+ |
| 22-2 | MS: 320 (M + H)+ |
| 22-3 | MS: 332 (M + H)+ |

Preparation 23

To a suspension of ethyl 6-[(3,4-dimethoxybenzyl)amino]-4-[(cis-5-hydroxy adamantan-2-yl)amino]-5-nitronicotinate (2.73 g) in ethanol (40 ml) was added 10% palladium on carbon (50% wet) (550 mg). In hydrogen atmosphere, catalytic reduction was carried out at 80° C. for 5 hours. After the reaction solution was cooled to ambient temperature, the catalyst was filtered and washed with dioxane, and the solvent was evaporated under reduced pressure. To the residue were added ethyl orthoformate (17 ml) and concentrated hydrochloric acid (864 µl), and the mixture was stirred at ambient temperature for overnight. The reaction solution was neutralized with saturated aqueous sodium hydrogencarbonate and extracted with ethyl acetate and tetrahydrofuran. The organic layer was washed with saturated brine, dried over magnesium sulfate, and filtered. The filtrate was evaporated under reduced pressure. The residue was purified by silica gel column chromatography (chloroform:methanol) to obtain ethyl 3-(3,4-dimethoxybenzyl)-7-[(cis-5-hydroxyadamantan-2-yl)amino]-3H-imidazo[4,5-b]pyridine-6-carboxylate (2.17 g).

The compound in Preparation 23-1 shown in the following table were produced using the corresponding starting compound according to the method similar to that described in Preparation 23.

TABLE 32

| Pr | Structure | Data |
|---|---|---|
| 23 | (structure) | MS: 507 (M + H) + |
| 23-1 | (structure) | MS: 357 (M + H) + |

Preparation 24

The compounds in Preparations 24-1 to 24-3 shown in the following table were produced using the corresponding starting compounds according to the method similar to that described in Example 35.

TABLE 33

| Pr | Structure | Data |
|---|---|---|
| 24-1 | (structure) cis/trans mix | MS: 182 (M + H) + |
| 24-2 | (structure) | MS: 299 (M + Na) + |
| 24-3 | (structure) | MS: 273 (M + Na) + |

Preparation 25

To a reaction solution of N-Boc-nortropinone (1.38 g) benzylamine (0.803 ml) and acetic acid (0.35 ml) in dichloromethane (10 ml) and 1,2-dichloroethane (32 ml) was added sodium triacetoxyborohydride (1.95 g). And the mixture was stirred at ambient temperature for 2 hours. To the reaction mixture was added benzylamine (0.201 ml) and sodium triacetoxyborohydride (649 mg), and the mixture was stirred at 50° C. for 3.5 hours. Furthermore, to the reaction mixture was added sodium triacetoxyborohydride (649 mg) and the mixture was stirred at 50° C. for 3 hours. The reaction solvent was evaporated under reduced pressure. To the residue were added saturated aqueous sodium hydrogencarbonate and 1M aqueous sodium hydroxide to alkalify the residue. The residue was extracted with ethyl acetate. The organic layer was washed with saturated aqueous sodium hydrogencarbonate, water, and saturated brine, dried over anhydrous sodium sulfate, and filtered. The filtrate was evaporated under reduced pressure. The residue was purified by silica gel column chromatography (chloroform:methanol) to obtain 3-(benzylamino)-8-azabicyclo[3.2.1]octane-8-carbamic acid t-butyl ester (1.78 g) as a white solid.

The compounds in Preparations 25-1 to 25-8 shown in the following table were produced using the corresponding starting compounds according to the method similar to that described in Preparation 25.

TABLE 34

| Pr | Structure |
|---|---|
| 25 | (structure) |

TABLE 34-continued

| Pr | Structure |
|---|---|
| 25-1 | 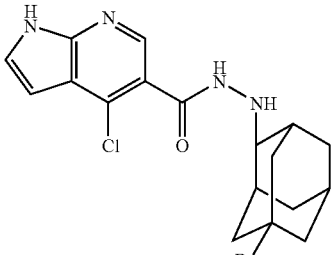<br>diastereomer of 25-8<br>cis or trans unknown |
| 25-2 | 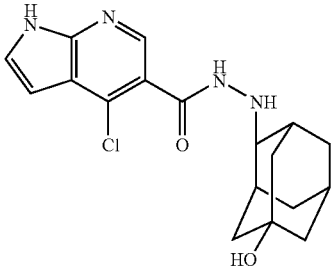<br>cis/trans mix |
| 25-3 | 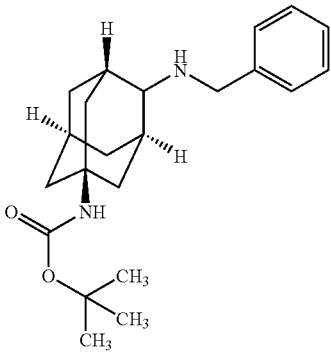<br>cis/trans mix |
| 25-4 | 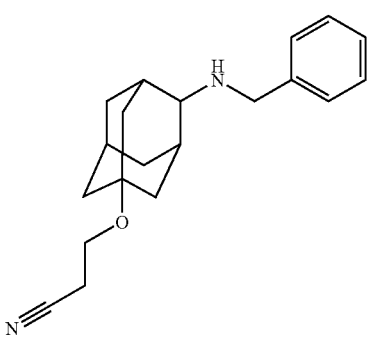<br>cis/trans mix |
| 25-5 | 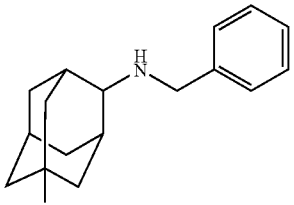<br>cis or trans unknown |
| 25-6 | 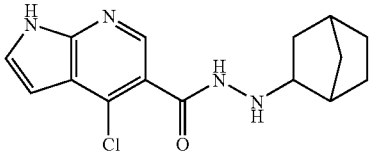 |
| 25-7 | 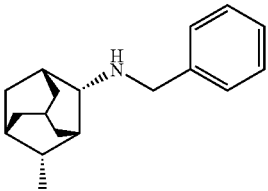 |
| 25-8 | 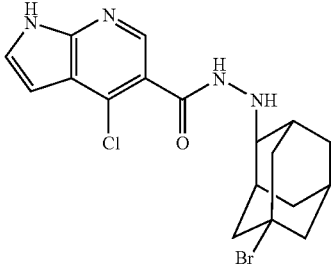<br>diastereomer of 25-1<br>cis or trans unknown |

TABLE 35

| Pr | Data |
|---|---|
| 25 | 1H-NMR (400 MHz, CDCl$_3$) δ: 1.35-1.66 (3H, m), 1.45 (9H, s), 1.86-2.22 (6H, m), 3.00 (1H, dd, J = 6.0, 6.0 Hz), 3.78 (2H, s), 4.04-4.28 (2H, m), 7.20-7.38 (5H, m) |
| 25-1 | MS: 423, 425 (M + H)+ |
| 25-2 | MS: 383 (M + Na)+ |
| 25-3 | MS: 357 (M + H)+ |
| 25-4 | MS: 311 (M + H)+ |
| 25-5 | MS: 320, 322 (M + H)+ |
| 25-6 | MS: 327 (M + Na)+ |
| 25-7 | MS: 258 (M + H)+ |
| 25-8 | MS: 423, 425 (M + H)+ |

Preparation 26

The compounds in Preparations 26-1 to 26-2 shown in the following table were produced using the corresponding starting compounds according to the method similar to that described in Example 50.

TABLE 36

| Pr | Structure | Data |
|---|---|---|
| 26-1 | [structure: 4-chloro-7-azaindole linked to 1,3,4-oxadiazole with C(CH3)2OH] | MS: 301 (M + Na)+ |
| 26-2 | [structure: 4-chloro-7-azaindole linked to 1,3,4-thiadiazole with C(CH3)2OH] | MS: 317 (M + Na)+ |

Preparation 27

To a solution of rel-(1'R,3'S,5'S,7's)-5'H-spiro[1,3-dioxolane-2,2'-tricyclo[3.3.1.1~3,7~]decane]-5'-carboxylic acid (100 mg) in toluene (1 ml) was added diphenylphosphate azide (99 μl) and triethylamine (64 μl). The mixture was stirred at 110° C. for 2 hours. After the reaction solution was cooled to ambient temperature, water was added, and the mixture was extracted with ethyl acetate. The organic layer was washed with brine, dried over magnesium sulfate, and filtered. The filtrate was evaporated under reduced pressure. The residue was dissolved in N,N-dimethylacetamide (1 ml), and potassium t-butoxide (49 mg) was added. The mixture was stirred at ambient temperature for overnight. To the reaction solution was added water, and the mixture was extracted with ethyl acetate. The organic layer was washed with saturated brine, dried over magnesium sulfate, and filtered. The filtrate was evaporated under reduced pressure. The residue was purified by silica gel column chromatography (n-hexane: ethyl acetate) to obtain t-butyl rel-(1'R,3'S,5'S,7's)-5'H-spiro[1,3-dioxolane-2,2'-tricyclo[3.3.1.1-3, 7-]decane]-5'-yl carbamate (40 mg).

The compounds in Preparations 27-1 to 27-3 shown in the following table were produced using the corresponding starting compounds according to the method similar to that described in Preparation 27.

TABLE 37

| Pr | Structure | Data |
|---|---|---|
| 27 | [structure: spiro dioxolane-adamantane with NHC(O)OC(CH3)3] | MS: 332 (M + Na)+ |

TABLE 37-continued

| Pr | Structure | Data |
|---|---|---|
| 27-1 | [structure: 7-azaindole-imidazolidinone with norbornane and triisopropylsilyloxymethyl] | MS: 455 (M + H)+ |
| 27-2 | [structure: benzylamino-nitro-pyridine imidazolidinone with hydroxyadamantane] cis or trans unknown | MS: 436 (M + H)+ |
| 27-3 | [structure: 7-azaindole-imidazolidinone with N-benzyl tropane] | MS: 374 (M + H)+ |

Preparation 28

To a concentrated sulfuric acid (175 ml) was added 70% nitric acid (20 ml) dropwise under ice cooling, and 2-adamantamine hydrochloride (25 g) was added slowly at 10° C. or less. The mixture was warmed to ambient temperature and stirred for 2 hours. The reaction solution was poured into ice water, and the mixture was neutralized with 6M aqueous sodium hydroxide and extracted with dichloromethane four times. The organic layers were combined, dried over anhydrous magnesium sulfate, and concentrated under reduced pressure to obtain 4-aminoadamantan-1-ol (17.7 g).

TABLE 38

| Pr | Structure | Data |
|---|---|---|
| 28 | [structure: 4-aminoadamantan-1-ol] cis/trans mix | MS: 168 (M + H)+ |

Preparation 29

A mixture of ethyl 4-{[3-exo(hydroxymethyl)bicyclo[2.2.1]heptyl-2-exo]amino}-1H-pyrrolo[2,3-b]pyridine-5-carboxylate (54 mg), triisopropylsilyl chloride (52 μl), imidazole (17 mg), and N,N-dimethylformamide (0.3 ml) was stirred at ambient temperature for 2 hours. The reaction solution was diluted with ethyl acetate (20 ml) and poured into saturated aqueous sodium hydrogencarbonate (15 ml). The mixture was extracted with ethyl acetate (15 ml) two times, and the extract was washed with brine (20 ml), dried over anhydrous magnesium sulfate, and filtered. The filtrate was concentrated. The residue was purified by silica gel column chromatography (n-hexane:ethyl acetate) to obtain ethyl 4-{[3-exo(triisopropylsilyl)oxy]methyl}bicyclo[2.2.1]heptyl-2-exo]amino}-1H-pyrrolo[2,3-b]pyridine-5-carboxylate (76 mg) as a pale brown solid.

TABLE 39

| Pr | Structure | Data |
|---|---|---|
| 29 | 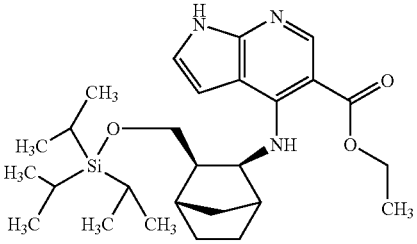 | MS: 486 (M + H)+ |

Preparation 30

To a solution of 4-chloro-2-methyl-1H-pyrrolo[2,3-b]pyridine (0.85 g) in N,N-dimethylformamide (8.5 ml) was added 60% oil-suspended NaH (245 mg) under nitrogen atmosphere while being cooled in an ice water bath. The reaction solution was stirred at ambient temperature for 1 hour and cooled again in the ice water bath. To the reaction solution was added triisopropylsilyl chloride (1.3 ml) slowly dropwise for 10 or more minutes. The reaction solution was stirred for 3 hours at ambient temperature and diluted with ethyl acetate (30 ml). The solution was washed with saturated aqueous sodium hydrogencarbonate (30 ml) and brine (20 ml). The solution was dehydrated with anhydrous magnesium sulfate and evaporated under reduced pressure. The residue was purified by silica gel column chromatography (n-hexane) to obtain 4-chloro-2-methyl-1-(triisopropylsilyl)-pyrrolo[2,3-b]pyridine (1.45 g) as a colorless transparent liquid.

TABLE 40

| Pr | Structure | Data |
|---|---|---|
| 30 | 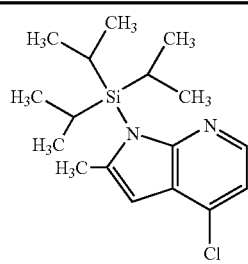 | MS: 323 (M + H)+ |

Preparation 31

The compounds in Preparations 31-1 to 31-2 shown in the following table were produced using the corresponding starting compounds according to the method similar to that described in Example 19.

TABLE 41

| Pr | Structure | Data |
|---|---|---|
| 31-1 | 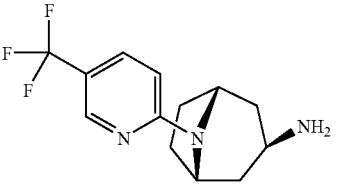 | MS: 272 (M + H)+ |

TABLE 41-continued

| Pr | Structure | Data |
|---|---|---|
| 31-2 | 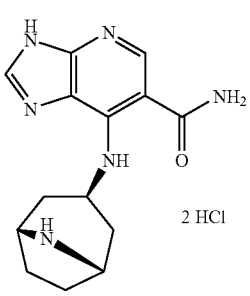 | MS: 287 (M + H)+ |

Preparation 32

A mixture of 4-chloro-2-methyl-1-(phenylsulfonyl)-1H-pyrrolo[2,3-b]pyridine (4.73 g), potassium carbonate (6.4 g), methanol (45 ml), and water (15 ml) was stirred at 90° C. for 2 hours. After the mixture was cooled, the obtained needle crystals were filtered and washed with water to obtain 4-chloro-2-methyl-1H-pyrrolo[2,3-b]pyridine (1.85 g).

TABLE 42

| Pr | Structure | Data |
|---|---|---|
| 32 | [structure: 2-methyl-4-chloro-7-azaindole] | MS: 167 (M + H)+ |

Preparation 33

To a solution of benzyl rel-[(1R,2S,3S,5s)-5-hydroxyadamantan-2-yl]carbamate (5.5 g) in methanol (55 ml) was added 10% palladium on carbon (50% wet) (1.1 g), and the mixture was stirred under hydrogen atmosphere at ambient temperature for 3 hours. After 10% palladium on carbon was removed with Celite, the filtrate was concentrated under reduced pressure to obtain rel-(1s,3R,4S,5S)-4-adamantamine-1-ol (3.8 g).

The compounds in Preparations 33-1 to 33-11 shown in the following table were produced using the corresponding starting compounds according to the method similar to that described in Preparation 33.

TABLE 43

| Pr | Structure |
|---|---|
| 33 | [structure: HO-adamantane-NH₂, trans] |
| 33-1 | [structure: adamantyl-NH₂ with H₃C-CH₂-O-C(O)-CH₂-NH-C(O)- substituent; diastereomer of 33-9, cis or trans unknown] |
| 33-2 | [structure: HO-adamantane-NH₂, cis] |
| 33-3 | [structure: adamantyl-NH₂ with N≡C-CH₂-NH-C(O)- substituent; diastereomer of 33-11, cis or trans unknown] |

TABLE 43-continued

| Pr | Structure |
|---|---|
| 33-4 | [structure: CH₃O-adamantane-NH₂, trans] |
| 33-5 | [structure: CH₃O-adamantane-NH₂, cis] |
| 33-6 | [structure: F-adamantane-NH₂, cis] |
| 33-7 | [structure: F-adamantane-NH₂, trans] |
| 33-8 | [structure: H₃C-CH₂-O-adamantane-NH₂, cis] |
| 33-9 | [structure: adamantyl-NH₂ with H₃C-CH₂-O-C(O)-CH₂-NH-C(O)- substituent; diastereomer of 33-1, cis or trans unknown] |
| 33-10 | [structure: F-adamantane-NH₂, cis/trans mix] |
| 33-11 | [structure: adamantyl-NH₂ with N≡C-CH₂-NH-C(O)- substituent; diastereomer of 33-3, cis or trans unknown] |

TABLE 44

| Pr | Data | Pr | Data |
|---|---|---|---|
| 33 | MS: 168 (M + H)+ | 33-1 | MS: 281 (M + H)+ |
| 33-2 | MS: 168 (M + H)+ | 33-3 | MS: 234 (M + H)+ |
| 33-4 | MS: 182 (M + H)+ | 33-5 | MS: 182 (M + H)+ |
| 33-6 | MS: 170 (M + H)+ | 33-7 | MS: 170 (M + H)+ |
| 33-8 | MS: 196 (M + H)+ | 33-9 | MS: 281 (M + H)+ |
| 33-10 | MS: 170 (M + H)+ | 33-11 | MS: 234 (M + H)+ |

Preparation 34

The compounds in Preparations 34-1 to 34-3 shown in the following table were produced using the corresponding starting compounds according to the method similar to that described in Example 21.

TABLE 45

| Pr | Structure | Data |
|---|---|---|
| 34-1 | (structure) | MS: 261 (M + Na)+ |
| 34-2 | (structure) | MS: 171 (M + H)+ |
| 34-3 | (structure) | MS: 323 (M + H)+ |

Preparation 35

To a solution of ethyl 5-(4-chloro-1H-pyrrolo[2,3-b]pyridine-5-yl)-1,2,4-oxadiazole-3-carboxylate (350 mg) in ethanol (3.5 ml) was added 1M aqueous sodium hydroxide (1.79 ml), and the reaction solution was stirred at 50° C. for 3 hours. The reaction solution was cooled to 4° C., and 1M hydrochloric acid was added to acidify the solution. The mixture was extracted with a mixture of chloroform and methanol (4:1) and washed with water. The organic layer was dried over magnesium sulfate and then filtered. The filtrate was concentrated under reduced pressure to obtain 4-chloro-5-(1,2,4-oxadiazole-5-yl)-1H-pyrrolo[2,3-b]pyridine (215 mg) as a white solid.

TABLE 46

| Pr | Structure | Data |
|---|---|---|
| 35 | (structure) | MS: 219 (M − H)+ |

Preparation 36 t-Butyl rel-(1'R,3'S,5'S,7's)-5'H-spiro[1,3-dioxolane-2,2'-tricyclo[3.3.1.1~3, 7~]decane]-5'-yl carbamate (420 mg) was dissolved in tetrahydrofuran (4.2 ml) and water (4.2 ml), para-tosylic acid monohydrate (516 mg) was added, and the mixture was stirred at 60° C. for 4 hours. The reaction solution was evaporated under reduced pressure, and saturated aqueous sodium hydrogencarbonate was added. The mixture was extracted with ethyl acetate. The organic layer was washed with saturated brine, dried over magnesium sulfate, and evaporated under reduced pressure. The residue was purified by silica gel column chromatography (n-hexane:ethyl acetate) to obtain t-butyl (cis-4-oxoadamantan-1-yl)carbamate (120 mg).

The compound in Preparation 36-1 shown in the following table was produced using the corresponding starting compound according to the method similar to that described in Preparation 36.

TABLE 47

| Pr | Structure | Data |
|---|---|---|
| 36 | (structure) | MS: 288 (M + H)+ |
| 36-1 | (structure) | MS: 220 (M + H)+ |

Preparation 37

To a reaction solution of 2-[(1R,2R,4S)-bicyclo[2.2.1]hept-2-yl]-1H-isoindole-1,3(2H)-dione (1.4 g) in tetrahydrofuran (28 ml) and ethanol (28 ml) was added 80% aqueous hydrazine monohydrate (1.1 ml), and the mixture was refluxed for 3 hours. After the reaction solution was cooled to ambient temperature, insoluble matter was removed by filtration. The filtrate was concentrated under reduced pressure to reduce the amount of the solvent. To the residue was added dichloromethane, and the mixture was washed with 1M aqueous sodium hydroxide, dried over anhydrous magnesium sulfate, and evaporated under reduced pressure. To the residue was added methanol, the mixture was converted into hydrochloride by adding 4M hydrochloric acid/dioxane solution, concentrated under reduced pressure and dried to hardness to obtain (1R,2R,4S)-bicyclo[2.2.1]heptane-2-amine hydrochloride (0.6 g).

The compound in Preparation 37-1 shown in the following table was produced using the corresponding starting compound according to the method similar to that described in Preparation 37.

TABLE 48

| Pr | Structure | Data |
|---|---|---|
| 37 | 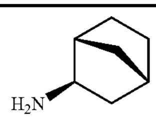 | MS: 112 (M + H)+ |
| 37-1 | 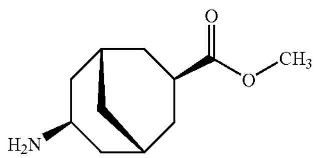 | MS: 198 (M + H)+ |

Preparation 38

To a suspension of methyl (2-{[4-chloro-6-(methylamino)-5-vinylpyridine-3-yl]carbonyl}hydrazino)(oxo)acetate (450 mg) in tetrahydrofuran (7 ml) and dioxane (7 ml) was added diphosphorus pentasulfide (383 mg) under cooling in an ice bath. After the mixture was stirred at ambient temperature for 5 hours. To the reaction mixture was added tetrahydrofuran (10 ml) and diphosphorus pentasulfide (190 mg). After the mixture was stirred at ambient temperature for 2 hours, water was added to the reaction solution, and the pH was adjusted to approximately 10 with aqueous sodium hydroxide, and the solution was extracted with ethyl acetate. The organic layer was dried over magnesium sulfate and filtered. The filtrate was concentrated under reduced pressure. The residue was purified by silica gel chromatography (chloroform:methanol) to obtain methyl-5-(4-chloro-1H-pyrrolo[2,3,b]pyridine-5-yl)-1,3,4-thiadiazole-2-carboxylate (90 mg).

TABLE 49

| Pr | Structure | Data |
|---|---|---|
| 38 | 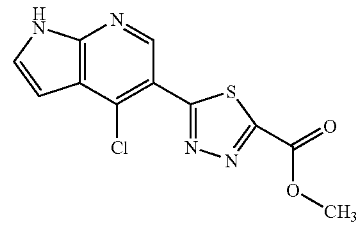 | MS: 317 (M + H)+ |

Preparation 39

The compounds in Preparations 39-1 to 39-4 shown in the following table were produced using the corresponding starting compounds according to the method similar to that described in Example 45.

TABLE 50

| Pr | Structure | Data |
|---|---|---|
| 39 | 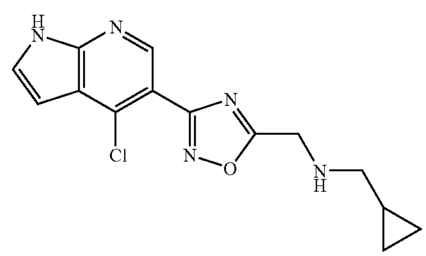 | MS: 304 (M + H)+, 326 (M + Na)+ |
| 39-1 | 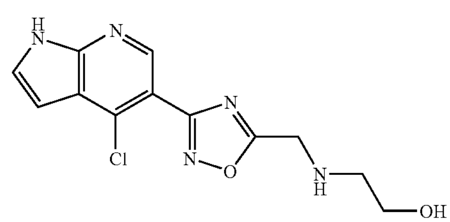 | MS: 316 (M + Na)+ |

TABLE 50-continued

| Pr | Structure | Data |
|---|---|---|
| 39-2 | 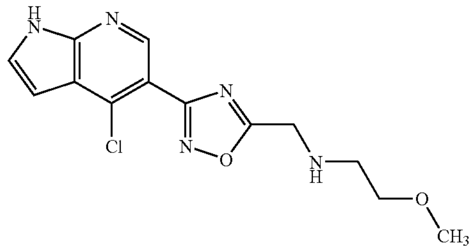 | MS: 330 (M + Na)+ |
| 39-3 | 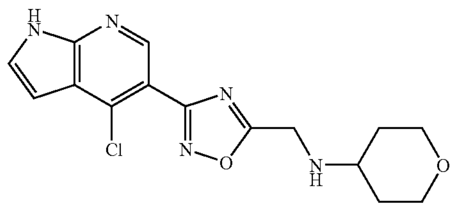 | MS: 356 (M + Na)+ |
| 39-4 | 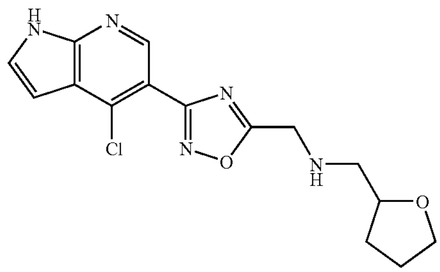 | MS: 356 (M + Na)+ |

Preparation 40

To a reaction solution of 4-Chloro-1-(triisopropylsilyl)-1H-pyrrolo[2,3-b]pyridine (2.26 g) in tetrahydrofuran (16 ml) was added sec-butyllithium (14.6 ml) dropwise in nitrogen atmosphere at −78° C. After the mixture was stirred at the same temperature for 30 minutes, a solution of benzyl chloroformate (2.1 ml) in tetrahydrofuran (16 ml) was added dropwise to the reaction mixture at −78° C. Furthermore, the reaction solution was stirred at −78° C. for 15 minutes, neutralized with saturated aqueous ammonium chloride (12 ml), and extracted with ethyl acetate. The organic layer was washed with saturated brine, dried over magnesium sulfate, and evaporated under reduced pressure. The residue was dissolved in tetrahydrofuran (17 ml), 1M tetrabutylammonium fluoride/tetrahydrofuran solution (16.9 ml) was added, and the mixture was stirred at ambient temperature for 3 hours. To the reaction solution were added ethyl acetate and water, the mixture was extracted with ethyl acetate. The organic layer was washed with saturated brine, dried over magnesium sulfate, and evaporated under reduced pressure. The residue was purified by silica gel column chromatography (n-hexane: ethyl acetate) to obtain benzyl 4-chloro-1H-pyrrolo[2,3-b]pyridine-5-carboxylate (690 mg).

The compounds in Preparations 40-1 to 40-3 shown in the following table were produced using the corresponding starting compounds according to the method similar to that described in Preparation 40.

TABLE 51

| Pr | Structure |
|---|---|
| 40 | 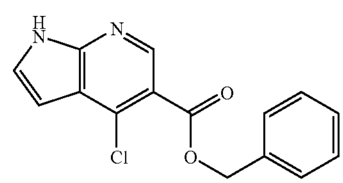 |
| 40-1 | 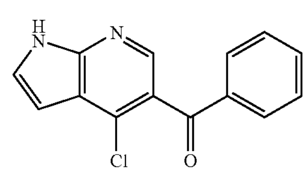 |
| 40-2 | 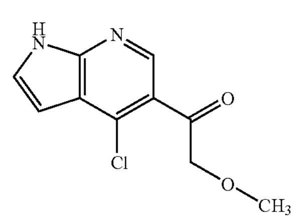 |

TABLE 51-continued

| Pr | Structure |
|---|---|
| 40-3 | (7-azaindole with Cl at 4-position, benzyl ester at 5-position) |

TABLE 52

| Pr | Data |
|---|---|
| 40 | 1H-NMR (d6-DMSO) δ: 5.40 (2H, s), 6.6 (1H, d, J = 1.8 Hz), 7.35-7.39 (3H, m), 7.41-7.45 (2H, m), 7.71 (1H, d, J = 3.5 Hz), 8.75 (1H, s), 12.42 (1H, br). MS: (+): 297 |
| 40-1 | MS: 279 (M + Na)+ |
| 40-2 | MS: 247 (M + H)+ |
| 40-3 | MS: 285 (M − H)− |

Preparation 41

Into a 100 ml metal sealed tube were put a stirring rod, ethyl 4-{[(3-exo)-8-benzyl-8-azabicyclo[3.2.1]oct-3-yl]amino}-6-chloro-5-nicotinic acid ester (1.5 g), 28% aqueous ammonia (4.6 ml), and ethanol (7.5 ml). The tube was closed and stirred at 90° C. for 2 hours. After being cooled, the reaction solution was diluted with methanol (20 ml) and evaporated under reduced pressure. The residue was recrystallised from ethyl acetate-methanol to obtain ethyl 6-amino-4-{[(3-exo)-8-benzyl-8-azabicyclo[3.2.1]oct -3-yl]amino}-5-nicotinic acid ester (1.3 g) as a yellow solid.

The compound in Preparation 41-1 shown in the following table was produced using the corresponding starting compound according to the method similar to that described in Preparation 41.

TABLE 53

| Pr | Structure | Data |
|---|---|---|
| 41 | (structure) | MS: 426 (M + H)+ |
| 41-1 | (structure) | MS: 361 (M + H)+ |
| 41-1 | (structure) | MS: 361 (M + H)+ |

Preparation 42

The compounds in Preparations 42-1 to 42-26 shown in the following table were produced using the corresponding starting compounds according to the method similar to that described in Example 7.

TABLE 54

| Pr | Structure |
|---|---|
| 42-1 | (7-azaindole-Cl-oxadiazole-tetrahydrofuran amide structure) |
| 42-2 | (7-azaindole-Cl-thiadiazole-N-methylpiperidine amide structure) |

TABLE 54-continued

| Pr | Structure |
|---|---|
| 42-3 | 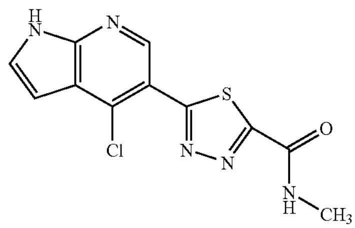 |
| 42-4 | 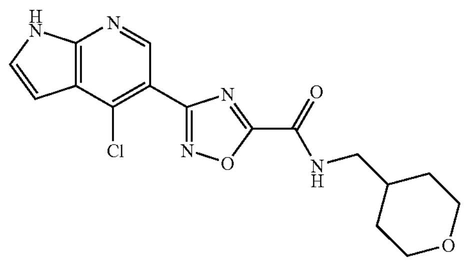 |
| 42-5 | 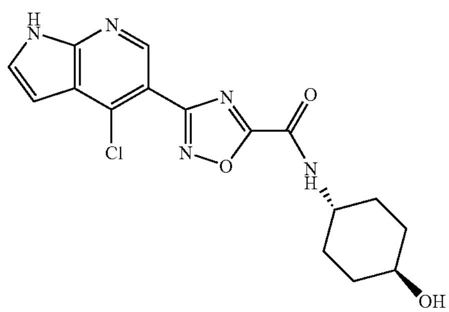 |
| 42-6 | 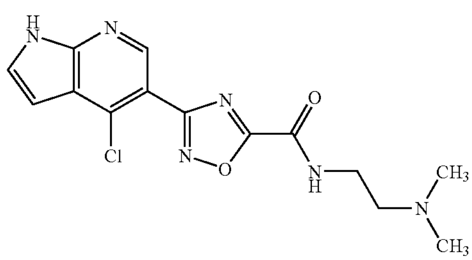 |
| 42-7 | 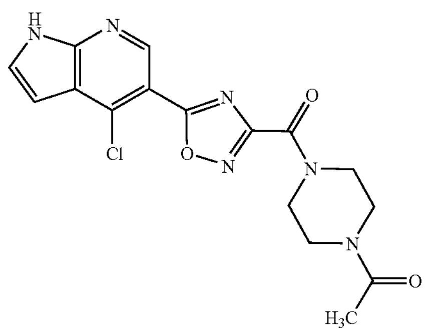 |

TABLE 54-continued

| Pr | Structure |
|---|---|
| 42-8 | (7-azaindole with Cl, 1,2,4-oxadiazole-C(O)NH-CH2-CH(OH)-CH3) |
| 42-9 | (7-azaindole with Cl, 1,2,4-oxadiazole-C(O)NH-CH2CH2-OH) |
| 42-10 | (7-azaindole with Cl, 1,2,4-oxadiazole-C(O)N(CH3)2) |
| 42-11 | (7-azaindole with Cl, 1,2,4-oxadiazole-C(O)NH-CH2-tetrahydropyran-4-yl) |
| 42-12 | (7-azaindole with Cl, 1,2,4-oxadiazole-C(O)NH2) |
| 42-13 | (7-azaindole with Cl, 1,2,4-oxadiazole-C(O)NH-trans-4-hydroxycyclohexyl) |

TABLE 54-continued

| Pr | Structure |
|---|---|
| 42-14 | 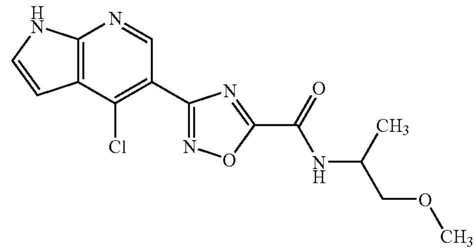 |
| 42-15 | 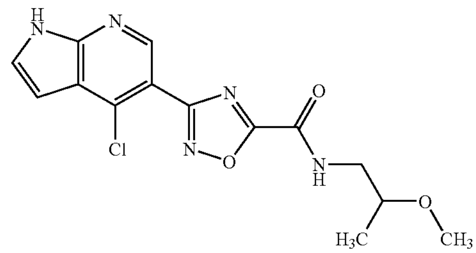 |
| 42-16 | 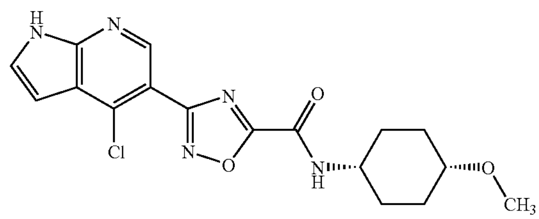 |
| 42-17 | 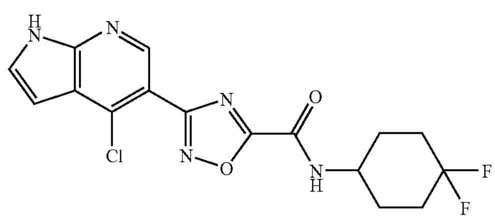 |
| 42-18 | 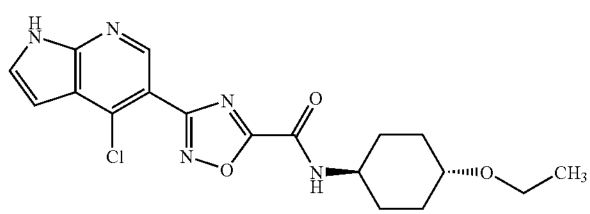 |
| 42-19 | 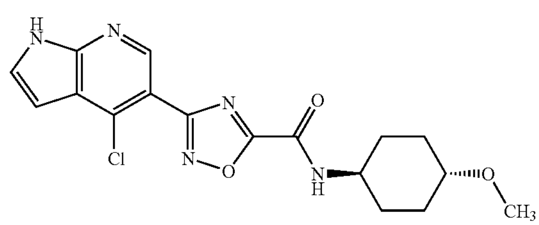 |

TABLE 54-continued
| Pr | Structure |
|---|---|
| 42-20 | 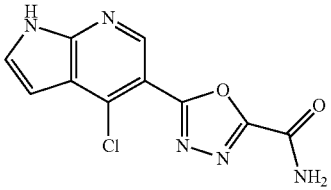 |
| 42-21 | 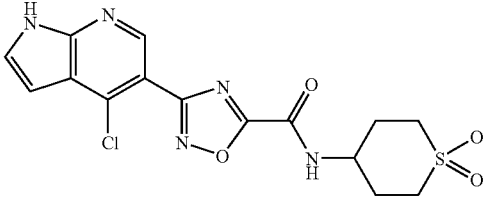 |
| 42-22 | 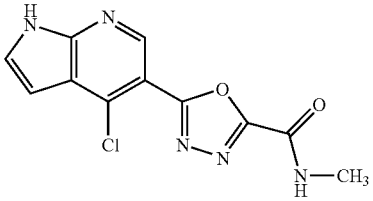 |
| 42-23 | 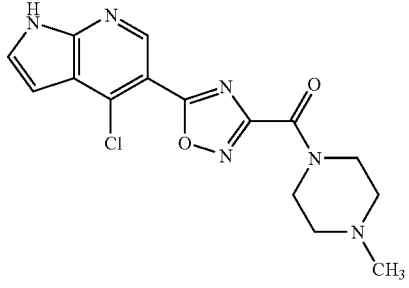 |
| 42-24 | 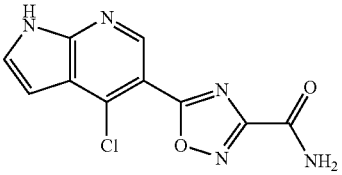 |
| 42-25 | 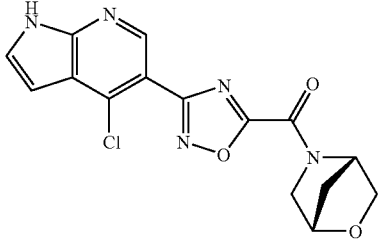 |

TABLE 54-continued

| Pr | Structure |
|---|---|
| 42-26 | 7-azaindole with Cl substituent connected to 1,2,4-oxadiazole bearing C(O)NH-CH2CH2-O-CH3 |

TABLE 55

| Pr | Data |
|---|---|
| 42-1 | MS: 348 (M + H)+ |
| 42-2 | MS: 377 (M + H)+ |
| 42-3 | MS: 316 (M + Na)+ |
| 42-4 | MS: 370 (M + H)+ |
| 42-5 | MS: 384 (M + Na)+ |
| 42-6 | MS: 335 (M + H)+ |
| 42-7 | MS: 375 (M + H)+ |
| 42-8 | MS: 322 (M + H)+ |
| 42-9 | MS: 308 (M + H)+ |
| 42-10 | MS: 314 (M + Na)+ |
| 42-11 | MS: 384 (M + Na)+ |
| 42-12 | MS: 286 (M + Na)+ |
| 42-13 | MS: 384 (M + Na)+ |
| 42-14 | MS: 358 (M + Na)+ |
| 42-15 | MS: 358 (M + Na)+ |
| 42-16 | MS: 398 (M + Na)+ |
| 42-17 | MS: 404 (M + Na)+ |
| 42-18 | MS: 412 (M + Na)+ |
| 42-19 | MS: 398 (M + Na)+ |
| 42-20 | MS: 286 (M + Na)+ |
| 42-21 | MS: 418 (M + Na)+, 394 (M − H)− |
| 42-22 | MS: 300 (M + Na)+ |
| 42-23 | MS: 369 (M + Na)+ |
| 42-24 | MS: 286 (M + Na)+ |
| 42-25 | MS: 346 (M + H)+ |
| 42-26 | MS: 322 (M + H)+, 344 (M + Na)+, 320 (M − H)− |

Preparation 43

The compound in Preparation 43 shown in the following table was produced using the corresponding starting compound according to the method similar to that described in Example 41.

TABLE 56

| Pr | Structure | Data |
|---|---|---|
| 43 | adamantane dioxolane with propionitrile ether substituent | MS: 264 (M + H)+ |

Preparation 44

To a solution of 4-aminoadamantan-1-ol (8.9 g) in tetrahydrofuran (89 ml) were added benzyloxycarbonyl chloride (7.6 ml) and 1M aqueous sodium hydroxide (53.4 ml) dropwise successively under ice cooling, and the mixture was stirred for 3 hours under ice cooling. The reaction solution was poured into aqueous potassium hydrogensulfate, and the mixture was extracted with ethyl acetate. The organic layer was washed with saturated brine, dried over anhydrous magnesium sulfate, and evaporated under reduced pressure. The residue was purified by silica gel column chromatography (n-hexane:ethyl acetate=1:1 to 1:3) to obtain benzyl rel-[(1R, 2S,3S,5s)-5-hydroxyadamantan-2-yl]carbamate (6.2 g) and benzyl rel-[(1R,2R,3S,5s)-5-hydroxyadamantan-2-yl]carbamate (5.3 g).

TABLE 57

| Pr | Structure | Data |
|---|---|---|
| 44 | trans-hydroxyadamantyl Cbz-carbamate; cis-hydroxyadamantyl Cbz-carbamate | MS: 324 (M + Na)+ 324 (M + Na)+ |

Preparation 45

To a solution of (1R,2S,4S)-bicyclo[2.2.1]heptane-2-ol (1.0 g) in tetrahydrofuran (10 ml) were added phthalimide (1.4 g) and triphenylphosphine (2.6 g), and diethylazodicarboxylate (1.5 ml) dropwise under ice cooling. The mixture was warmed to ambient temperature and stirred for 24 hours. The reaction solution was concentrated under reduced pressure, and the residue was purified by silica gel column chromatography (n-hexane:ethyl acetate)=100:0 to 95:5) to obtain 2-[(1R,2R,4S)-bicyclo[2.2.1]hept-2-yl]-1H-isoindole-1,3(2H)-dione (1.4 g) as a colorless solid.

The compound in Preparation 45-1 shown in the following table was produced using the corresponding starting compound according to the method similar to that described in Preparation 45.

TABLE 58

| Pr | Structure | Data |
| --- | --- | --- |
| 45 | 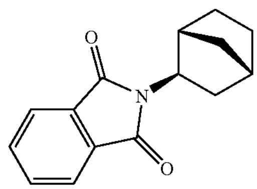 | MS: 264 (M + Na)+ |
| 45-1 | 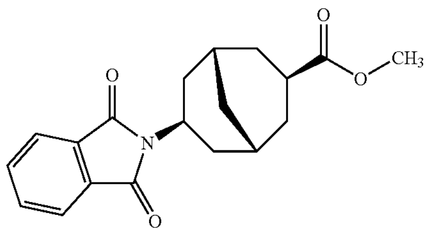 | MS: 350 (M + Na)+ |

Preparation 46

A mixture of ethyl 6-chloro-4-{[5-methoxyadamantan-2-yl]amino}-5-nicotinic acid ester (635 mg), benzylamine (253 μl), diisopropylethylamine (270 μl), and 2-propanol (3 ml) was subjected to microwave irradiation under nitrogen atmosphere and heated at 90° C. for 30 minutes. After being cooled, the reaction solution was diluted with ethyl acetate (20 ml) and poured into ½ saturated aqueous ammonia chloride (20 ml). The mixture was extracted with ethyl acetate (20 ml) two times, washed with brine (30 ml), dehydrated with anhydrous magnesium sulfate, and concentrated under reduced pressure. The residue was purified by silica gel column chromatography (n-hexane:ethyl acetate) to obtain ethyl 6-benzylamino-4-{[5-methoxyadamantan-2-yl]amino}-5-nicotinic acid ester (550 mg) as an orange solid.

The compounds in Preparations 46-1 to 46-2 shown in the following table were produced using the corresponding starting compounds according to the method similar to that described in Preparation 46.

TABLE 59

| Pr | Structure | Data |
| --- | --- | --- |
| 46 | 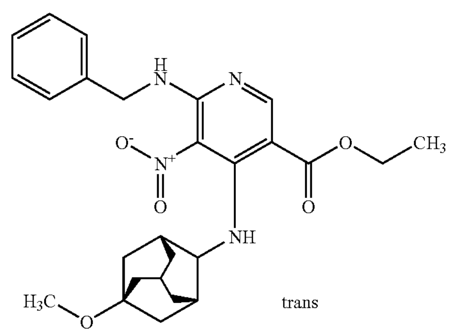 | MS: 481 (M + H)+ |
| 46-1 | | MS: 481 (M + H)+ | trans diastereomer of 46-2
cis trans unknown

TABLE 59-continued

| Pr | Structure | Data |
|---|---|---|
| 46-2 | [Structure: diastereomer of 46-1, cis trans unknown] | MS: 481 (M + H)+ |

Preparation 47

A solution of 4-chloro-2-methyl-1-(triisopropylsilyl)-1H-pyrrolo[2,3-b]pyridine (525 mg) in tetrahydrofuran (10 ml) was cooled to −78° C. under nitrogen atmosphere, and to the reaction mixture was added 0.99M sec-butyllithium/cyclohexane solution (4.1 ml) dropwise. After the mixture was stirred at −78° C., ethyl chlorocarbonate (389 μl) was added dropwise. The reaction solution was stirred at −78° C. for 30 minutes, saturated aqueous ammonium chloride (20 ml) was added, and the temperature was returned to ambient temperature. The reaction solution was transferred into a separating funnel and extracted with ethyl acetate. The organic layer was washed with brine, dried over anhydrous magnesium sulfate, filtered, and evaporated under reduced pressure. The residue was purified by silica gel column chromatography (n-hexane) to obtain ethyl 4-chloro-2-methyl-1-(triisopropylsilyl)-1H-pyrrolo[2,3-b]pyridine-5-carboxylate (645 mg) as a colorless viscous liquid.

The compound in Preparation 47-1 shown in the following table was produced using the corresponding starting compound according to the method similar to that described in Preparation 47.

TABLE 60

| Pr | Structure | Data |
|---|---|---|
| 47 | [Structure] | MS: 417 (M + Na)+ |

TABLE 60-continued

| Pr | Structure | Data |
|---|---|---|
| 47-1 | [Structure] | |

Preparation 48

A mixture of ethyl 4,6-dichloro-5-nitronicotinic acid ester (1 g), 2-adamantamine hydrochloride (708 mg), diisopropylethylamine (1.3 ml), and 2-propanol (4 ml) was subjected to microwave irradiation under nitrogen atmosphere, and heated at 90° C. for 10 minutes. After being cooled, the reaction solution was diluted with ethyl acetate (20 ml), and poured into ½ saturated aqueous ammonium, chloride (20 ml). The mixture was extracted with ethyl acetate (20 ml) two times, washed with brine (30 ml), dehydrated with anhydrous magnesium sulfate, and evaporated under reduced pressure. The residue was purified by silica gel column chromatography (n-hexane:ethyl acetate) to obtain ethyl 4-(2-adamantylamino)-6-chloro-5-nicotinic acid ester (1.23 g) as an orange solid.

The compounds in Preparations 48-1 to 48-5 shown in the following table were produced using the corresponding starting compounds according to the method similar to that described in Preparation 48.

TABLE 61

| Pr | Structure |
|---|---|
| 48 | ethyl 6-chloro-5-nitro-4-(2-adamantylamino)nicotinate |
| 48-1 | ethyl 6-chloro-5-nitro-4-[(5-hydroxy-2-adamantyl)amino]nicotinate, cis/trans mix |
| 48-2 | ethyl 6-chloro-5-nitro-4-[(5-methoxy-2-adamantyl)amino]nicotinate, trans |
| 48-3 | ethyl 6-chloro-5-nitro-4-[(8-benzyl-8-azabicyclo[3.2.1]oct-3-yl)amino]nicotinate |
| 48-4 | ethyl 6-chloro-5-nitro-4-[(5-hydroxy-2-adamantyl)amino]nicotinate, cis/trans mix |

TABLE 61-continued

| Pr | Structure |
|---|---|
| 48-5 | ethyl 6-chloro-5-nitro-4-{[5-(hydroxymethyl)-2-adamantyl]amino}nicotinate, cis or trans unknown |

TABLE 62

| Pr | Data |
|---|---|
| 48 | MS: 380 (M + H)+ |
| 48-1 | MS: 396 (M + H)+ |
| 48-2 | MS: 410 (M + H)+ |
| 48-3 | MS: 445 (M + H)+ |
| 48-4 | MS: 377 (M + H)+ |
| 48-5 | MS: 410 (M + H)+ |

Preparation 49

A mixture of ethyl 4,6-dichloro-5-nitronicotinic acid ester (333 mg), 4-amino-1-adamantanol (200 mg), diisopropylethylamine (219 μl), and isopropylalcohol (1 ml) was subjected to microwave irradiation under nitrogen atmosphere and heated at 90° C. for 10 minutes. After the mixture was cooled, benzylamine (157 μl) was added to the reaction solution, the mixture was subjected to microwave irradiation again and heated at 90° C. for 10 minutes. After being cooled, the reaction solution was diluted with ethyl acetate (20 ml), poured into ½ saturated aqueous ammonium-chloride (20 ml), extracted with ethyl acetate (20 ml) two times, washed with brine (30 ml), dried over anhydrous magnesium sulfate, and filtered. The filtrate was evaporated under reduced pressure. The residue was purified by silica gel column chromatography (chloroform:methanol) to obtain ethyl 6-(benzylamino)-4-[(5-hydroxy-2-adamantyl)amino]-nicotinic acid ester (515 mg) as an orange solid.

The compounds in Preparations 49-1 to 49-5 shown in the following table were produced using the corresponding starting compounds according to the method similar to that described in Preparation 49.

TABLE 63
| Pr | Structure |
|---|---|
| 49 | 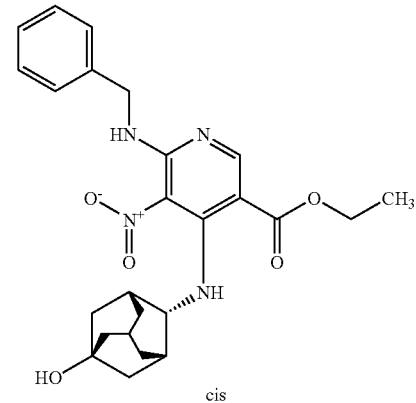 cis/trans mix |
| 49-1 | (structure with F-adamantyl) cis/trans mix |
| 49-2 | (structure with CN-adamantyl) cis or trans unknown |
TABLE 63-continued
| Pr | Structure |
|---|---|
| 49-3 | (structure with HO-adamantyl) cis |
| 49-4 | (structure with HO-adamantyl) trans |
| 49-5 | (structure with 3,4-dimethoxybenzyl and HO-adamantyl) cis |
TABLE 64
| Pr | Data |
|---|---|
| 49 | MS: 467 (M + H)+ |
| 49-1 | MS: 469 (M + H)+ |
| 49-2 | MS: 476 (M + H)+ |
| 49-3 | MS: 467 (M + H)+ |
| 49-4 | |
| 49-5 | MS: 527 (M + H)+ |

Preparation 50

The compound in Preparation 50 shown in the following table was produced using the corresponding starting compound according to the method similar to that described in Example 10.

TABLE 65

| Pr | Structure |
|---|---|
| 50 | (structure: 4-nitrophenyl N-methyl-N-(cyanomethyl)carbamate) |

Preparation 51

The compound in Preparation 51 shown in the following table was produced using the corresponding starting compound according to the method similar to that described in Example 28.

TABLE 66

| Pr | Structure | Data |
|---|---|---|
| 51 | (structure) | MS: 211 (M + H)+ |

Preparation 52

10% Palladium on carbon (50% wet) (40 mg) was added to a solution of benzyl 4-[(5-carbamoyladamantan-2-yl)amino]-1H-pyrrolo-[2,3-b]pyridine-5-carboxylate (183 mg) in methanol (5 ml) and 1,4-dioxane (5 ml), and hydrogenated under hydrogen atmosphere for 5 hours. Resulting precipitates were dissolved by tetrahydrofuran and filtered out the catalysts. The filtrates were evaporated in vacuo to give 4-[(5-carbamoyladamantan-2-yl)amino]-1H-pyrrolo[2,3-b]pyridine-5-carboxylic acid (117 mg).

The compounds in Preparations 52-1 to 52-17 shown in the following table were produced using the corresponding starting compounds according to the method similar to that described in Preparation 52.

TABLE 67

| Pr | Structure |
|---|---|
| 52-1 | (structure) |
| 52-2 | (structure) cis/tans mix |
| 52-3 | (structure) |
| 52-4 | (structure) cis/trans mix |
| 52-5 | (structure) |

TABLE 67-continued

| Pr | Structure |
|---|---|
| 52-6 | (7-azaindole-5-carboxylic acid ethyl ester with adamantyl-NH substituent at 4-position) |
| 52-7 | (7-azaindole-5-carboxylic acid with bromo-adamantyl-NH substituent) cis or trans unknown |
| 52-8 | (bromo-adamantyl amine, NH₂) cis/trans unknown |
| 52-9 | (7-azaindole-5-carboxylic acid with (2-cyanoethoxy)-adamantyl-NH substituent) cis or trans unknown |
| 52-10 | (2-cyanoethoxy-adamantyl amine, NH₂) cis/trans mix |
| 52-11 | (tricyclic pyrrolopyridine imidazolone with azabicyclic substituent) |
| 52-12 | (7-azaindole-5-carboxylic acid with cyanoacetamido-adamantyl-NH substituent) diastereomer of 53-17 cis or trans unknown |
| 52-13 | (7-azaindole-5-carboxylic acid with Boc-amino-adamantyl-NH substituent) cis or trans unknown |
| 52-14 | (7-azaindole-5-carboxylic acid with carbamoyl-adamantyl-NH substituent) diastereomer of 53-1 cis or trans unknown |
| 52-15 | (hydroxy-bicyclic amine, NH₂, OH) |
| 52-16 | (Boc-protected azabicyclic amine with NH₂) |
| 52-17 | (7-azaindole-5-carboxylic acid with cyanoacetamido-adamantyl-NH substituent) diastereomer of 53-12 cis or trans unknown |

TABLE 68

| Pr | Data |
|---|---|
| 52-1 | MS: 355 (M + H)+ |
| 52-2 | MS: 370 (M + H)+ |
| 52-3 | MS: 168 (M + H)+ |
| 52-4 | MS: 267 (M + H)+ |
| 52-5 | MS: 316 (M + H)+ |
| 52-6 | MS: 313 (M − H)− |
| 52-7 | MS: 390, 392 (M + H)+ |
| 52-8 | MS: 230, 232 (M + H)+ |
| 52-9 | MS: 381 (M + H)+ |
| 52-10 | MS: 221 (M + H)+ |
| 52-11 | MS: 284 (M + H)+ |
| 52-12 | MS: 394 (M + H)+ |
| 52-13 | MS: 427 (M + H)+ |
| 52-14 | MS: 355 (M + H)+ |
| 52-15 | MS: 168 (M + H)+ |
| 52-16 | 1H-NMR (400 MHz, CDCl$_3$) δ: 1.46 (9H, s), 1.61-2.29 (10H, m), 3.33 (1H, dd, J = 6.2, 6.2 Hz), 4.06-4.29 (2H, m) MS: 227 (M + H)+ |
| 52-17 | MS: 394 (M + H)+ |

Preparation 53

The compound in Preparation 53-1 to 53-4 shown in the following table was produced using the corresponding starting compound according to the method similar to that described in Example 16.

TABLE 69

| Pr | Structure |
|---|---|
| 53-1 | (structure) |
| 53-2 | (structure) cis or trans mix |
| 53-3 | (structure) |
| 53-4 | (structure) |

TABLE 70

| Pr | Structure |
|---|---|
| 53-1 | MS: 143 (M − H)− |
| 53-2 | MS: 430 (M + Na)+ |
| 53-3 | MS: 176 (M − H)− |
| 53-4 | MS: 372, 374 (M + H)+ |

Example 1

To a solution of 5-(4-chloro-1H-pyrrolo[2,3-b]pyridine-5-yl)-N-methyl-1,3,4-oxadiazole-2-carboxamide (18 mg) in 1-methyl-2-pyrrolidone (0.18 ml) were added N,N-dibutyl-1-butaneamine (0.046 ml) and cis-(1S,3R,4R,5S)-4-aminoadamantan-1-ol (32.5 mg) under ambient temperature. The mixture was heated immediately to 150° C. and stirred for 2 hours. After the disappearance of the starting compound was ascertained, the residue was purified by silica gel column chromatography (chloroform:methanol=97:3 to 85:15) to obtain cis-5-(4-{[(1R,2R,3S,5s)-5-hydroxyadamantan-2-yl]amino}-1H-pyrrolo[2,3-b]pyridine-5-yl)-N-methyl-1,3,4-oxadiazole-2-carboxamide (19.8 mg) as a white solid.

Example 2

To 1-[(1S,2R,5S)-6,6-dimethylbicyclo[3.1.1]hept-2-yl]methaneamine (61 mg) were added a solution of 4-chloro-1H-pyrrolo[2,3-b]pyridine-5-carboxamide (39 mg) in 1-methyl-2-pyrrolidone (0.6 ml), triethylamine (0.056 ml), and sodium iodide (3 mg), and the mixture was stirred at 130° C. for 17 hours. After the reaction mixture was left to cool, to the reaction mixture were added N,N-dimethylformamide (0.3 ml) and water (0.1 ml), and the reaction mixture was dissolved. The reaction mixture was directly purified by preparative HPLC (101M-NH$_4$HCO$_3$+NH$_3$ (pH=9.2):CH$_3$CN=98:2 to 30:70). The active fraction was concentrated and dried to hardness to obtain 4-({[(1S,2R,5S)-6,6-dimethylbicyclo[3.1.1]hept-2-yl]methyl}amino)-1H-pyrrolo[2,3-b]pyridine-5-carboxamide (33.5 mg) as a solid.

Example 3

To a suspension methyl 4-(2-oxo-3,6-dihydropyrazolo[4,5-d]pyrrolo[2,3-b]pyridine-1(2H)-yl)adamantan-1-carboxylate (40 mg) in methanol (0.4 ml) and dioxane (0.4 ml) was added 1M aqueous sodium hydroxide (0.22 ml), and the suspension was refluxed for 2 hours. The reaction solution was cooled to ambient temperature, the pH was adjusted to 5 with 1M aqueous hydrochloric acid and pH 4 buffer solution, and the reaction solution was evaporated under reduced pressure. The obtained solid was collected by filtration and washed with water to obtain 4-(2-oxo-3,6-dihydroimidazo[4,5-d]pyrrolo[2,3-b]pyridine-1(2H)-yl)adamantan-1-carboxylic acid (32 mg).

Example 4

4-(2-Oxo-3,6-dihydroimidazo[4,5-d]pyrrolo[2,3-b]pyridine-1(2H)-yl)adamantan-1-carboxylic acid (50 mg) was suspended in N,N-dimethyl formamide (1 ml). To the suspension were added aminoacetonitrile hydrochloride (17 mg), 1-hydroxybenzotriazole (28 mg), diisopropylethylamine (62 µl), and 1-ethyl-3-(3-dimethylaminopropyl)-carbodiimide hydrochloride (41 mg) successively, and the mixture was stirred overnight at ambient temperature. To the reaction solution were added ethyl acetate and water, and the organic layer was extracted. The organic layer was washed with saturated brine, dried over magnesium sulfate, and evaporated under reduced pressure. The residue was purified by silica gel column chromatography (chloroform:methanol) to obtain N-(cyanomethyl)-4-(2-oxo-3,6-dihydroimidazo[4,5-d]pyrrolo[2,3-b]pyridine-1(2H)-yl)adamantan-1-carboxamide (23 mg).

Example 5

To a solution of 3-methylbenzoic acid (22.4 mg) in 1-methyl-2-pyrrolidone (0.6 ml) were added 4-[(3-exo-8-azabicyclo[3.2.1]oct-3-yl)amino]-1H-pyrrolo[2,3-b]pyridine-5-carboxamide (42.8 mg) and 1-hydroxybenzotriazole (22.3 mg) Furthermore, 1M 1-ethyl-3-(3-dimethylaminopropyl)-1-carbodiimide/1-methyl-2-pyrrolidone solution (0.225 ml) was added, and the mixture was stirred for 4 hours at 50° C. After being cooled, the reaction solution was directly purified by preparative HPLC system (10 mM-$NH_4HCO_3$+$NH_3$ (pH=9.2):$CH_3CN$=98:2 to 30:70). The active fraction was concentrated and dried to hardness to obtain 4-{[(3-exo)-8-(3-methylbenzoyl)-8-azabicyclo[3.2.1]oct-3-yl)amino]}-1H-pyrrolo[2,3-b]pyridine-5-carboxamide (34.8 mg) as a solid.

Example 6

To a solution of 2-aminoethanol (18.6 mg) in 1-methyl-2-pyrrolidone (0.6 ml) were added cis-4-{[(1R,2R,3S,5s)-5-hydroxyadamantan-2-yl]amino}-1H-pyrrolo[2,3-b]pyridine-5-carboxylic acid (41 mg) and 1-hydroxybenzotriazole (18.6 mg). Furthermore, 1-ethyl-3-(3-dimethylaminopropyl)-carbodiimide/1-methyl-2-pyrrolidone solution (0.188 ml) was added, and the mixture was stirred for 6 hours at 60° C. After being cooled, the reaction solution was directly purified by preparative HPLC (10M-$NH_4HCO_3$+$NH_3$ (pH=9.2):$CH_3CN$=98:2 to 30:70). The active fraction was concentrated and dried to hardness to obtain 4-{[(2r,5s)-5-hydroxyadamantan-2-yl]amino}-N-(2-hydroxyethyl)-1H-pyrrolo[2,3-b]pyridine-5-carboxamide (22.9 mg) as a solid.

Example 7

To a solution of ethyl 3-(4-{[(2r,5s)-5-hydroxyadamantan-2-yl]amino}-1H-pyrrolo[2,3-b]pyridine-5-yl)-1,2,4-oxadiazole-5-carboxylate (25 mg) in 1-methyl-2-pyrrolidone (0.25 ml) was added 2-piperazin-1-ylethanol (8.5 mg) under ambient temperature. The mixture was immediately warmed to 50° C. and stirred for 0.5 hour. After the disappearance of the starting compound was ascertained, the residue was purified by silica gel column chromatography (chloroform:methanol=96:4 to 87:13) to obtain cis-(1s,3R,4R,5S)-4-{[5-(5-{[4-(2-hydroxyethyl)piperazin-1-yl]carbonyl}-1,2,4-oxadiazole-3-yl)-1H-pyrrolo[2,3-b]pyridine-4-yl]amino}adamantan-1-ol (22.6 mg) as a yellowish white solid.

Example 8

To a solution of methylamine hydrochloride (4.7 mg) in 1-methyl-2-pyrrolidone (0.3 ml) were added ethyl cis-5-(4-{[(1R,2R,3S,5s)-5-hydroxyadamantan-2-yl]amino}-1H-pyrrolo[2,3-b]pyridine-5-yl)-1,2,4-oxadiazole-5-carboxylate (14.8 mg) and diisopropylamine (0.0183 ml), and the mixture was stirred for 6 hours at 90° C. After being cooled, the reaction solution was directly purified by preparative HPLC system (10 mM-$NH_4HCO_3$+$NH_3$ (pH=9.2):$CH_3CN$=90:10 to 20:80). The active fraction was concentrated and dried to hardness to obtain 5-(4-{[(2r,5s)-5-hydroxyadamantan-2-yl]amino}-1H-pyrrolo[2,3-b]pyridine-5-yl)-N-methyl-1,2,4-oxadiazole-3-carboxamide (6.74 mg) as a solid.

Example 9

To a solution of cis-5-(4-{[(1R,2R,3S,5s)-5-hydroxyadamantan-2-yl]amino}-1H-pyrrolo[2,3-b]pyridine-5-yl)-N-piperidine-4-yl-1,2,4-oxadiazole-3-carboxamide dihydrochloride (20 mg) in 1-methyl-2-pyrrolidone (0.25 ml) were added N-ethyl-N-isopropylpropan-2-amine (0.025 ml) and acetic anhydride (0.043 ml) under ambient temperature, and the mixture was stirred for 1 hour. The residue was purified by silica gel column chromatography (chloroform:methanol=99:1 to 89:11) to obtain cis-N-(1-acetylpiperidine-4-yl)-5-(4-{[(1R,2R,3S,5s)-5-hydroxyadamantan-2-yl]amino}-1H-pyrrolo[2,3-b]pyridine-5-yl)-1,2,4-oxadiazole-3-carboxamide (7.8 mg) as a yellowish white solid.

Example 10

To 1-(5-aminoadamantan-2-yl)-3,6-dihydroimidazo[4,5-d]pyrrolo[2,3-b]pyridine-2(1H)-one dihydrochloride (15 mg) were added dichloromethane-methanol and, saturated aqueous sodium hydrogencarbonate, and the organic layer was extracted. The organic layer was dried over magnesium sulfate and filtered. The filtrate was evaporated under reduced pressure. The residue was suspended in dichloromethane (7.5 ml), and triethylamine (13 µl) and propanoyl chloride (4 µl) were added. The mixture was stirred overnight at ambient temperature. The reaction solution was purified by NH silica gel-column chromatography (chloroform:methanol) to obtain N-[4-(2-oxo-3,6-dihydroimidazo[4,5-d]pyrrolo[2,3-b]pyridine-1(2H)-yl)adamantan-1-yl]propanamide (2 mg).

Example 11

To a solution of cis-4-{[(1R,2R,3S,5s)-5-hydroxyadamantan-2-yl]amino}-1H-pyrrolo[2,3-b]pyridine-5-carboxylic acid (30 mg) in N,N-dimethylformamide (0.21 ml) were added N,N'-carbonyl diimidazole (22.3 mg) and 2M dimethylamine/methanol solution (0.183 ml) successively under ambient temperature. The mixture was stirred at ambient temperature for 18 hours. Water was added to the reaction solution, and the reaction solution was filtered. The solid residue was washed with water and dried. The residue was purified by thin-layer silica gel column chromatography (chloroform:methanol=10:1) to obtain methyl cis-4-{[(1R,2R,3S,5s)-5-hydroxyadamantan-2-yl]amino}-1H-pyrrolo[2,3-b]pyridine-5-carboxylate (18 mg) as a yellowish white solid.

Example 12

To a suspension of rel-4-{[(1R,2R,3S,5s)-5-hydroxyadamantan-2-yl]amino}-1H-pyrrolo[2,3-b]pyridine-5-carboxylic acid (25 mg) in N,N-dimethylformamide (0.4 ml) were added potassium carbonate (15.8 mg) and 1-chloroacetone (0.0073 ml), and the mixture was stirred at ambient temperature for 5 hours. The reaction solution was diluted with ethyl acetate, washed with water and saturated brine, dried over anhydrous sodium sulfate, and filtered. The filtrate was evaporated under reduced pressure. The residue was purified by silica gel column chromatography (chloroform:methanol) to obtain rel-4-{[(1R,2R,3S,5s)-5-hydroxyadamantan-2-yl]amino}-1H-pyrrolo[2,3-b]pyridine-5-carboxylic acid 2-oxopropyl ester (20.8 mg) as a white solid.

Example 13

To a suspension of rel-4-{[(1R,2R,3S,5s)-5-hydroxyadamantan-2-yl]amino}-1H-pyrrolo[2,3-b]pyridine-5-carboxylic acid (45 mg), acetamide oxime (25.5 mg), and 1-hydroxybenzotriazole (27.9 mg) in N,N-dimethylformamide (1.08 ml) were added triethylamine (0.077 ml) and N-[3-(dimethylamino)propyl]-N'-ethylcarbodiimide hydrochloride (39.5 mg). The mixture was stirred for 2 hours at 60° C. The reaction solution was diluted with chloroform and ethanol, washed with saturated brine, dried over anhydrous sodium sulfate, and filtered. The filtrate was evaporated under reduced pressure. The residue was purified by silica gel column chromatography (chloroform:methanol) to obtain rel-(1Z)-N'-{[(4-{[(1R,2R,3S,5s)-5-hydroxyadamantan-2-yl]amino}-1H-pyrrolo[2,3-b]pyridine-5-yl)carbonyl]oxy}ethanimidamide (38.9 mg) as white powder.

Example 14

To a solution of cis-4-{[(1R,2R,3S,5s)-5-hydroxyadamantan-2-yl]amino}-1H-pyrrolo[2,3-b]pyridine-5-carboxylic acid (30 mg) in N,N-dimethylformamide (0.9 ml) were added N,N'-carbonyldiimidazole (83 mg), N-ethyl-N-isopropylpropane-2-amine (0.018 ml), and carbonic acid-guanidine (1:2) (82.5 mg) successively under ambient temperature. Furthermore, after 1-methyl-2-pyrrolidone (0.3 ml) was added, the mixture was immediately warmed to 60° C. and stirred for 5 hours. The mixture was evaporated under reduced pressure and dried. The residue was purified by basic thin-layer silica gel column chromatography (chloroform:methanol=6:1) to obtain cis-N-(diaminomethylene)-4-{[(1R,2R,3S,5s)-5-hydroxyadamantan-2-yl]amino}-1H-pyrrolo[2,3-b]pyridine-5-carboxamide (18.1 mg) as a yellowish white solid.

Example 15

To a solution of cis-4-{[(1R,2R,3S,5s)-5-hydroxyadamantan-2-yl]amino}-1H-pyrrolo[2,3-b]pyridine-5-carboxylic acid (80 mg) in 1-methyl-2-pyrrolidone (0.8 ml) were added (O-(7-azabenzotriazol-1-yl)-1,1,3,3-tetramethyluronium hexafluorophosphate) (HATU) (139 mg), N-ethyl-N-isopropylpropane-2-amine (0.17 ml), and hydrazine carboxamide hydrochloride (32.7 mg) successively under ambient temperature. The mixture was stirred for 3 hours at ambient temperature. To the reaction solution were added ethyl acetate and diisopropyl ether, and the mixture was filtered. The solid residue was washed with ethyl acetate-diisopropyl ether and dried to obtain cis-2-[(4-{[(1R,2R,3S,5s)-5-hydroxyadamantan-2-yl]amino}-1H-pyrrolo[2,3-b]pyridine-5-yl)carbonyl]hydrazinecarboxamide (90 mg) as a yellowish white solid.

Example 16

4-(2-Oxo-3,6-dihydroimidazo[4,5-d]pyrrolo[2,3-b]pyridine-1(2H)-yl)adamantan-1-carboxamide (70 mg) was suspended in N,N-dimethylformamide (1 ml), and 2,4,6-trichloro-1,3,5-triazine (37 mg) was added under ice cooling. The mixture was stirred at ambient temperature for 4 hours. To the reaction solution was added saturated aqueous sodium hydrogencarbonate, and the obtained solid was collected by filtration, washed with water and ethyl acetate to obtain 4-(2-oxo-3,6-dihydroimidazo[4,5-d]pyrrolo[2,3-b]pyridine-1(2H)-yl)adamantan-1-carbonitrile (30 mg).

Example 17

To a solution of 5-(4-{[(2r,5s)-5-hydroxyadamantan-2-yl]amino}-1H-pyrrolo[2,3-b]pyridine-5-yl)-1,2,4-oxadiazole-3-carboxamide (30 mg) in tetrahydrofuran (1 ml) were added pyridine (37 µl) and trifluoroacetic anhydride (64 µl) under ice cooling, and the reaction solution was stirred under ambient temperature for 30 minutes. Water was added to the reaction solution, and the precipitate was collected by filtration and dissolved in tetrahydrofuran (1 ml). To the reaction solution was added 1M aqueous sodium hydroxide (0.114 ml) under ice cooling, and the reaction solution was stirred for 1 hour under ambient temperature. The reaction solution was extracted with chloroform and washed with water. The organic layer was dried over magnesium sulfate and filtered. The filtrate was concentrated under reduced pressure. The residue was purified by silica gel column chromatography (chloroform:methanol=100:0 to 90:10) to obtain 5-(4-{[(2r,5s)-5-hydroxyadamantan-2-yl]amino}-1H-pyrrolo[2,3-b]pyridine-5-yl)-1,2,4-oxadiazole-3-carbonitrile (5 mg) as a white solid.

Example 18 t-Butyl [4-(2-oxo-3,6-dihydroimidazo[4±5-d]pyrrolo[2,3-b]pyridine-1(2H)-yl)adamantan-1-yl]carbamate (118 mg) was suspended in dioxane (1.2 ml). 4M hydrochloric acid/dioxane (0.7 ml) was added, and the mixture was stirred overnight at ambient temperature. To the reaction solution was added ethyl acetate, and the obtained solid was collected by filtration and washed with ethyl acetate to obtain 1-(5-adamantan-2-yl)-3,6-dihydroimidazo[4,5-d]pyrrolo[2,3-b]pyridine-2(1H)-one dihydrochloride (108 mg).

Example 19

To 3-(3,4-dimethoxybenzyl)-N-(4-fluorobenzyl)-7-{(5-hydroxyadamantan-2-yl)amino}-3H-imidazo[4,5-b]pyridine-6-carboxamide (170 mg) was added trifluoroacetic acid (1.7 ml), and the mixture was stirred at ambient temperature for overnight. The reaction solution was neutralized with saturated aqueous sodium hydrogencarbonate and extracted with ethyl acetate and tetrahydrofuran. The organic layer was washed with saturated brine, dried over magnesium sulfate, and filtered. The filtrate was evaporated under reduced pressure. The residue was purified by silica gel column chromatography (chloroform:methanol) to obtain N-(4-fluorobenzyl)-7-{(5-hydroxyadamantan-2-yl)amino}-3H-imidazo[4,5-b]pyridine-6-carboxamide (31 mg).

Example 20

To a solution of 4-{[(2r, 5s)-5-hydroxyadamantan-2-yl]amino}-N-(tetrahydro-2H-pyran-2-yloxy)-1H-pyrrolo[2,3- b]pyridine-5-carboxamide (35 mg) in ethanol (0.525 ml) was added 2M hydrochloric acid/ethanol solution (0.205 ml) under ambient temperature. The reaction solution was stirred under ambient temperature for 2 hours. To the reaction solution was added ethyl acetate, and the precipitate was collected by filtration to obtain N-hydroxy-4-{[(2r,5s)-5-hydroxyadamantan-2-yl]amino}-1H-pyrrolo[2,3-b]pyridine-5-carboxamide hydrochloride (18 mg) as a white solid.

Example 21

To a solution of 3-{[(triisopropylsilyl)oxy]methyl}bicyclo[2.2.1]hept-2-yl]-3,6-dihydroimidazo[4,5-d]pyrrolo[2,3-b]pyridine-2(1H)-one (45 mg) in tetrahydrofuran (0.15 ml) was added 1M tetrabutylammoniumfluoride/tetrahydrofuran solution (297 µl), and the mixture was stirred overnight at ambient temperature. The reaction solution was evaporated under reduced pressure. The residue was purified by silica gel column chromatography (ethyl acetate:methanol) to obtain 1-[3-(hydroxymethyl)bicyclo[2.2.1]hept-2-yl]-3,6-dihydroimidazo[4,5-d]pyrrolo[2,3-b]pyridine-2(1H)-one (14.8 mg) as a white solid. To a solution of rel-4-{[(1R,2R,3S,5s)-5-hydroxyadamantan-2-yl]amino}-1H-pyrrolo[2,3-b]pyridine-5-carbohydrazide in 1-methyl-2-pyrrolidone (1 ml) were added triethyl orthoformate (340 µl) and p-toluene sulfonic acid monohydrate (5.6 mg). After stirring at 120° C. for 30 minutes, triethyl orthoformate (340 µl) and p-toluene sulfonic acid monohydrate (5.6 mg) were added. After the mixture was stirred at 120° C. for 40 minutes, the reaction solution was extracted with 20% chloroform/methanol solution, and washed with saturated aqueous sodium bicarbonate. The organic layer was dried over magnesium sulfate and filtered. The filtrate was evaporated under reduced pressure. The residue was purified by silica gel chromatography (chloroform:methanol) to obtain rel-(1s,3R,4R,5S)-4-{[1-(diethoxymethyl)-5-(1,3,4-oxazole-2-yl)-1H-pyrrolo[2,3-b]pyridine-4-yl]amino}adamantan-1-ol (28 mg) and rel-(1s,3R,4R,5S)-4-{[5-(1,3,4-oxazole-2-yl)-1H-pyrrolo[2,3-b]pyridine-4-yl]amino}.adamantan-1-ol (70 mg).

Example 22

The cis-trans mixture of N-(cyanomethyl)-4-(2-oxo-3,6-dihydropyrazolo[4,5-d]pyrrolo[2,3-b]pyridine-1(2H)-yl)adamantan-1-carboxylate was separated by HPLC (aqueous (NH$_4$)HCO$_3$-aqueous ammonia (pH=9.2):acetonitrile) to obtain a fraction (8 mg) having a peak with a short retention time and another fraction (15 mg) having a peak with a long retention time.

Example 23

4-(Adamantan-1-ylamino)-1H-pyrrolo[2,3-b]pyridine-5-carboxylic acid (17 mg) and triethylamine (15 µl) were dissolved in dioxane (0.5 ml). To the mixture was added diphenylphosphoryl azide (DPPA) (18 µl) at 120° C. under stirring. The mixture was stirred at the same temperature for 2 hours and cooled to ambient temperature. The obtained solid was collected by filtration and washed with acetonitrile to obtain (adamantan-1-yl)-3,6-dihydroimidazo[4,5-d]pyrrolo[2,3-b]pyridine-2(1H)-one (11 mg).

Example 24

To a mixture of 5,6-diamino-4-{cis-5-hydroxyl-2-adamantyl]amino}-N-methylnicotinamide (9 mg) and triethyl orthoformate (0.15 ml) was added concentrated hydrochloric acid (5 µl), and the mixture was heated at 90° C. for 3 hours. After being cooled, the reaction solution was diluted with ethyl acetate (10 ml), and saturated aqueous sodium hydrogencarbonate (10 ml) was added. The organic layer was extracted, dried over magnesium sulfate, and concentrated. The residue was purified by silica gel column chromatography (chloroform:methanol) to obtain 7-{[cis-5-hydroxyadamantan-2-yl]amino}-N-methyl-3H-imidazo[4,5-b]pyridine-6-carboxyamide (0.5 mg) as a pale yellow solid.

Example 25

A mixture of acetic anhydride (897 µl) and formic acid (342 µl) was stirred at 60° C. for 2 hours. After the mixture was cooled, a solution of 4-(2-adamantylamino)-6-amino-5-nicotinamide (200 mg) in dichloromethane (1 ml) was added dropwise. The reaction mixture was stirred at ambient temperature for 1 hour and at 50° C. for 2 hours. After being cooled, the reaction mixture was evaporated under reduced pressure. To the residue were added ethanol (2 ml), tetrahydrofuran (1 ml), and water (1 ml). Then, iron powder (169 mg) and ammonium chloride (16 mg) were added to the mixture. The mixture was stirred at 120° C. for 6 hours. After being cooled, the mixture was evaporated under reduced pressure. To the residue was added saturated aqueous sodium hydroxide (10 ml), and the mixture was extracted with ethyl acetate. The organic layer was dried over magnesium sulfate and filtered. The filtrate was concentrated under reduced pressure. The residue was purified by silica gel column chromatography (chloroform:methanol) to obtain 7-(2-adamantylamino)-3H-imidazo[4,5-b]pyridine-6-carboxyamide (110 mg) as a white solid.

Example 26

To a mixture of isopropyl 6-(benzylamino)-4-{[cis-5-hydroxyadamantan-2-yl]amino}-5-nicotinate (90 mg), ammonium formate (236 mg), and methanol was added 10% palladium on carbon (50% wet) (40 mg), and the mixture was stirred for 5 hours under refluxing. After being cooled, the reaction mixture was filtered to remove catalyst. The filtrate was concentrated under reduced pressure. To the residue were added triethyl orthoformate (0.6 ml) and concentrated hydrochloric acid (31 µl), and the mixture was stirred at ambient temperature for 3 hours. After the reaction mixture was diluted with ethyl acetate (20 ml), saturated aqueous sodium hydrogencarbonate (20 ml) was added. The organic layer was extracted, dried over magnesium sulfate, and filtered. The filtrate was concentrated under reduced pressure. The residue was purified by silica gel column chromatography (chloroform:methanol) to obtain isopropyl-rel-7-{[(1R,2R,3S,5S)-5-hydroxyadamantan-2-yl]amino}-3H-imidazo[4,5-b]pyridine-6-carboxylate (45 mg) as a white solid.

Example 27

To a solution of 4-[(5-hydroxyadamantan-2-yl)amino]-1H-pyrrolo[2,3-b]pyridine-5-carbonitrile (100 mg) in methanol (3 ml) were added hydroxylamine hydrochloride (34 mg) and sodium hydrogencarbonate (82 mg), and the reaction solution was stirred at 90° C. for 18 hours. The reaction solution was concentrated under reduced pressure, and the residue was purified by silica gel column chromatography (chloroform:methanol=100:0 to 90:10) to obtain N'-hydroxy-4-{[(2r,5s)-hydroxyadamantan-2-yl]amino}-1H-pyrrolo[2,3-b]pyridine-5-carboxylmidamide (32 mg) as a white solid and to obtain N'-hydroxy-4-{[(2s,5r)-hydroxyadamantan-2-yl]amino}-1H-pyrrolo[2,3-b]pyridine-5-carboxylmidamide (35 mg) as a white solid.

Example 28

A solution of rel-(1Z)-N'-{[(4-{[(1R,2R,3S,5s)-5-hydroxyadamantan-2-yl]amino}-1H-pyrrolo[2,3-b]pyridin-5-yl)carbonyl]oxy}ethanimidamide (16.2 mg) in N,N-dimethylformamide (0.4 mL) was stirred at 160° C. for 3 hours, then stirred at 165° C. for 1 hour. The reaction mixture was diluted with ethyl acetate, washed with 10% sodium chloride aqueous solution, water (three times), and brine, dried over magnesium sulfate, filtered and evaporated in vacuo. The residue was purified by silica gel column chromatography (chloroform:methanol, 15:1) to give rel-(1s,3R,4R,5S)-4-{[5-(3-methyl-1,2,4-oxadiazol-5-yl)-1H-pyrrolo[2,3-b]pyridin-4-yl]amino}adamantan-1-ol (6.0 mg) as a orange crystals.

Example 29

To a solution of rel-4-{[(1R,2R,3S,5s)-5-hydroxyadamantan-2-yl]amino}-1H-pyrrolo[2,3-b]pyridine-5-carbohydrazide in 1-methyl-2-pyrrolidone (1 ml) were added triethyl orthoformate (340 µl) and p-toluene sulfonic acid monohydrate (5.6 mg). After the mixture was stirred at 120° C. for 30 minutes, triethyl orthoformate (340 µl) and p-toluene sulfonic acid monohydrate (5.6 mg) were added. After the mixture was stirred at 120° C. for 40 minutes, the reaction solution was extracted with 20% chloroform/methanol solution and washed with saturated aqueous sodium bicarbonate. The organic layer was dried over magnesium sulfate and filtered. The filtrate was concentrated under reduced pressure. The residue was purified by silica gel chromatography (chloroform:methanol) to obtain rel-(1s,3R,4R,5S)-4-{[1-(diethoxymethyl)-5-(1,3,4-oxazole-2-yl)-1H-pyrrolo[2,3-b]pyridine-4-yl]amino}adamantan-1-ol (28 mg) and to obtain rel-(1s,3R,4R,5S)-4-{[5-(1,3,4-oxazole-2-yl)-1H-pyrrolo[2,3-b]pyridine-4-yl]amino}adamantan-1-ol (70 mg).

Example 30

To a solution of N'-hydroxy-4-{[(2r,5s)-5-hydroxyadamantan-2-yl]amino}-1H-pyrrolo[2,3-b]pyridine-5-carboximidamide (45 mg) in dichloromethane (0.45 ml) were added pyridine (32 µl) and acetic anhydride (19 µl). The reaction solution was stirred under ambient temperature for 2 hours. To the reaction solution were further added pyridine (32 µl) and acetic anhydride (19 µl), and the reaction solution was stirred at 60° C. for 2 hours. To the reaction solution was further added pyridine (0.5 ml), and the mixture was stirred at 90° C. for 16 hours. The reaction solution was extracted with chloroform and washed with water. The organic layer was dried over magnesium sulfate and filtered. The filtrate was concentrated under reduced pressure. The residue was purified by silica gel column chromatography (chloroform:methanol=100:0 to 90:10) to obtain (1s,4r)-4-{[5-(5-methyl-1,2,4-oxadiazol-3-yl)-1H-pyrrolo[2,3-b]pyridine-4-yl]amino}adamantan-1-ol (10 mg) as a white solid.

Example 31

To a solution of N'-hydroxy-4-{[(2r,5s)-5-hydroxyadamantan-2-yl]amino}-1H-pyrrolo[2,3-b]pyridine-5-carboxylmidamide (25 mg) in N,N-dimethylformamide (0.5 ml) were added pyridine (9 µl) and 2-ethylhexyl chlorocarbonate (14 µl) under ice cooling. The reaction solution was stirred at ambient temperature for 2 hours. To the reaction solution was added water. The mixture was extracted with chloroform and washed with water. The organic layer was dried over magnesium sulfate and filtered. The filtrate was concentrated under reduced pressure. The residue was dissolved in N,N-dimethylformamide (0.5 ml) and xylene (0.5 ml), and the reaction solution was stirred at 150° C. for 2 hours. After the reaction solution was cooled to ambient temperature, the precipitate was collected by filtration and washed with a small amount of ethyl acetate to obtain (1s,4r)-4-(3-aminopyrazolo[3,4-d]pyrrolo[2,3-b]pyridine-1(6H)-yl)adamantan-1-ol (8 mg) as a white solid.

Example 32

To a solution of 3-(4-chloro-1H-pyrrolo[2,3-b]pyridine-5-yl)-N-(2-methoxyethyl)-1,2,4-oxadiazole-5-carboxamide (35 mg) in 1-methyl-2-pyrrolidone (0.35 ml) were added N,N-dibutyl-1-butanamine (0.078 ml) and cis-(1S,3R,4R,5S)-4-aminoadamantan-1-ol (36 mg) under ambient temperature. The mixture was immediately heated to 190° C. and stirred for 1 hour. After the disappearance of the starting compound was ascertained, water was added to the reaction solution, and the solution was filtered. The solid residue was washed with water and dried. The solid residue was purified by thin-layer silica gel column chromatography (chloroform:methanol=12:1) to obtain cis-N-{1-[(1R,2R,3S,5s)-5-hydroxyadamantan-2-yl]-1,6-dihydropyrazolo[3,4-d]pyrrolo[2,3-b]pyridine-3-yl}-N'-(2-methoxyethyl)ethanediamide (18.1 mg) as a yellowish white solid.

Example 33

To a solution of 3-(4-chloro-1H-pyrrolo[2,3-b]pyridine-5-yl)-N-methyl-1,2,4-oxadiazole-5-carboxamide (14.2 mg) in 1-methyl-2-pyrrolidone (0.142 ml) were added N,N-dibutyl-1-butanamine (0.0487 ml) and cis-(1S,3R,4R,5S)-4-aminoadamantan-1-ol (25.7 mg). The mixture was stirred for 100 minutes using a microwave reaction system at 200° C. After being cooled, the reaction solution was directly purified by preparative HPLC system (10 mM $NH_4HCO_3+NH_3$ (pH=9.2):$CH_3CN$=95:5 to 20:80). The active fraction was concentrated to obtain cis-N-{1-[(1R,2R,3S,5s)-5-hydroxyadamantan-2-yl]-1,6-dihydropyrazolo[3,4-d]pyrrolo[2,3-b]pyridine-3-yl}-N'-methylethanediamide (11.1 mg) as a solid.

Example 34

To a suspension of 4-{[(2r,5s)-5-hydroxyadamantan-2-yl]amino}-1H-pyrrolo[2,3-b]pyridine-5-carbonitrile (60 mg) in toluene (0.6 ml) were added thiosemicarbazide (35.5 mg) and trifluoroacetic acid (0.15 ml), and the mixture was stirred at 70° C. for 6 hours. To the mixture were further added thiosemicarbazide (35.5 mg) and trifluoroacetic acid (0.15 ml), and the mixture was stirred at 90° C. for 51 hours. Furthermore, thiosemicarbazide (17.8 mg) was added, and the mixture was stirred at 90° C. for 48 hours. The reaction solution was alkalified with saturated aqueous sodium hydrogencarbonate and extracted with ethyl acetate. The organic layer was washed with water and saturated brine, dried over anhydrous sodium, sulfate, and evaporated under reduced pressure. The residue was purified by silica gel column chromatography (chloroform:methanol) to obtain (1s,4r)-4-{[5-(5-amino-1,3, 4-thiadiazole-2-yl)-1H-pyrrolo[2,3-b]pyridine-4-yl]amino}adamantan-1-ol (8.3 mg) as a white solid.

Example 35

To a solution of ethyl 5-[4-(2-oxo-3,6-dihydroimidazo[2,3-b]pyridine-1(2H)-yl)adamantan-1-yl]-1,2,4-oxadiazole-3-carboxylate (30 mg) in tetrahydrofuran (1 ml) was added lithium aluminum hydride (10 mg) under ice cooling, and the mixture was stirred for 1 hour at ambient temperature. To the reaction solution was added 1M aqueous sodium hydroxide. The mixture was stirred for 30 minutes at ambient temperature and extracted with chloroform. The organic layer was dried over magnesium sulfate and filtered, and the filtrate was concentrated under reduced pressure. The residue was purified by silica gel column chromatography (chloroform:methanol) to obtain 1-{5-[3-(hydroxymethyl)-1,2,4-oxadiazole-5-yl]adamantan-2-yl}-3,6-dihydroimiazo[4,5-d]pyrrolo[2,3-b]pyridine-2(1H)-one (3 mg).

Example 36

To a solution of 4-{[(2r,5s)-hydroxyadamantan-2-yl]amino}-1H-pyrrolo[2,3-b]pyridine-5-carbonitrile (27 mg) in ethanol (0.5 ml) were added 10% palladium on carbon (30 mg) and 2M hydrochloric acid/ethanol solution (0.5 ml). The reaction solution was stirred for 3 hours under hydrogen atmosphere at 60° C. The catalyst was filtered with Celite, and the filtrate was concentrated under reduced pressure to obtain (1s,4r)-4-{[5-(aminomethyl)-1H-pyrrolo[2,3-b]pyridine-4-yl]amino}adamantan-1-ol trihydrochloride (37 mg) as a white solid.

Example 37

To a solution of 1-(4-{[(2r,5s)-5-hydroxyadamantan-2-yl]amino}-1H-pyrrolo[2,3-b]pyridine-5-yl)ethanone (20 mg) in tetrahydrofuran (2.5 ml) was added lithium aluminum hydride (19.4 mg)-under ambient temperature. Furthermore, the mixture was stirred at ambient temperature for 2 hours. After the disappearance of the starting compound was ascertained, to the reaction solution were added water (19 µl), 2M aqueous sodium hydroxide (19 µl), and water (57 µl) successively. The precipitated solid was removed by Celite filtration and washed with tetrahydrofuran. The filtrate was concentrated under reduced pressure and purified by thin-layer silica gel column chromatography (chloroform:methanol 4:1) to obtain (1s, 4r)-4-{[5-(1-hydroxyethyl)-1H-pyrrolo[2,3-b]pyridine-4-yl]amino}adamantan-1-ol (9.1 mg).

Example 38

To a solution of 4-{[(3-exo)-8-(5-nitropyridine-2-yl)-8-azabicyclo[3.2.1]oct-3-yl]amino}-1H-pyrrolo[2,3-b]pyridine-5-carboxamide (25 mg) in methanol (0.5 ml) were added ammonium formate (38.6 mg) and palladium on carbon (50% wet) (1.3 mg), and the mixture was heated for 5 hours under refluxing. After the mixture was cooled to ambient temperature, the insoluble matter was removed by Celite filtration and washed with methanol. The filtrate was evaporated under reduced pressure and purified by thin-layer silica gel column chromatography (chloroform:methanol=4:1) to obtain 4-{[(3-exo)-8-(5-aminopyridine-2-yl)-8-azabicyclo[3.2.1]oct-3-yl]amino}-1H-pyrrolo[2,3-b]pyridine-5-carboxamide (12 mg).

Example 39

To a solution of N'-(5-bromoadamantan-2-yl)-4-chloro-1H-pyrrolo[2,3-b]pyridine-5-carbohydrazide (200 mg) in 1-methyl-2-pyrrolidone (1.5 ml) was added triethylamine (0.2 ml), and the mixture was stirred at 200° C. using a microwave reaction system for 2 hours. After the reaction solution was cooled, water was added to the reaction solution, and the mixture was extracted with chloroform. The organic layer was dried over magnesium sulfate and filtered. The filtrate was concentrated under reduced pressure. The residue was purified by silica gel column chromatography (chloroform:methanol) to obtain 1-(5-bromoadamantan-2-yl)-1,6-dihydropyrazolo[3,4-d]pyrrolo[2,3-b]pyridine-3(2H)-one (91 mg).

Example 40

To a suspension of 4-{[(2R,5S)-5-hydroxyadamantan-2-yl]amino}-1H-pyrrolo[2,3-b]pyridine-5-carbonitrile (50 mg) in a mixture of toluene (1.5 ml) and N,N'-dimethylformamide (1.5 ml) were added sodium azide (105 mg) and triethylamine hydrochloride (223 mg), and the mixture was stirred for at 100° C. for 3 hours. To the reaction mixture was added sodium azide (210 mg) and triethylamine hydrochloride (446 mg), and the mixture was stirred at 100° C. for 3.5 hours. The reaction solution was diluted with a mixture solvent of dichloromethane:methanol (=10:1), and the organic layer was separated. Furthermore, the water layer was extracted with a mixture solvent of dichloromethane: methanol (=10:1) three times. The obtained organic layers were combined, dried over anhydrous sodium sulfate, and filtered. The filtrate was concentrated under reduced pressure. The residue was purified by preparative TLC (dichloromethane: methanol=10:1) to obtain rel-(1s,3R,4R,5S)-4-{[5-(2H-tetrazole-5-yl)-1H-pyrrolo[2,3-b]pyridine-4-yl]amino}adamantan-1-ol (35 mg) as a solid.

Example 41

To 4-[(5-bromoadamantan-2-yl)amino]-1H-pyrrolo[2,3-b]pyridine-5-carboxamide (52 mg) were added ethylene cyanhydrin (250 µl) and triethylamine (56 µl), and the mixture was stirred for 20 minutes using a microwave reaction system at 150° C. The reaction solution was cooled and purified by silica gel column chromatography (chloroform:methanol). The obtained fraction was concentrated under reduced pressure, and water was added. The obtained solid was collected by filtration to obtain 4-{[5-(2-cyanoethoxy)adamantan-2-yl]amino}-1H-pyrrolo[2,3-b]pyridine-5-carboxamide (16 mg).

Example 42

To a solution of 4-({5-[5-(trichloromethyl)-1,2,4-oxadiazole-3-yl]-1H-pyrrolo[2,3-b]pyridine-4-yl}amino) adamantan-1-ol (80 mg) in 1-methyl-2-pyrrolidinone (1.6 ml) was added ethylamine/methanol solution (2.0M) (1.7 ml) under ice cooling. The reaction solution was stirred for 5 hours under ambient temperature. To the reaction solution were added ethyl acetate, tetrahydrofuran, and water. The mixture was extracted with a mixture solvent of tetrahydrofuran and ethyl acetate, and washed with saturated brine. The organic layer was dried over magnesium sulfate and filtered. The filtrate was concentrated under reduced pressure. The residue was purified by silica gel (NH silica gel) column chromatography (chloroform:methanol=100:0 to 91:9) to obtain 4-({5-[5-(ethylamino)-1,2,4-oxadiazole-3-yl]-1H -pyrrolo[2,3-b]pyridine-4-yl}amino)adamantan-1-ol (50 mg) as a yellow solid.

Example 43

4-[(5-Hydroxyadamantan-2-yl)amino]-1H-pyrrolo[2,3-b]pyridine-5-carboxamide (100 mg) was dissolved in 45% aqueous HBr (0.5 ml), and the mixture was refluxed for 1.5 hours. The reaction solution was cooled, and the obtained solid was collected by filtration and washed with water. The obtained solid was dissolved in dichloromethane and methanol, and purified by silica gel column chromatography (chloroform:methanol) to obtain 4-[5-bromoadamantan-2-yl]amino}-1H-pyrrolo[2,3-b]pyridine-5-carboxamide (85 mg).

Example 44

(5-Hydroxyadamantan-2-yl)-3,6-dihydroimidazo[4,5-d]pyrrolo[2,3-b]pyridine-2(1H)-one (92 mg) was suspended in dichloromethane, and diethyl aminosulfur trifluoride (DAST) was added. The mixture was stirred at ambient temperature for 1 hour. The saturated aqueous sodium hydrogencarbonate and ethyl acetate were added. The obtained solid was collected by filtration and washed with diisopropyl ethylether to obtain (5-fluoroadamantan-2-yl)-3,6-dihydroimidazo[4,5-d]pyrrolo[2,3-b]pyridine-2(1H)-one (34 mg).

Example 45

To a solution of cis-(1s,3R,4R,5S)-4-{[5-(2H -tetrazole-5-yl)-1H-pyrrolo[2,3-b]pyridine-4-yl]amino}adamantan-1-ol (55 mg) in 1-methyl-2-pyrrolidone (0.65 ml) were added N-ethyl-N-isopropylpropane-2-amine (0.11 ml) and iodomethane (0.015 ml) under ambient temperature, and the mixture was stirred at ambient temperature for 4 hours. The residue was purified by silica gel column chromatography (chloroform:methanol=99:1 to 90:10) to obtain cis-(1s,3R,4R,5S)-4-{[5-(2-methyl-2H-tetrazol-5-yl)-1H-pyrrolo[2,3-b]pyridine-4-yl]amino}adamantan-1-ol (19.5 mg) as a major product (having a larger Rf value obtained by TLC (chloroform-methanol=10:1)) and to obtain cis-(1s,3R,4R,5S)-4-{[5-(1-methyl-1H-tetrazole-5-yl)-1H-pyrrolo[2,3-b]pyridine-4-yl]amino}adamantan-1-ol (4.5 mg) as a minor product (having a smaller Rf value obtained by TLC (chloroform-methanol=10:1)), the major and minor products each being obtained as a yellowish white solid.

Example 46

To a solution of 2-chloronicotinonitrile (56.7 mg) and 4-[(3-exo)-8-azabicyclo[3.2.1]oct-3-ylamino]-1H -pyrrolo[2,3-b]pyridine-5-carboxamide (58.4 mg) in 1-methyl-2-pyrrolidone (0.6 ml) were added triethylamine (0.057 ml) and sodium iodide (3 mg), and the mixture was stirred for 10 hours at 130° C. After the reaction mixture was left to cool, 1-methyl-2-pyrrolidone (0.3 ml) was added to the reaction mixture, and the reaction mixture was dissolved. The mixture was directly purified by preparative HPLC system (10 mM NH$_4$HCO$_3$+NH$_3$ (pH=9.2):CH$_3$CN=98:2 to 60:40). The active fraction was concentrated and dried to hardness to obtain 4-{[(3-exo)-8-(3-cyanopyridine-2-yl)-8-azabicyclo[3.2.1]oct-3-yl]amino}-1H-pyrrolo[2,3-b]pyridine-5-carboxamide (10.1 mg) as a solid.

Example 47

To a solution of 4-{[(3-exo)-8-(5-aminopyridine-2-yl)-8-azabicyclo[3.2.1]oct-3-yl]amino}-1H-pyrrolo[2,3-b]pyridine-5-carboxamide (11 mg) in methanol/dichloromethane was added aqueous formalin (0.022 ml), and the mixture was stirred at ambient temperature for 0.5 hours. Sodium triacetoxyborohydride (30.9 mg) was further added, and the mixture was stirred for 16 hours at ambient temperature. To the reaction solution was added saturated aqueous sodium hydrogencarbonate, and the mixture was stirred for 30 minutes at ambient temperature and extracted with chloroform-methanol. The extract was concentrated, and the obtained yellow oily matter was purified by thin-layer silica gel column chromatography (chloroform:methanol=7:1) to obtain 4-{[(3-exo)-8-(5-(dimethylamino)pyridine-2-yl)-8-azabicyclo[3.2.1]oct-3-yl]amino}-1H-pyrrolo[2,3-b]pyridine-5-carboxamide (5.2 mg) as a yellowish white solid.

Example 48

To a suspension of 4-[(3-endo)-8-azabicyclo[3.2.1]oct-3-ylamino]-1H-pyrrolo[2,3-b]pyridine-5-carboxamide dihydrochloride (25 mg) in 1,3-dimethyl-2-imidazolidinone (0.5 ml) was added triethylamine (0.029 ml). Furthermore, mesyl chloride (0.0059 ml) was added under ice cooling. After the mixture was stirred for 1 hour at ambient temperature, diluted aqueous sodium hydrogencarbonate was added, and the mixture was stirred. The precipitated white solid was collected by filtration, washed with water, and dried to obtain 4-{[(3-endo)-8-(methylsulfonyl)-8-azabicyclo[3.2.1]oct-3-yl]amino}-1H-pyrrolo[2,3-b]pyridine-5-carboxamide (14.1 mg) as a white solid.

Example 49

To a solution of 1-[(3-exo)-8-azabicyclo[3.2.1]oct-3-yl]-3,6-dihydroimidazo[4,5-d]pyrrolo[2,3-b]pyridine-2(1H)-one (12 mg) in N,N-dimethylacetamide (0.48 ml) and N,N-dimethylformamide (0.24 ml) were added N-ethyl-N-isopropylpropane-2-amine (0.015 ml) and 6-chloronicotinonitrile (11.7 mg). The mixture was immediately heated to 90° C. and stirred for 12 hours. After the disappearance of the starting compound was ascertained, the reaction solution was evaporated under reduced pressure and dried. The solid residue was purified by thin-layer silica gel column chromatography (chloroform:methanol=8:1) to obtain 6-[(3-exo)-3-(2-oxo-3,6-dihydroimidazo[4,5-d]pyrrolo[2,3-b]pyridine-1(2H)-yl)-8-azabicyclo[3.2.1]oct-8-yl]nicotinonitrile (5.2 mg) as a yellowish white solid.

Example 50

To a solution of ethyl 3-(4-{[(2r, 5s)-hydroxyadamantan-2-yl]amino}-1H-pyrrolo[2,3-b]pyridine-5-yl)-1,2,4-oxadiazole-5-carboxylate (80 mg) in tetrahydrofuran (3.2 ml) was added 3M iodo(methyl)magnesium/diethyl ether solution (0.315 ml) under ice cooling, and the reaction solution was stirred for 16 hours under ambient temperature. To the reaction solution was further added 3M iodo(methyl)magnesium/diethyl ether solution (0.189 ml) under ice cooling. The reaction solution was stirred under ambient temperature for 16 hours. To the reaction solution was added water under ice cooling, and the mixture was stirred at the same temperature for 15 minutes. To the reaction solution were added chloroform and saturated aqueous ammonium chloride. The mixture was extracted with chloroform and washed with saturated brine. The organic layer was dried over magnesium sulfate and filtered. The filtrate was concentrated under reduced pressure. The residue was purified by silica gel column chromatography (chloroform:methanol=100:0 to 90:10) to obtain rel-(1s,3R,4R,5S)-4-({5-[5-(1-hydroxy-1-methylethyl)-1,2,4-oxadiazol-3-yl]-1H-pyrrolo[2,3-b]pyridine-4-yl}amino) adamantan-1-ol (15 mg) as a white solid.

Example 51

To a solution of 4-{[(3-exo)-8-(5-bromopyrimidine-2-yl)-8-azabicyclo[3.2.1]oct-3-yl]amino}-1H-pyrrolo[2,3-b]pyridine-5-carboxamide (22.2 mg) in N,N-dimethylformamide (0.67 ml) and 1,3-dimethyl-2-imidazolidinone (0.67 ml) were added tetrakis (triphenylphosphine)palladium (0) (5.8 mg) and dicyanozinc (17.7 mg). Reaction was carried out at 160° C. using a microwave reaction system for 1 hour. To the reaction solution was added dichloromethane, and the mixture was filtered. The solid residue was washed with dichloromethane and dried. The solid residue was purified by thin-layer silica gel column chromatography (chloroform:methanol=8:1) to obtain 4-{[(3-exo)-8-(5-cyanopyrimidine-2-yl)-8-azabicyclo[3.2.1]oct-3-yl]amino}-1H-pyrrolo[2,3-b]pyridine-5-carboxamide (15 mg) as a yellowish white solid.

Example 52

To a solution of 4-{[(2r,5s)-5-hydroxyadamantan-2-yl]amino}-1H-pyrrolo[2,3-b]pyridine-5-carbonitrile (30 mg) in tetrahydrofuran (0.6 ml) was added diisobutylaluminum hydride (0.99M toluene solution) (0.49 ml) at 5° C. The mixture was stirred for 2 hours at 5° C. and further stirred for 3 hours at ambient temperature. To the reaction solution was added 6M aqueous hydrochloric acid (0.09 ml) at 5° C. The mixture was stirred for 0.5 hour at ambient temperature. Solid sodium hydroxide (23.3 mg) and magnesium sulfate were added, and the mixture was stirred for 0.5 hour at ambient temperature. The insoluble matter was removed by Celite filtration and washed with tetrahydrofuran. The filtrate was evaporated under reduced pressure and purified by thin-layer silica gel column chromatography (chloroform:methanol=9:1) to obtain 4-{[(2r,5s)-5-hydroxyadamantan-2-yl]amino}-1H-pyrrolo[2,3-b]pyridine-5-carboaldehyde (18 mg) as a yellowish white solid.

Example 53

To a solution of 4-{[(2r,5s)-5-hydroxyadamantan-2-yl]amino}-1H-pyrrolo[2,3-b]pyridine-5-carboaldehyde-(20 mg) in ethanol (0.6 ml) were added pyridine (0.052 ml) and O-methylhydroxyamine hydrochloride (32.1 mg), and the mixture was heated for 6 hours under refluxing. After being cooled to ambient temperature, the reaction solution was evaporated under reduced pressure, dried, and purified by thin-layer silica gel column chromatography (chloroform:methanol=10:1) to obtain 4-{[(2r, 5s)-5-hydroxyadamantan-2-yl]amino}-1H-pyrrolo[2,3-b]pyridine-5-carboaldehyde O-methyloxime (11 mg) as a yellowish white solid.

Example 54

To acetic acid (0.8 ml) were added pyrrolidine (0.013 ml) and para-formaldehyde (5.72 mg), and the mixture was stirred for 5 minutes at 60° C. To the reaction solution was added cis-4-{[(1R,2R,3S,5s)-5-hydroxyadamantan-2-yl]amino}-1H-pyrrolo[2,3-b]pyridine-5-carboxamide (40.0 mg) at 60° C., and the mixture was stirred at 60° C. for 2 hours. The reaction solution was evaporated under reduced pressure, and toluene and N-ethyl-N-isopropylpropane-2-amine were added, and the mixture was subjected to azeotropy. The solid residue was purified by NH thin-layer silica gel column chromatography (chloroform:methanol=10:1) to obtain cis-4-{[(1R,2R,3S,5s)-5-hydroxyadamantan-2-yl]amino}-3-(pyrrolidine-1-ylmethyl)-1H-pyrrolo[2,3-b]pyridine-5-carboxamide (10.8 mg) as a yellowish white solid.

Example 55

To a solution of 4-{[(2r,5s)-5-hydroxyadamantan-2-yl]amino}-1H-pyrrolo[2,3-b]pyridine-5-carboaldehyde (40 mg) in tetrahydrofuran (1 ml) was added methyl (triphenylphosphoranylidene) acetate (56 mg), and the reaction solution was stirred at 80° C. for 16 hours. To the reaction solution was further added methyl (triphenylphosphoranylidene) acetate (43 mg), and the reaction solution was stirred at 90° C. for 3 hours. To the reaction solution was further added methyl (triphenylphosphoranylidene)acetate (129 mg), and the reaction solution was stirred at 90° C. for 16 hours. The reaction solution was concentrated under reduced pressure, and the residue was purified by silica gel column chromatography (chloroform:methanol 100:0 to 90:10) to obtain methyl (2E)-3-(4-{[(2r,5s)-5-hydroxyadamantan-2-yl]amino}-1H-pyrrolo[2,3-b]pyridine-5-yl)acrylate (7 mg) as a yellow solid.

Example 56

To a solution of cis-4-{[(1R,2R,3S,5s)-5-hydroxyadamantan-2-yl]amino}-1H-pyrrolo[2,3-b]pyridine-5-carboxamide (50 mg) in N,N-dimethylformamide (0.6 ml) was added 1-chloro-2,5-pyrrolidinedione (18.4 mg) at ambient temperature. After the mixture was stirred at ambient temperature for 2 hours, water was added to the reaction solution, and the solution was filtered. The solid residue was washed with water and dried. The solid residue was purified by thin-layer silica gel column chromatography (chloroform:methanol=4:1) to obtain cis-3-chloro-4-{[(1R,2R,3S,5s)-hydroxyadamantan-2-yl]amino}-1H -pyrrolo[2,3-b]pyridine-5-carboxamide (5 mg) as a yellowish white solid.

Example 57

To a solution of N'-hydroxy-4-{[(2r,5s)-5-hydroxyadamantan-2-yl]amino}-1H-pyrrolo[2,3-b]pyridine-5-carboxylmidamide (30 mg) in acetic acid (0.5 ml) was added acetic anhydride (11 µl), and the reaction solution was stirred for 30 minutes under ambient temperature. To the reaction solution was added 10% palladium on carbon (10 mg), and the mixture was stirred under hydrogen atmosphere at 50° C. for 3 hours. After the reaction solution was cooled to ambient temperature, the catalyst was filtered off with Celite. The filtrate was concentrated under reduced pressure, and the residue was washed with acetonitrile under stirring. The precipitate was collected by filtration to obtain 4-{[(2r,5s)-5-hydroxyadamantan-2-yl]amino}-1H-pyrrolo[2,3-b]pyridine-5-carboxylmidamide acetate (20 mg) as a yellow solid.

Example 58

To a solution of cis-4-{[(1R,2R,3S,5s)-5-hydroxyadamantan-2-yl]amino}-1H-pyrrolo[2,3-b]pyridine-5-carboxylic acid (30 mg) in 1-methyl-2-pyrrolidone (0.18 ml) was added pyridine hydrochloride (10.6 mg) at ambient temperature. Reaction was carried out at 200° C. for 1 hour using a microwave reaction system. To the reaction solution was added saturated aqueous sodium hydrogencarbonate, and the mixture was extracted with ethyl acetate and washed with water. The extract was dried over magnesium sulfate and filtered. The filtrate was concentrated under reduced pressure. The residue was purified by thin-layer silica gel column chromatography (chloroform:methanol=10:1) to obtain cis-(1s,3R,4R,5S)-4-(1H-pyrrolo[2,3-b]pyridine-4-ylamino)adamantan-1-ol (14.1 mg) as a yellowish white solid.

Example 59

To absolution of cis-4-{[(1R,2R,3S,5s)-5-hydroxyadamantan-2-yl]amino}-1H-pyrrolo[2,3-b]pyridine-5-carboxylic acid (30 mg) in N,N-dimethylformamide (0.1 ml) was added N,N'-carbonyldiimidazole (29.7 mg), and the mixture was stirred for 0.5 hours at 60° C. To the reaction mixture was added methanesulfonamide (17.4 mg) and 1,8-diazabicyclo[5.4.0]undec-7-ene (DBU) (0.027 ml). After being further stirred at 60° C. for 3 hours, the reaction solution was concentrated under reduced pressure. The residue was purified by thin-layer silica gel column chromatography (chloroform:methanol=4:1) to obtain cis-4-{[(1R,2R,3S,5s)-5-hydroxyadamantan-2-yl]amino}-N-(methylsulfonyl)-1H-pyrrolo[2,3-b]pyridine-5-carboxamide (7.8 mg) as a yellowish white solid.

Example 60

To a solution of cis-4-{[(1R,2R,3S,5s)-5-hydroxyadamantan-2-yl]amino}-1H-pyrrolo[2,3-b]pyridine-5-carboxamide (75 mg) in tetrahydrofuran (0.5 ml) and methanol (0.375 ml) was added 1,1-dimethoxy-N,N-dimethylmethaneamine (1.54 ml) at ambient temperature. After being stirred for 1 hour under heating and refluxing, the mixture was cooled to ambient temperature and stirred for 1 hour. The precipitated solid was collected by filtration, washed and dried to obtain cis-N-[(dimethylamino)methylene]-4-{[(1R,2R,3S,5s)-5-hydroxyadamantan-2-yl]amino}-1H-pyrrolo[2,3-b]pyridine-5-carboxamide (70 mg) as a white solid.

Example 61

A solution of cis-2-[(4-{[(1R,2R,3S,5s)-5-hydroxyadamantan-2-yl]amino}-1H-pyrrolo[2,3-b]pyridine-5-yl)carbonyl]hydrazine carboxamide (30 mg) in a mixture of xylene (0.45 ml) and acetic acid (0.45 ml) was stirred at 120° C. for 3 hours. Furthermore, 1-methyl-2-pyrrolidone (0.45 ml) was added, and the mixture was stirred at 150° C. for 4 hours. The reaction solution was concentrated under reduced pressure and dried. The residue was purified by thin-layer silica gel column chromatography (chloroform:methanol=10:1) to obtain cis-5-(4-{[(1R,2R,3S,5s)-5-hydroxyadamantan-2-yl]amino}-1H-pyrrolo[2,3-b]pyridine-5-yl)-2,4-dihydro-3H-1,2,4-triazol-3-one (5.6 mg) as a product (having a higher Rf value obtained by TLC (chloroform-methanol=10:1)) and to obtain cis-5-(4-{[(1R,2R,3S,5s)-5-hydroxyadamantan-2-yl]amino}-1H-pyrrolo[2,3-b]pyridine-5-yl)-1,3,4-oxadiazole-2(3H)-one (8.9 mg) as another product (having a lower Rf value obtained by TLC (chloroform-methanol=10:1)), these products each being obtained as a yellowish white solid.

Example 62

To a solution of ethyl 4-{[(2r,5s)-5-hydroxyadamantan-2-yl]amino}-1H-pyrrolo[2,3-b]pyridine-5-carboxylmidate trihydrochloride (75 mg) in ethanol (1 ml) was added 1,2-ethanediamine (0.11 ml), the reaction solution was stirred at 120° C. for 2 hours. The reaction solution was concentrated under reduced pressure, and the residue was purified by NH-silica gel column chromatography (chloroform:methanol=100:0 to 95:5) to obtain (1s,4r)-4-{[5-(4,5-dihydro-1H-imidazole-2-yl)-1H-pyrrolo[2,3-b]pyridine-4-yl]amino}adamantan-1-ol (17 mg) as a white solid.

Example 63

To a solution of ethyl 4-{[(2r,5s)-5-hydroxyadamantan-2-yl]amino}-1H-pyrrolo[2,3-b]pyridine-5-carboxylmidate trihydrochloride (150 mg) in ethanol (1.5 ml) were added 2-aminoethanol (78 µl) and triethylamine (0.225 ml), and the reaction solution was stirred at 110° C. for 2 hours. The reaction solution was cooled to ambient temperature and filtered, and the filtrate was concentrated under reduced pressure. The residue was purified by silica gel column chromatography (chloroform:methanol=100:0 to 90:10). The obtained solid was washed with ethyl acetate under stirring and collected by filtration to obtain (1s,4r)-4-{[5-(4,5-dihydro-1,3-oxazole-2-yl)-1H-pyrrolo[2,3-b]pyridine-4-yl]amino}adamantan-1-ol (5 mg) as a white solid.

Example 64

4-[(5-Hydroxyadamantan-2-yl)amino]-1H-pyrrolo[2,3-b]pyridine-5-carbonitrile (200 mg) and Raney nickel were added to ethanol (5 ml), and the reaction solution was stirred under hydrogen atmosphere at 60° C. for 8 hours. The catalyst was filtered off with Celite. The filtrate was concentrated under reduced pressure. The residue was dissolved in dioxane (3 ml), and 1M aqueous sodium hydroxide (0.65 ml) was added. To the reaction solution was added di-t-butyl dicarbonate (0.22 ml) under ambient temperature, and the mixture was stirred for 16 hours. The reaction solution was extracted with chloroform and washed with water. The organic layer was dried over magnesium sulfate and filtered. The filtrate was concentrated under reduced pressure. The residue was purified by silica gel column chromatography (chloroform:methanol=100:0 to 90:10) to obtain t-butyl ({4-[(5-hydroxyadamantan-2-yl)amino]-1H-pyrrolo[2,3-b]pyridine-5-yl}methyl)carbamate (40 mg) as a pale yellow solid.

The compounds shown in the following Table 71 were produced according to the above-mentioned production methods, the methods obvious to those skilled in the art, or modified methods of these. The tables 71 and 72 show the structures and physicochemical data of the compounds described in these Examples and also show the methods for producing the compounds.

TABLE 71
| Ex | Structure |
|---|---|
| 1 | 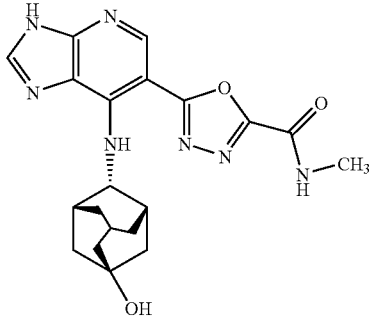<br>cis |
| 2 | 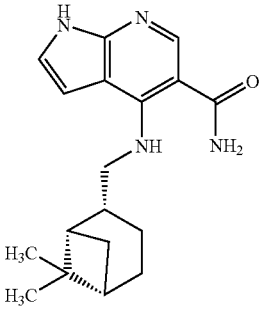 |
| 3 | 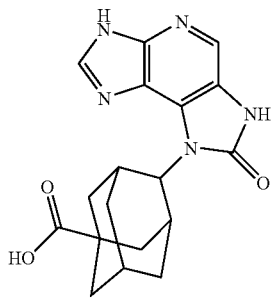<br>cis/trans mix |
| 4 | 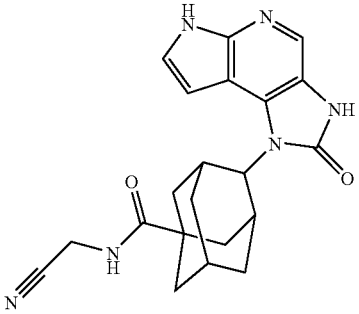<br>cis/trans mix |

TABLE 71-continued
| Ex | Structure |
|---|---|
| 5 | 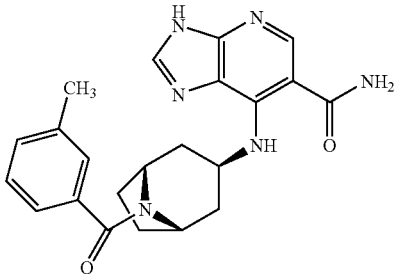 |
| 6 | 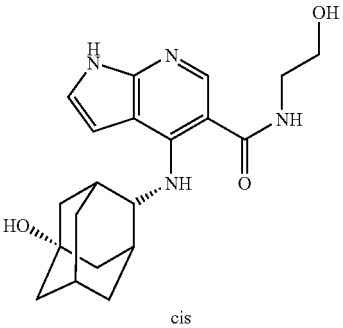<br>cis |
| 7 | 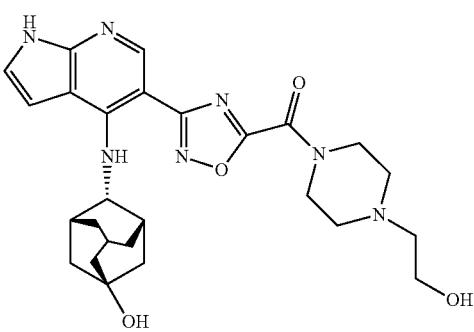<br>cis |
| 8 | 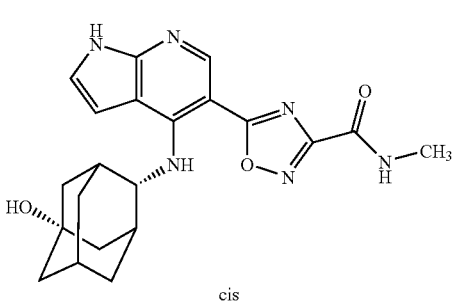<br>cis |

TABLE 71-continued
| Ex | Structure |
|---|---|
| 9 | 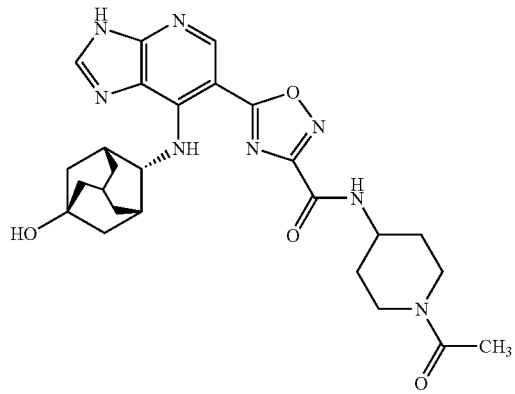cis |
| 10 | 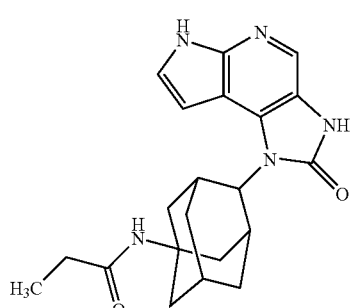cis/trans mix |
| 11 | 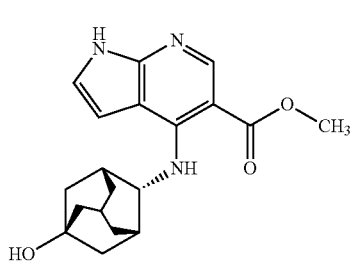cis |
| 12 | 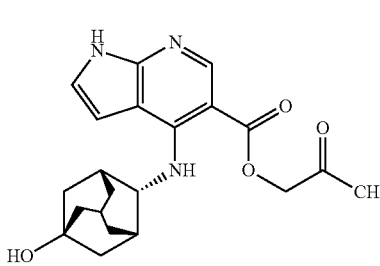cis |

TABLE 71-continued
| Ex | Structure |
|---|---|
| 13 | 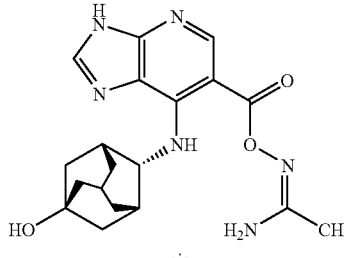<br>cis |
| 14 | 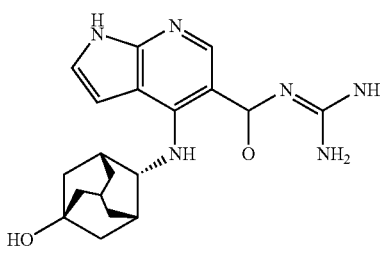<br>cis |
| 15 | 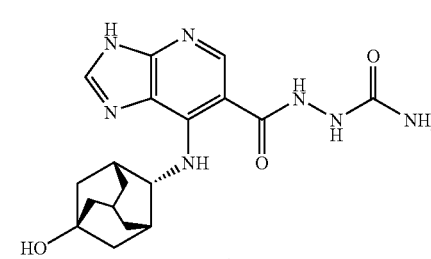<br>cis |
| 16 | 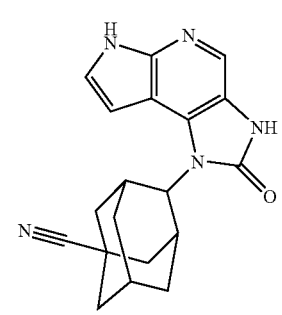<br>diastereomer of 365<br>cis or trans unknown |
| 17 | 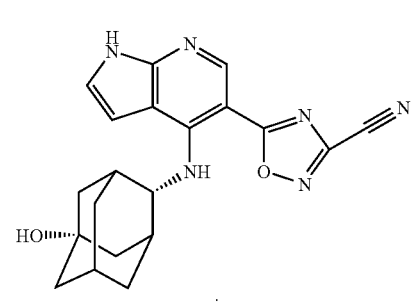<br>cis |

TABLE 71-continued
| Ex | Structure |
|---|---|
| 18 | 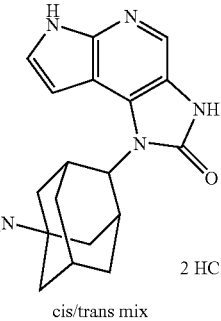<br>2 HCl<br>cis/trans mix |
| 19 | 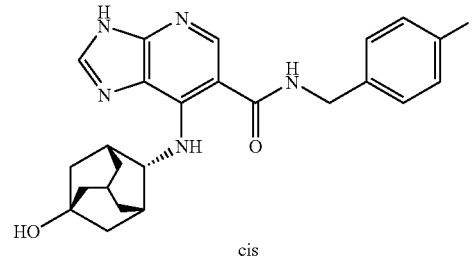<br>cis |
| 20 | 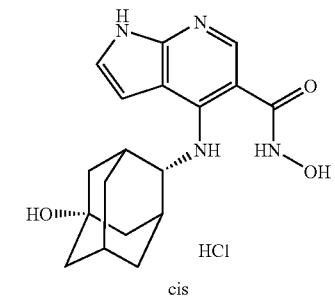<br>HCl<br>cis |
| 21 | 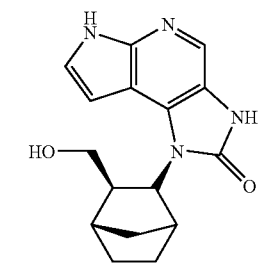 |
| 22 | 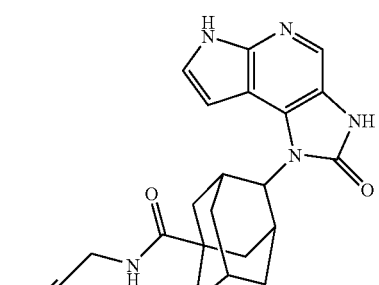<br>diastereomer of 382<br>cis or trans unknown |

TABLE 71-continued
| Ex | Structure |
|---|---|
| 23 | 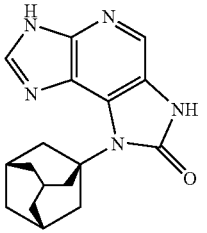 |
| 24 | 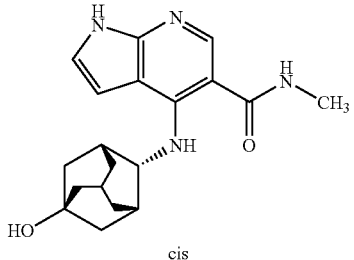 |
| 25 | 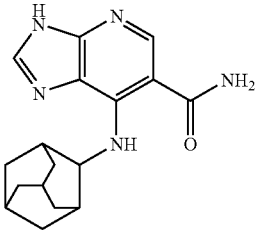 |
| 26 | 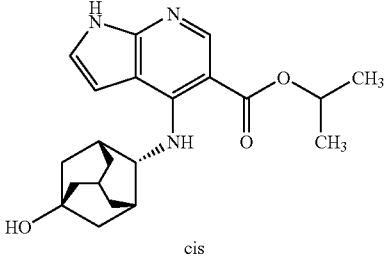 |
| 27 | 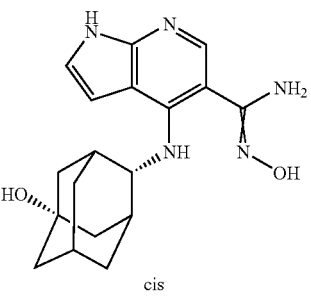 |

TABLE 71-continued
| Ex | Structure |
|---|---|
| 28 | 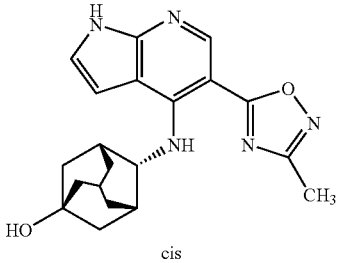 cis |
| 29 | 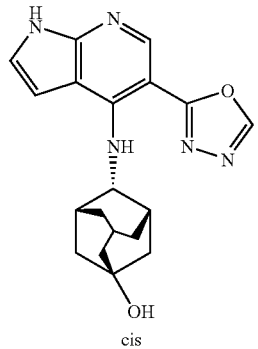 cis |
| 30 | 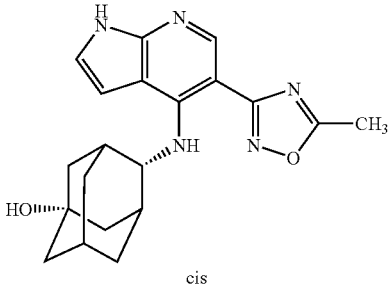 cis |
| 31 | 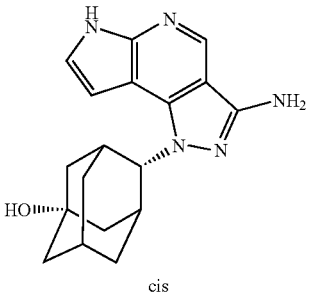 cis |
| 32 | 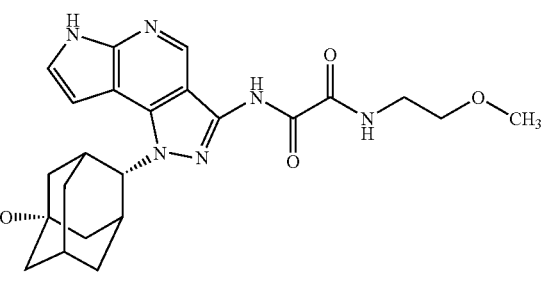 cis |

TABLE 71-continued
| Ex | Structure |
|---|---|
| 33 | 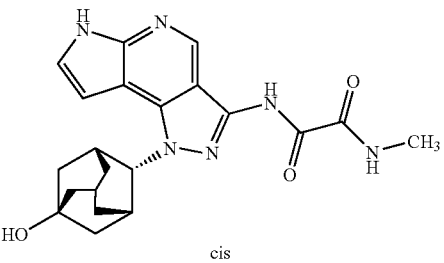<br>cis |
| 34 | 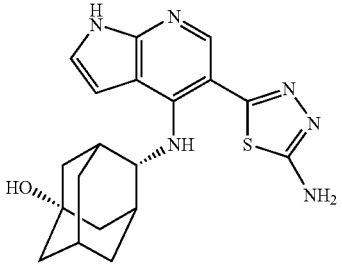<br>cis |
| 35 | 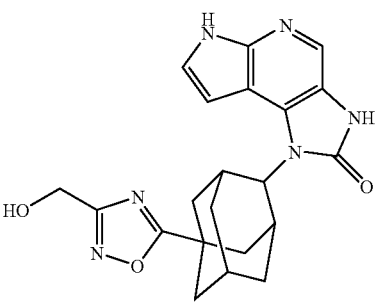<br>cis/trans mix |
| 36 | 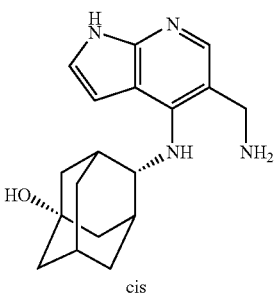<br>cis |
| 37 | 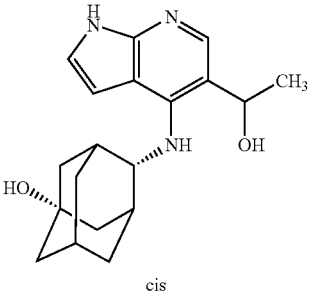<br>cis |

TABLE 71-continued
| Ex | Structure |
|---|---|
| 38 | 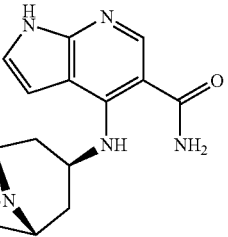 |
| 39 | 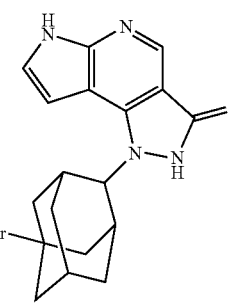<br>cis/trans mix |
| 40 | 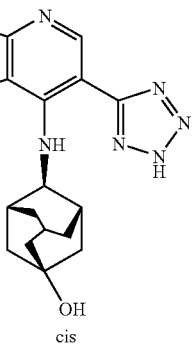<br>cis |
| 41 | 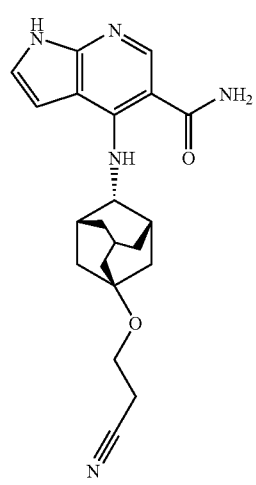<br>cis |

TABLE 71-continued
| Ex | Structure |
|---|---|
| 42 | 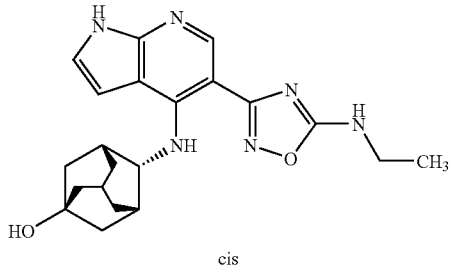 cis |
| 43 | 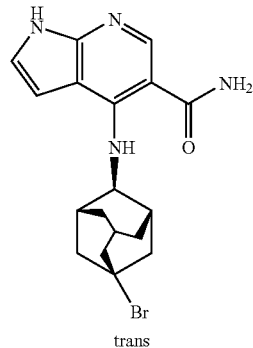 trans |
| 44 | 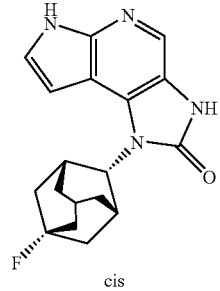 cis |
| 45 | 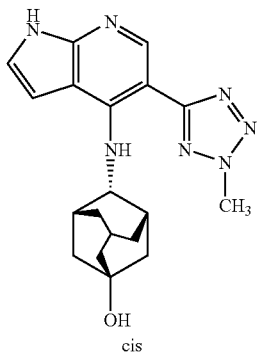 cis |

TABLE 71-continued

| Ex | Structure |
|---|---|
| 46 | 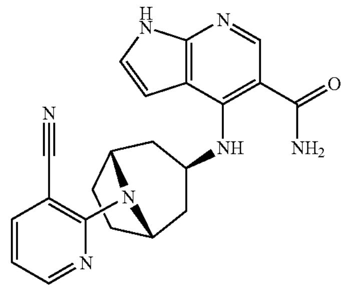 |
| 47 | 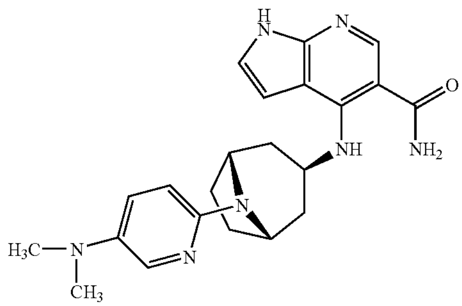 |
| 48 | 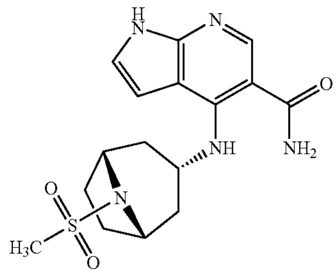 |
| 49 | 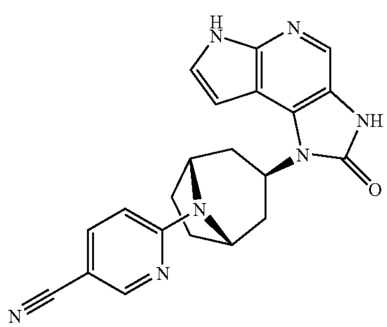 |
| 50 | 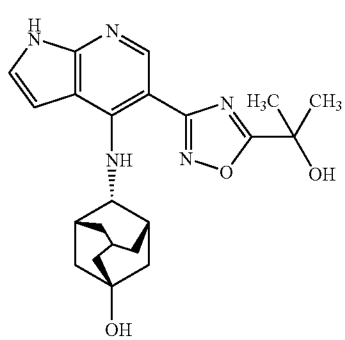 |

TABLE 71-continued
| Ex | Structure |
|---|---|
| 51 | 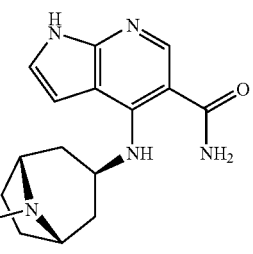 |
| 52 | 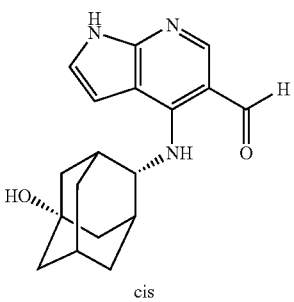 cis |
| 53 | 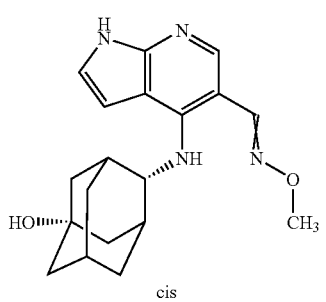 cis |
| 54 | 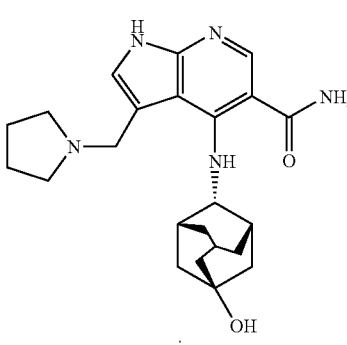 cis |
| 55 | 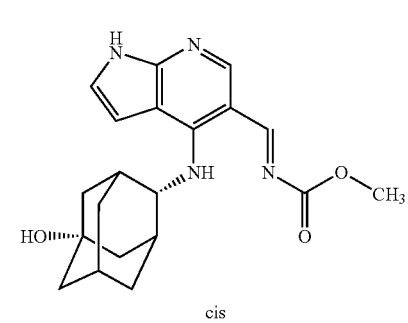 cis |

TABLE 71-continued
| Ex | Structure |
|---|---|
| 56 | 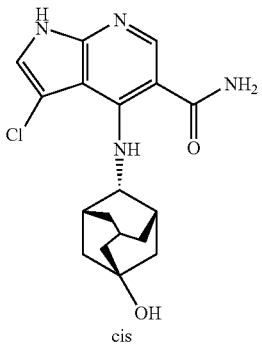 cis |
| 57 | 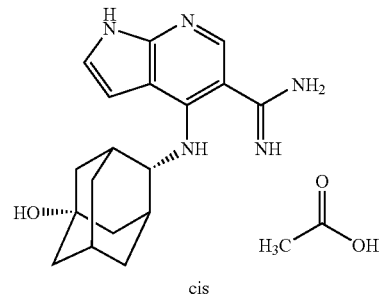 cis |
| 58 | 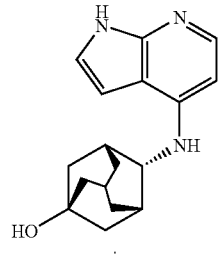 cis |
| 59 | 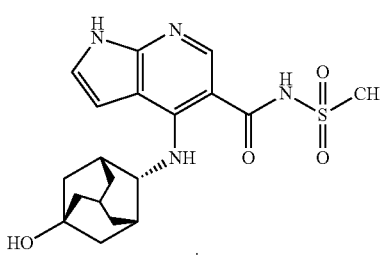 cis |
| 60 | 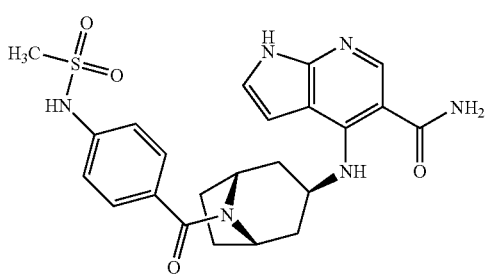 |

TABLE 71-continued
| Ex | Structure |
|---|---|
| 61 | 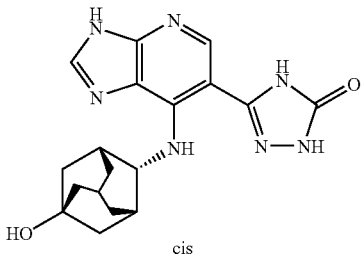 cis |
| 62 | 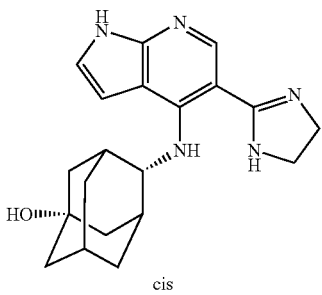 cis |
| 63 | 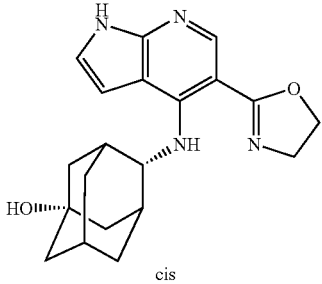 cis |
| 64 | 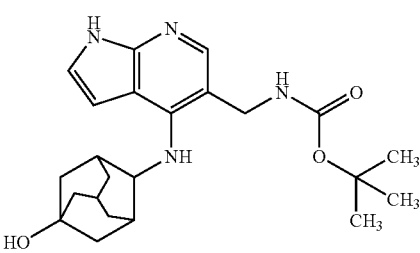 cis/trans mix |
| 65 | 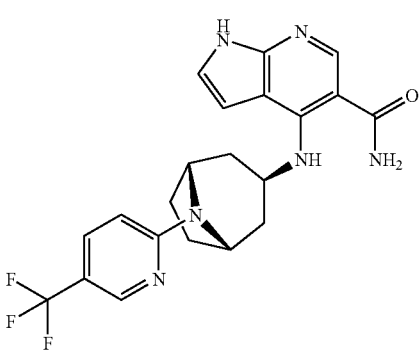 |

TABLE 71-continued
| Ex | Structure |
|---|---|
| 66 | 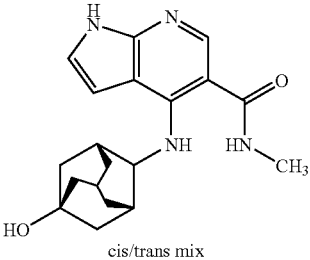<br>cis/trans mix |
| 67 | 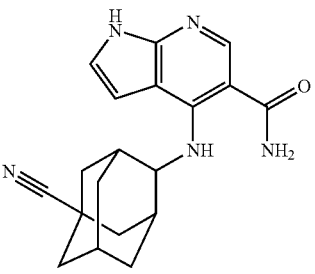<br>diastereomer of 68<br>cis or trans unknown |
| 68 | 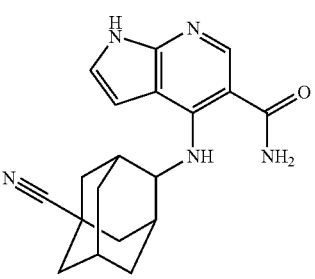<br>diastereomer of 67<br>cis or trans unknown |
| 69 | 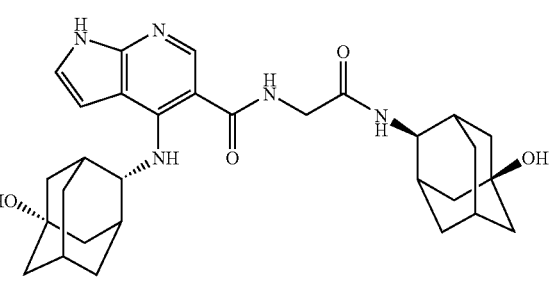<br>cis |
| 70 | 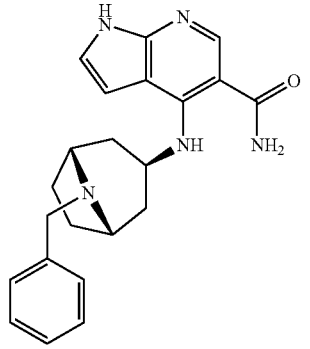 |

TABLE 71-continued

| Ex | Structure |
|---|---|
| 71 | 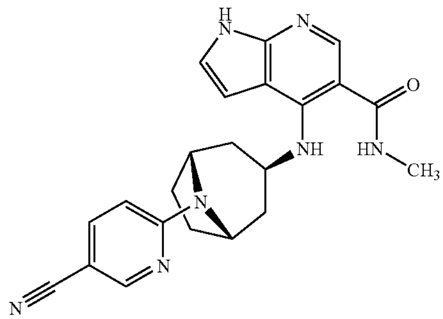 |
| 72 | trans |
| 73 | cis |
| 74 | trans |

TABLE 71-continued
| Ex | Structure |
|---|---|
| 75 | 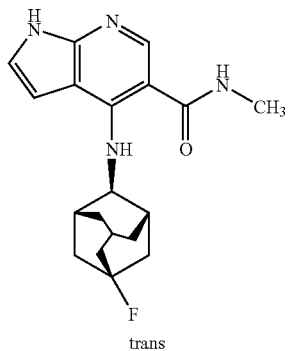 trans |
| 76 | 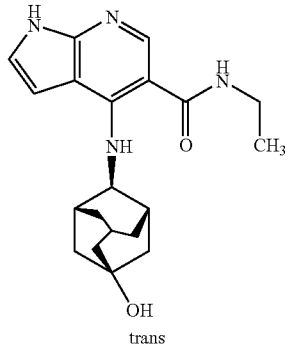 trans |
| 77 | 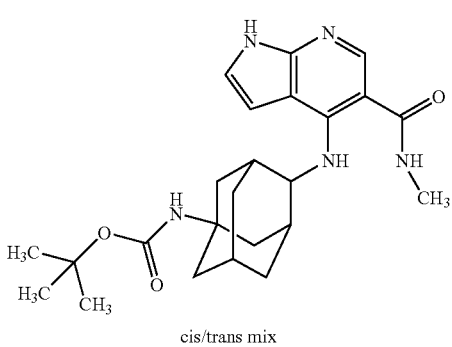 cis/trans mix |
| 78 | 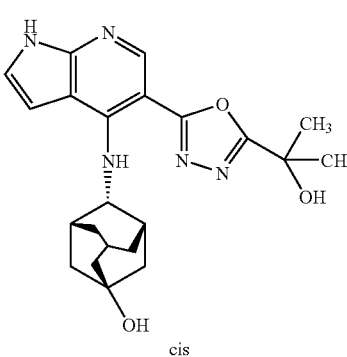 cis |

TABLE 71-continued
| Ex | Structure |
|---|---|
| 79 | 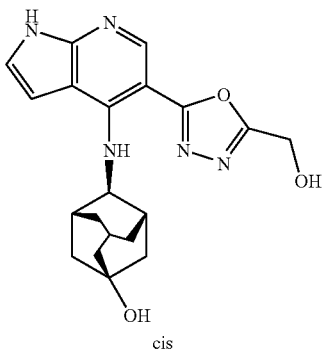cis |
| 80 | 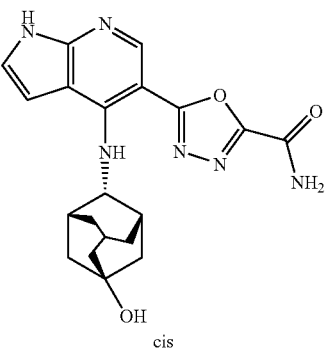cis |
| 81 | 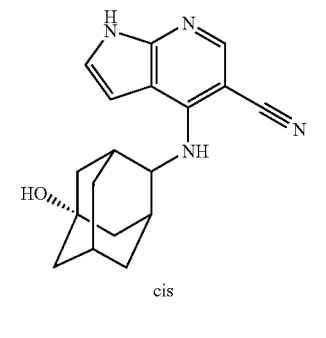cis |
| 82 | 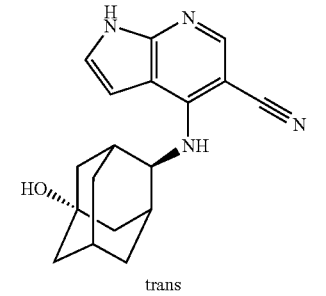trans |

TABLE 71-continued
| Ex | Structure |
|---|---|
| 83 | 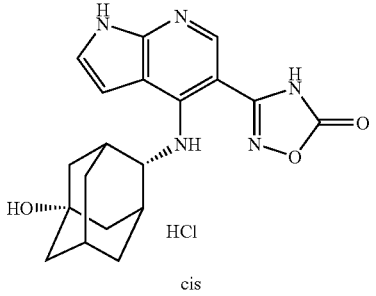  HCl  cis |
| 84 | 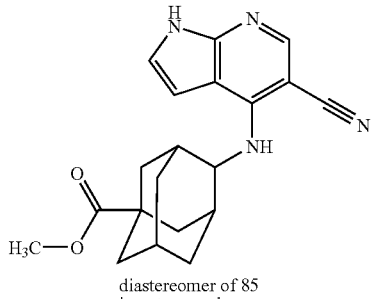  diastereomer of 85  cis or trans unknown |
| 85 | 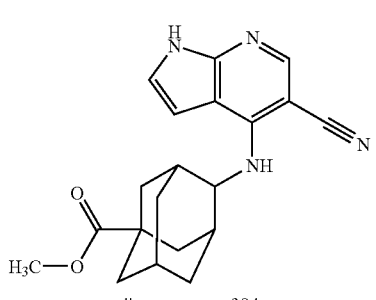  diastereomer of 84  cis or trans unknown |
| 86 | 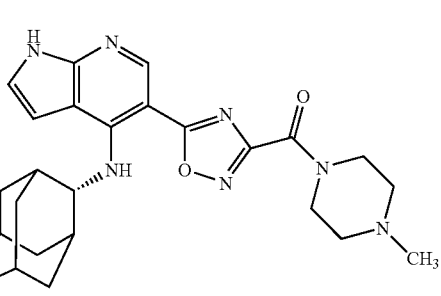  cis |
| 87 | 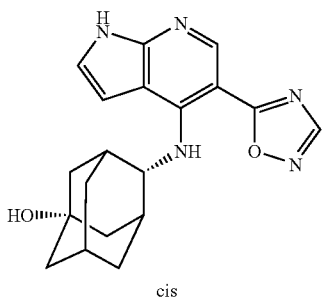  cis |

TABLE 71-continued
| Ex | Structure |
|---|---|
| 88 | 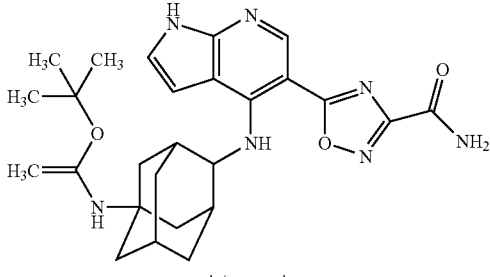 cis/trans mix |
| 89 | 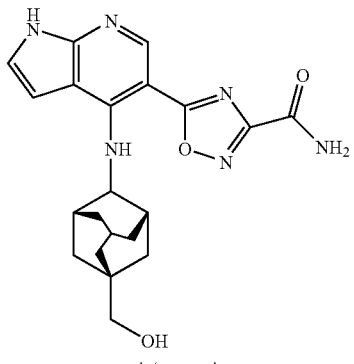 cis/trans mix |
| 90 | 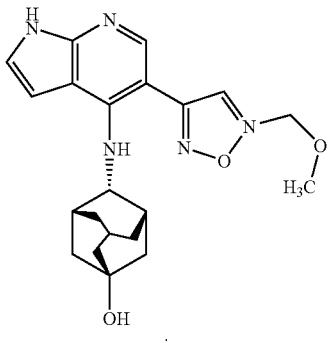 cis |
| 91 | 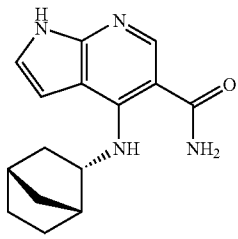 |
| 92 | 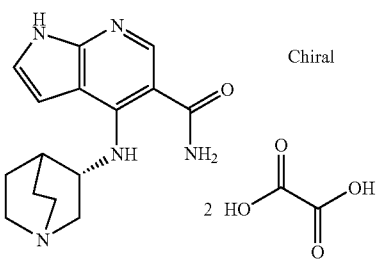 Chiral |

TABLE 71-continued
| Ex | Structure |
|---|---|
| 93 | 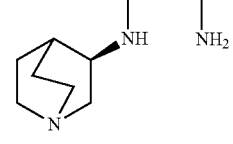 Chiral |
| 94 | 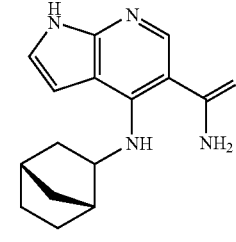 |
| 95 | 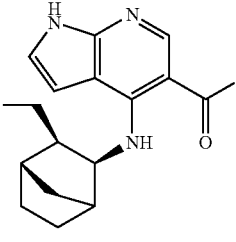 |
| 96 | 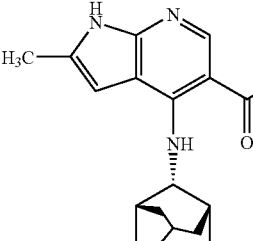 cis |
| 97 | 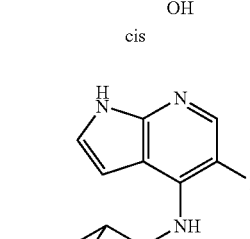 cis/trans mix |

TABLE 71-continued
| Ex | Structure |
|---|---|
| 98 | 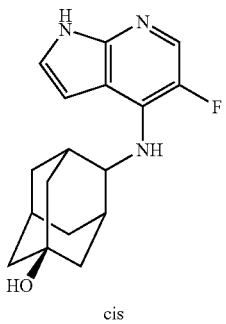 cis |
| 99 | 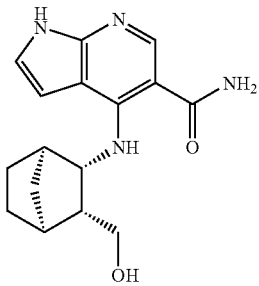 |
| 100 | 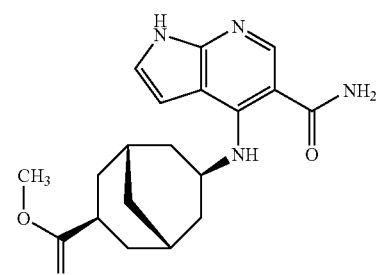 |
| 101 | 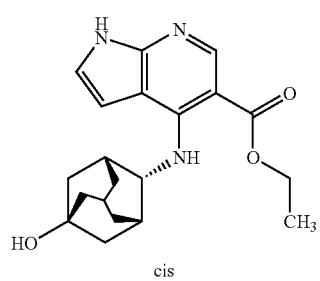 cis |
| 102 | 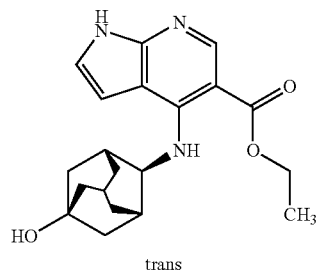 trans |

TABLE 71-continued
| Ex | Structure |
|---|---|
| 103 | 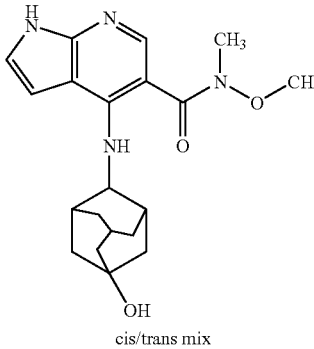<br>cis/trans mix |
| 104 | 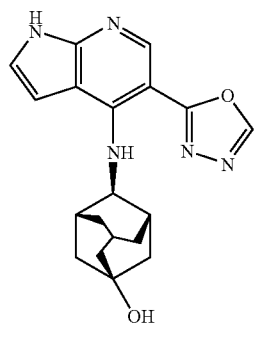<br>trans |
| 105 | 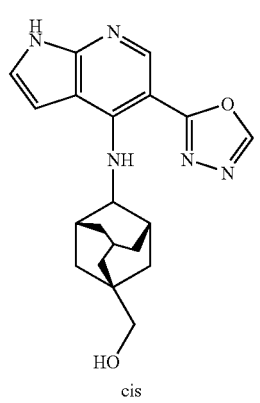<br>cis |
| 106 | 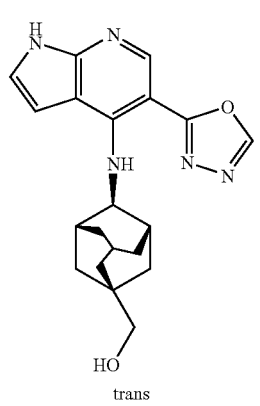<br>trans |

TABLE 71-continued
| Ex | Structure |
|---|---|
| 107 | 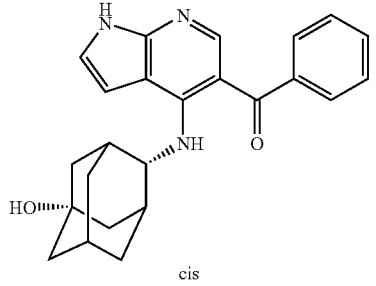 cis |
| 108 | 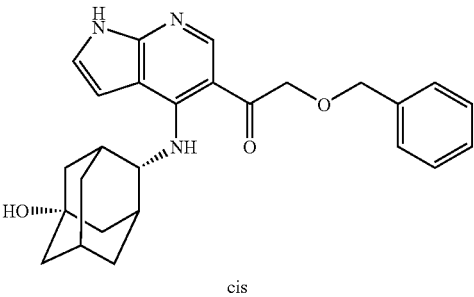 cis |
| 109 | 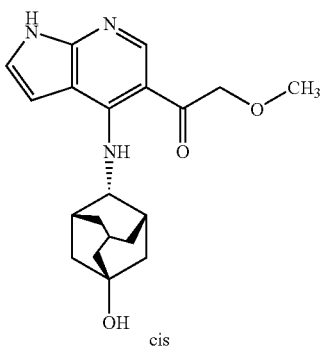 cis |
| 110 | 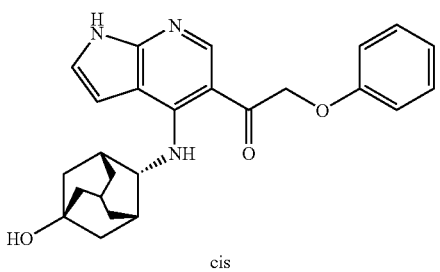 cis |
| 111 | 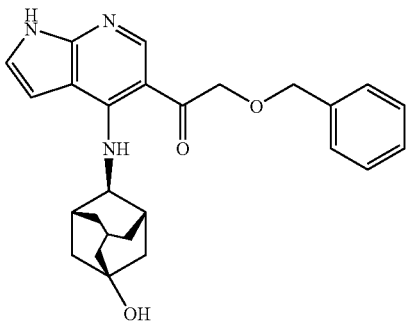 trans |

TABLE 71-continued

| Ex | Structure |
|---|---|
| 112 | [structure: 7-azaindole with NH-adamantyl(CH2OH) substituent and C(=O)CH2-O-CH2-phenyl group; cis/trans mix] |
| 113 | [structure: 7-azaindole with NH-(hydroxyadamantyl) and 1,3,4-thiadiazole-CH2OH substituent] |
| 114 | [structure: 7-azaindole with NH-(hydroxyadamantyl) and 1,3,4-thiadiazole-C(CH3)2OH substituent] |
| 115 | [structure: 7-azaindole with NH-(hydroxyadamantyl) and 1,3,4-thiadiazole-C(=O)NHCH3; cis] |
| 116 | [structure: 7-azaindole with NH-(hydroxyadamantyl) and 1,3,4-thiadiazole-C(=O)NH-(1-methylpiperidin-4-yl); cis] |

TABLE 71-continued

| Ex | Structure |
|---|---|
| 117 | 1H-pyrrolo[2,3-b]pyridine-5-carboxamide, 4-(2-adamantylamino)- |
| 118 | 1H-pyrrolo[2,3-b]pyridine-5-carboxamide, 4-(1-adamantylamino)- |
| 119 | 1H-pyrrolo[2,3-b]pyridine-5-carboxamide, 4-[(5-hydroxy-2-adamantyl)amino]-, cis |
| 120 | 1H-pyrrolo[2,3-b]pyridine-5-carboxamide, 4-[(3-hydroxy-1-adamantyl)amino]- |
| 121 | 1H-pyrrolo[2,3-b]pyridine-5-carboxamide, 4-[(5-hydroxy-2-adamantyl)amino]-, trans |

TABLE 71-continued
| Ex | Structure |
|---|---|
| 122 | 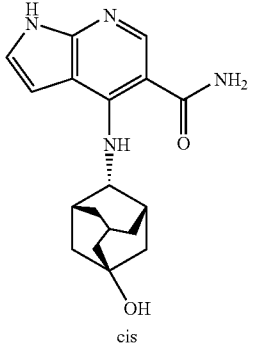<br>cis |
| 123 | 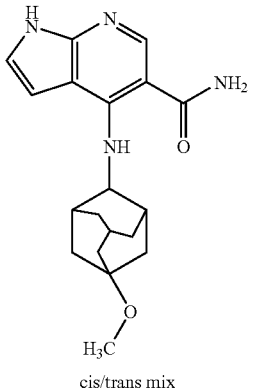<br>cis/trans mix |
| 124 | 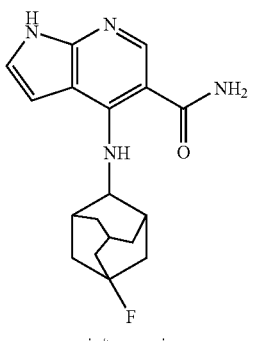<br>cis/trans mix |
| 125 | 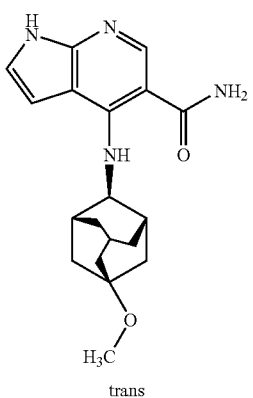<br>trans |

TABLE 71-continued
| Ex | Structure |
|---|---|
| 126 | 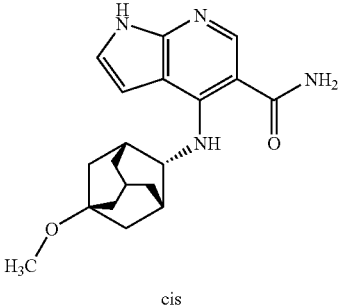<br>cis |
| 127 | 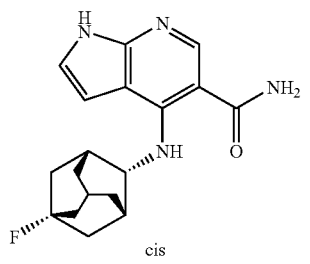<br>cis |
| 128 | 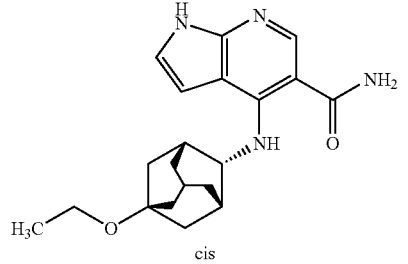<br>cis |
| 129 | 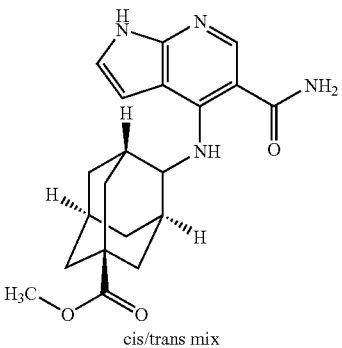<br>cis/trans mix |
| 130 | 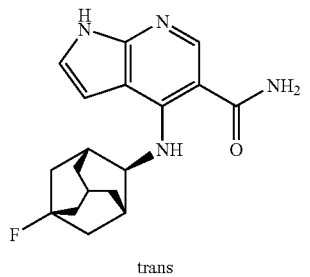<br>trans |

TABLE 71-continued
| Ex | Structure |
|---|---|
| 131 | 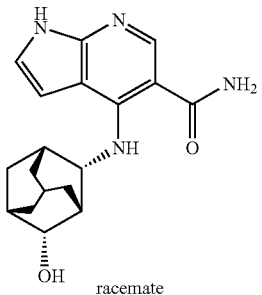 racemate |
| 132 | 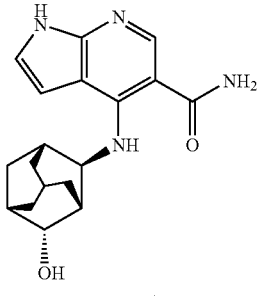 racemate |
| 133 | 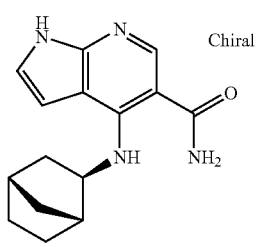 Chiral |
| 134 | 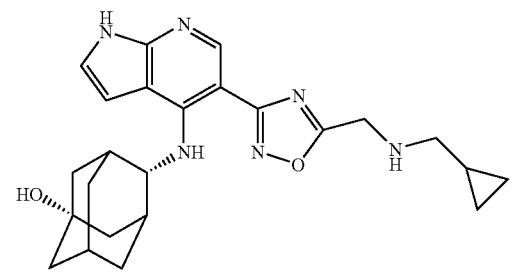 cis |
| 135 | 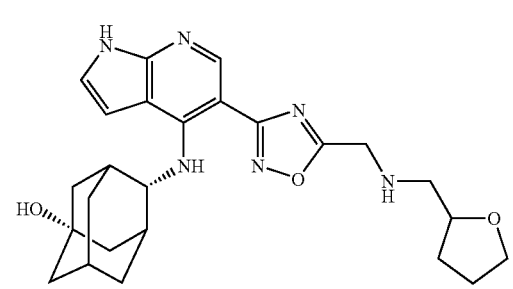 cis |

TABLE 71-continued
| Ex | Structure |
|---|---|
| 136 | 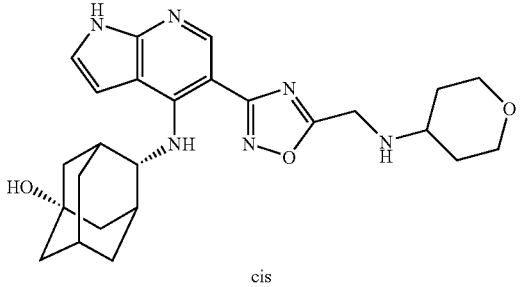 cis |
| 137 | 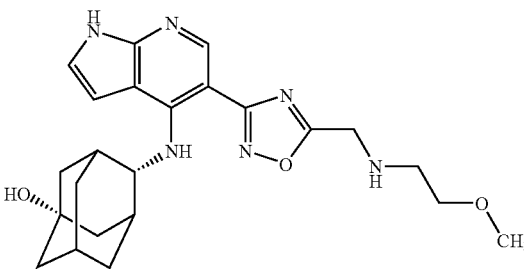 cis |
| 138 | 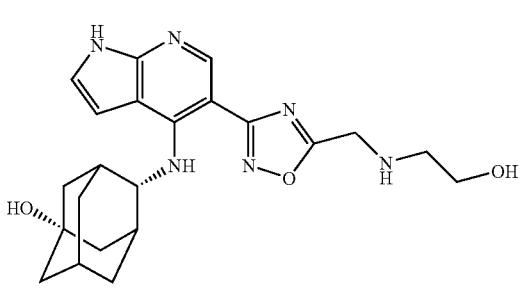 cis |
| 139 | 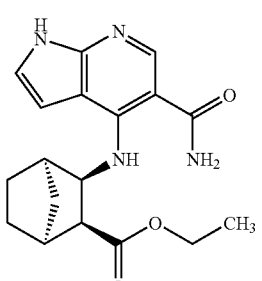 |
| 140 | 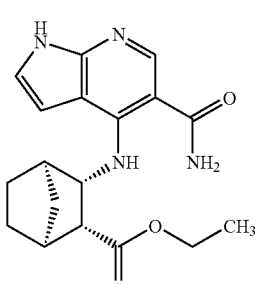 |

TABLE 71-continued

| Ex | Structure |
|---|---|
| 141 | 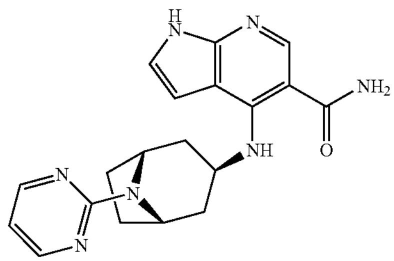 |
| 142 | Chiral |
| 143 | 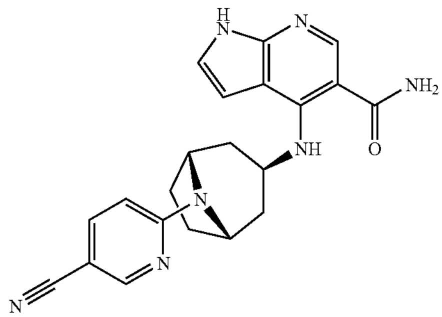 |
| 144 | cis/trans mix |
| 145 | cis |

TABLE 71-continued
| Ex | Structure |
|---|---|
| 146 | 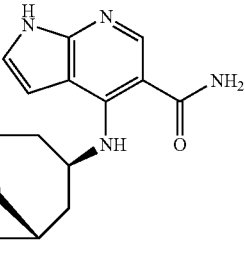 |
| 147 | 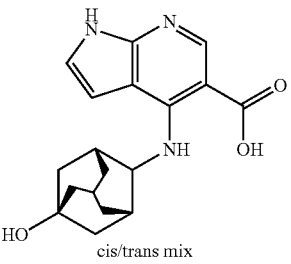
cis/trans mix |
| 148 | 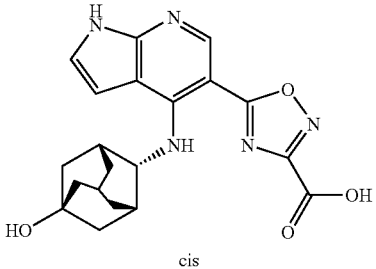
cis |
| 149 | 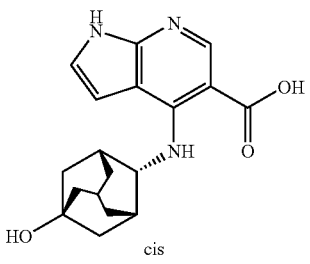
cis |
| 150 | 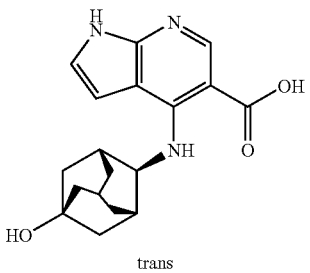
trans |

TABLE 71-continued
| Ex | Structure |
|---|---|
| 151 | 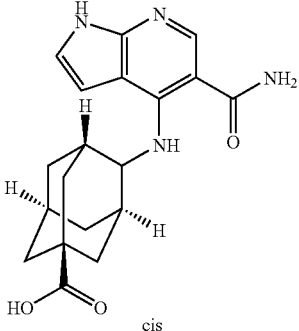
cis |
| 152 | 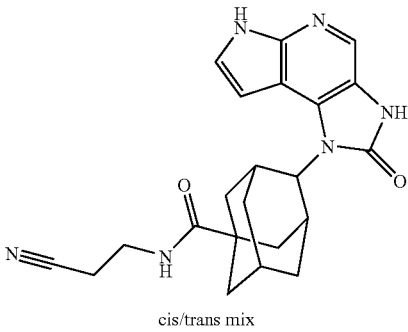
cis/trans mix |
| 153 | 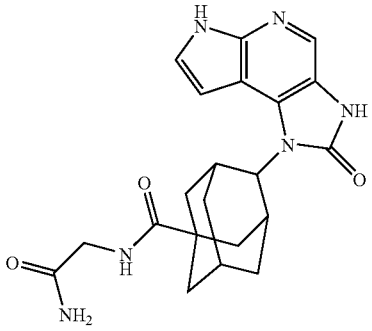
diastereomer of 154
cis or trans unknown |
| 154 | 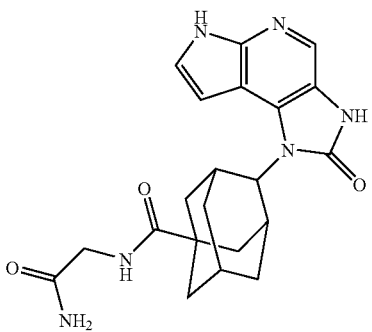
diastereomer of 153
cis or trans unknown |

TABLE 71-continued
| Ex | Structure |
|---|---|
| 155 | 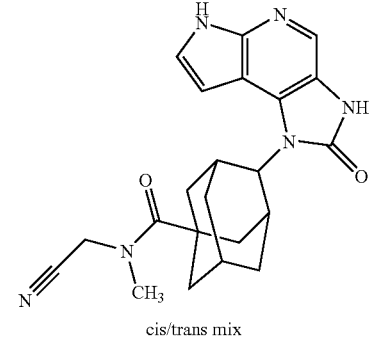<br>cis/trans mix |
| 156 | 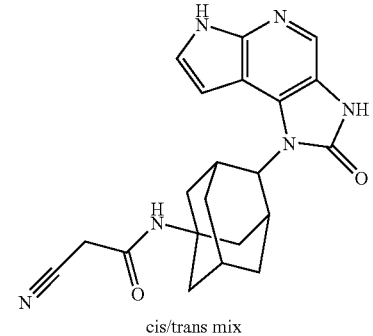<br>cis/trans mix |
| 157 | 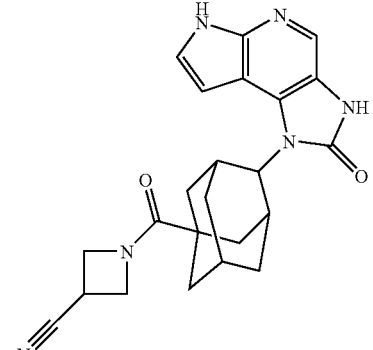<br>cis/trans mix |
| 158 | 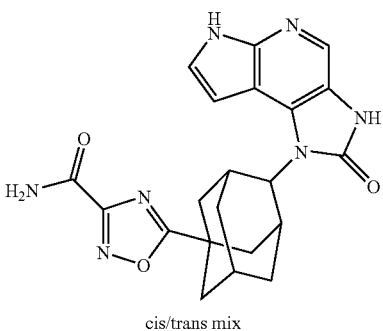<br>cis/trans mix |

TABLE 71-continued
| Ex | Structure |
|---|---|
| 159 | 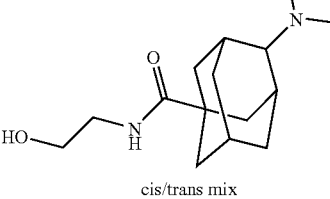<br>cis/trans mix |
| 160 | 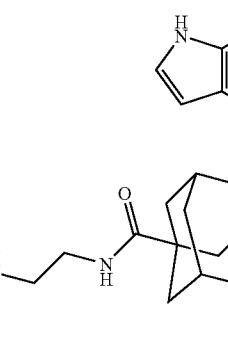<br>cis/trans mix |
| 161 | 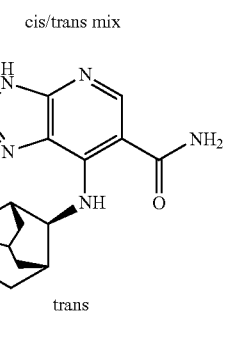<br>trans |
| 162 | 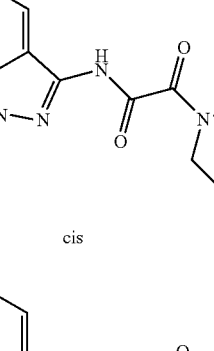<br>cis |
| 163 | 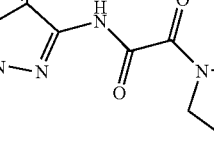<br>cis |

TABLE 71-continued
| Ex | Structure |
|---|---|
| 164 | 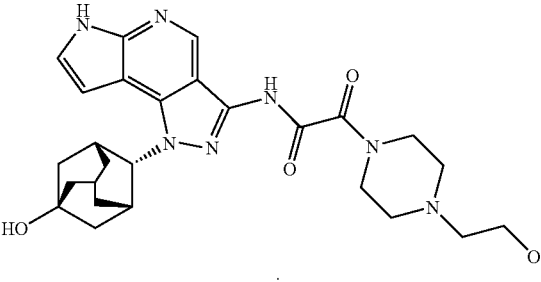<br>cis |
| 165 | 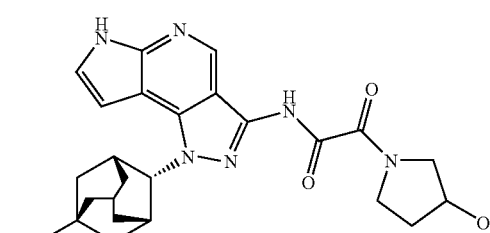<br>cis |
| 166 | 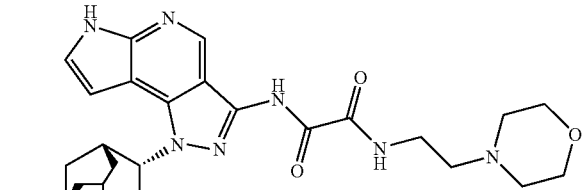<br>cis |
| 167 | 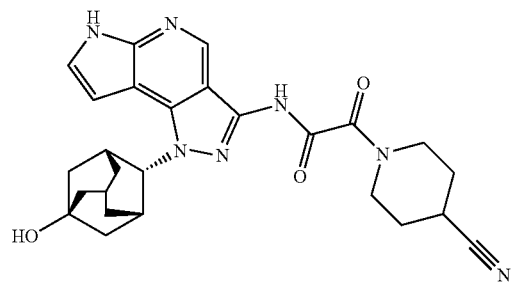<br>cis |
| 168 | 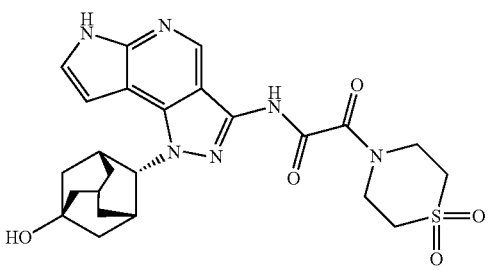<br>cis |

TABLE 71-continued
| Ex | Structure |
|---|---|
| 169 | 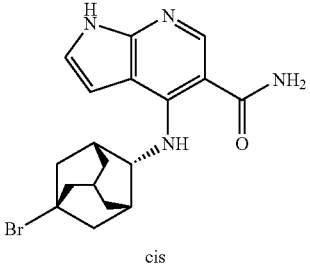 cis |
| 170 | 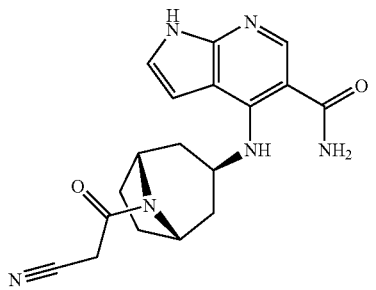 |
| 171 | 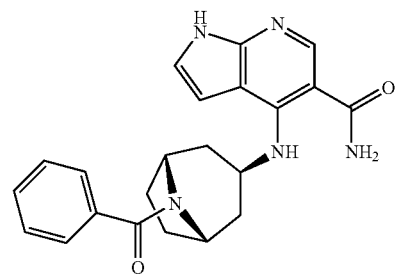 |
| 172 | 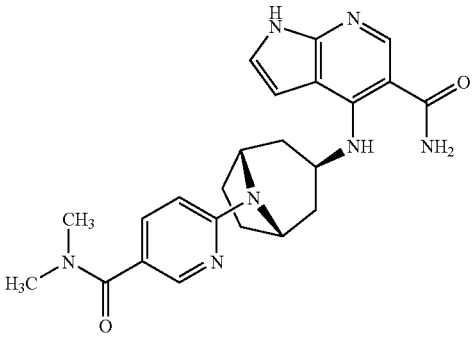 |
| 173 | 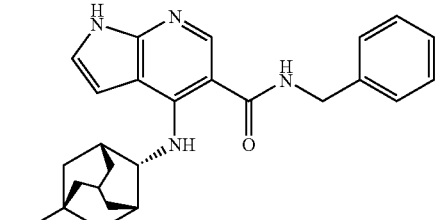 cis |

TABLE 71-continued
| Ex | Structure |
|---|---|
| 174 | 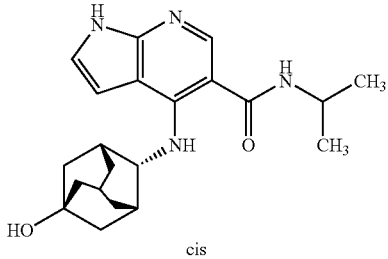 cis |
| 175 | 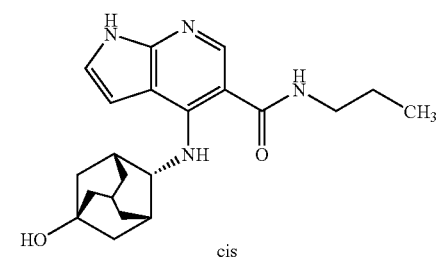 cis |
| 176 | 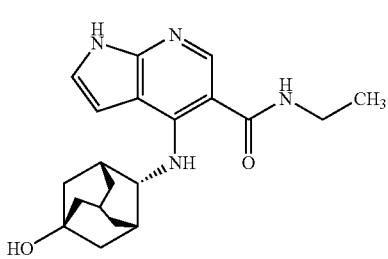 cis |
| 177 | 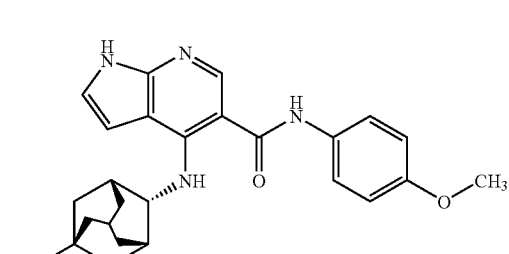 cis |
| 178 | 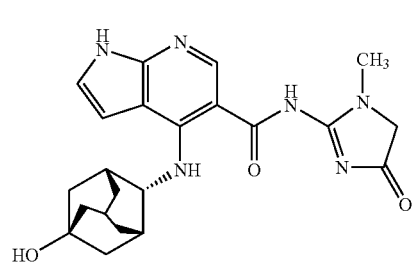 cis |

TABLE 71-continued
| Ex | Structure |
|---|---|
| 179 | 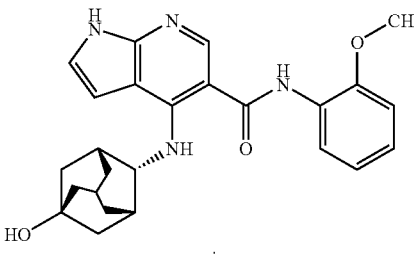 cis |
| 180 | 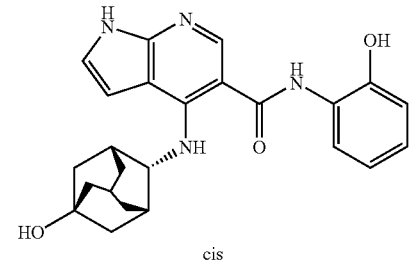 cis |
| 181 | 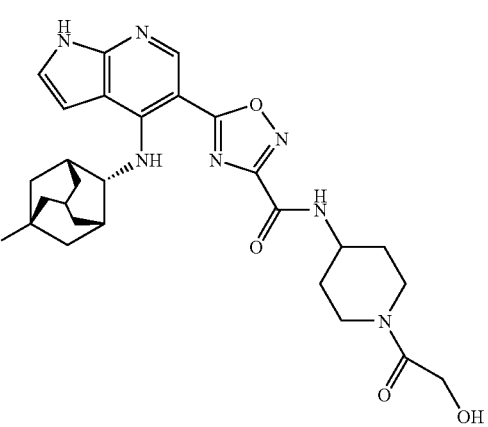 cis |
| 182 | 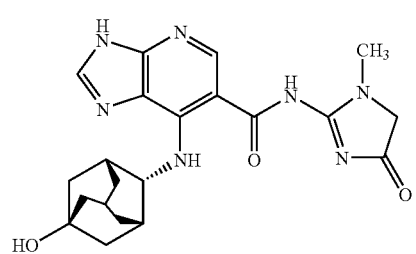 cis |
| 183 | 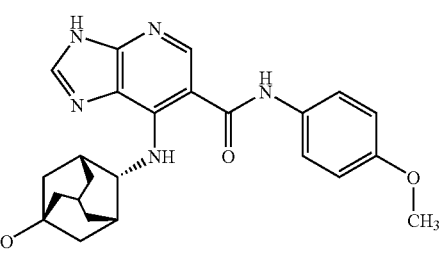 cis |

TABLE 71-continued

| Ex | Structure |
|---|---|
| 184 | 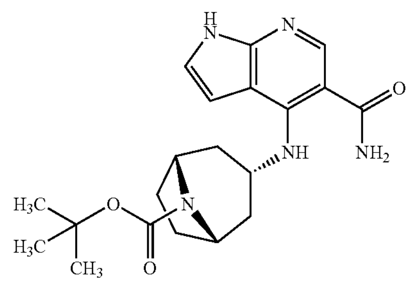 |
| 185 | 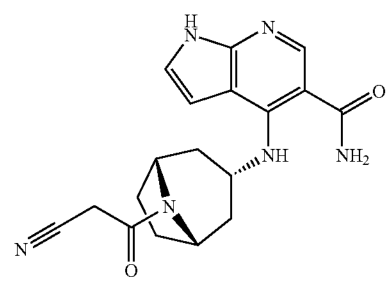 |
| 186 | 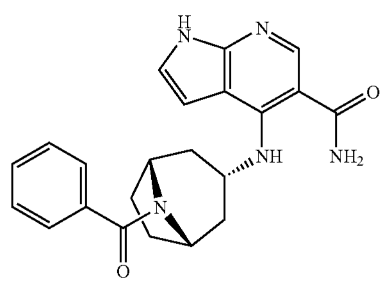 |
| 187 | 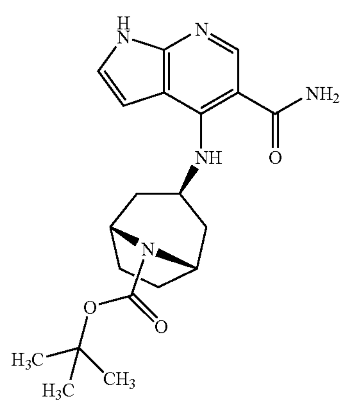 |
| 188 | 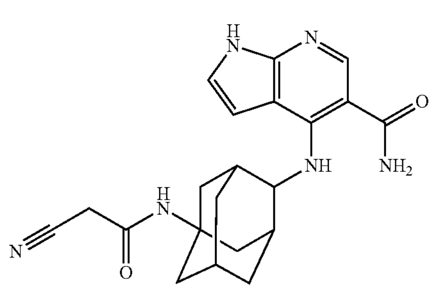 |

TABLE 71-continued
| Ex | Structure |
|---|---|
| 189 | 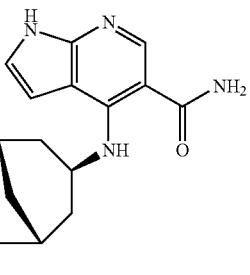 |
| 190 | 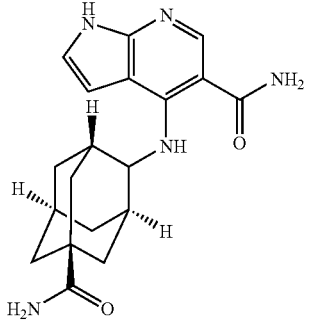
cis/trans mix |
| 191 | 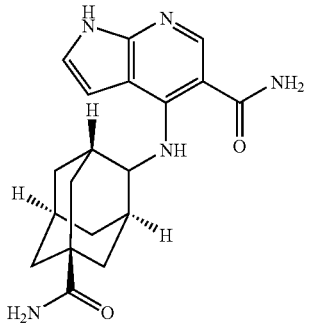
diastereomer of 192
cis or trans unknown |
| 192 | 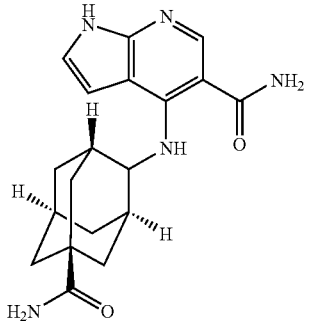
diastereomer of 191
cis or trans unknown |

TABLE 71-continued
| Ex | Structure |
|----|-----------|
| 193 | 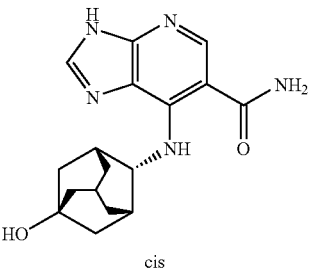 cis |
| 194 | 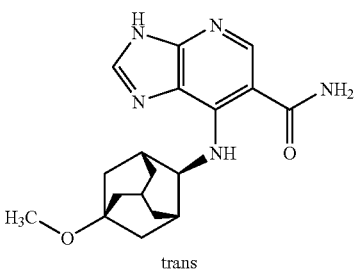 trans |
| 195 | 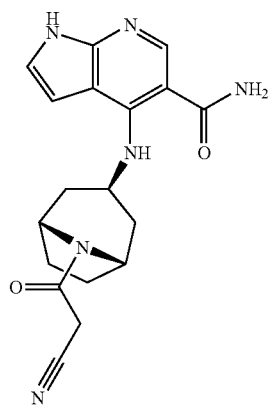 |
| 196 | 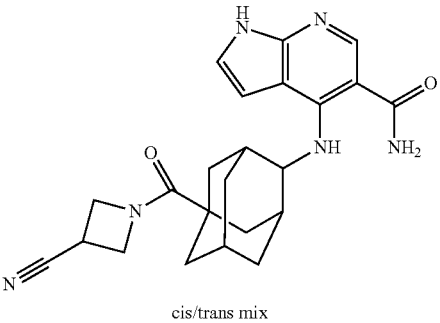 cis/trans mix |

TABLE 71-continued
| Ex | Structure |
|---|---|
| 197 | 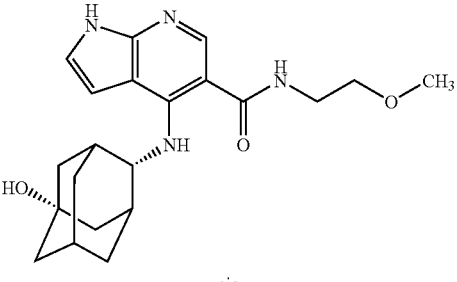<br>cis |
| 198 | 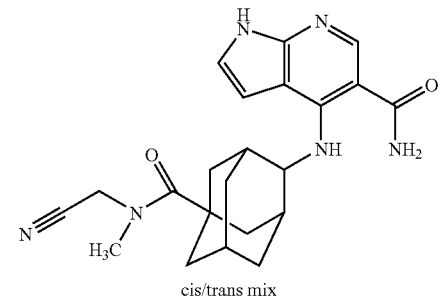<br>cis/trans mix |
| 199 | 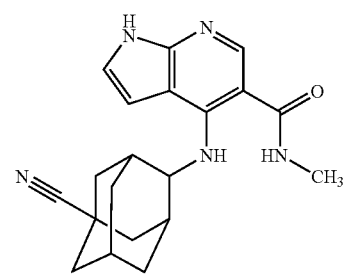<br>diastereomer of 200<br>cis or trans unknown |
| 200 | 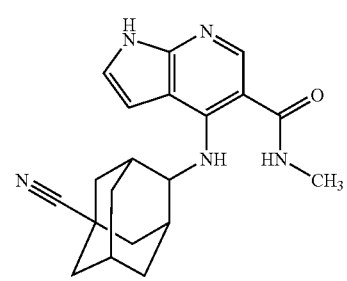<br>diastereomer of 199<br>cis or trans unknown |
| 201 | 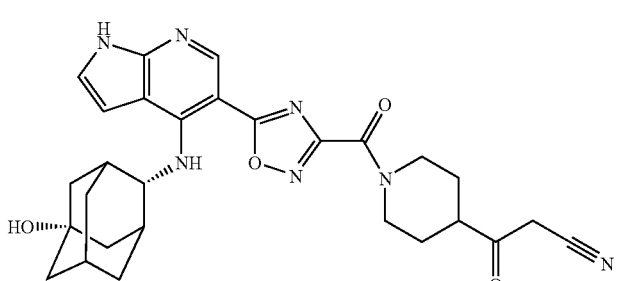<br>cis |

TABLE 71-continued

| Ex | Structure |
|---|---|
| 202 | 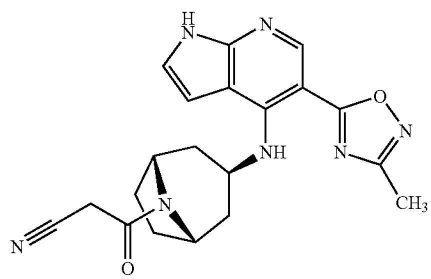 |
| 203 | cis |
| 204 | cis |
| 205 | cis |
| 206 | cis |

TABLE 71-continued
| Ex | Structure |
|---|---|
| 207 | 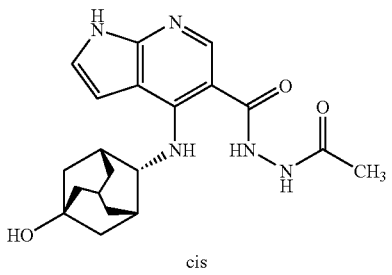 cis |
| 208 | 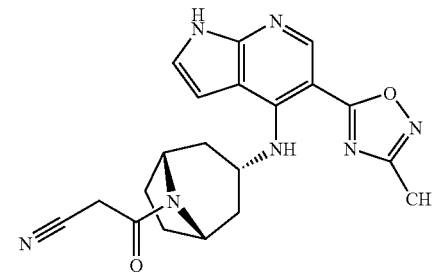 |
| 209 | 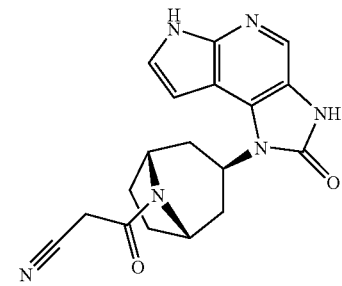 |
| 210 | 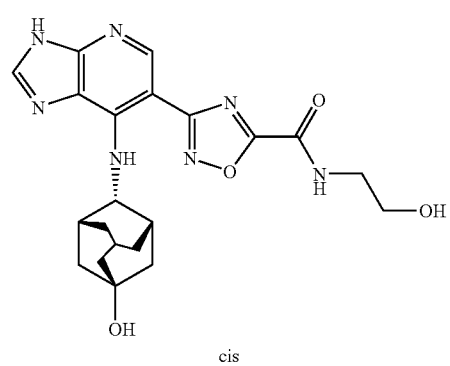 cis |
| 211 | 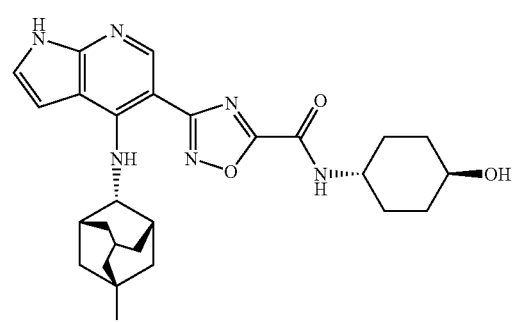 cis |

TABLE 71-continued

| Ex | Structure |
|---|---|
| 212 | 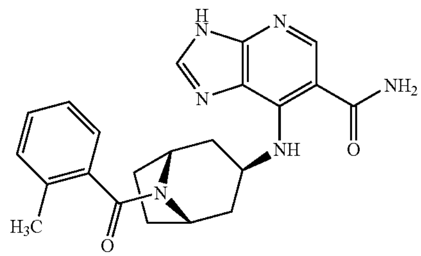 |
| 213 | 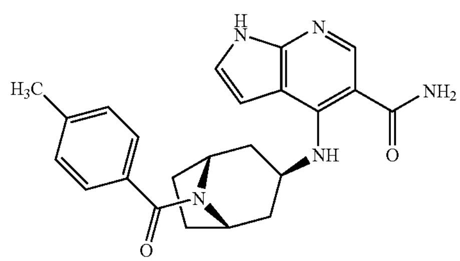 |
| 214 | 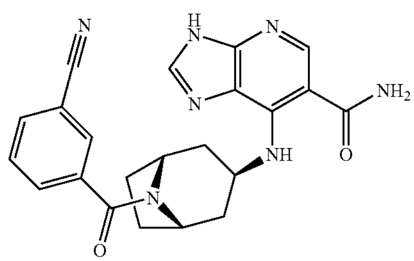 |
| 215 | 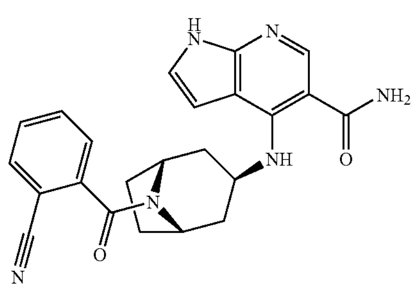 |
| 216 | 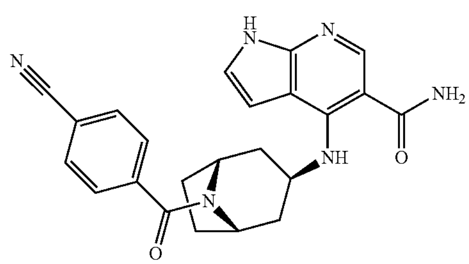 |

TABLE 71-continued

| Ex | Structure |
|---|---|
| 217 | 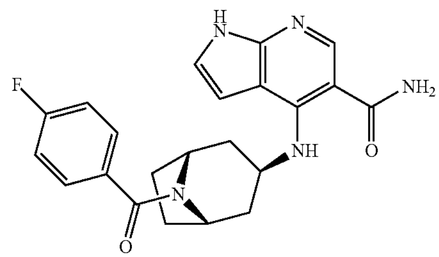 |
| 218 | 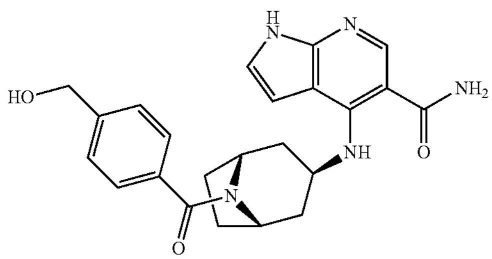 |
| 219 | 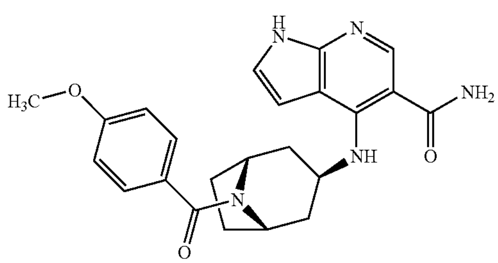 |
| 220 | 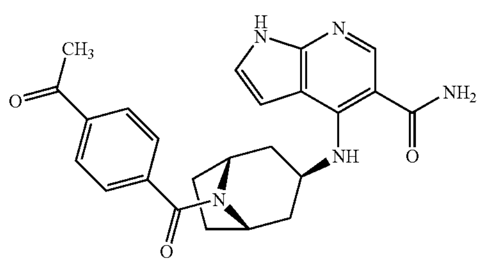 |
| 221 | 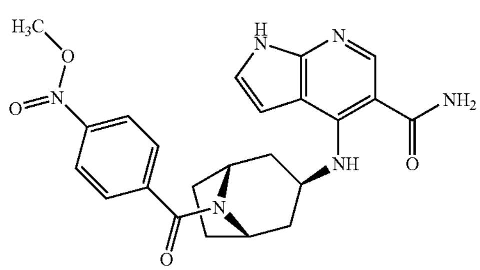 |
| 222 | 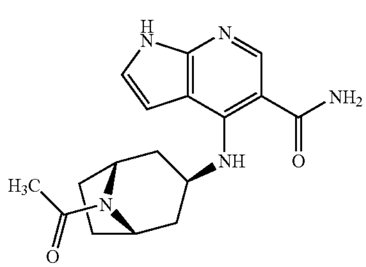 |

TABLE 71-continued
| Ex | Structure |
|---|---|
| 223 | 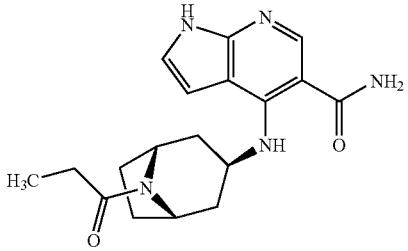 |
| 224 | 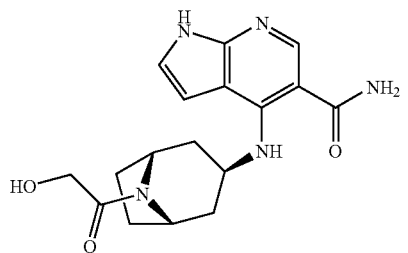 |
| 225 | 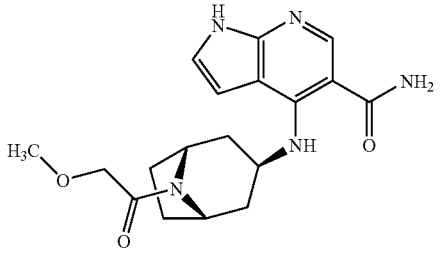 |
| 226 | 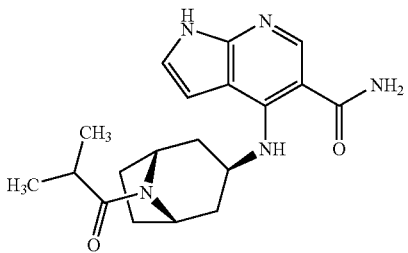 |
| 227 | 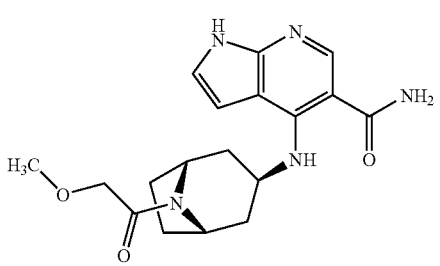 |

TABLE 71-continued

| Ex | Structure |
|---|---|
| 228 | 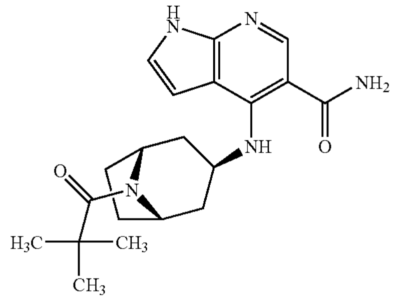 |
| 229 | 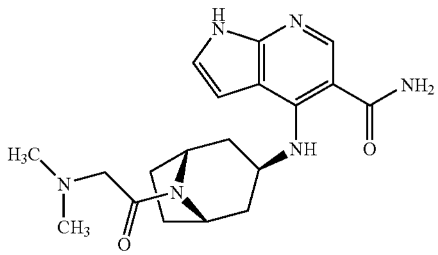 |
| 230 | 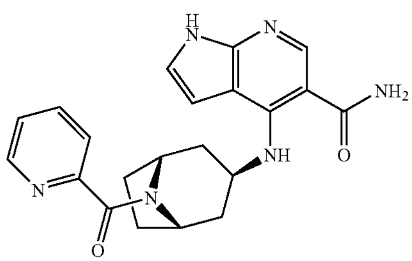 |
| 231 | 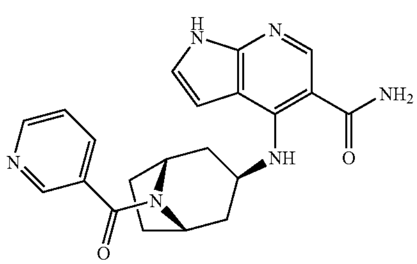 |
| 232 | 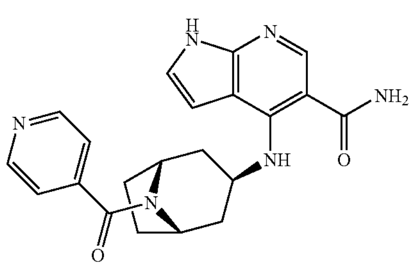 |

TABLE 71-continued

| Ex | Structure |
|---|---|
| 233 | 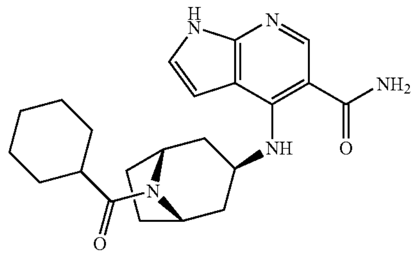 |
| 234 | 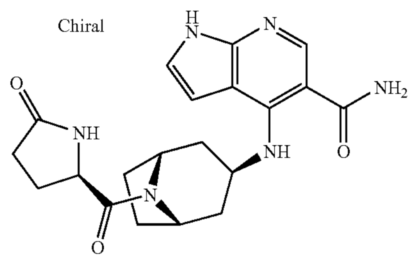 |
| 235 | 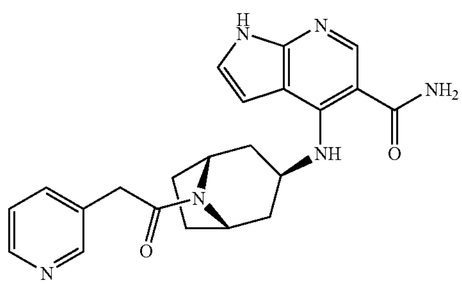 |
| 236 | 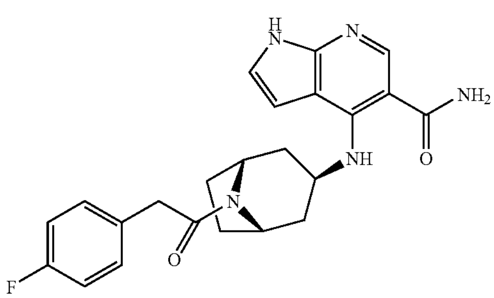 |
| 237 | 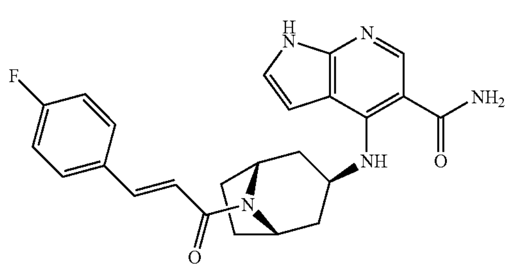 |

TABLE 71-continued

| Ex | Structure |
|---|---|
| 238 | 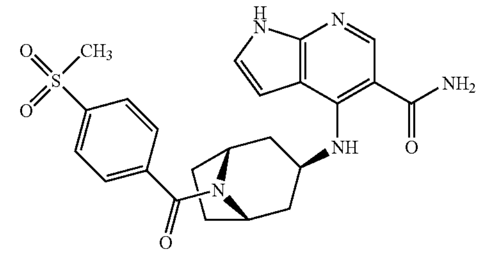 |
| 239 | 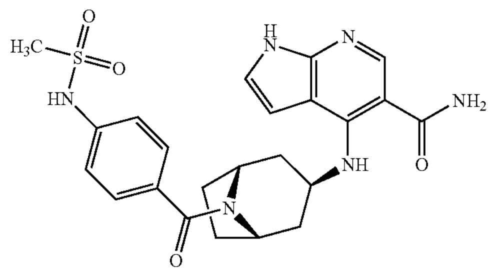 |
| 240 | cis |
| 241 | cis |
| 242 | Chiral / cis |

TABLE 71-continued
| Ex | Structure |
|---|---|
| 243 | 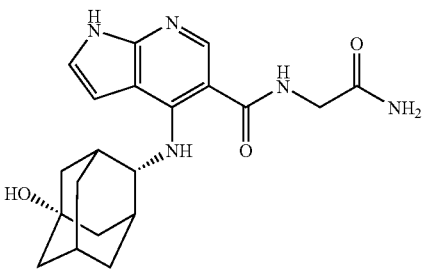 cis |
| 244 | 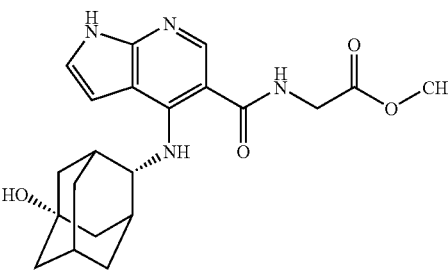 cis |
| 245 | 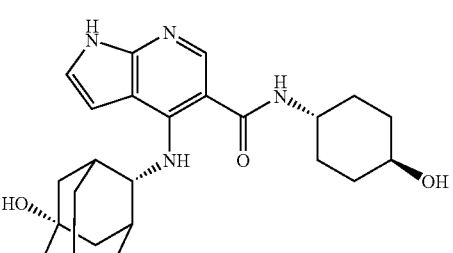 cis |
| 246 | 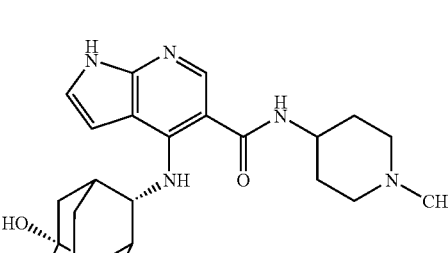 cis |
| 247 | 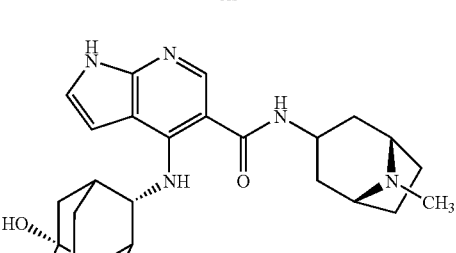 cis |

TABLE 71-continued

| Ex | Structure |
|---|---|
| 248 | (structure with 7-azaindole-4-amino(hydroxyadamantyl)-5-carboxamide-N-(tetrahydropyran-4-yl)) cis |
| 249 | (structure with 7-azaindole-4-amino(hydroxyadamantyl)-5-carboxamide-N-CH₂CH(OCH₃)₂) cis |
| 250 | (structure with 7-azaindole-4-amino(hydroxyadamantyl)-5-carboxamide-N-CH₂-(tetrahydropyran-4-yl)) cis |
| 251 | (structure with 7-azaindole-4-amino(hydroxyadamantyl)-5-carboxamide-N-CH₂-(tetrahydrofuran-2-yl)) cis |
| 252 | (structure with 7-azaindole-4-amino(hydroxyadamantyl)-5-carboxamide-N-CH₂CH₂-piperidinyl) cis |

TABLE 71-continued
| Ex | Structure |
|---|---|
| 253 | 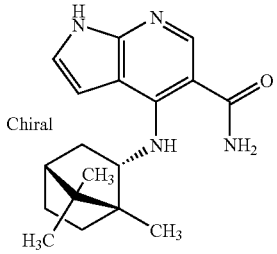 |
| 254 | 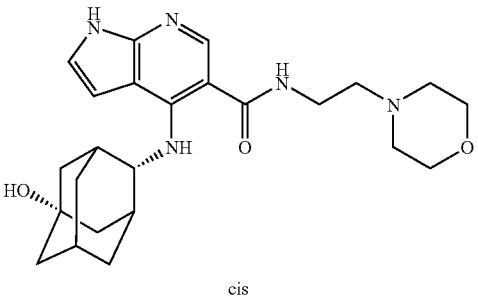
cis |
| 255 | 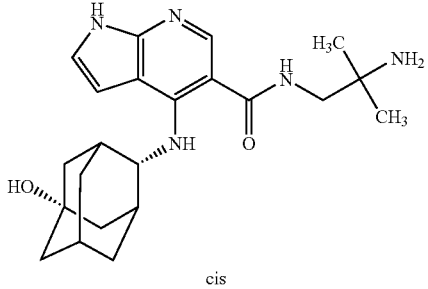
cis |
| 256 | 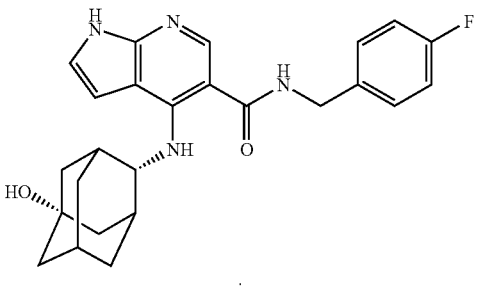
cis |
| 257 | 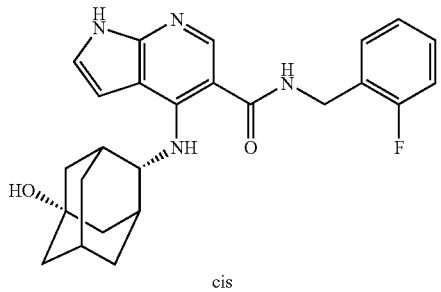
cis |

TABLE 71-continued
| Ex | Structure |
|---|---|
| 258 | 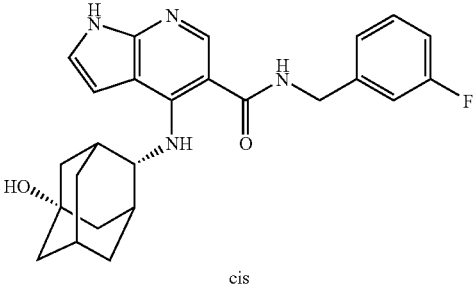 cis |
| 259 | 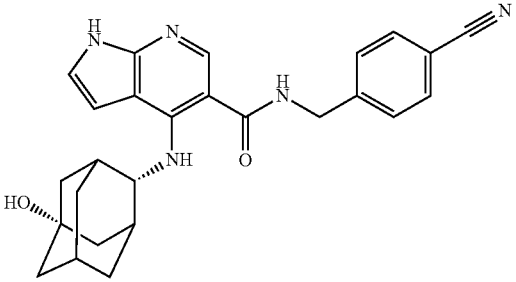 cis |
| 260 | 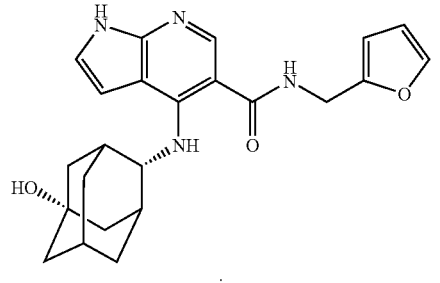 cis |
| 261 | 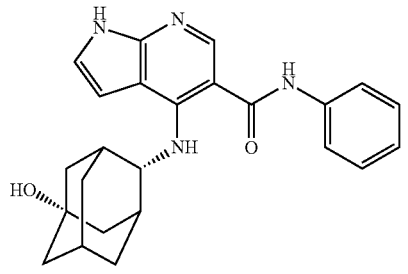 cis |
| 262 | 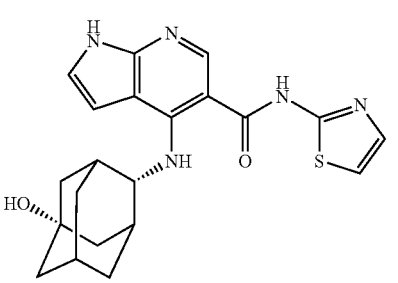 cis |

TABLE 71-continued
| Ex | Structure |
|---|---|
| 263 | 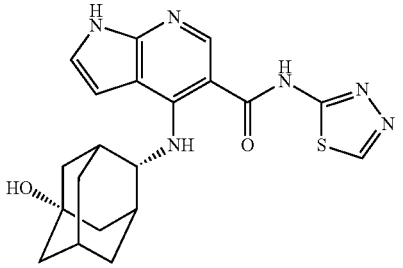 cis |
| 264 | 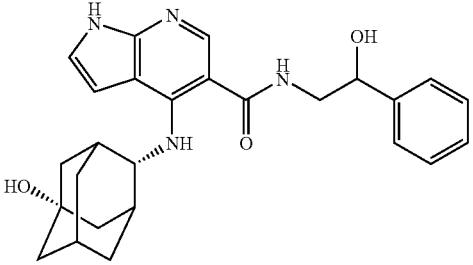 cis |
| 265 | 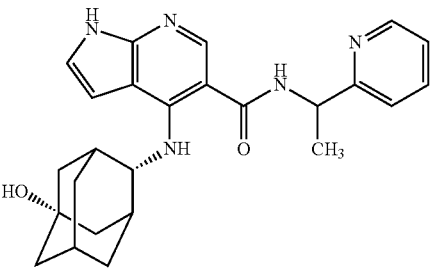 cis |
| 266 | 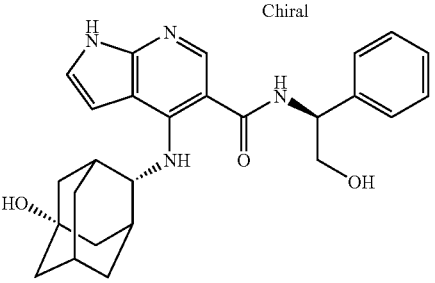 Chiral<br>cis |
| 267 | 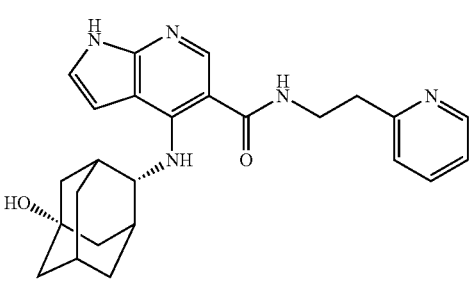 cis |

TABLE 71-continued
| Ex | Structure |
|---|---|
| 268 | 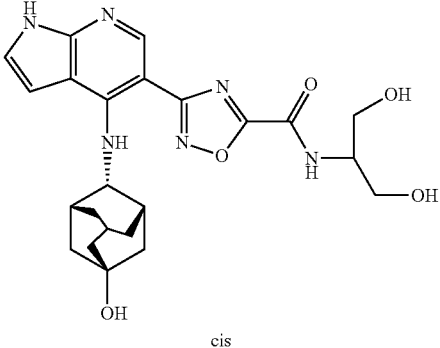 cis |
| 269 | 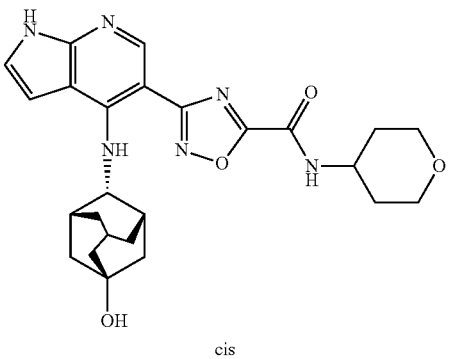 cis |
| 270 | 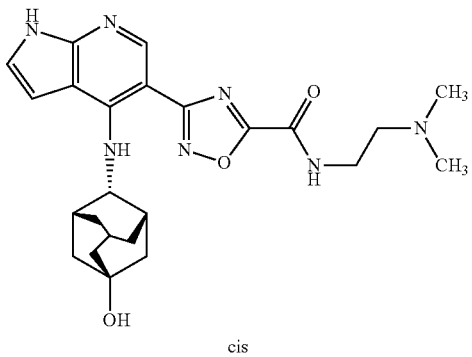 cis |
| 271 | 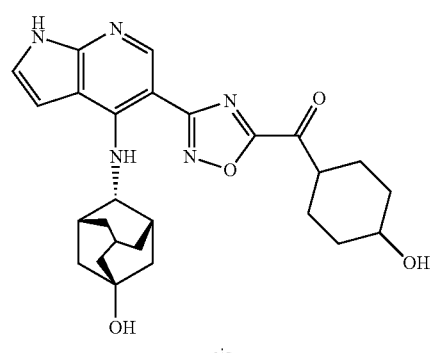 cis |

TABLE 71-continued
| Ex | Structure |
|---|---|
| 272 | 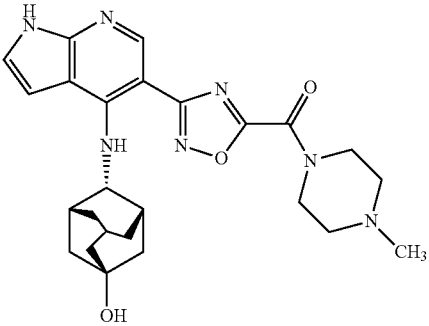<br>cis |
| 273 | 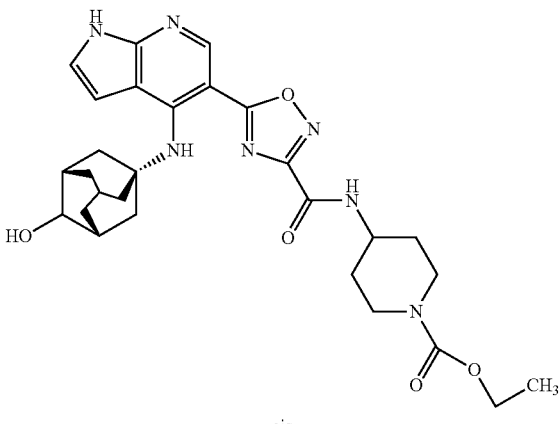<br>cis |
| 274 | 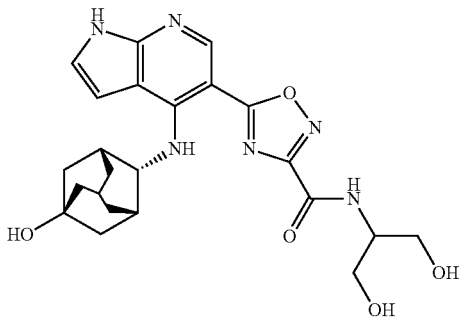<br>cis |
| 275 | 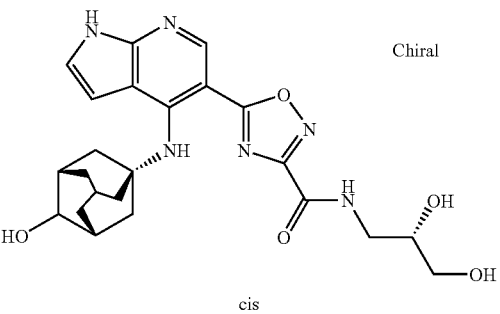<br>cis |

TABLE 71-continued
| Ex | Structure |
|---|---|
| 276 | 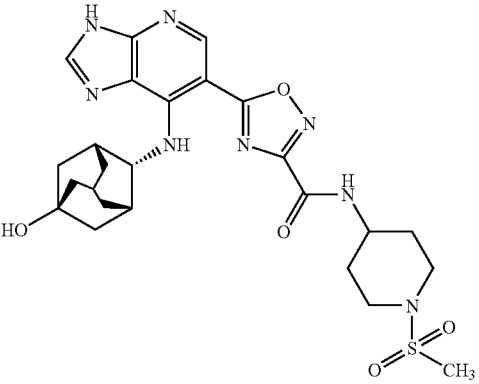<br>cis |
| 277 | 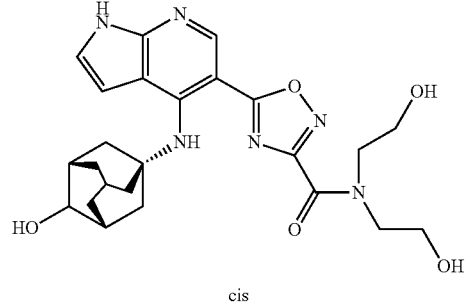<br>cis |
| 278 | 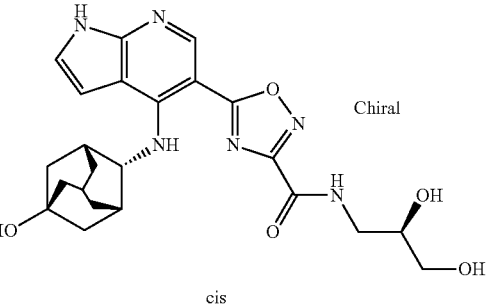<br>cis |
| 279 | 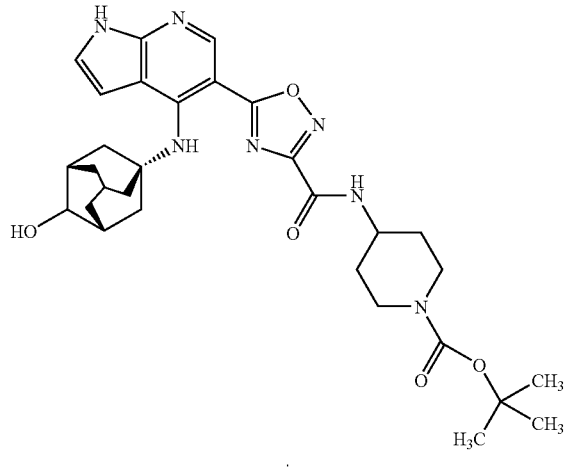<br>cis |

TABLE 71-continued
| Ex | Structure |
|---|---|
| 280 | 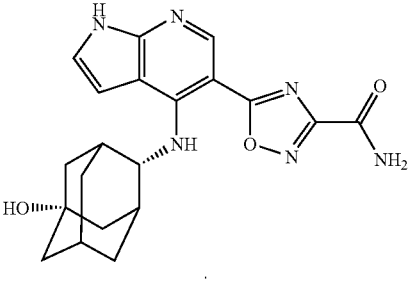<br>cis |
| 281 | 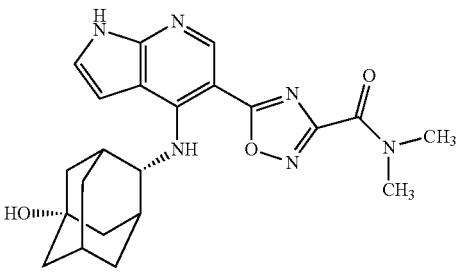<br>cis |
| 282 | 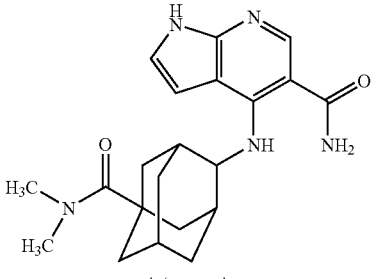<br>cis/trans mix |
| 283 | 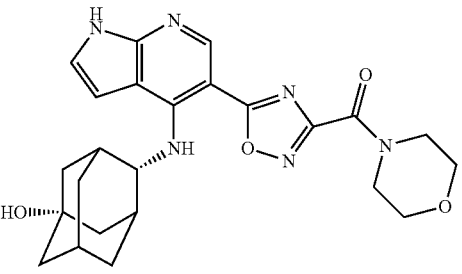<br>cis |
| 284 | 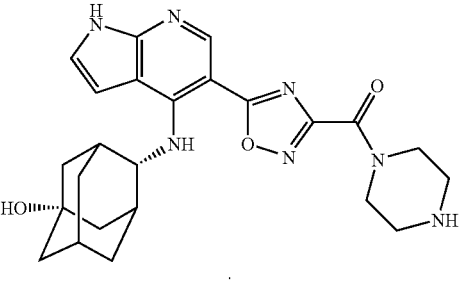<br>cis |

TABLE 71-continued
| Ex | Structure |
|---|---|
| 285 | 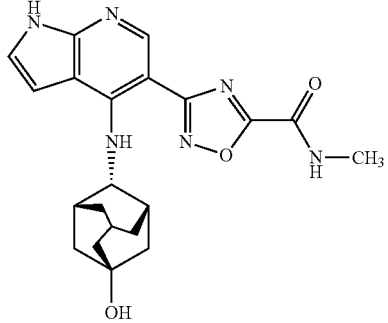 cis |
| 286 | 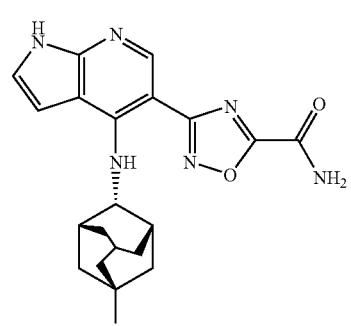 cis |
| 287 | 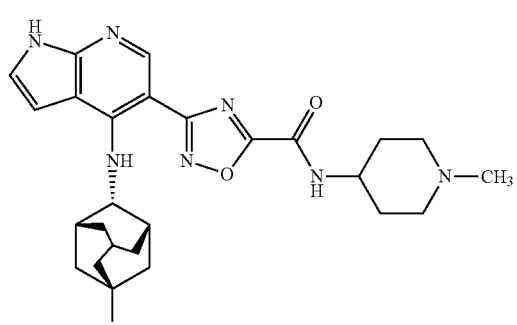 cis |
| 288 | 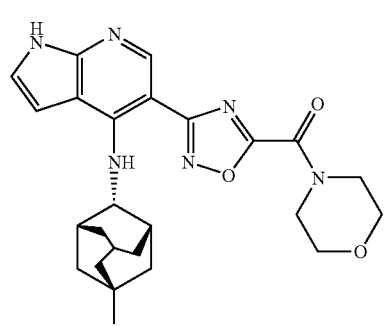 cis |

TABLE 71-continued
| Ex | Structure |
|---|---|
| 289 | 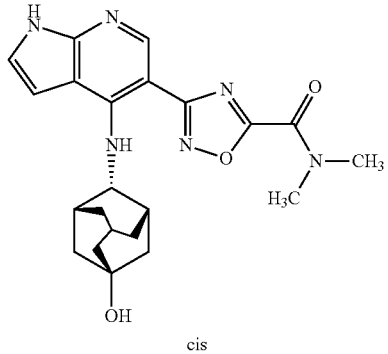 cis |
| 290 | 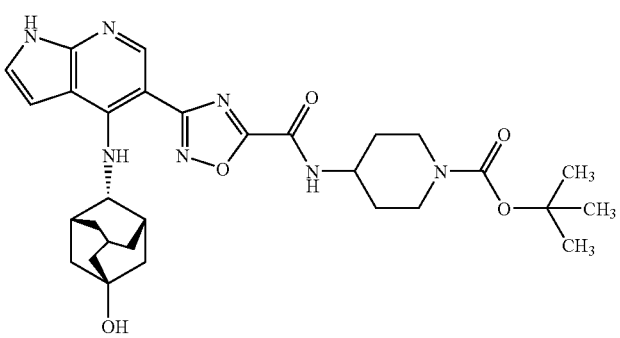 cis |
| 291 | Chiral 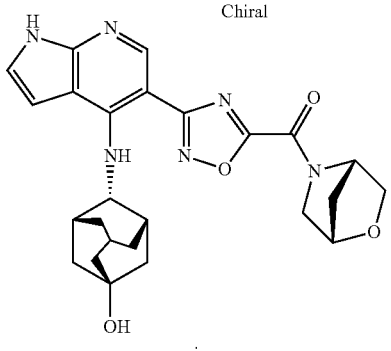 cis |
| 292 | 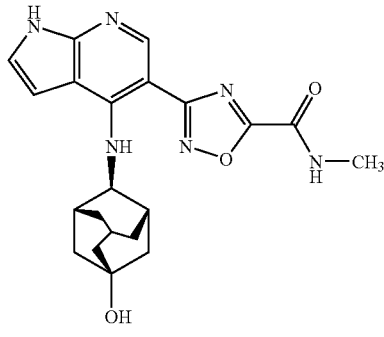 trans |

TABLE 71-continued
| Ex | Structure |
|---|---|
| 293 | 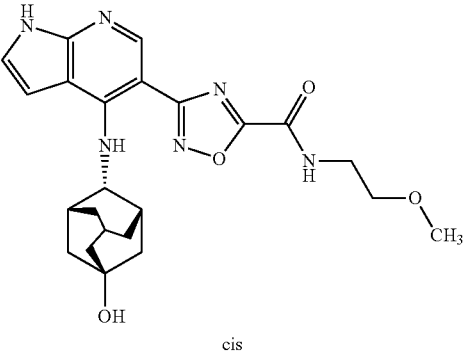 cis |
| 294 | 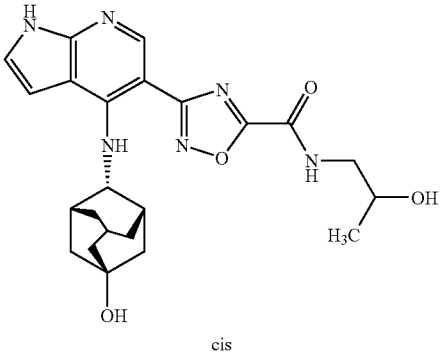 cis |
| 295 | 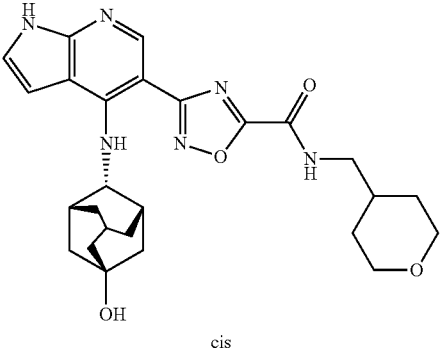 cis |
| 296 | 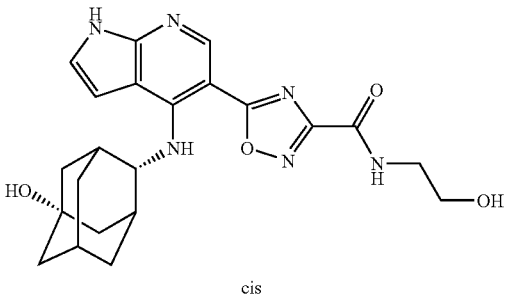 cis |

TABLE 71-continued
| Ex | Structure |
|---|---|
| 297 | 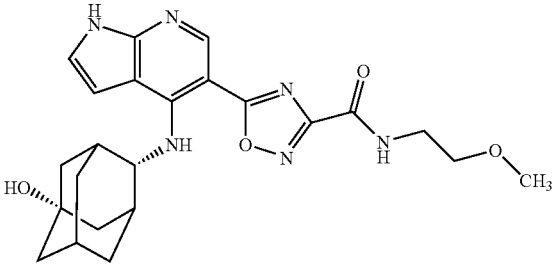 cis |
| 298 | 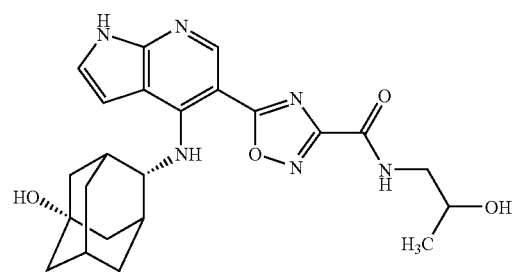 cis |
| 299 | 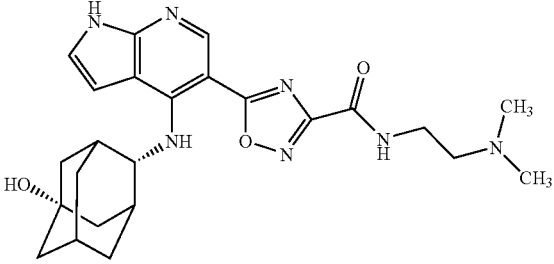 cis |
| 300 | 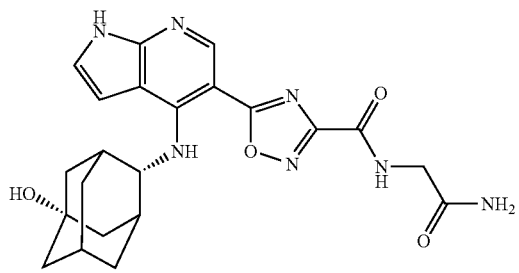 cis |
| 301 | 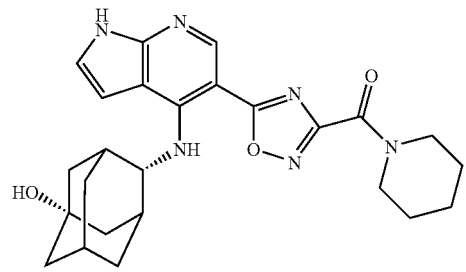 cis |

TABLE 71-continued
| Ex | Structure |
|----|-----------|
| 302 | 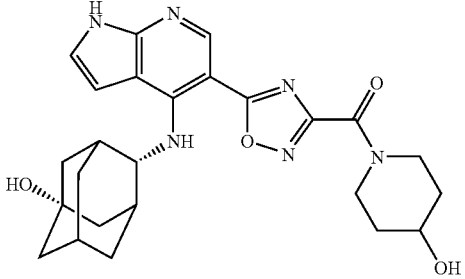 cis |
| 303 | 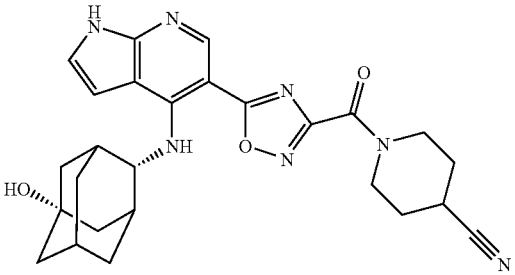 cis |
| 304 | 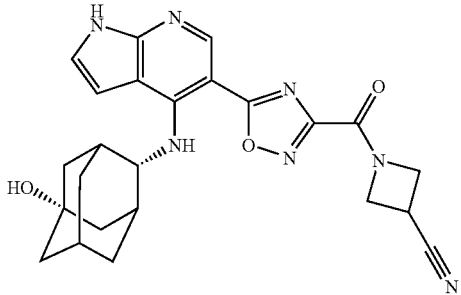 cis |
| 305 | 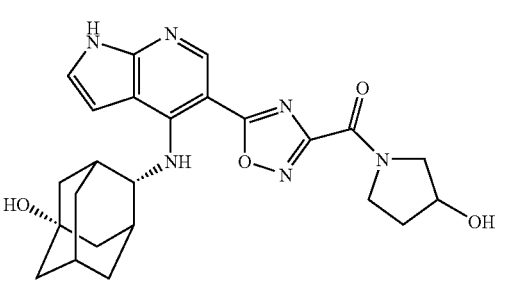 cis |
| 306 | 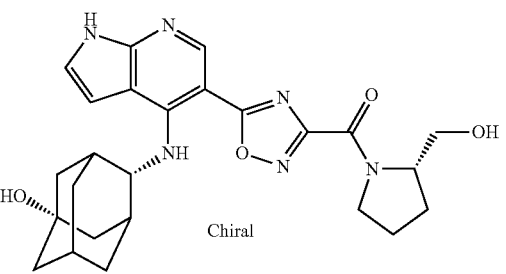 Chiral cis |

TABLE 71-continued
| Ex | Structure |
|---|---|
| 307 | 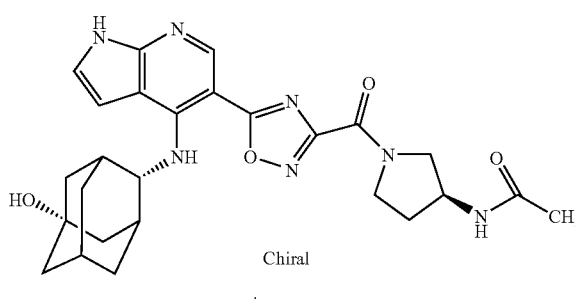
Chiral
cis |
| 308 | 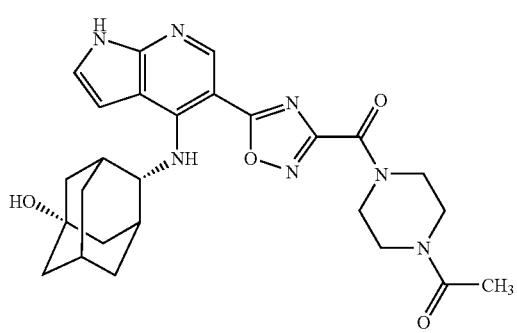
cis |
| 309 | 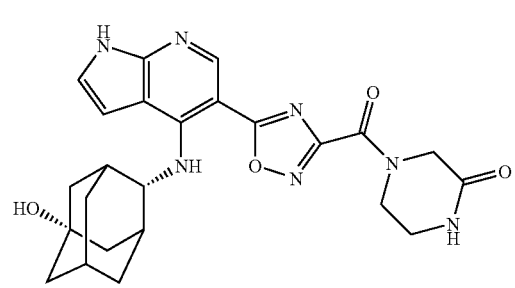
cis |
| 310 | 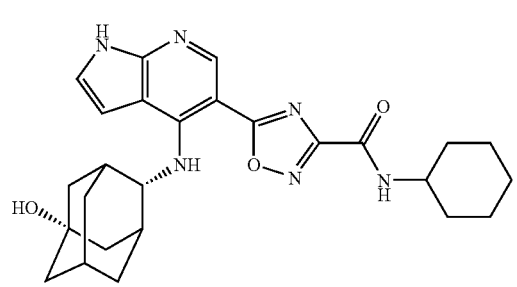
cis |

TABLE 71-continued
| Ex | Structure |
|---|---|
| 311 | 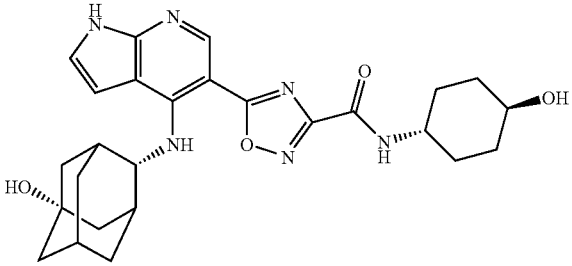 cis |
| 312 | 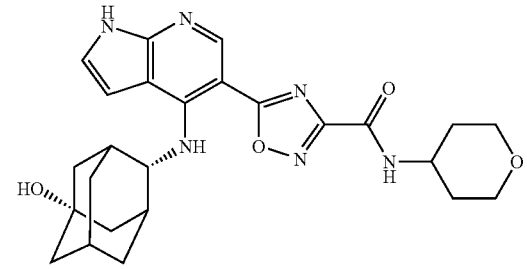 cis |
| 313 | 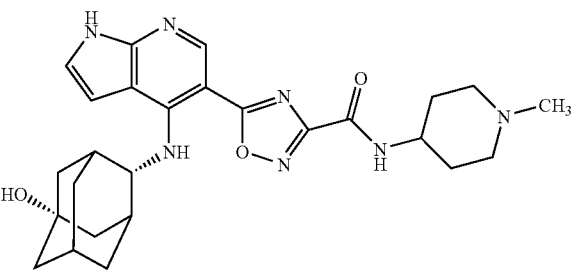 cis |
| 314 | 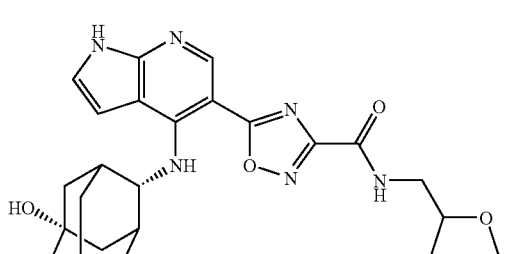 cis |
| 315 | 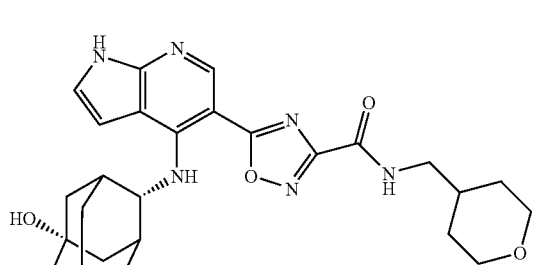 cis |

TABLE 71-continued
| Ex | Structure |
|---|---|
| 316 | 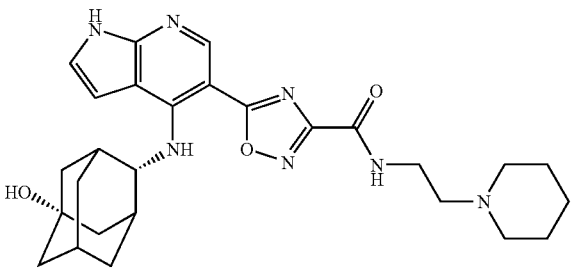<br>cis |
| 317 | 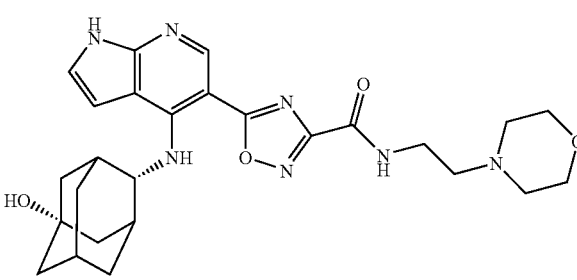<br>cis |
| 318 | 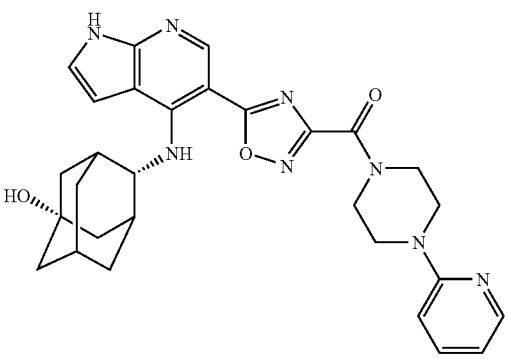<br>cis |
| 319 | 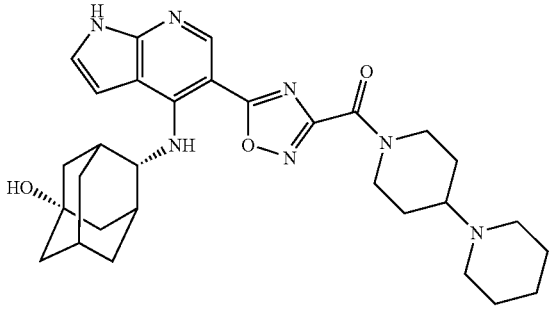<br>cis |

TABLE 71-continued

| Ex | Structure |
|---|---|
| 320 | 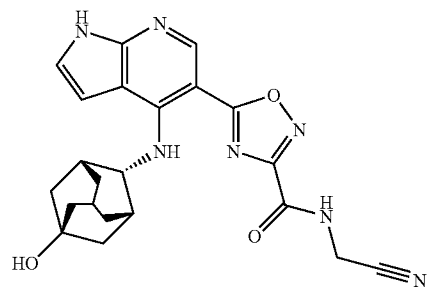 |
| 321 | cis |
| 322 | cis |
| 323 | cis |
| 324 | cis |

TABLE 71-continued
| Ex | Structure |
|---|---|
| 325 | 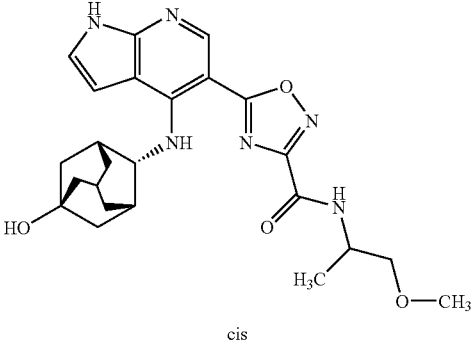 cis |
| 326 | 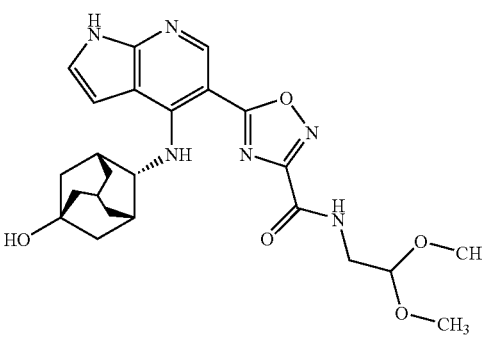 cis |
| 327 | 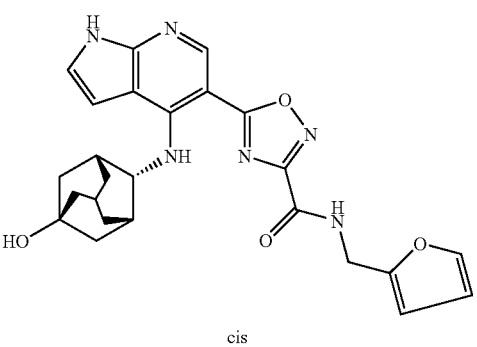 cis |
| 328 | 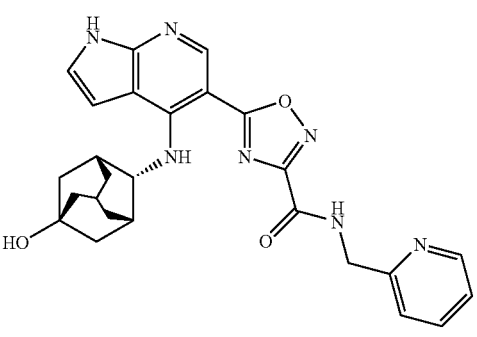 cis |

TABLE 71-continued
| Ex | Structure |
|---|---|
| 329 | 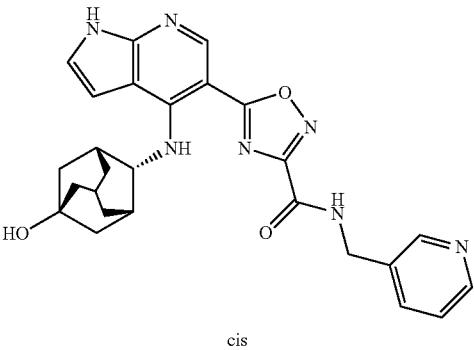<br>cis |
| 330 | 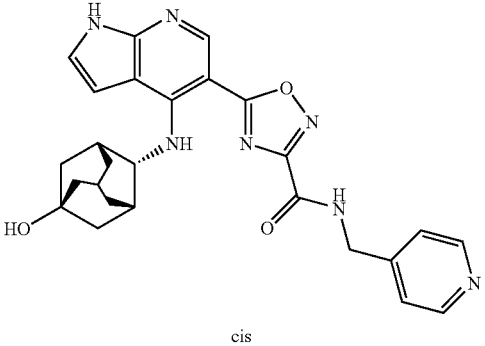<br>cis |
| 331 | 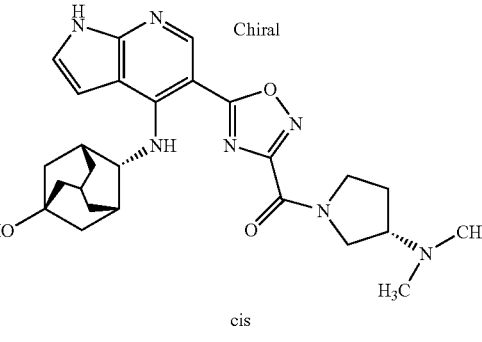<br>cis |
| 332 | 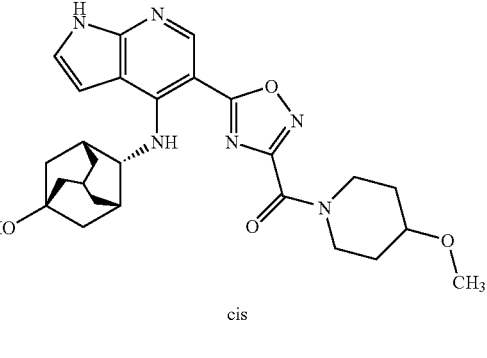<br>cis |

TABLE 71-continued
| Ex | Structure |
|---|---|
| 333 | 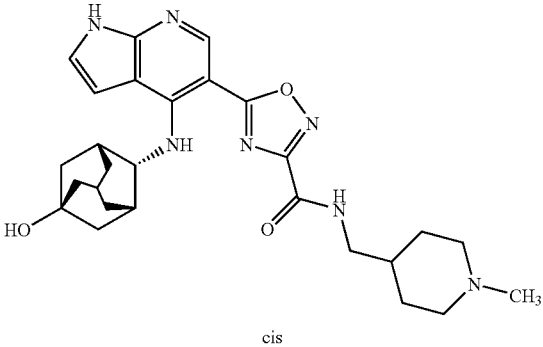 cis |
| 334 | 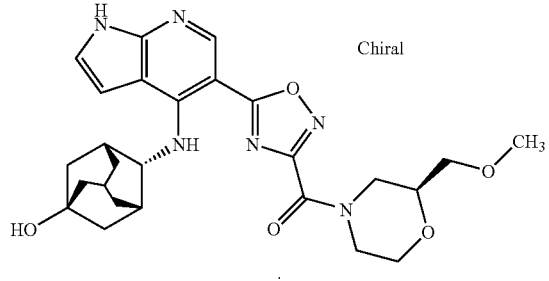 cis |
| 335 | 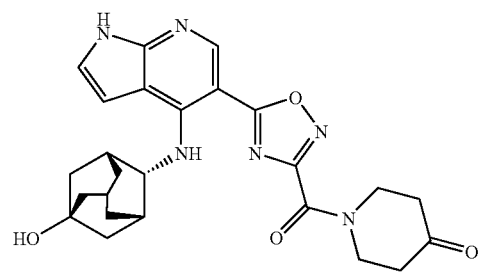 cis |
| 336 | 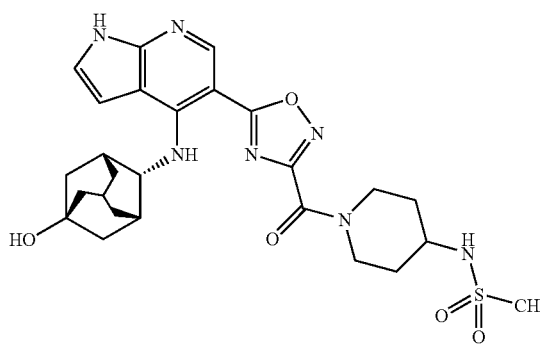 cis |

TABLE 71-continued
| Ex | Structure |
|---|---|
| 337 | 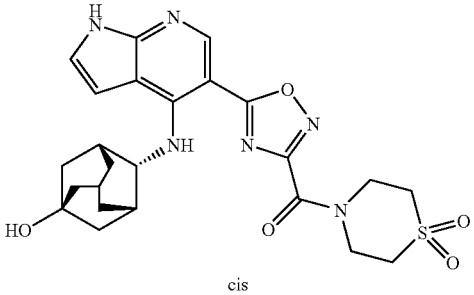 cis |
| 338 | 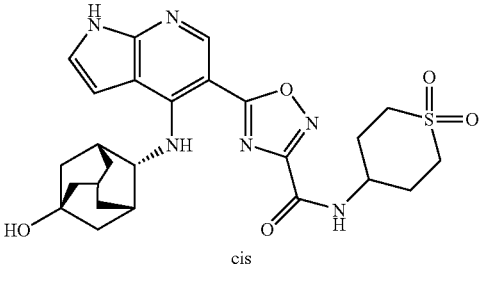 cis |
| 339 | 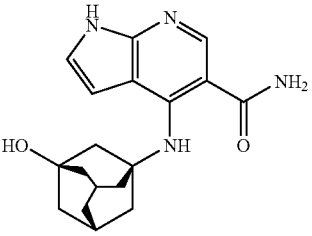 |
| 340 | 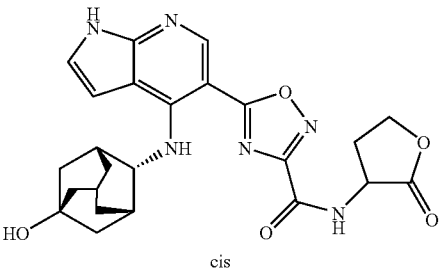 cis |
| 341 | 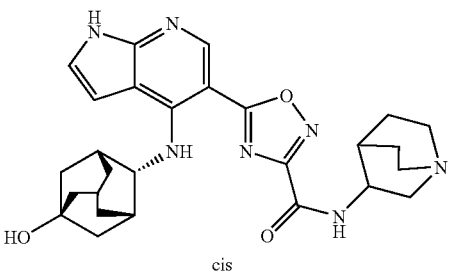 cis |

TABLE 71-continued
| Ex | Structure |
|---|---|
| 342 | 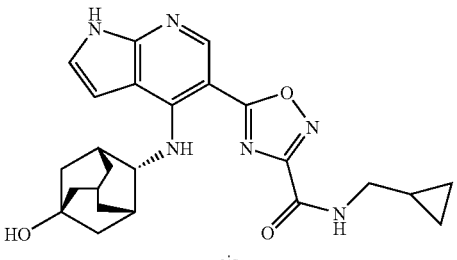 cis |
| 343 | 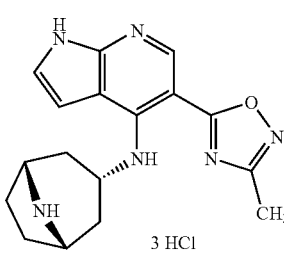 3 HCl |
| 344 | 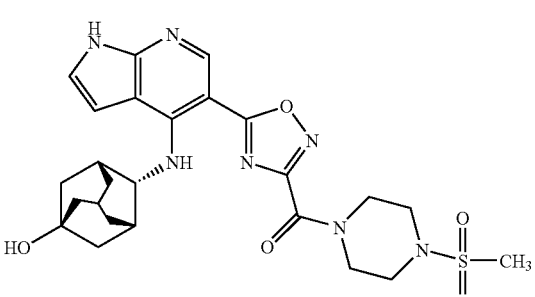 cis |
| 345 | 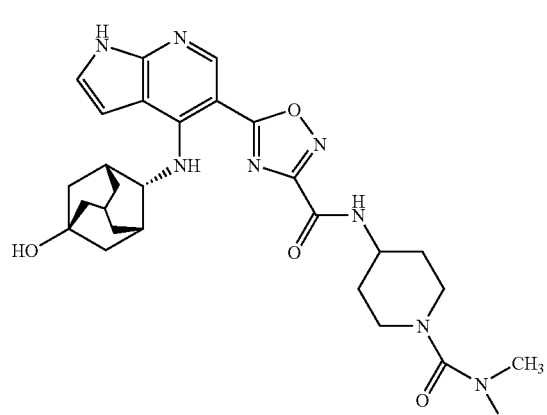 cis |

TABLE 71-continued
| Ex | Structure |
|---|---|
| 346 | 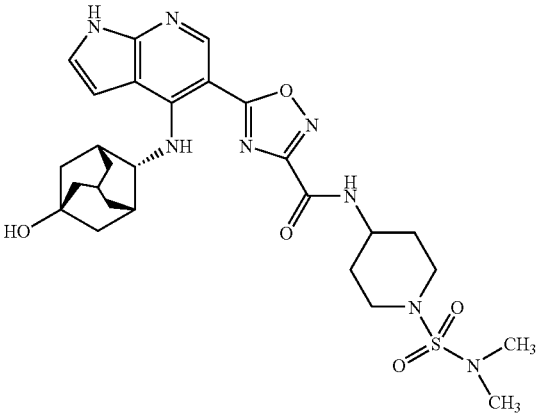 cis |
| 347 | 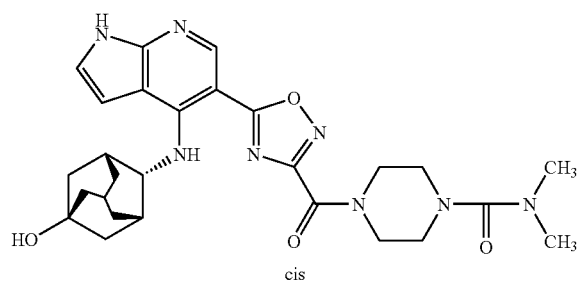 cis |
| 348 | 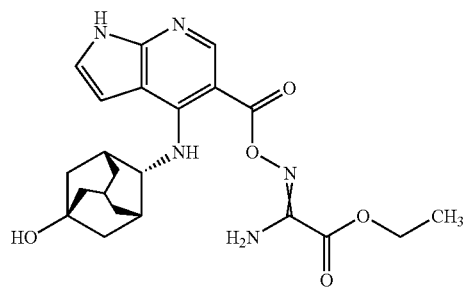 cis |
| 349 | 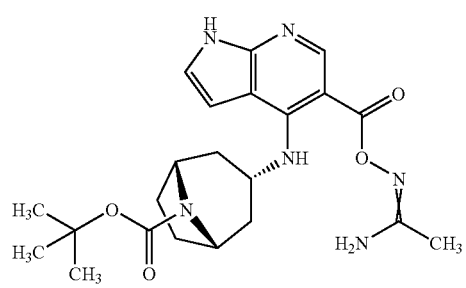 |

TABLE 71-continued
| Ex | Structure |
|---|---|
| 350 | 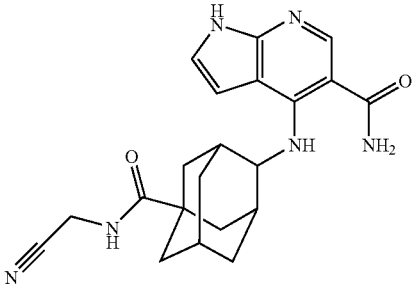<br>diastereomer of 351<br>cis or trans unknown |
| 351 | 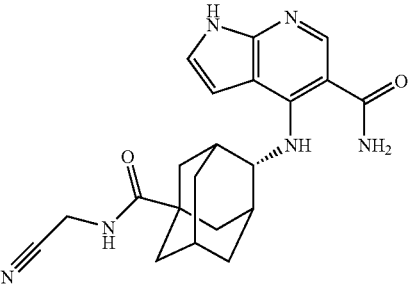<br>diastereomer of 350<br>cis or trans unknown |
| 352 | 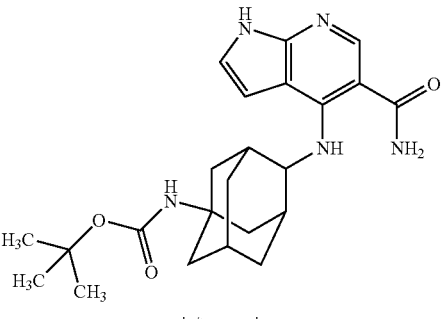<br>cis/trans mix |
| 353 | 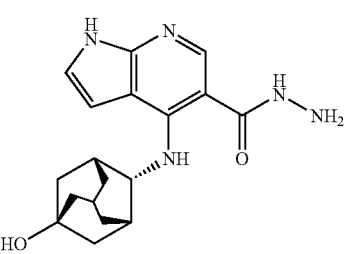<br>cis |

TABLE 71-continued
| Ex | Structure |
|---|---|
| 354 | 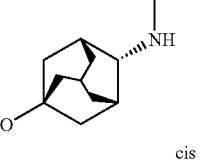 cis |
| 355 | 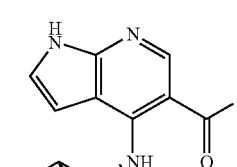 cis |
| 356 | 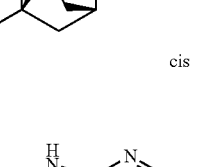 cis |
| 357 | 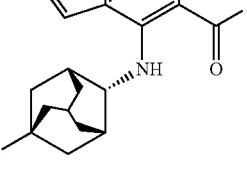 cis |
| 358 | 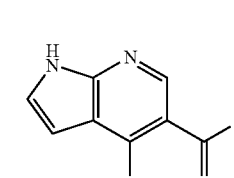 cis |

TABLE 71-continued
| Ex | Structure |
|---|---|
| 359 | 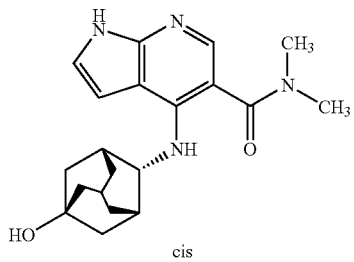 cis |
| 360 | 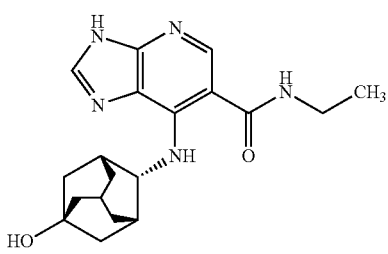 cis |
| 361 | 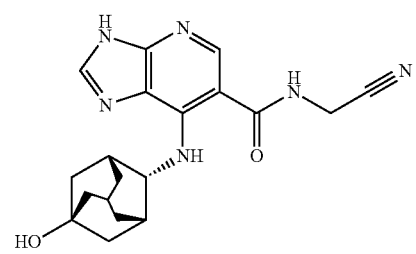 cis |
| 362 | 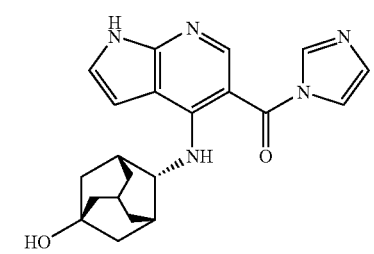 cis |
| 363 | 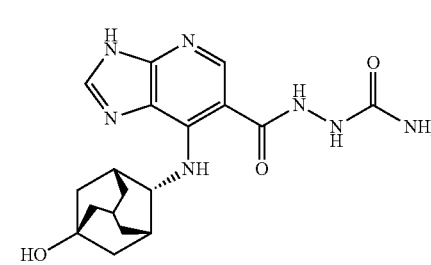 cis |

TABLE 71-continued
| Ex | Structure |
|---|---|
| 364 | 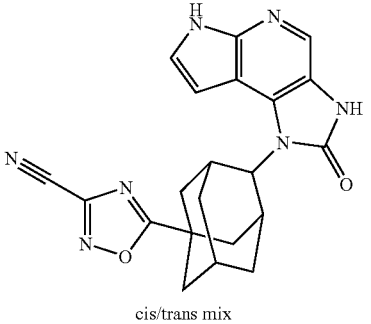<br>cis/trans mix |
| 365 | 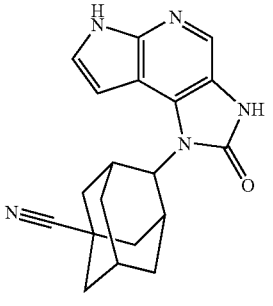<br>diastereomer of 16<br>cis or trans unknown |
| 366 | 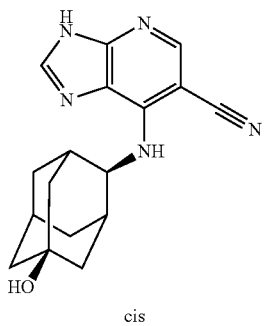<br>cis |
| 367 | 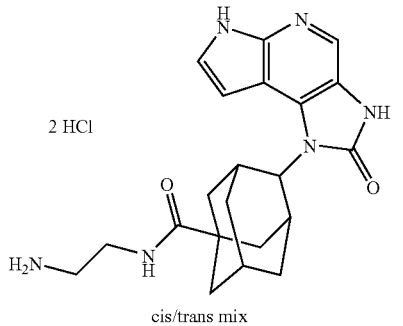<br>cis/trans mix |

TABLE 71-continued
| Ex | Structure |
|---|---|
| 368 | 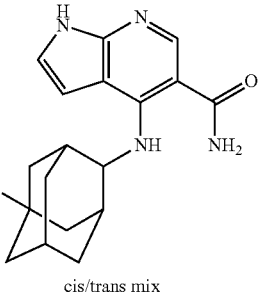<br>3 HCl<br>cis/trans mix |
| 369 | <br>3 HCl<br>cis/trans mix |
| 370 | <br>cis |
| 371 | 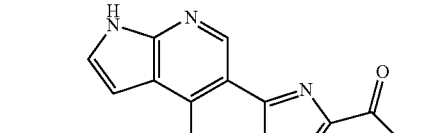<br>3 HCl<br>cis/trans mix |

TABLE 71-continued
| Ex | Structure |
|---|---|
| 372 | 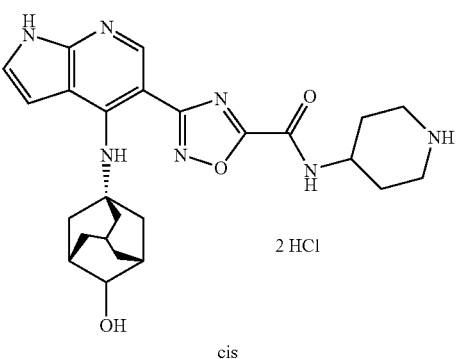  cis |
| 373 | 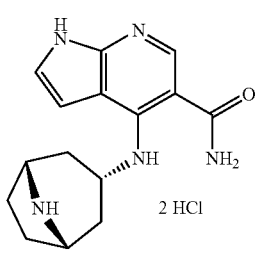 |
| 374 | 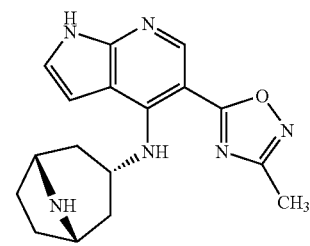 |
| 375 | 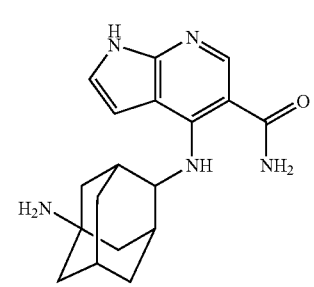  diastereomer of 376 cis or trans unknown |
| 376 | 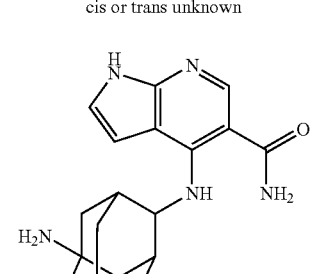  diastereomer of 375 cis or trans unknown |

TABLE 71-continued
| Ex | Structure |
|---|---|
| 377 | 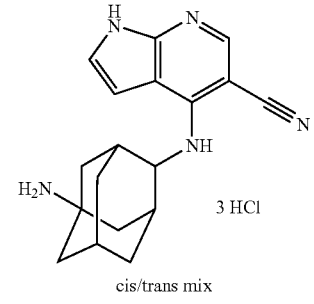 cis/trans mix |
| 378 | 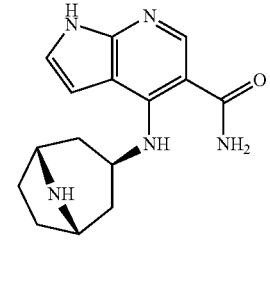 |
| 379 | 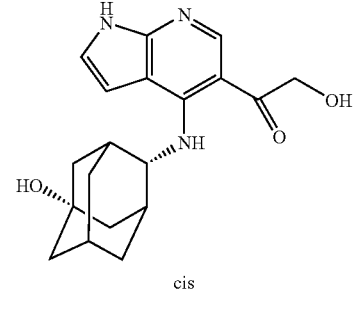 cis |
| 380 | 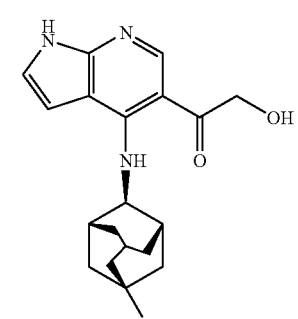 trans |

TABLE 71-continued
| Ex | Structure |
|---|---|
| 381 | 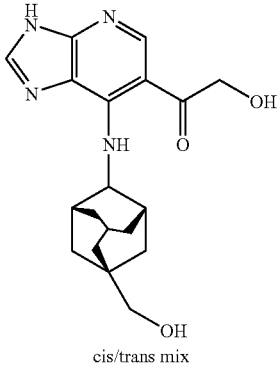<br>cis/trans mix |
| 382 | 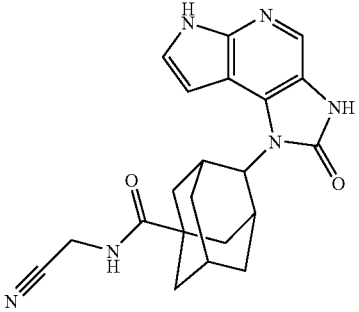<br>diastereomer of 22<br>cis or trans unknown |
| 383 | 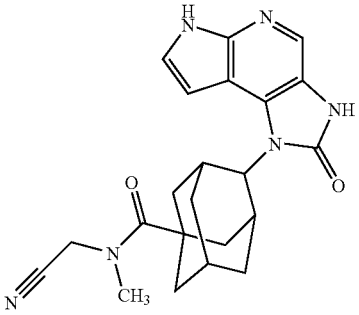<br>diastereomer of 384<br>cis or trans unknown |
| 384 | 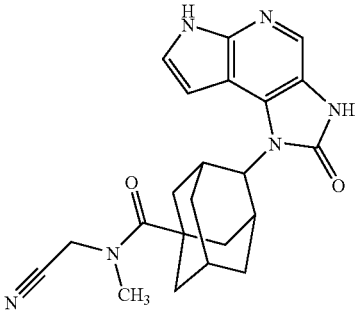<br>diastereomer of 383<br>cis or trans unknown |

TABLE 71-continued

| Ex | Structure |
|---|---|
| 385 | (structure) diastereomer of 386 cis or trans unknown |
| 386 | (structure) diastereomer of 385 cis or trans unknown |
| 387 | (structure) diastereomer of 388 cis or trans unknown |
| 388 | (structure) diastereomer of 387 cis or trans unknown |

TABLE 71-continued
| Ex | Structure |
|---|---|
| 389 | 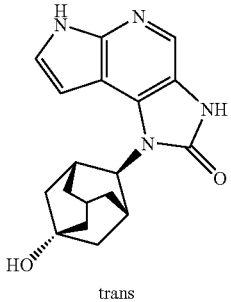<br>trans |
| 390 | 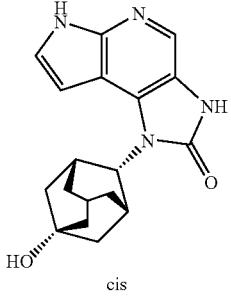<br>cis |
| 391 | 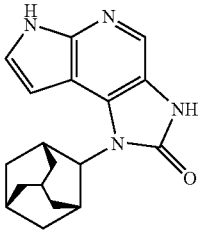 |
| 392 | 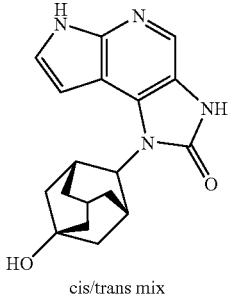<br>cis/trans mix |
| 393 | 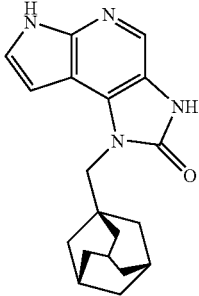 |

TABLE 71-continued
| Ex | Structure |
|---|---|
| 394 | 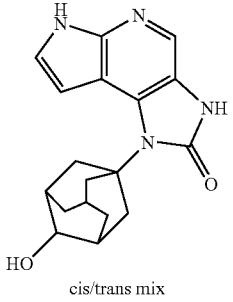<br>cis/trans mix |
| 395 | 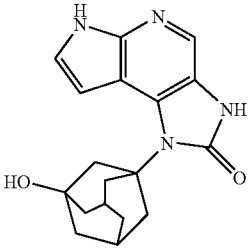 |
| 396 | 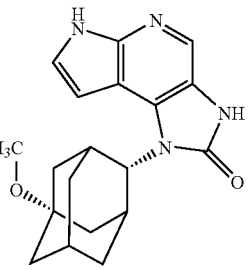<br>cis |
| 397 | 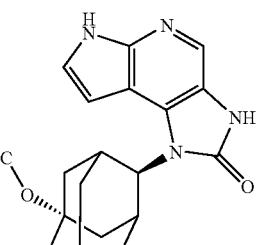<br>trans |
| 398 | 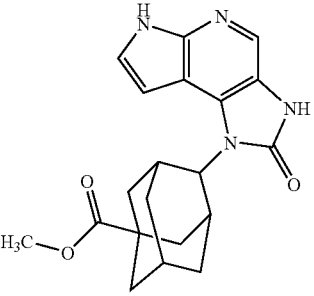<br>cis/trans mix |

TABLE 71-continued

| Ex | Structure |
|---|---|
| 399 | diastereomer of 400<br>cis or trans unknown |
| 400 | diastereomer of 399<br>cis or trans unknown |
| 401 | diastereomer of 402<br>cis or trans unknown |
| 402 | diastereomer of 401<br>cis or trans unknown |

TABLE 71-continued
| Ex | Structure |
|---|---|
| 403 | 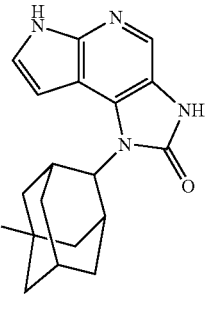<br>cis/trans mix |
| 404 | 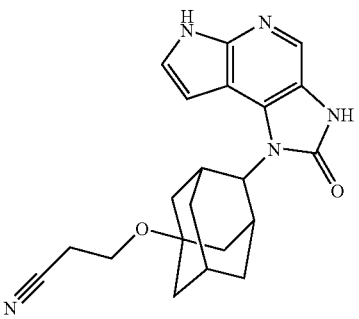<br>diastereomer of 405<br>cis or trans unknown |
| 405 | 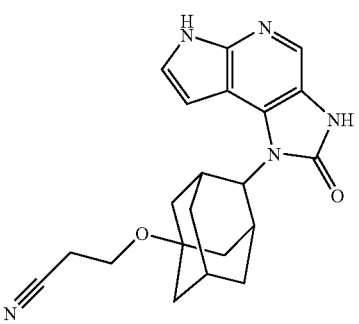<br>diastereomer of 404<br>cis or trans unknown |
| 406 | 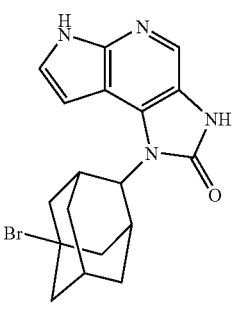<br>cis or trans unknown |

TABLE 71-continued
| Ex | Structure |
|---|---|
| 407 | 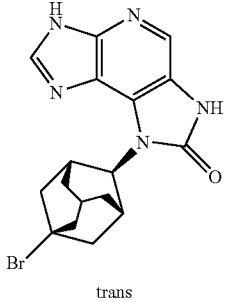 trans |
| 408 | 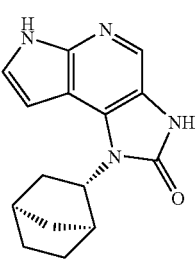 |
| 409 | 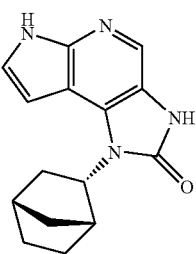 |
| 410 | 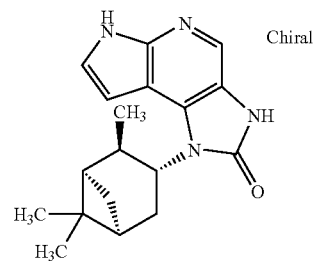 Chiral |
| 411 | 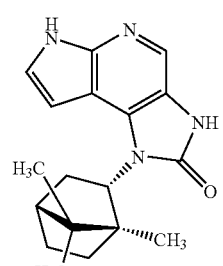 Chiral |

TABLE 71-continued
| Ex | Structure |
|---|---|
| 412 | 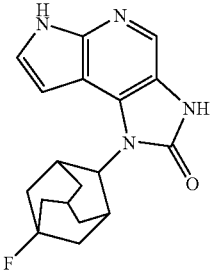<br>cis/trans mix |
| 413 | 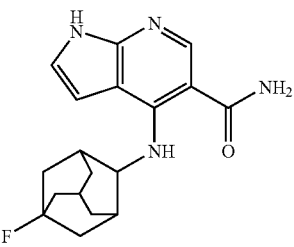<br>cis/trans mix |
| 414 | 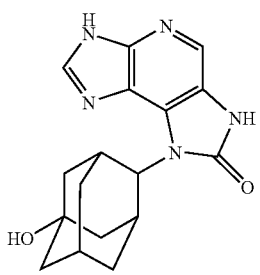<br>diastereomer of 415<br>cis or trans unknown |
| 415 | 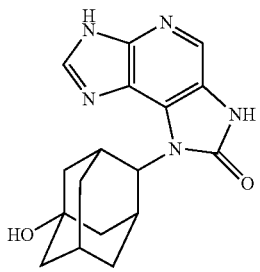<br>diastereomer of 414<br>cis or trans unknown |
| 416 | 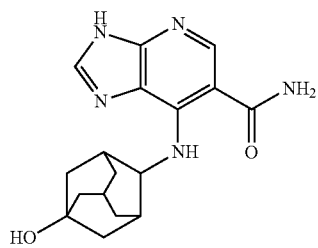<br>cis/trans mix |

TABLE 71-continued
| Ex | Structure |
|---|---|
| 417 | 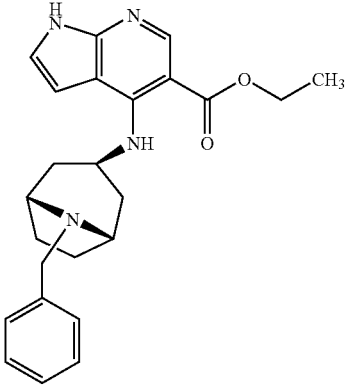 |
| 418 | 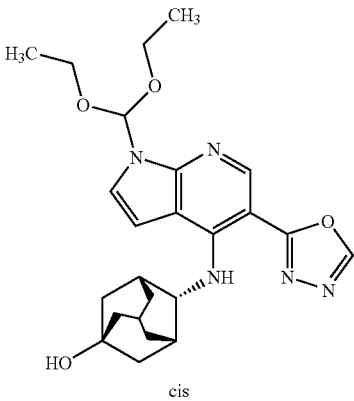 cis |
| 419 | 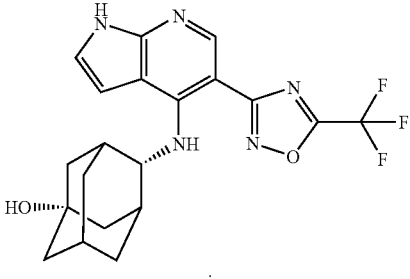 cis |
| 420 | 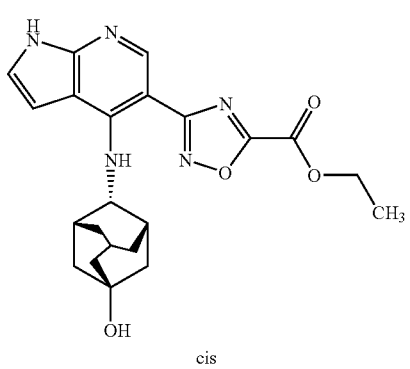 cis |

TABLE 71-continued
| Ex | Structure |
|---|---|
| 421 | 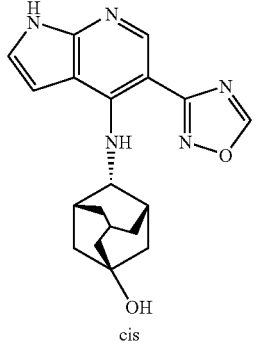<br>cis |
| 422 | 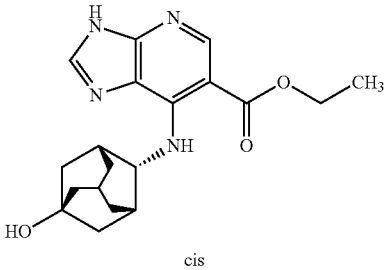<br>cis |
| 423 | 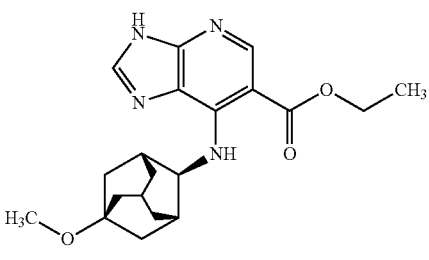<br>trans |
| 424 | 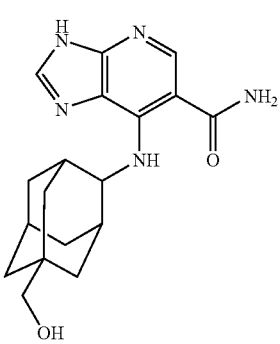<br>diastereomer of 425<br>cis or trans unknown |

TABLE 71-continued
| Ex | Structure |
|---|---|
| 425 | 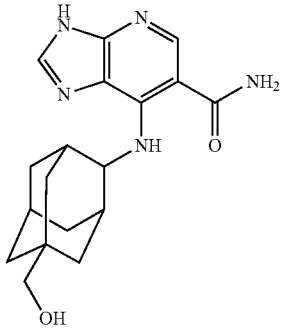<br>diastereomer of 424<br>cis or trans unknown |
| 426 | 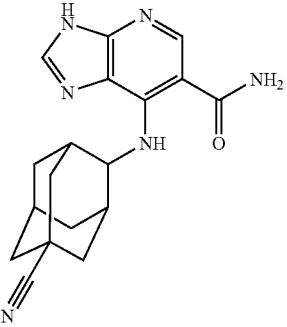<br>cis or trans unknown |
| 427 | 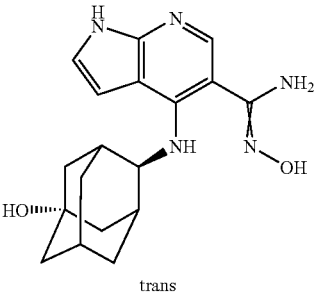<br>trans |
| 428 | 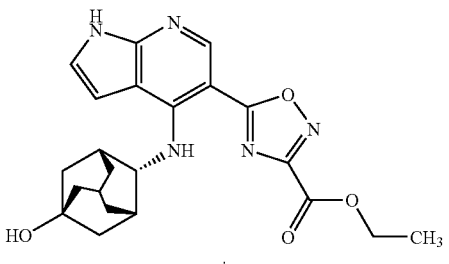<br>cis |

TABLE 71-continued
| Ex | Structure |
|---|---|
| 429 | 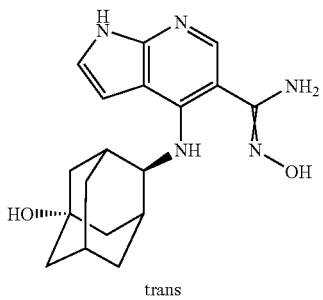<br>trans |
| 430 | 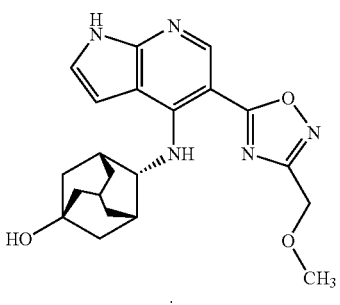<br>cis |
| 431 | 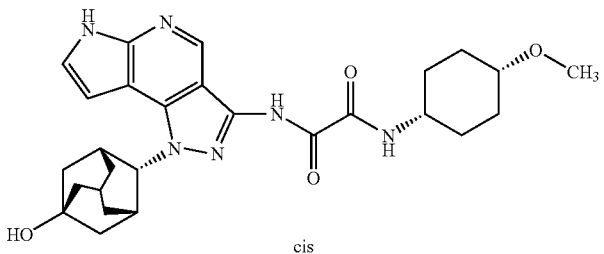<br>cis |
| 432 | 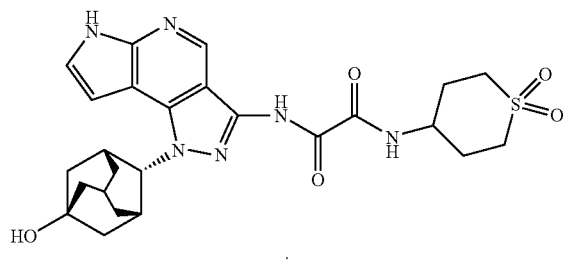<br>cis |
| 433 | 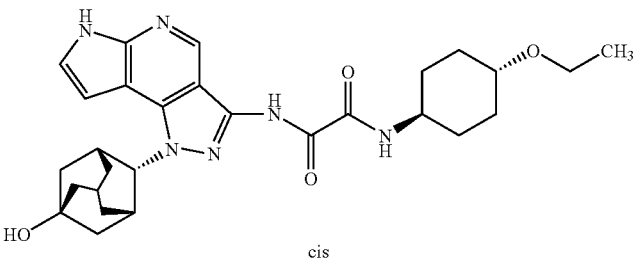<br>cis |

TABLE 71-continued

| Ex | Structure |
|---|---|
| 434 | (structure) cis |
| 435 | (structure) cis |
| 436 | (structure) cis |
| 437 | (structure) cis |
| 438 | (structure) cis |

TABLE 71-continued
| Ex | Structure |
|---|---|
| 439 | 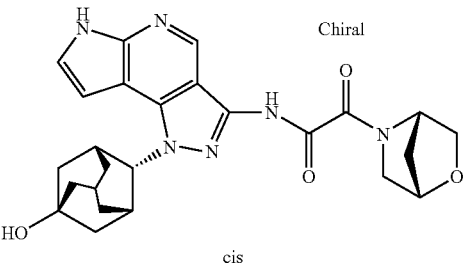 cis |
| 440 | 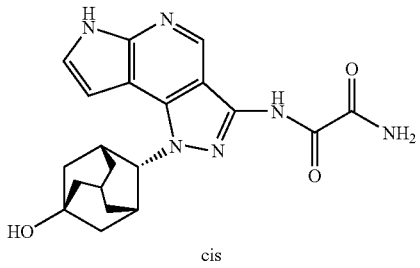 cis |
| 441 | 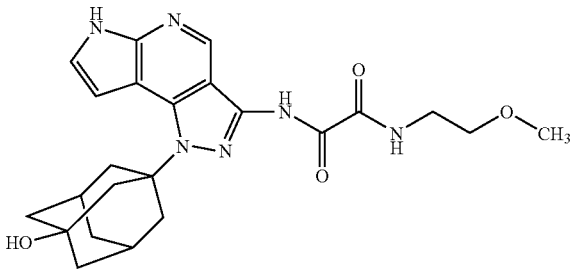 |
| 442 | 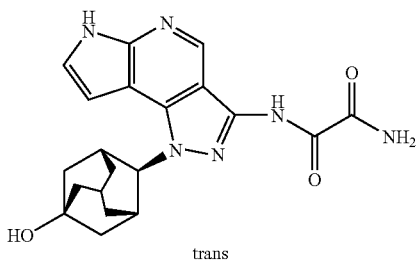 trans |
| 443 | 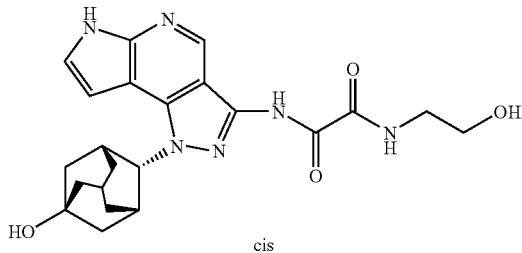 cis |

TABLE 71-continued
| Ex | Structure |
|---|---|
| 444 | 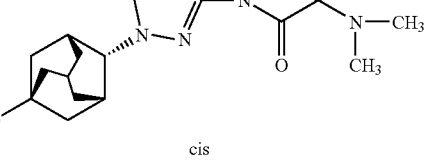 cis |
| 445 | 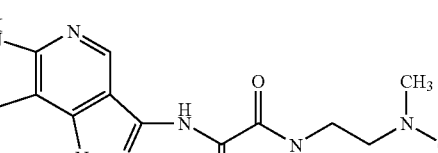 cis |
| 446 |  cis |
| 447 | 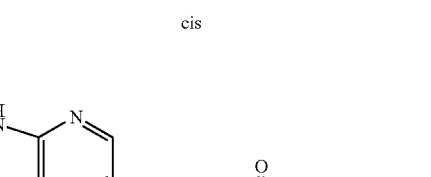 cis |
| 448 | 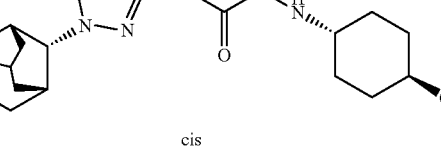 cis |

TABLE 71-continued
| Ex | Structure |
|---|---|
| 449 | 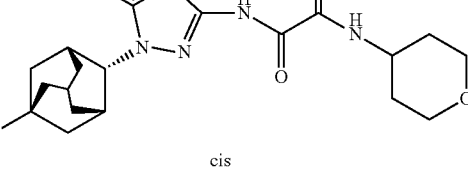 cis |
| 450 | 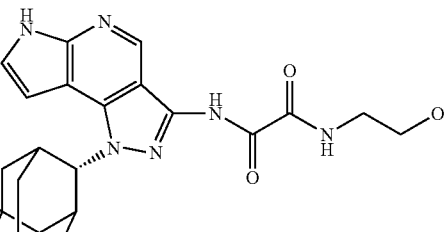 cis or trans unknown |
| 451 | 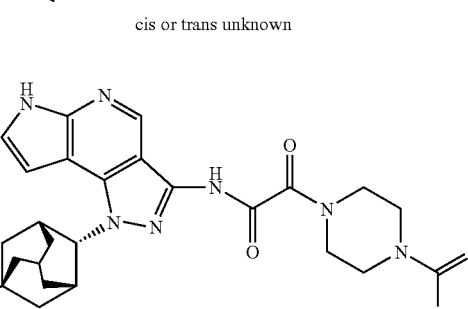 cis |
| 452 | 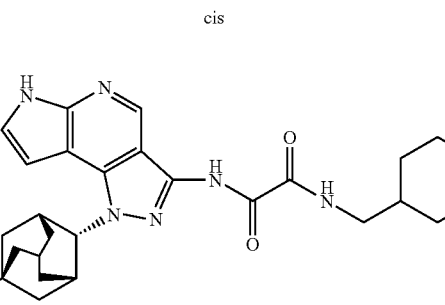 cis |
| 453 | 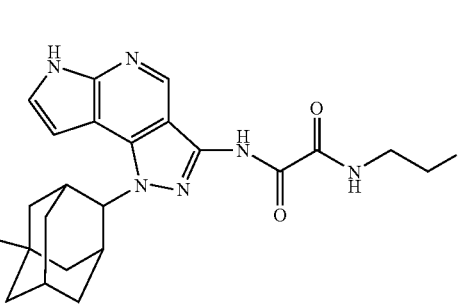 cis/trans mix |

TABLE 71-continued
| Ex | Structure |
|---|---|
| 454 | 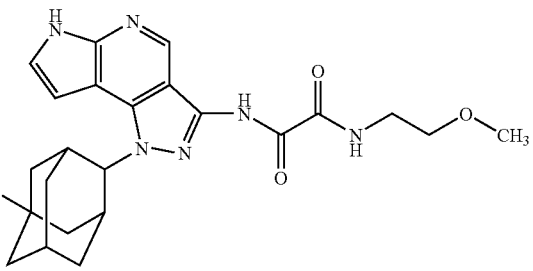<br>cis or trans unknown |
| 455 | 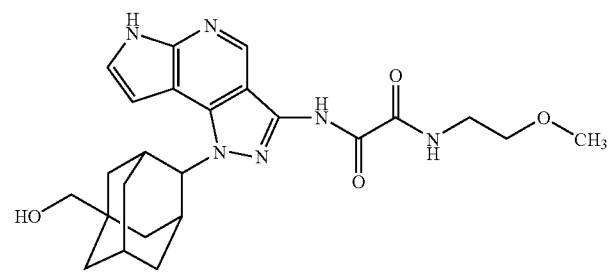<br>cis/trans mix |
| 456 | 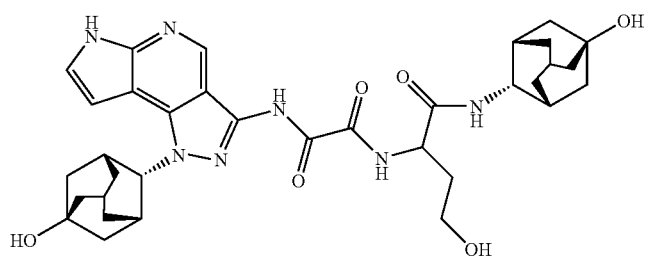<br>cis |
| 457 | 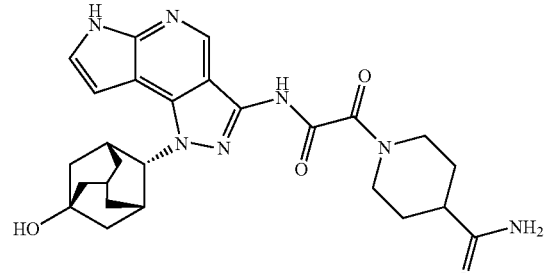<br>cis |
| 458 | 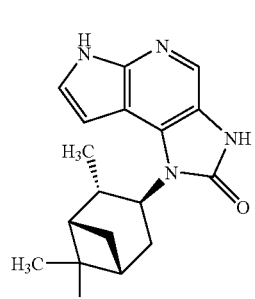<br>cis |

TABLE 71-continued
| Ex | Structure |
|---|---|
| 459 | 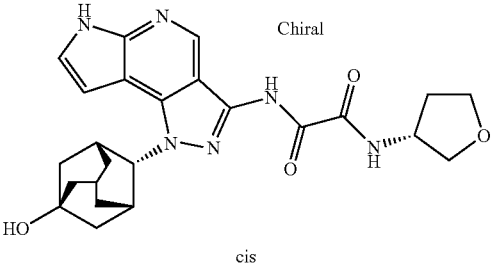 Chiral, cis |
| 460 | 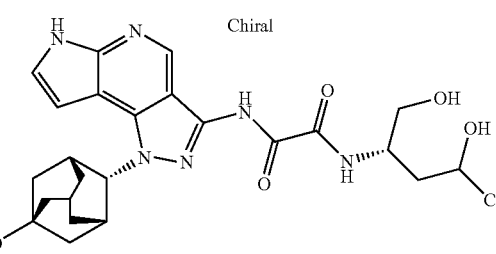 Chiral, cis |
| 461 | 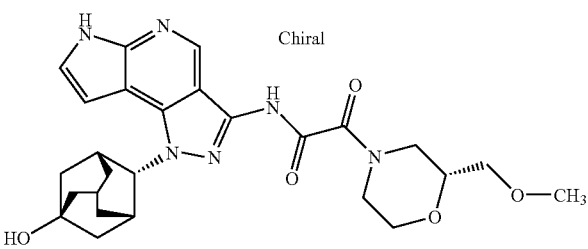 Chiral, cis |
| 462 | 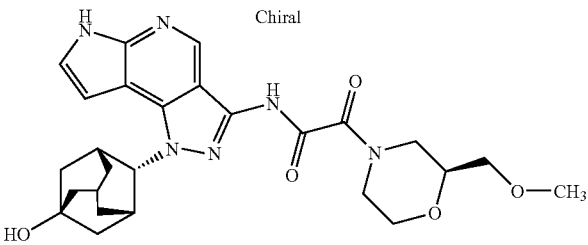 Chiral, cis |
| 463 | 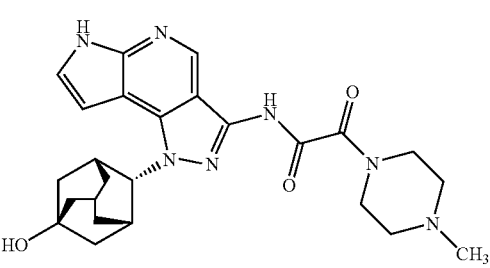 cis |

TABLE 71-continued
| Ex | Structure |
|---|---|
| 464 | 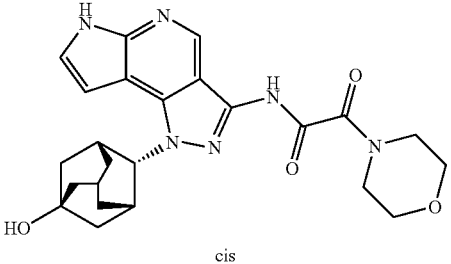 cis |
| 465 | 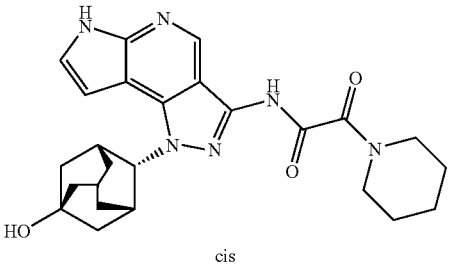 cis |
| 466 | 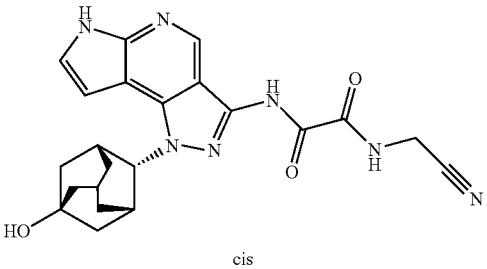 cis |
| 467 | 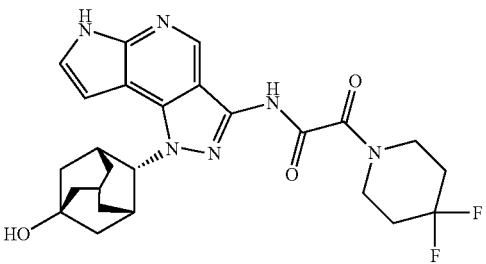 cis |
| 468 | 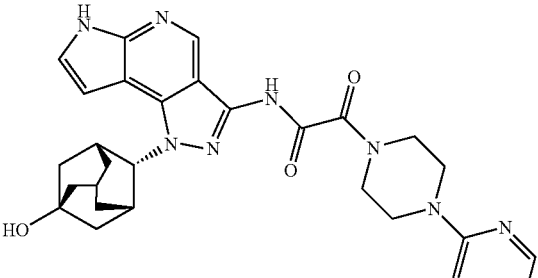 cis |

TABLE 71-continued
| Ex | Structure |
|---|---|
| 469 | 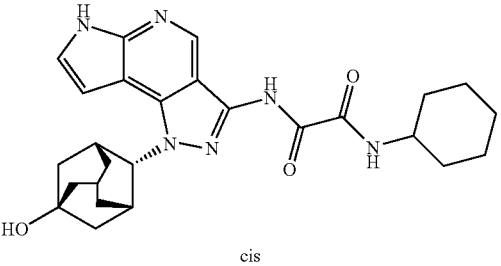 cis |
| 470 | 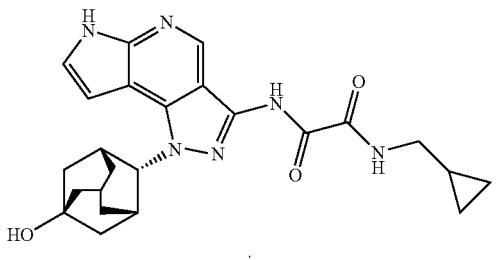 cis |
| 471 | 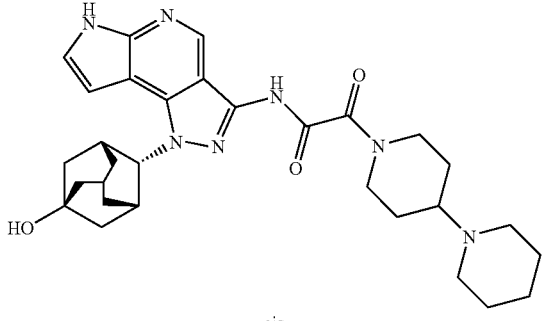 cis |
| 472 | 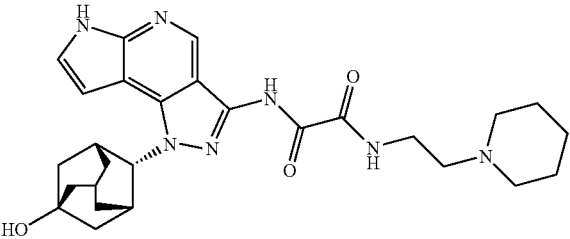 cis |
| 473 | 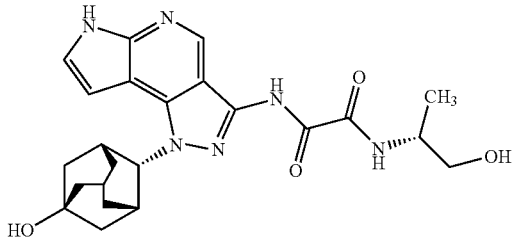 cis |

TABLE 71-continued
| Ex | Structure |
|---|---|
| 474 | 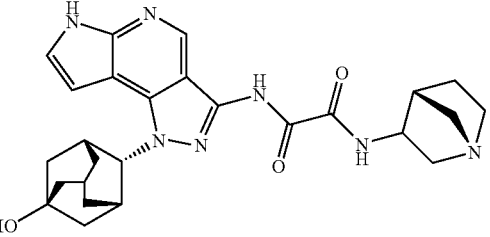 cis |
| 475 | 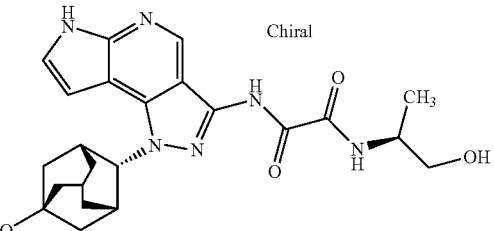 cis |
| 476 | 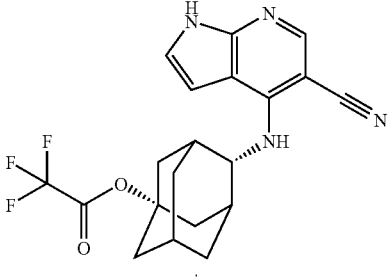 cis |
| 477 | 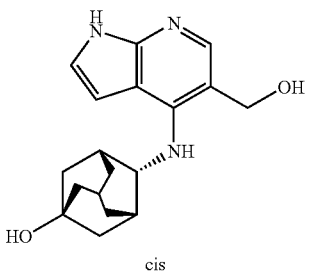 cis |
| 478 | 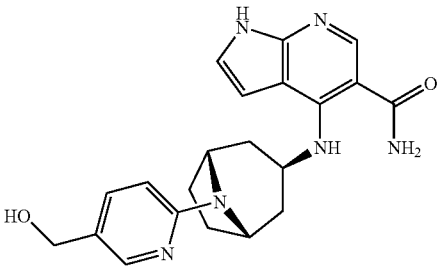 |

TABLE 71-continued
| Ex | Structure |
|---|---|
| 479 | 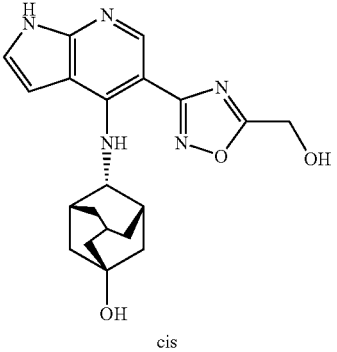 cis |
| 480 | 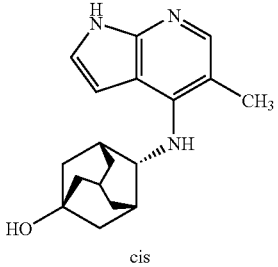 cis |
| 481 | 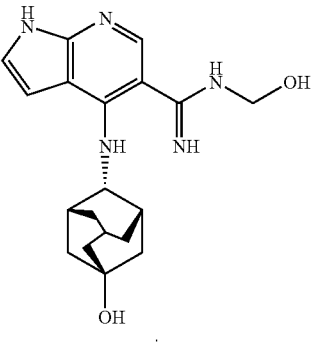 cis |
| 482 | 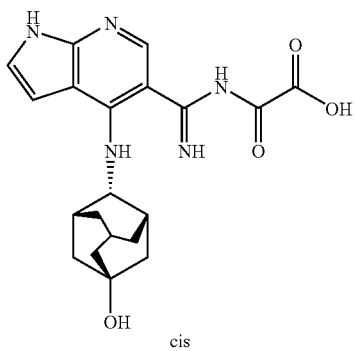 cis |

TABLE 71-continued
| Ex | Structure |
|---|---|
| 483 | 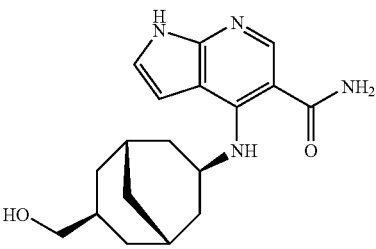 |
| 484 | 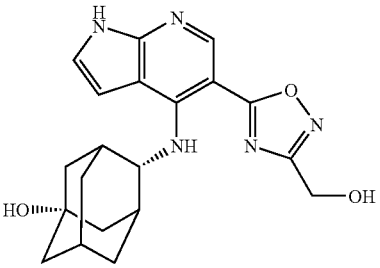<br>cis |
| 485 | 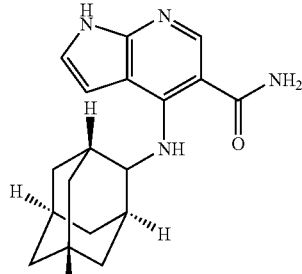<br>diastereomer of 486<br>cis or trans unknown |
| 486 | 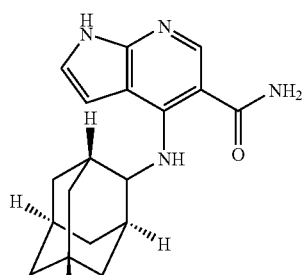<br>diastereomer of 485<br>cis or trans unknown |

TABLE 71-continued

| Ex | Structure |
|---|---|
| 487 | (structure) 3 HCl<br>cis/trans mix |
| 488 | (structure)<br>diastereomer of 490<br>cis or trans unknown |
| 489 | (structure) |
| 490 | (structure)<br>diastereomer of 488<br>cis or trans unknown |
| 491 | (structure) |

TABLE 71-continued

| Ex | Structure |
|---|---|
| 492 | cis or trans unknown |
| 493 | diastereomer of 494<br>cis or trans unknown |
| 494 | diastereomer of 493<br>cis or trans unknown |
| 495 | trans |

TABLE 71-continued

| Ex | Structure |
|---|---|
| 496 | cis/trans mix |
| 497 | diastereomer of 498<br>cis or trans unknown |
| 498 | diastereomer of 497<br>cis or trans unknown |
| 499 | cis |

TABLE 71-continued
| Ex | Structure |
|---|---|
| 500 | 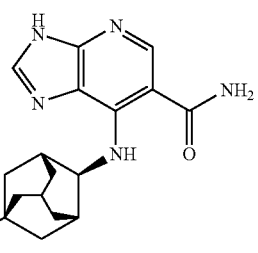 trans |
| 501 | 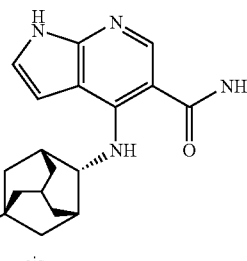 cis |
| 502 | 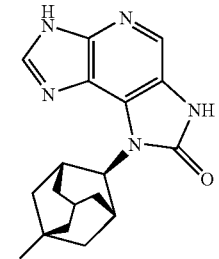 trans |
| 503 | 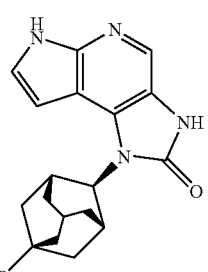 trans |

TABLE 71-continued
| Ex | Structure |
|---|---|
| 504 | 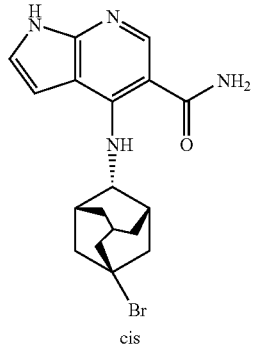<br>cis |
| 505 | 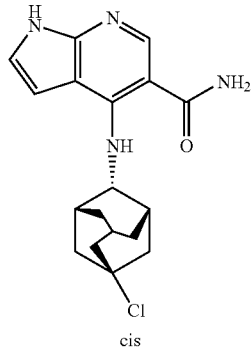<br>cis |
| 506 | 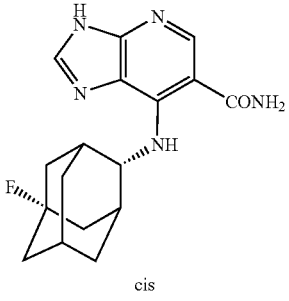<br>cis |
| 507 | 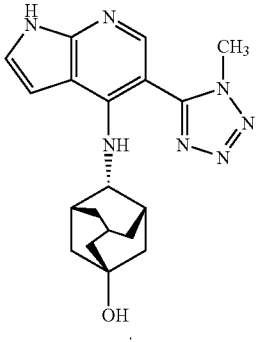<br>cis |

TABLE 71-continued

| Ex | Structure |
|---|---|
| 508 | 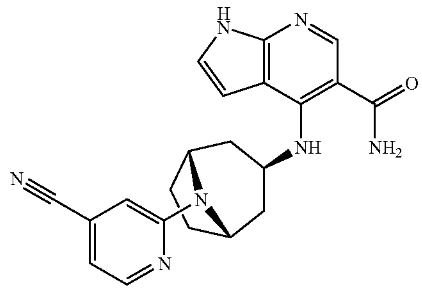 |
| 509 | 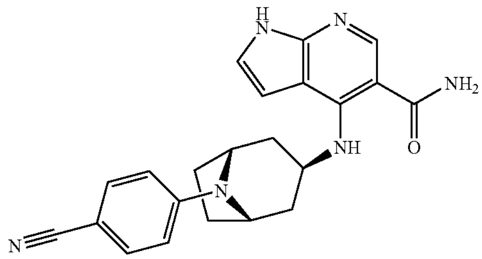 |
| 510 | 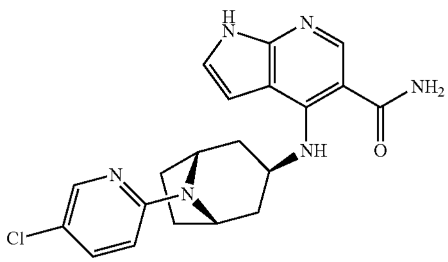 |
| 511 | 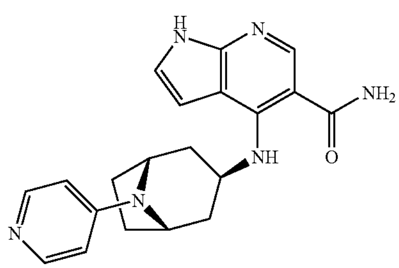 |
| 512 | 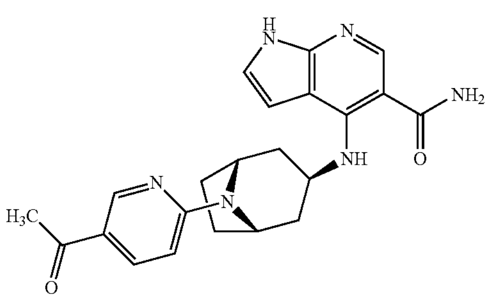 |

TABLE 71-continued
| Ex | Structure |
|---|---|
| 513 | 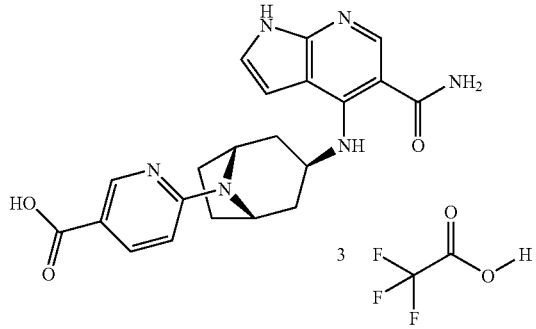 |
| 514 | 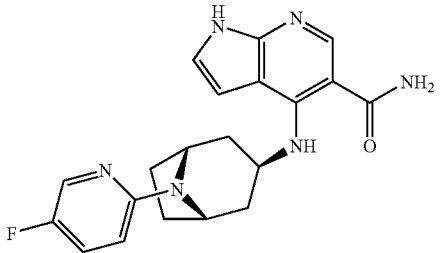 |
| 515 | 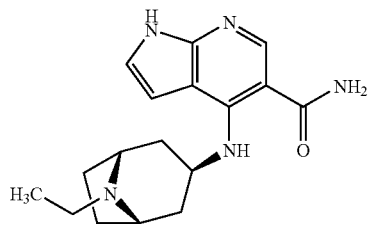 |
| 516 | 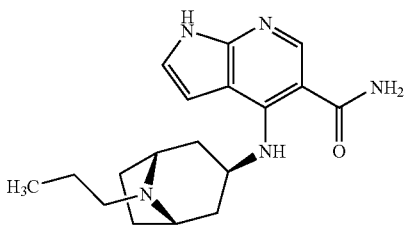 |
| 517 | 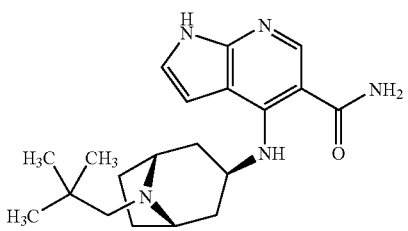 |
| 518 | 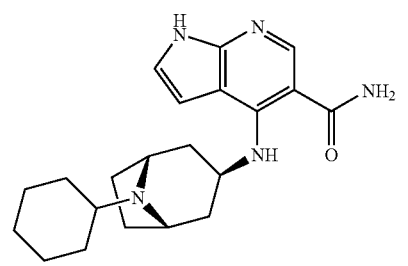 |

TABLE 71-continued

| Ex | Structure |
|---|---|
| 519 | 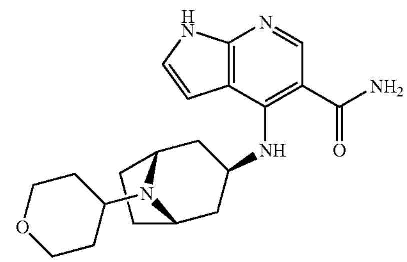 |
| 520 | 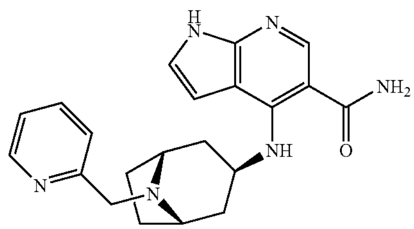 |
| 521 | 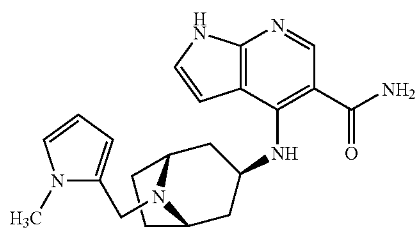 |
| 522 | 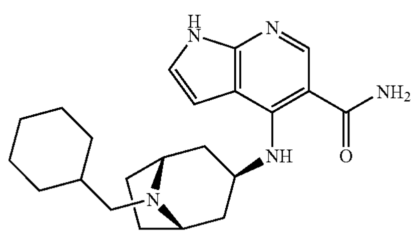 |
| 523 | 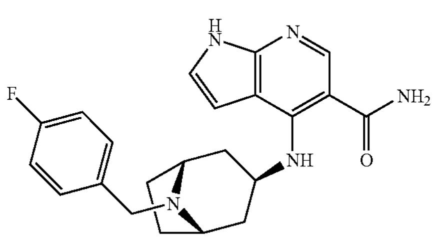 |
| 524 | 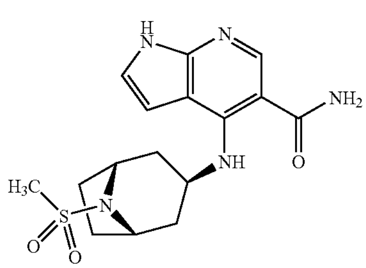 |

TABLE 71-continued
| Ex | Structure |
|---|---|
| 525 | 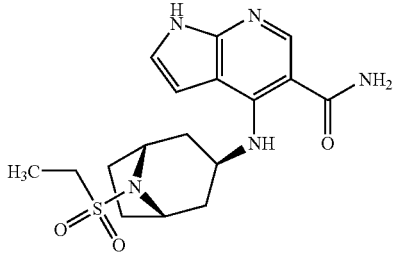 |
| 526 | 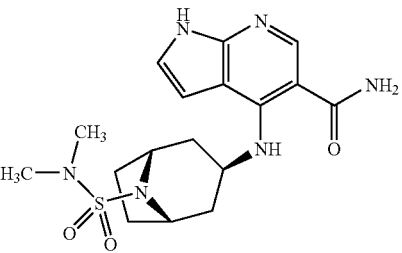 |
| 527 | 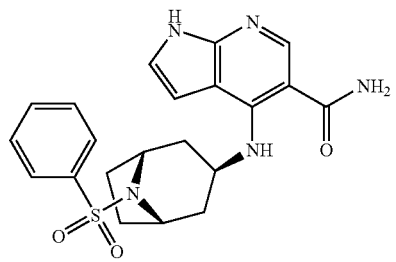 |
| 528 | 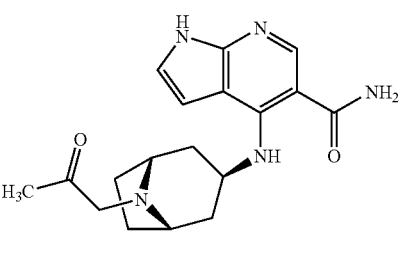 |
| 529 | 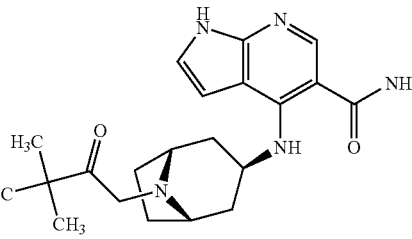 |

TABLE 71-continued
| Ex | Structure |
|---|---|
| 530 | 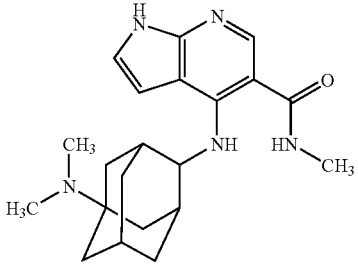
diastereomer of 534
cis or trans unknown |
| 531 | 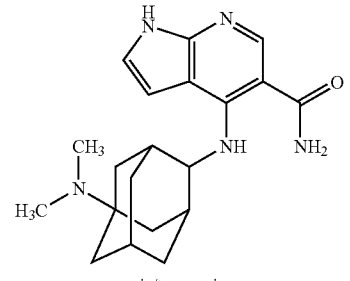
cis/trans mix |
| 532 | 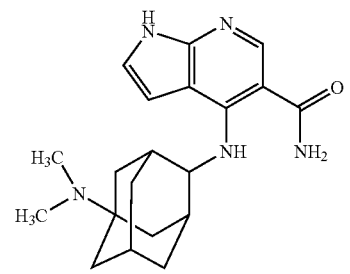
diastereomer of 533
cis or trans unknown |
| 533 | 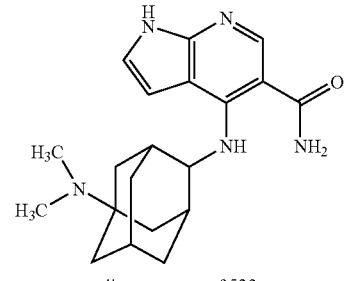
diastereromer of 532
cis or trans unknown |

TABLE 71-continued

| Ex | Structure |
|---|---|
| 534 | (diastereomer of 530, cis or trans unknown) |
| 535 | (cis/trans mix) |
| 536 | 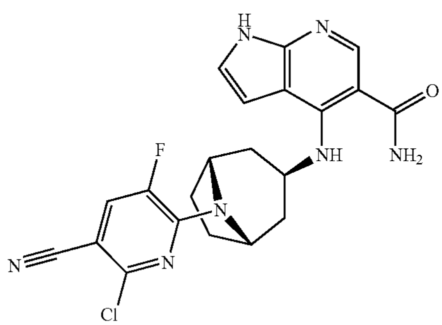 |
| 537 | 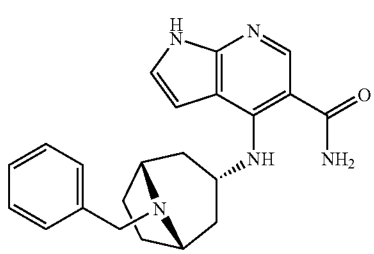 |
| 538 | 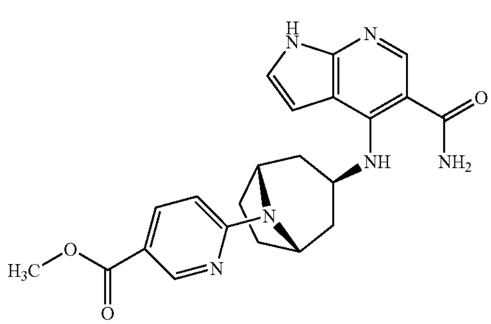 |

TABLE 71-continued

| Ex | Structure |
|---|---|
| 539 | 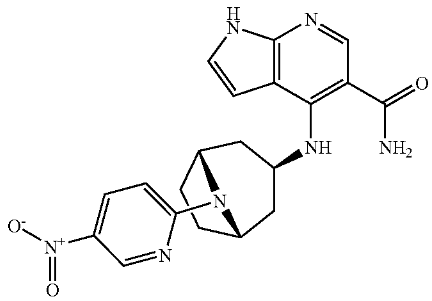 |
| 540 | 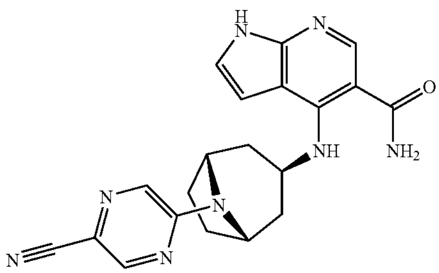 |
| 541 | 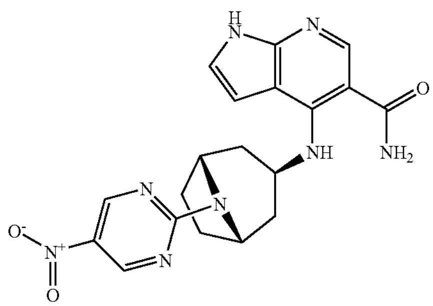 |
| 542 | 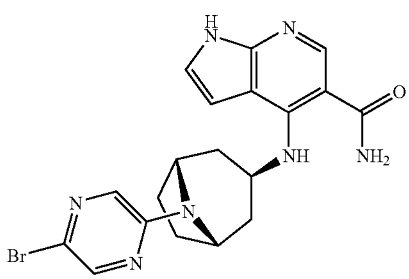 |
| 543 | 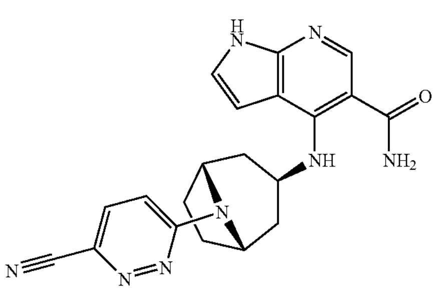 |

TABLE 71-continued

| Ex | Structure |
|---|---|
| 544 | 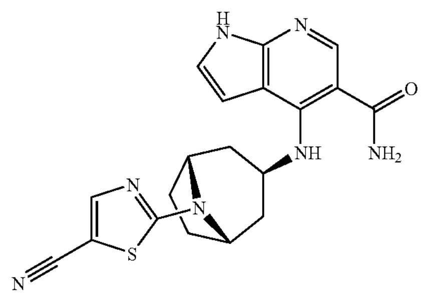 |
| 545 | 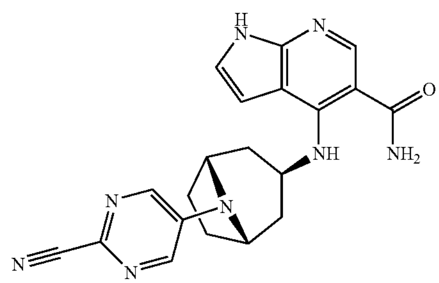 |
| 546 | cis |
| 547 | 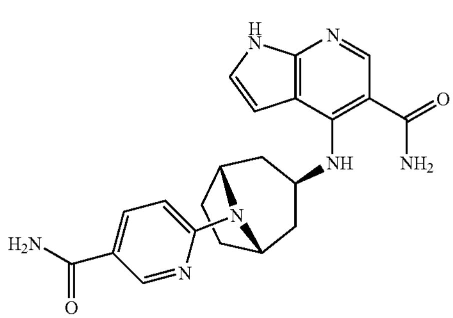 |

TABLE 71-continued

| Ex | Structure |
|---|---|
| 548 | 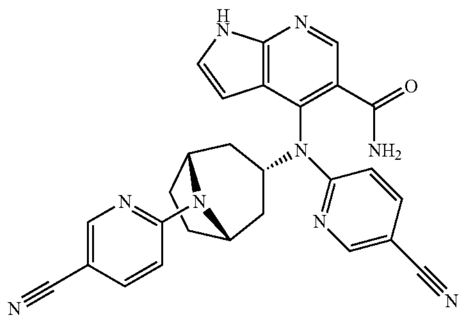 |
| 549 | 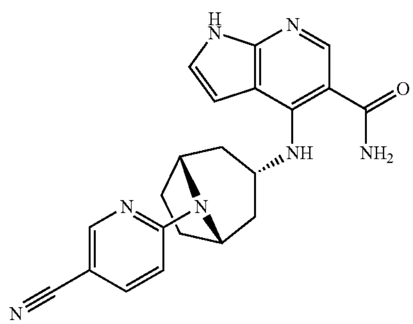 |
| 550 | 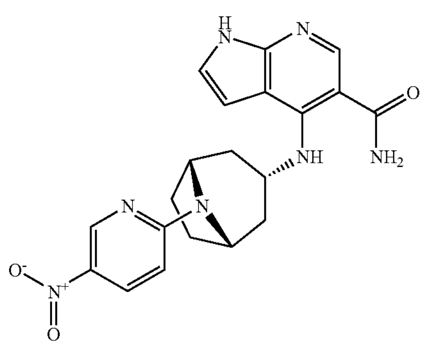 |
| 551 | 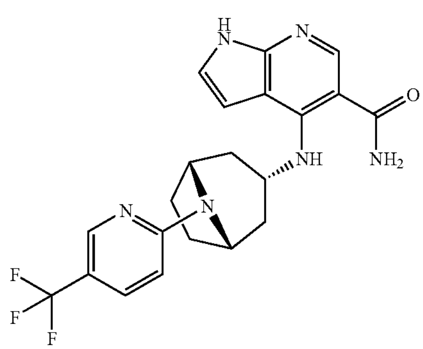 |

TABLE 71-continued
| Ex | Structure |
|---|---|
| 552 | 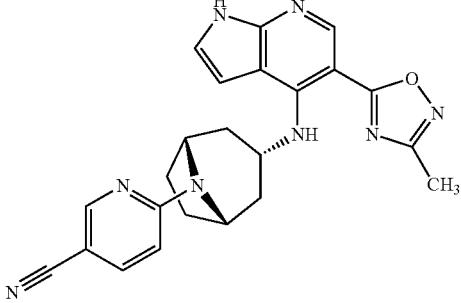 |
| 553 | 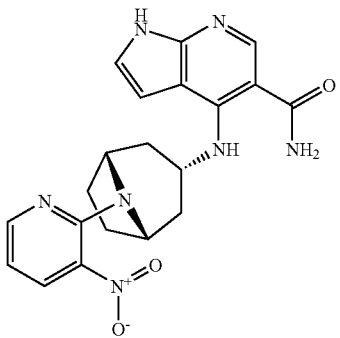 |
| 554 | 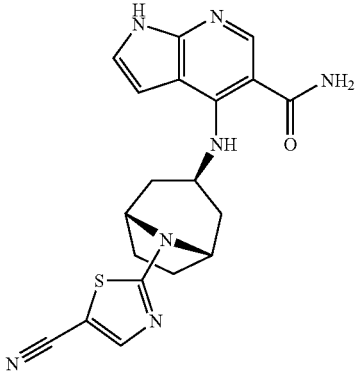 |
| 555 | 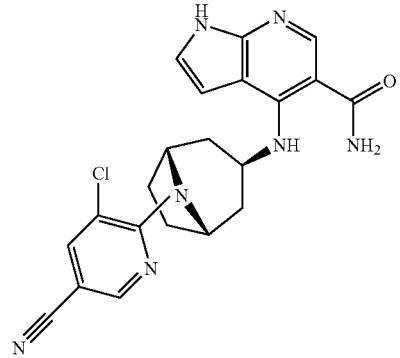 |

TABLE 71-continued

| Ex | Structure |
|---|---|
| 556 | 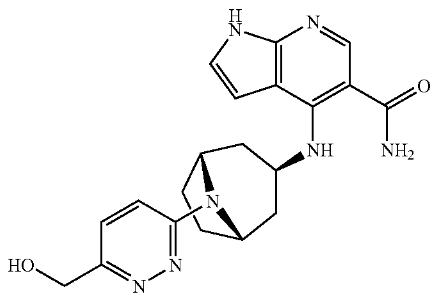 |
| 557 | 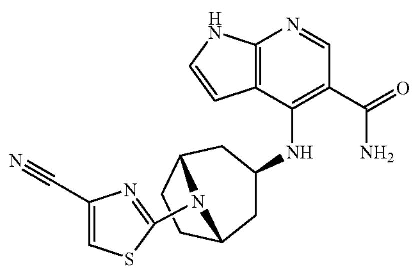 |
| 558 | 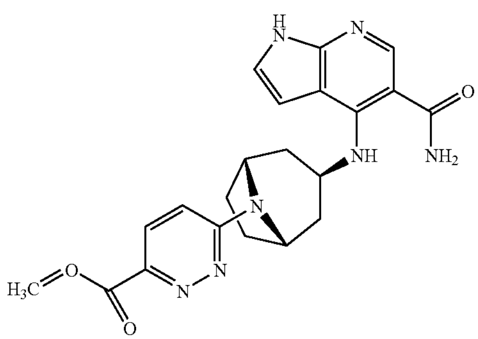 |
| 559 | 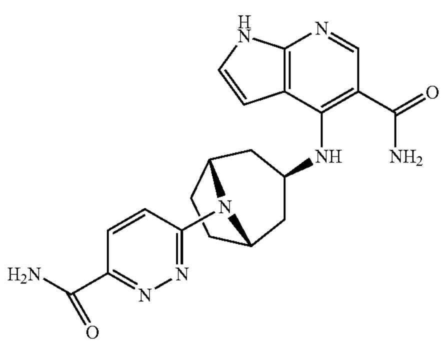 |
| 560 | 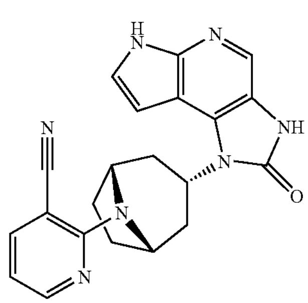 |

TABLE 71-continued

| Ex | Structure |
|---|---|
| 561 | 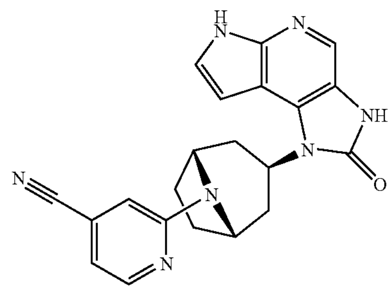 |
| 562 | 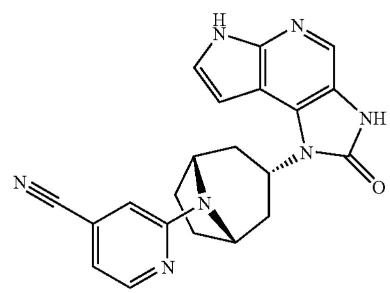 |
| 563 | 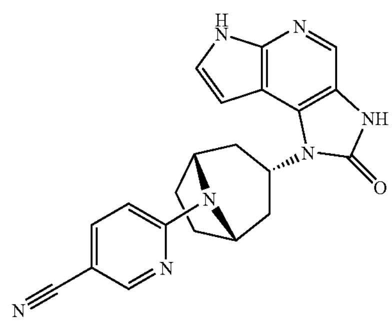 |
| 564 | 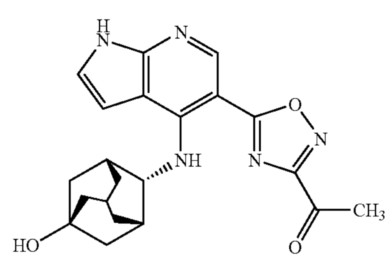 |
| 565 | 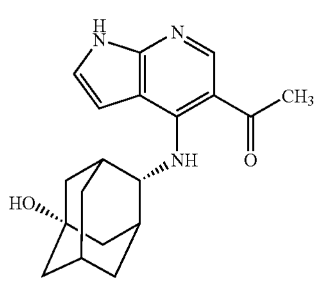 |

TABLE 71-continued
| Ex | Structure |
|---|---|
| 566 | 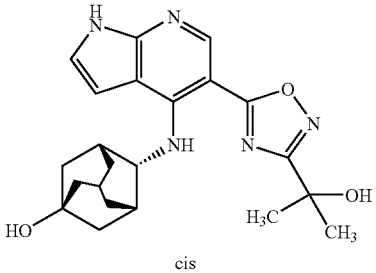 cis |
| 567 | 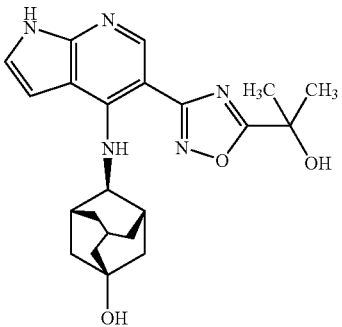 trans |
| 568 | 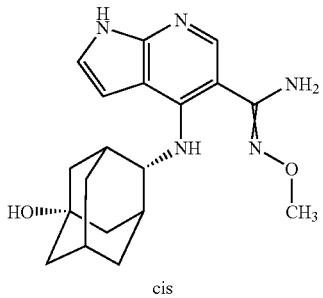 cis |
| 569 | 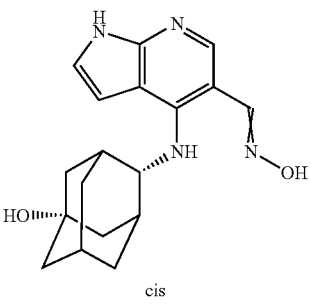 cis |
| 570 | 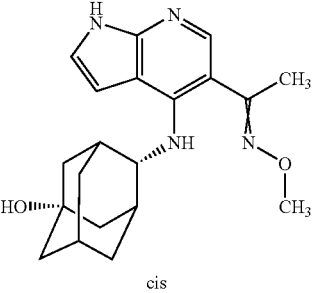 cis |

TABLE 71-continued
| Ex | Structure |
|---|---|
| 571 | 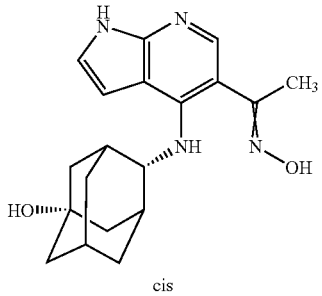 cis |
| 572 | 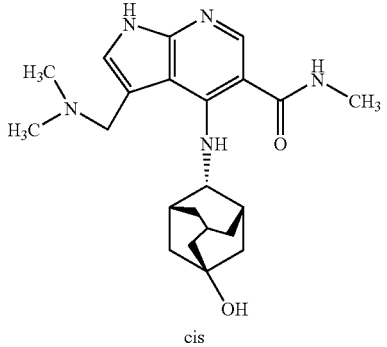 cis |
| 573 | 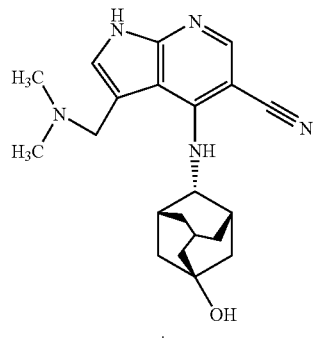 cis |
| 574 | 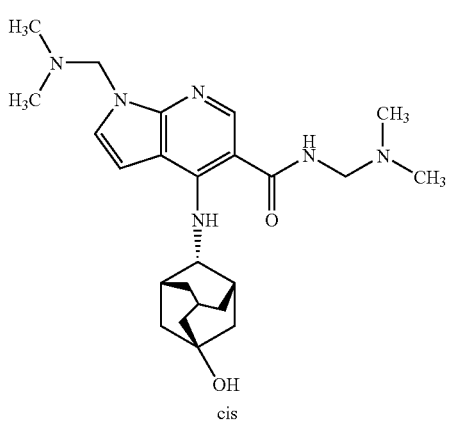 cis |

TABLE 71-continued
| Ex | Structure |
|---|---|
| 575 | 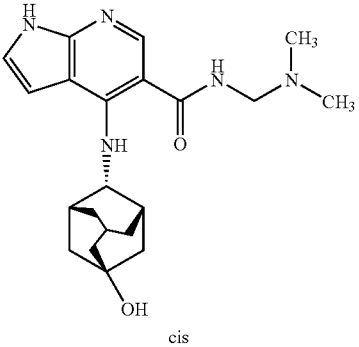 cis |
| 576 | 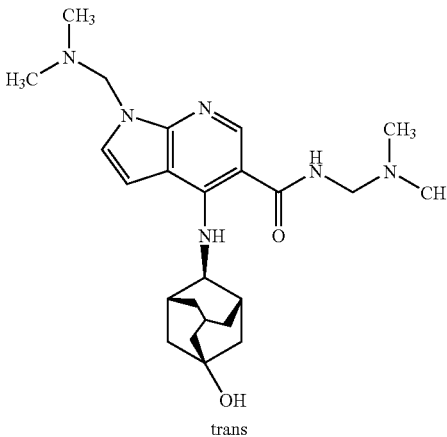 trans |
| 577 | 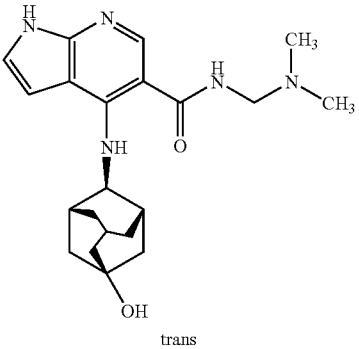 trans |
| 578 | 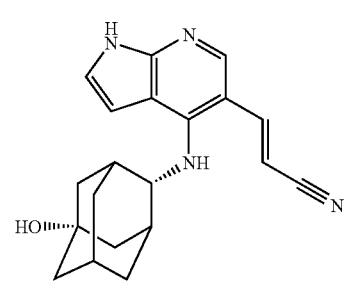 cis |

TABLE 71-continued

| Ex | Structure |
|---|---|
| 579 | 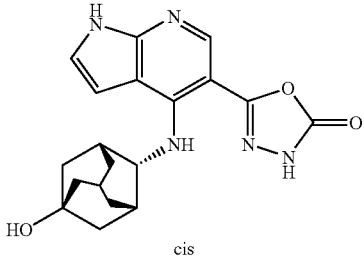 cis |

TABLE 72

| Ex | Ref-Ex | Data |
|---|---|---|
| 1 | — | 1H-NMR (400 MHz, d6-DMSO) δ: 1.44-2.38 (10H, m), 2.85 (3H, d, J = 4.8 Hz), 4.23 (1H, m), 4.53 (1H, s), 6.58 (1H, m), 7.27 (1H, m), 8.58 (1H, s), 8.78 (1H, m), 9.25 (1H, m), 11.79 (1H, s). MS: 409 (M + H)+ |
| 2 | — | MS: 313 (M + H)+ |
| 3 | — | 1H-NMR (400 MHz, d6-DMSO) δ: 1.52-2.46 (11H, m), 2.63-2.72 (2H, m), 4.49-4.53 (1H, m), 6.31-6.35 (1H, m), 7.42-7.45 (1H, m), 7.89-7.90 (1H, m), 10.75-10.77 (1H, m), 11.55-11.58 (1H, m), 12.10 (1H, br). MS: 353 (M + H)+ |
| 4 | — | 1H-NMR (400 MHz, d6-DMSO) δ: 1.51-2.13 (8H, m), 2.18-2.47 (3H, m), 2.65-2.76 (2H, m), 4.02-4.13 (2H, m), 4.50-4.55 (1H, m), 6.34-6.39 (1H, m), 7.44-7.46 (1H, m), 7.90 (1H, s), 8.14-8.39 (1H, m), 10.77-10.78 (1H, m), 11.58 (1H, s). MS: 391 (M + H)+ |
| 5 | — | MS: 404 (M + H)+ |
| 6 | — | MS: 371 (M + H)+ |
| 7 | — | MS: 508 (M + H)+ |
| 8 | — | MS: 409 (M + H)+ |
| 9 | — | MS: 542 (M + Na)+ |
| 10 | — | 1H-NMR (400 MHz, d6-DMSO) δ: 1.38-2.77 (18H, m), 4.38-4.54 (1H, m), 6.29-6.35 (1H, m), 7.25-7.37 (1H, m), 7.42-7.45 (1H, m), 7.89-7.90 (1H, m), 10.75 (1H, br), 11.57 (1H, s). MS: 380 (M + H)+ |
| 11 | — | 1H-NMR (400 MHz, d6-DMSO) δ: 1.46-2.29 (9H, m), 3.83 (3H, s), 4.10 (1H, m), 4.56 (1H, s), 6.50 (1H, m), 7.18 (1H, m), 8.55 (1H, s), 9.27 (1H, m), 11.68 (1H, s). MS: 342 (M + H)+ |
| 12 | — | 1H-NMR (400 MHz, d6-DMSO) δ: 1.43-1.54 (2H, m), 1.58-1.73 (4H, m), 1.73-1.86 (4H, m), 2.05-2.12 (1H, m), 2.17 (3H, s), 2.21-2.29 (2H, m), 4.08-4.16 (1H, m), 4.56 (1H, s), 4.99 (2H, s), 6.48-6.55 (1H, m), 7.18-7.24 (1H, m), 8.63 (1H, s), 9.12 (1H, d, J = 7.8 Hz), 11.74 (1H, s). MS: 384 (M + H)+ |
| 13 | — | 1H-NMR (400 MHz, d6-DMSO) δ: 1.43-1.53 (2H, m), 1.57-1.74 (4H, m), 1.74-1.90 (4H, m), 1.80 (3H, s), 2.04-2.12 (1H, m), 2.20-2.29 (2H, m), 4.06-4.14 (1H, m), 4.56 (1H, s), 6.45 (2H, brs), 6.47-6.52 (1H, m), 7.14-7.19 (1H, m), 8.76 (1H, s), 9.41 (1H, d, J = 8.0 Hz), 11.64 (1H, s). MS: 384 (M + H)+ |
| 14 | — | MS: 369 (M + H)+ |
| 15 | — | MS: 383 (M − H)− |
| 16 | — | 1H-NMR (400 MHz, d6-DMSO) δ: 1.57-1.63 (2H, m), 1.95-2.09 (3H, m), 2.17-2.24 (2H, m), 3.31-3.71 (6H, m), 4.62 (1H, s), 6.38-6.40 (1H, m), 7.44 (1H, t, J = 3.0 Hz), 7.90 (1H, s), 10.80 (1H, s), 11.58 (1H, s). MS: 334 (M + H)+ |
| 17 | — | 1H-NMR (400 MHz, d6-DMSO) δ: 1.51-1.56 (2H, m), 1.63-1.74 (4H, m), 1.83-1.91 (4H, m), 2.09-2.13 (1H, m), 2.30-2.34 (2H, m), 4.22-4.25 (1H, m), 4.58 (1H, s), 6.62 (1H, d, J = 3.6 Hz), 7.31 (1H, d, J = 3.6 Hz), 8.50 (1H, d, J = 7.6 Hz), 8.66 (1H, s), 12.00 (1H, brs). MS: 399 (M + Na)+ |
| 18 | — | 1H-NMR (400 MHz, d6-DMSO) δ: 1.49-2.48 (10H, m), 2.72-2.85 (2H, m), 4.61 (1H, s), 6.44-6.61 (1H, m), 7.64-7.71 (1H, m), 8.02-8.35 (4H, m), 11.59-11.64 (1H, m), 12.51-12.53 (1H, m). MS: 324 (M + H)+ |
| 19 | — | 1H-NMR (400 MHz, d6-DMSO) δ: 1.39-1.48 (2H, m), 1.59-1.74 (6H, m), 1.79-1.85 (2H, m), 2.02-2.07 (1H, m), 2.16-2.20 (2H, m), 4.45-4.48 (3H, m), 4.97 (1H, d, J = 7.4 Hz), |

TABLE 72-continued

| Ex | Ref-Ex | Data |
|---|---|---|
| | | 7.13-7.19 (2H, m), 7.36-7.40 (2H, m), 8.06 (1H, s), 8.48 (1H, s), 8.89 (1H, t, J = 5.9 Hz), 9.62. MS: 436 (M + H)+ |
| 20 | — | 1H-NMR (400 MHz, d6-DMSO) δ: 1.50-1.56 (2H, m), 1.62-1.72 (4H, m), 1.77-1.88 (4H, m), 2.08-2.11 (1H, m), 2.24-2.28 (2H, m), 3.56 (1H, m), 4.15-4.20 (1H, m), 6.67-6.69 (1H, m), 7.36-7.38 (1H, m), 8.28 (1H, s), 9.40 (1H, br), 10.36-10.41 (1H, m), 11.55 (1H, s), 12.53 (1H, brs), 14.29 (1H, br). MS: 343 (M − HCl + H)+ |
| 21 | — | 1H-NMR (400 MHz, d6-DMSO) δ: 0.86-1.37 (3H, m), 1.58-1.69 (2H, m), 2.20-2.24 (1H, m), 2.41-2.51 (2H, m), 2.77-2.80 (1H, m), 2.90 (1H, s), 3.03-3.05 (1H, m), 4.29-4.35 (2H, m), 6.63 (1H, s), 7.43 (1H, s), 7.87 (1H, s), 10.7 (1H, s), 11.6 (1H, s). MS: 299 (M + H)+ |
| 22 | — | 1H-NMR (400 MHz, d6-DMSO) δ: 1.68-1.93 (6H, m), 2.02-2.13 (3H, m), 2.40-2.47 (2H, m), 2.71-2.75 (2H, m), 4.04 (2H, d, J = 5.5 Hz), 4.50 (1H, s), 6.34-6.36 (1H, m), 7.45 (1H, t, J = 3.0 Hz), 7.90 (1H, s), 8.16 (1H, t, J = 5.6 Hz), 10.77 (1H, s), 11.59 (1H, s). MS: 391 (M + H)+ |
| 23 | — | 1H-NMR (400 MHz, d6-DMSO) δ: 1.71-1.89 (6H, m), 2.21-2.25 (3H, m), 2.53-2.56 (6H, m), 6.63 (1H, s), 7.46 (1H, t, J = 3.2 Hz), 7.90 (1H, s), 10.77 (1H, s), 11.61 (1H, s). MS: 309 (M + H)+ |
| 24 | — | MS: 342 (M + H)+ |
| 25 | — | MS: 312 (M + H)+ |
| 26 | — | 1H-NMR (400 MHz, d6-DMSO) δ: 1.33 (6H, d, J = 6.2 Hz), 1.46-1.86 (10H, m), 2.06 (1H, brs), 2.22 (2H, brs), 4.54 (1H, s), 5.05 (1H, d, J = 8.8 Hz), 5.18-5.15 (1H, m), 8.12 (1H, s), 8.63 (1H, s), 9.16 (1H, d, J = 8.8 Hz), 13.0 (1H, brs). MS: 371 (M + H)+ |
| 27 | — | 1H-NMR (400 MHz, d6-DMSO) δ: 1.41-1.45 (2H, m), 1.59-1.62 (2H, m), 1.65-1.70 (2H, m), 1.74-1.79 (2H, m), 1.88-1.92 (2H, m), 2.05-2.09 (1H, m), 2.18-2.21 (2H, m), 4.02-4.05 (1H, m), 4.32 (1H, s), 5.82 (2H, brs), 6.41-6.42 (1H, m), 7.09-7.11 (1H, m), 8.13 (1H, s), 8.96 (1H, d, J = 8.1 Hz), 9.50 (1H, s), 11.23 (1H, brs). MS: 342 (M + H)+ |
| 28 | — | 1H-NMR (400 MHz, d6-DMSO) δ: 1.45-1.57 (2H, m), 1.57-1.78 (4H, m), 1.78-1.97 (4H, m), 2.05-2.14 (1H, m), 2.26-2.34 (2H, m), 2.44 (3H, s), 4.17-4.24 (1H, m), 4.53 (1H, s), 6.56-6.61 (1H, m), 7.24-7.28 (1H, m), 8.58 (1H, s), 9.10 (1H, d, J = 7.8 Hz), 11.82 (1H, brs). MS: 366 (M + H)+ |
| 29 | — | 1H-NMR (400 MHz, d6-DMSO) δ: 1.49-2.32 (13H, m), 4.20-4.22 (1H, m), 4.55 (1H, s), 6.55-6.57 (1H, m), 7.25-7.27 (1H, m), 8.49 (1H, s), 8.79 (1H, d, J = 8.0 Hz), 9.27 (1H, s), 11.73 (1H, brs). MS: 374 (M + Na)+ |
| 30 | — | 1H-NMR (400 MHz, d6-DMSO) δ: 1.47-1.52 (2H, m), 1.62-1.64 (2H, m), 1.68-1.73 (2H, m), 1.81-1.91 (4H, m), 2.09-2.11 (1H, m), 2.28-2.31 (2H, m), 2.67 (3H, s), 4.19-4.22 (1H, m), 4.53 (1H, s), 6.53-6.54 (1H, m), 7.22-7.24 (1H, m), 7.88 (1H, d, J = 7.8 Hz), 8.69 (1H, s), 11.61 (1H, brs). MS: 366 (M + H)+ |
| 31 | — | 1H-NMR (400 MHz, d6-DMSO) δ: 1.44-1.49 (2H, m), 1.62-1.64 (2H, m), 1.74-1.79 (2H, m), 1.98-2.03 (4H, m), 2.15-2.18 (1H, m), 3.00-3.03 (2H, m), 4.45 (1H, brs), 4.61 (1H, brs), 5.77 (2H, s), 6.35-6.37 (1H, m), 7.33-7.35 (1H, m), 8.14 (1H, s), 11.44 (1H, brs). MS: 324 (M + H)+ |
| 32 | — | 1H-NMR (400 MHz, d6-DMSO) δ: 1.45-2.60 (13H, m), 3.27 (3H, s), 3.37-3.49 (4H, m), 4.44 (1H, m), 4.77 (1H, s), 6.66 (1H, m), 7.46 (1H, m), 8.71 (1H, s), 8.98 (1H, m), 10.92 (1H, s), 12.08 (1H, s). MS: 453 (M + H)+ |
| 33 | — | MS: 409 (M + H)+ |
| 34 | — | 1H-NMR (400 MHz, d6-DMSO) δ: 1.42-1.51 (2H, m), 1.58-1.75 (4H, m), 1.76-1.95 (4H, m), 2.05-2.13 (1H, m), 2.25-2.32 (2H, m), 4.11-4.19 (1H, m), 4.50 (1H, brs), 6.49-6.54 (1H, m), 7.17-7.22 (1H, m), 7.24 (2H, s), 8.06 (1H, s), 9.70 (1H, d, J = 7.6 Hz), 11.57 (1H, s). MS: 383 (M + H)+ |
| 35 | — | 1H-NMR (400 MHz, d6-DMSO) δ: 1.46-2.49 (10H, m), 2.72-2.80 (2H, m), 4.49-4.56 (2H, m), 4.60-4.67 (1H, m), 5.64-5.71 (1H, m), 6.34-6.39 (1H, m), 7.42-7.47 (1H, m), 7.89-7.92 (1H, m), 8.62 (1H, s), 10.77-10.83 (1H, m), 11.55-11.61 (1H, m). MS: 407 (M + H)+ |
| 36 | — | 1H-NMR (400 MHz, d6-DMSO) δ: 1.32-1.87 (12H, m), 2.09 (1H, m), 2.08 (2H, m), 4.18-4.22 (1H, m), 4.68 (1H, m), 6.70-6.71 (1H, m), 7.09 (1H, s), 7.25 (1H, s), 7.37-7.39 (1H, m), 8.32 (1H, s), 10.32 (1H, m), 12.68 (1H, brs). MS: 313 (M − 3HCl + H)+ |
| 37 | — | MS: 328 (M + H)+ |

TABLE 72-continued

| Ex | Ref-Ex | Data |
|---|---|---|
| 38 | — | MS: 378 (M + H)+ |
| 39 | — | 1H-NMR (400 MHz, d6-DMSO) δ: 1.54-1.63 (2H, m), 1.86-2.56 (10H, m), 2.77-2.85 (1H, m), 4.91 (1H, s), 6.64-6.66 (1H, m), 7.36-7.38 (1H, m), 8.50 (1H, s), 10.82 (1H, s), 11.93-11.95 (1H, m). MS: 387, 389 (M + H)+ |
| 40 | — | 1H-NMR (400 MHz, d6-DMSO) δ: 1.50-1.53 (2H, m), 1.64-2.01 (8H, m), 2.11 (1H, s), 2.32 (2H, s), 4.21 (1H, d, J = 7.5 Hz), 4.56 (2H, s), 6.58 (1H, s), 7.26 (1H, s), 8.61 (1H, s), 9.86 (1H, brs), 11.77 (1H, s). MS: 350 (M − H)− |
| 41 | — | 1H-NMR (400 MHz, d6-DMSO) δ: 1.54-1.60 (2H, m), 1.68-1.77 (4H, m), 1.78-1.86 (2H, m), 1.90-1.98 (2H, m), 2.12-2.16 (1H, m), 2.25-2.30 (2H, m), 2.68 (2H, t, J = 6.0 Hz), 3.57 (2H, t, J = 6.0 Hz), 4.08 (1H, d, J = 7.8 Hz), 6.46 (1H, dd, J = 2.0, 3.6 Hz), 7.04 (1H, br), 7.13 (1H, dd, J = 2.6, 3.6 Hz), 7.80 (1H, br), 8.38 (1H, s), 10.17 (1H, d, J = 8.2 Hz), 11.47 (1H, s). MS: 380 (M + H)+ |
| 42 | — | 1H-NMR (400 MHz, d6-DMSO) δ: 1.21 (3H, t, J = 7.2 Hz), 1.41-2.34 (13H, m), 3.33-3.42 (2H, m), 4.12-4.18 (1H, m), 4.50 (1H, s), 6.48-6.51 (1H, m), 7.17-7.21 (1H, m), 8.02 (1H, brd, J = 7.6 Hz), 8.42 (1H, brt, J = 5.6 Hz), 8.58 (1H, s), 11.51 (1H, brs). MS: 395 (M + H)+ |
| 43 | — | 1H-NMR (400 MHz, d6-DMSO) δ: 1.58-1.69 (2H, m), 1.86-1.96 (2H, m), 2.04-2.11 (1H, m), 2.14-2.23 (2H, m), 2.34-2.44 (4H, m), 2.61-2.71 (2H, m), 4.38-4.42 (1H, m), 6.63-6.67 (1H, m), 7.25 (1H, s), 7.35 (1H, br), 8.05 (1H, br), 10.58 (1H, s), 10.58 (1H, s), 11.94 (1H, s). MS: 389, 391 (M + H)+ |
| 44 | — | 1H-NMR (400 MHz, d6-DMSO) δ: 1.72-2.04 (9H, m), 2.29-2.91 (4H, m), 4.42-4.45 (1H, m), 6.37 (1H, d, J = 3.5 Hz), 7.44 (1H, d, J = 3.5 Hz), 7.90 (1H, s), 10.80 (1H, br, s), 11.58 (1H, s). MS: 327 (M + H)+ |
| 45 | — | MS: 366 (M + H)+ |
| 46 | — | MS: 388 (M + H)+ |
| 47 | — | MS: 406 (M + H)+ |
| 48 | — | 1H-NMR (400 MHz, d6-DMSO) δ: 1.84-1.97 (2H, m), 1.97-2.17 (4H, m), 2.19-2.34 (2H, m), 2.96 (3H, s), 4.12-4.24 (2H, m), 4.30-4.40 (1H, m), 6.44-6.51 (1H, m), 7.04 (1H, br), 7.08-7.15 (1H, m), 7.81 (1H, br), 8.38 (1H, s), 10.22 (1H, d, J = 7.6 Hz), 11.47 (1H, s). MS: 364 (M + H)+ |
| 49 | — | MS: 386 (M + H)+ |
| 50 | — | 1H-NMR (400 MHz, d6-DMSO) δ: 1.48-1.53 (2H, m), 1.62-1.65 (2H, m), 1.64 (6H, s), 1.69-1.74 (2H, m), 1.81-1.93 (4H, m), 2.08-2.12 (1H, m), 2.29-2.32 (2H, m), 4.19-4.23 (1H, m), 4.53 (1H, s), 6.07 (1H, s), 6.53-6.55 (1H, m), 7.22-7.24 (1H, m), 7.87-7.90 (1H, m), 8.72 (1H, s), 11.62 (1H, brs). MS: 410 (M + H)+ |
| 51 | — | MS: 389 (M + H)+ |
| 52 | — | 1H-NMR (400 MHz, d6-DMSO) δ: 1.45-2.47 (9H, m), 3.17 (1H, m), 4.10 (1H, m), 4.58 (1H, s), 6.51 (1H, m), 7.21 (1H, m), 8.22 (1H, s), 9.79 (1H, s), 9.90 (1H, m), 11.84 (1H, s). MS: 312 (M + H)+ |
| 53 | — | 1H-NMR (400 MHz, d6-DMSO) δ: 1.48-2.33 (8H, m), 3.90 (3H, s), 4.15 (1H, m), 4.51 (1H, s), 6.48 (1H, m), 7.17 (1H, m), 7.90 (1H, s), 8.43 (1H, s), 8.46 (1H, m), 11.50 (1H, s). MS: 341 (M + H)+ |
| 54 | — | MS: 410 (M + H)+ |
| 55 | — | 1H-NMR (400 MHz, d6-DMSO) δ: 1.37-1.48 (2H, m), 1.57-1.91 (8H, m), 2.04-2.08 (1H, m), 2.24-2.33 (2H, m), 3.71 (3H, s), 3.99-4.02 (1H, m), 4.50 (1H, s), 5.85-5.87 (1H, m), 6.34-6.38 (1H, m), 6.43-6.46 (1H, m), 7.14-7.17 (1H, m), 7.93-7.98 (1H, m), 8.20 (1H, s), 11.49 (1H, brs). MS: 368 (M + H)+ |
| 56 | — | MS: 361 (M + H)+ |
| 57 | — | 1H-NMR (400 MHz, d6-DMSO) δ: 1.39-1.45 (2H, m), 1.59-1.61 (2H, m), 1.64-1.70 (2H, m), 1.73-1.79 (2H, m), 1.85-1.91 (5H, m), 2.05-2.08 (1H, m), 2.20-2.23 (2H, m), 4.01-4.04 (1H, m), 4.42-4.52 (1H, m), 6.44 (1H, d, J = 3.6 Hz), 7.12 (1H, d, J = 3.6 Hz), 8.15 (1H, s), 10.05 (1H, br), 11.38 (1H, brs). MS: 326 (M − AcOH + H)+ |
| 58 | — | MS: 284 (M + H)+ |
| 59 | — | MS: 427 (M + Na)+, 403 (M − H)− |
| 60 | — | 1H-NMR (400 MHz, d6-DMSO) δ: 1.45-2.27 (7H, m), 3.12 (3H, s), 3.18 (3H, s), 4.07 (1H, m), 4.46 (1H, s), 6.44 (1H, m), 7.09 (1H, m), 8.58 (1H, s), 9.08 (1H, s), 10.56 (1H, m), 11.45 (1H, s). MS: 382.3 (M + H)+ |

TABLE 72-continued

| Ex | Ref-Ex | Data |
|---|---|---|
| 61 | — | 1H-NMR (400 MHz, d6-DMSO) δ: 1.45-2.69 (13H, m), 4.19 (1H, m), 4.53 (1H, s), 6.54 (1H, m), 7.25 (1H, m), 8.43 (1H, s), 8.75 (1H, m), 11.68 (1H, s). MS: 367.3 (M + H), 365.0 (M − H)− |
| 62 | — | 1H-NMR (400 MHz, d6-DMSO) δ: 1.39-1.45 (2H, m), 1.59-1.70 (4H, m), 1.75-1.81 (2H, m), 1.90-1.95 (2H, m), 2.06-2.09 (1H, m), 2.20-2.23 (2H, m), 3.35 (2H, m), 3.89 (2H, t, J = 9.6 Hz), 4.04-4.08 (1H, m), 4.43 (1H, br), 6.44 (1H, d, J = 3.6 Hz), 6.87 (1H, brs), 7.10 (1H, d, J = 3.5 Hz), 8.21 (1H, s), 10.97 (1H, d, J = 7.8 Hz), 11.34 (1H, brs). MS: 352 (M + H)+ |
| 63 | — | 1H-NMR (400 MHz, d6-DMSO) δ: 1.43-1.48 (2H, m), 1.60-1.63 (2H, m), 1.66-1.72 (2H, m), 1.77-1.83 (2H, m), 1.87-1.92 (2H, m), 2.06-2.10 (1H, m), 2.22-2.26 (2H, m), 4.05 (2H, t, J = 9.0 Hz), 4.09-4.13 (1H, m), 4.32 (2H, t, J = 9.0 Hz), 4.47 (1H, s), 6.47-6.49 (1H, m), 7.15-7.17 (1H, m), 8.34 (1H, s), 9.98 (1H, d, J = 7.8 Hz), 11.49 (1H, brs). MS: 353 (M + H)+ |
| 64 | — | 1H-NMR (400 MHz, d6-DMSO) δ: 1.02-1.05 (4H, m), 1.37-1.41 (9H, m), 1.53-1.67 (5H, m), 1.74-1.85 (2H, m), 2.01-2.23 (5H, m), 4.11-4.18 (2H, m), 6.29-6.36 (1H, m), 7.09-7.13 (1H, m), 7.28-7.32 (1H, m), 7.64-7.65 (1H, m), 11.11 (1H, brs). MS: 413 (M + H)+ |
| 65 | 1 | MS: 431 (M + H)+ |
| 66 | 1 | MS: 341 (M + H)+ |
| 67 | 1 | 1H-NMR (400 MHz, d6-DMSO) δ: 1.81-2.02 (8H, m), 2.09-2.62 (5H, m), 4.15-4.20 (1H, m), 6.43-6.46 (1H, m), 7.09 (1H, br), 7.14-7.16 (1H, m), 7.86 (1H, br), 8.40 (1H, s), 10.25 (1H, d, J = 8.2 Hz), 11.50 (1H, s). MS: 336 (M + H)+ |
| 68 | 1 | 1H-NMR (400 MHz, d6-DMSO) δ: 1.54-1.60 (2H, m), 1.86-1.97 (3H, m), 1.99-2.03 (2H, m), 2.08-2.15 (4H, m), 2.27-2.35 (2H, m), 4.27 (1H, d, J = 7.6 Hz), 6.50-6.52 (1H, m), 6.99 (1H, br), 7.14 (1H, t), 7.81 (1H, s), 8.38 (1H, s), 10.17 (1H, d, J = 8.3 Hz), 11.48 (1H, s). MS: 336 (M + H)+ |
| 69 | 1 | MS: 534 (M + H)+, 532 (M − H)− |
| 70 | 1 | MS: 376 (M + H)+ |
| 71 | 1 | MS: 402 (M + H)+ |
| 72 | 1 | 1H-NMR (400 MHz, d6-DMSO) δ: 1.39-1.43 (2H, m), 1.62-1.72 (4H, m), 1.79-1.89 (4H, m), 2.02-2.09 (1H, m), 2.11-2.17 (2H, m), 2.75 (3H, d, J = 4.3 Hz), 4.09-4.16 (1H, m), 4.49 (1H, brs), 6.39-6.41 (1H, m), 7.11-7.15 (1H, m), 8.18-8.25 (1H, m), 8.30 (1H, s), 9.87 (1H, d, J = 8.3 Hz), 11.42 (1H, brs). MS: 341 (M + H)+ |
| 73 | 1 | MS: 341 (M + H)+ |
| 74 | 1 | MS: 355 (M + H)+ |
| 75 | 1 | 1H-NMR (400 MHz, d6-DMSO) δ: 1.44-2.27 (9H, m), 2.76 (3H, d, J = 4.4 Hz), 4.23 (1H, m), 6.48 (1H, m), 7.14 (1H, m), 8.25 (1H, m), 8.32 (1H, s), 9.87 (1H, m), 11.45 (1H, s). MS: 343 (M + H)+ |
| 76 | 1 | MS: 355 (M + H)+ |
| 77 | 1 | MS: 440 (M + H)+ |
| 78 | 1 | 1H-NMR (400 MHz, d6-DMSO) δ: 1.43-2.36 (8H, m), 1.63 (6H, s), 4.22 (1H, m), 4.54 (1H, s), 5.90 (1H, s), 6.55 (1H, m), 7.25 (1H, m), 8.50 (1H, s), 8.80 (1H, s), 11.72 (1H, s). MS: 410 (M + H)+ |
| 79 | 1 | MS: 382 (M + H)+, 380 (M − H)− |
| 80 | 1 | MS: 417 (M + Na)+, 395 (M + H)+ |
| 81 | 1 | 1H-NMR (400 MHz, d6-DMSO) δ: 1.44-1.48 (2H, m), 1.60-1.68 (4H, m), 1.76-1.85 (4H, m), 2.06-2.08 (1H, m), 2.29-2.31 (2H, m), 4.13-4.15 (1H, m), 4.53-4.54 (1H, m), 5.99 (1H, d, J = 7.0 Hz), 6.68 (1H, d, J = 3.6 Hz), 7.28 (1H, d, J = 3.6 Hz), 8.11 (1H, s), 11.86 (1H, brs). MS: 331 (M + Na)+ |
| 82 | 1 | 1H-NMR (400 MHz, d6-DMSO) δ: 1.40-1.43 (2H, m), 1.64-1.69 (4H, m), 1.83-1.88 (4H, m), 2.05-2.07 (1H, m), 2.21-2.23 (2H, m), 4.25-4.27 (1H, m), 4.52 (1H, brs), 6.04 (1H, d, J = 7.2 Hz), 6.68 (1H, d, J = 3.5 Hz), 7.28 (1H, d, J = 3.4 Hz), 8.10 (1H, s), 11.85 (1H, brs). MS: 309 (M + H)+ |
| 83 | 1 | 1H-NMR (400 MHz, d6-DMSO) δ: 1.50-1.55 (2H, m), 1.62-1.73 (4H, m), 1.79-1.89 (4H, m), 2.08-2.12 (1H, m), 2.28-2.32 (2H, m), 4.24-4.28 (1H, m), 6.68-6.71 (1H, m), 7.39-7.41 (1H, m), 8.42 (1H, s), 8.44-8.48 (1H, m), 12.48 (1H, brs). MS: 368 (M + H)+ |
| 84 | 1 | 1H-NMR (400 MHz, d6-DMSO) δ: 1.50-1.57 (2H, m), 1.81-1.87 (2H, m), 1.92-2.00 (5H, m), 2.04-2.09 (2H, m), 2.18-2.24 (2H, m), 3.62 (3H, s), 4.30-4.33 (1H, m), 6.16 (1H, d, J = 7.1 Hz), 6.72 (1H, d, J = 3.4 Hz), 7.28 (1H, d, J = 3.3 Hz), 8.11 (1H, s), 11.85 (1H, brs). MS: 373 (M + Na)+ |

TABLE 72-continued

| Ex | Ref-Ex | Data |
|---|---|---|
| 85 | 1 | 1H-NMR (400 MHz, d6-DMSO) δ: 1.70-1.75 (2H, m), 1.78-1.91 (5H, m), 1.94-2.02 (2H, m), 2.04-2.12 (2H, m), 2.19-2.26 (2H, m), 3.60 (3H, s), 4.25-4.28 (1H, m), 6.19 (1H, d, J = 7.1 Hz), 6.70-6.72 (1H, m), 7.27-7.29 (1H, m), 8.10 (1H, s), 11.85 (1H, brs). MS: 373 (M + Na)+ |
| 86 | 1 | 1H-NMR (400 MHz, d6-DMSO) δ: 1.48-1.53 (2H, m), 1.63-1.74 (4H, m), 1.81-1.91 (4H, m), 2.08-2.11 (1H, m), 2.21 (3H, s), 2.29-2.36 (4H, m), 2.39-2.42 (2H, m), 3.49-3.53 (2H, m), 3.66-3.70 (2H, m), 4.19-4.23 (1H, m), 4.49 (1H, s), 6.57-6.59 (1H, m), 7.27-7.29 (1H, m), 8.64 (1H, s), 8.83-8.86 (1H, m), 11.86 (1H, brs). MS: 478 (M + H)+ |
| 87 | 1 | 1H-NMR (400 MHz, d6-DMSO) δ: 1.46-1.52 (2H, m), 1.61-1.81 (8H, m), 2.05-2.08 (1H, m), 2.20-2.24 (2H, m), 4.09-4.12 (1H, m), 4.53 (1H, s), 6.63-6.65 (1H, m), 6.82-6.86 (1H, m), 7.30-7.32 (1H, m), 8.65 (1H, s), 10.52-10.56 (1H, m), 11.80 (1H, brs). MS: 352 (M + H)+ |
| 88 | 1 | 1H-NMR (400 MHz, d6-DMSO) δ: 0.85-0.93 (1H, m), 1.34, 1.40 (9H, s), 1.47-1.53 (1H, m), 1.67-1.79 (1H, m), 1.85-1.92 (3H, m), 1.99-2.06 (3H, m), 2.13-2.34 (4H, m), 4.21-4.25, 4.30-4.34 (1H, m), 6.37-6.41, 6.54-6.56 (1H, m), 6.51-6.63, 6.57-6.59 (1H, m), 7.28-7.29 (1H, m), 8.06-8.32 (2H, m), 8.63, 8.64 (1H, s), 8.87-8.89, 8.99-9.01 (1H, m), 11.88 (1H, brs). MS: 516 (M + Na)+ |
| 89 | 1 | 1H-NMR (400 MHz, d6-DMSO) δ: 1.31-1.36 (1H, m), 1.47-1.53 (3H, m), 1.59-1.64 (1H, m), 1.67-1.80 (2H, m), 1.89-2.00 (3H, m), 2.06-2.11 (1H, m), 2.16-2.20 (2H, m), 3.02-3.09 (2H, m), 4.27-4.44 (2H, m), 6.52-6.54, 6.61-6.63 (1H, m), 7.26-7.29 (1H, m), 8.10-8.31 (2H, m), 8.63 (1H, s), 8.92-8.95, 9.04-9.07 (1H, m), 11.86 (1H, brs). MS: 431 (M + Na)+ |
| 90 | 1 | 1H-NMR (400 MHz, d6-DMSO) δ: 1.48-1.53 (2H, m), 1.62-1.73 (4H, m), 1.81-1.92 (4H, m), 2.09-2.12 (1H, m), 2.29-2.32 (2H, m), 3.46 (3H, s), 4.20-4.24 (1H, m), 4.54 (1H, s), 4.86 (2H, s), 6.54-6.56 (1H, m), 7.24-7.25 (1H, m), 7.84-7.86 (1H, m), 8.72 (1H, s), 11.65 (1H, s). MS: 396 (M + H)+ |
| 91 | 1 | 1H-NMR (400 MHz, d6-DMSO) δ: 0.74-0.88 (1H, m), 1.13-1.75 (7H, m), 2.10-2.30 (2H, m), 4.27-4.44 (1H, m), 6.55 (1H, brs), 6.56 (1H, d, J = 3.4 Hz), 7.11 (1H, m), 7.65 (1H, d, J = 3.4 Hz), 8.35 (1H, s), 9.86 (1H, d, J = 7.9 Hz), 11.43 (1H, brs). MS: 271 (M + H)+ |
| 92 | 1 | 1H-NMR (400 MHz, d6-DMSO) δ: 1.75-2.33 (5H, m), 2.97-3.36 (5H, m), 3.73-3.88 (1H, m), 4.38-4.64 (1H, d, J = 3.4 Hz), 7.17 (1H, brs), 7.23 (1H, d, J = 3.4 Hz), 7.92 (1H, brs), 8.44 (1H, s), 10.25 (1H, d, J = 7.8 Hz), 11.68 (1H, s). MS: 286 (M + H)+ |
| 93 | 1 | 1H-NMR (400 MHz, d6-DMSO) δ: 1.29-2.02 (5H, m), 2.41 (1H, dd, J = 3.8, 13.8 Hz), 2.65-2.83 (4H, m), 4.05-4.20 (1H, m), 4.36 (1H, t, J = 5.1 Hz), 6.51-6.58 (1H, m), 6.88-7.94 (3H, m), 8.37 (1H, s), 9.99 (1H, d, J = 7.9 Hz), 11.46 (1H, brs). MS: 286 (M + H)+ |
| 94 | 1 | 1H-NMR (400 MHz, d6-DMSO) δ: 1.12-1.65 (7H, m), 1.82-1.97 (1H, m), 2.25-2.34 (2H, m), 3.85-3.96 (1H, m), 6.57 (1H, d, J = 3.3 Hz), 7.12 (1H, d, J = 2.4 Hz), 6.78-7.92 (2H, brs), 8.35 (1H, s), 9.57 (1H, d, J = 7.1 Hz), 11.5 (1H, brs). MS: 271 (M + H)+ |
| 95 | 1 | 1H-NMR (400 MHz, d6-DMSO) δ: 1.17-1.64 (10H, m) 2.0-2.07 (1H, m), 2.18-2.22 (1H, m), 2.38-2.40 (1H, m), 3.18-3.23 (1H, m), 4.14 (1H, t, J = 7.8 Hz), 4.25 (2H, q, J = 7.0 Hz), 4.46 (1H, t, J = 4.8 Hz), 7.17 (1H, s), 6.70 (1H, s), 8.51 (1H, s), 8.78 (1H, d, J = 8.0 Hz), 11.7 (1H, s). MS: 330 (M + H)+ |
| 96 | 1 | 1HNMR (400 MHz, d6-DMSO) δ: 1.38-1.86 (10H, m), 2.07 (1H, brs), 2.19 (2H, brs), 2.29 (3H, s), 3.97 (1H, d, J = 8.0 Hz), 4.49 (1H, s), 6.14 (1H, s), 6.98 (1H, brs), 7.78 (1H, brs), 8.28 (1H, s), 9.99 (1H, d, J = 8.0 Hz), 11.3 (1H, s). MS: 341 (M + H)+ |
| 97 | 1 | 1HNMR (400 MHz, CDCl3) δ: 1.35-2.67 (13H, m), 3.75 (1H, brs), 4.05-4.20 (1H, m), 5.00-5.12 (1H, brs), 6.45-6.48 (1H, m), 7.15-7.16 (1H, m), 7.95 (1H, d, J = 4.7 Hz), 10.0 (1H, brs).. MS: 302 (M + H)+ |
| 98 | 1 | 1HNMR (400 MHz, d6-DMSO) δ: 1.40-2.30 (13H, m), 3.92-3.96 (1H, m), 4.44 (1H, s), 5.27-5.29 (1H, m), 6.51 (1H, dd, J = 2.0, 3.2 Hz), 7.21 (1H, dd, J = 2.8, 3.2 Hz), 7.88 (1H, d, J = 4.8 Hz), 11.3 (1H, s). MS: 302 (M + H)+ |
| 99 | 1 | 1H-NMR (400 MHz, d6-DMSO) δ: 1.13-1.40 (3H, m), 1.48-1.63 (3H, m), 1.93-2.00 (1H, m), 2.14-2.18 (1H, m), 2.35-2.38 (1H, m), 3.12-3.20 (1H, m), 3.41-3.47 (1H, m), |

TABLE 72-continued

| Ex | Ref-Ex | Data |
|---|---|---|
| | | 4.04-4.10 (1H, m), 4.38-4.41 (1H, m), 6.61-6.65 (1H, m), 6.81-7.03 (1H, br), 7.09-7.13 (1H, m), 7.61-7.86 (1H, br), 8.33 (1H, s), 9.64 (1H, d, J = 8.0 Hz), 11.45 (1H, brs). MS: 301 (M + H)+. |
| 100 | 1 | 1H-NMR (400 MHz, d6-DMSO) δ: 1.38-2.28 (12H, m), 2.87-2.98 (1H, m), 3.63 (3H, s), 4.45-4.57 (1H, m), 6.42-6.45 (1H, m), 6.80-7.13 (1H, br), 7.18-7.22 (1H, m), 7.51-7.93 (1H, br), 8.34 (1H, s), 9.44 (1H, d, J = 8.0 Hz), 11.49 (1H, brs). MS: 357 (M + H)+. |
| 101 | 1 | 1H-NMR (400 MHz, d6-DMSO) δ: 1.33 (3H, t, J = 8.0 Hz), 1.47-1.51 (2H, m), 1.61-1.72 (4H, m), 1.78-1.85 (4H, m), 2.07-2.10 (1H, m), 2.23-2.27 (2H, m), 4.09-4.12 (1H, m), 4.30 (2H, q, J = 8.0 Hz), 4.56 (1H, brs), 6.48-6.50 (1H, m), 7.17-7.19 (1H, m), 8.56 (1H, s), 9.28 (1H, d, J = 7.6 Hz), 11.69 (1H, brs). MS: 356 (M + H)+. |
| 102 | 1 | 1H-NMR (400 MHz, d6-DMSO) δ: 1.32 (3H, t, J = 6.8 Hz), 1.43-1.50 (2H, m), 1.65-1.73 (4H, m), 1.78-1.90 (4H, m), 2.06-2.10 (1H, m), 2.16-2.21 (2H, m), 4.19-4.23 (1H, m), 4.29 (2H, q, J = 6.8 Hz), 4.54 (1H, brs), 6.45-6.46 (1H, m), 7.18-7.20 (1H, m), 8.56 (1H, s), 9.26 (1H, d, J = 8.0 Hz), 11.68 (1H, brs). MS: 356 (M + H)+. |
| 103 | 1 | 1H-NMR (400 MHz, d6-DMSO) δ: 1.38-1.48 (2H, m), 1.59-1.70 (4H, m), 1.73-1.86 (4H, m), 2.03-2.09 (1H, m), 2.11-2.16 (1H, m), 2.18-2.23 (1H, m), 3.258 (1.5H, s), 3.263 (1.5H, s), 3.53 (1.5H, s), 3.54 (1.5H, s), 4.00-4.05 (0.5H, m), 4.10-4.15 (0.5H, m), 4.50 (0.5H, brs), 4.52 (0.5H, brs), 6.42-6.45 (0.5H, m), 6.46-6.48 (0.5H, m), 7.16-7.19 (1H, m), 7.89 (0.5H, d, J = 8.4 Hz), 7.94 (0.5H, d, J = 8.4 Hz), 8.15-8.16 (1H, m), 11.52 (1H, brs). MS: 371 (M + H)+. |
| 104 | 1 | 1H-NMR (400 MHz, d6-DMSO) δ: 1.46-2.24 (13H, m), 4.31-4.33 (1H, m), 4.52 (1H, s), 6.52-6.53 (1H, m), 7.25-7.27 (1H, m), 8.49 (1H, s), 8.76 (1H, d, J = 8.0 Hz), 9.25 (1H, s), 11.72 (1H, s). MS: 352 (M + H)+ |
| 105 | 1 | 1H-NMR (400 MHz, d6-DMSO) δ: 1.51-2.17 (13H, m), 3.07-3.08 (2H, m), 4.31-4.32 (1H, m), 4.40-4.42 (1H, m), 6.50-6.51 (1H, m), 7.24-7.25 (1H, m), 8.49 (1H, s), 8.84 (1H, d, J = 8.0 Hz), 9.25 (1H, s), 11.71 (1H, s). MS: 366.3 (M + H)+ |
| 106 | 1 | 1H-NMR (400 MHz, d6-DMSO) δ: 1.13-2.19 (13H, m), 2.97-3.00 (2H, m), 3.82-3.83 (1H, m), 4.31-4.40 (1H, m), 6.57-6.58 (1H, m), 7.26-7.27 (1H, m), 8.48 (1H, s), 8.78 (1H, d, J = 8.0 Hz), 9.24-9.25 (1H, m), 11.70 (1H, s). MS: 366 (M + H)+ |
| 107 | 1 | H-NMR (400 MHz, d6-DMSO) δ: 1.51-2.31 (13H, m), 4.17-4.18 (1H, m), 4.58 (1H, brs), 6.56 (1H, d, J = 3.4 Hz), 7.22 (1H, d, J = 2.7 Hz), 7.50-7.57 (5H, m), 8.06 (1H, s), 10.58 (1H, d, J = 7.9 Hz), 11.82 (1H, brs). MS: 388 (M + H)+. |
| 108 | 1 | 1H-NMR (400 MHz, d6-DMSO) δ: 0.88-2.26 (13H, m), 4.10-4.11 (1H, m), 4.58 (1H, brs), 4.60 (2H, s), 4.82 (2H, s), 6.51-6.52 (1H, s), 7.17-7.18 (1H, s), 7.30-7.38 (5H, m), 10.52 (1H, d, J = 7.9 Hz), 11.76 (1H, brs). MS: 432 (M + H)+ |
| 109 | 1 | 1H-NMR (400 MHz, d6-DMSO) δ: 1.48-2.25 (13H, m), 3.36 (3H, s), 4.10-4.12 (1H, m), 4.57 (1H, s), 4.69 (2H, s), 6.51-6.52 (1H, m), 7.16-7.18 (1H, m), 8.49 (1H, s), 10.51 (1H, d, J = 8.0 Hz), 11.76 (1H, brs). MS: 356 (M + H)+ |
| 110 | 1 | 1H-NMR (400 MHz, d6-DMSO) δ: 1.46-2.25 (14H, m), 4.10 (1H, d, J = 7.9 Hz), 5.48 (2H, s), 6.51-6.53 (1H, m), 6.92-6.99 (3H, m), 7.18 (1H, brs), 7.28-7.30 (2H, m), 8.65 (1H, s), 10.44 (1H, d, J = 7.9 Hz), 11.8 (1H, s). MS: 418 (M + H)+ |
| 111 | 1 | 1H-NMR (400 MHz, d6-DMSO) δ: 1.45-2.19 (13H, m), 4.21-4.23 (1H, m), 4.51 (1H, s), 4.59 (2H, s), 4.80 (2H, s), 6.46-6.48 (1H, m), 7.17-7.18 (1H, m), 7.29-7.37 (6H, m), 10.45 (1H, d, J = 8.0 Hz), 11.73 (1H, s). MS: 432 (M + H)+ |
| 112 | 1 | 1H-NMR (400 MHz, d6-DMSO) δ: 1.23-2.33 (13H, m), 2.99-3.11 (2H, m), 4.21 (1H, brs), 4.40-4.41 (1H, m), 4.59 (2H, s), 4.79 (2H, s), 6.51 (1H, s), 7.16-7.37 (6H, m), 8.51 (1H, s), 10.50 (1H, d, J = 8.0 Hz), 11.72 (1H, s). MS: 446 (M + H)+ |
| 113 | 1 | 1H-NMR (400 MHz, d6-DMSO) δ: 1.47-2.33 (13H, m), 3.53-3.75 (2H, m), 4.16-4.17 (1H, m), 4.40 (1H, s), 4.87 (1H, s), 6.19-6.20 (1H, m), 6.82 (1H, s), 7.21-7.22 (1H, m), 9.80 (1H, d, J = 8.0 Hz), 11.64 (1H, s). MS: 398 (M + H)+ |
| 114 | 1 | 1H-NMR (400 MHz, d6-DMSO) δ: 1.49-1.52 (2H, m), 1.62 (6H, s), 1.64-2.31 (11H, m), 4.19-4.20 (1H, m), 4.54 (1H, s), 6.27 (1H, s), 6.53 (1H, brs), 7.20-7.22 (1H, m), 8.30 (1H, s), 9.80 (1H, d, J = 8.0 Hz), 11.64 (1H, brs). MS: 426 (M + H)+ |
| 115 | 1 | 1H-NMR (400 MHz, d6-DMSO) δ: 1.49-2.32 (13H, m), 2.82 (3H, d, J = 4.8 Hz), 4.27-4.28 (1H, m), 4.52 (1H, s), |

TABLE 72-continued

| Ex | Ref-Ex | Data |
|---|---|---|
| | | 6.55-6.57 (1H, m), 7.22-7.23 (1H, m), 8.83 (1H, m), 9.31-9.32 (1H, m), 9.82-9.83 (1H, m), 11.76 (1H, s). MS: 424.9 (M − H)− |
| 116 | 1 | 1H-NMR (400 MHz, d6-DMSO) δ: 1.27-2.77 (24H, m), 3.75-3.77 (1H, m), 4.24-4.25 (1H, m), 4.53 (1H, s), 6.55-6.56 (1H, m), 7.23-7.24 (1H, m), 8.38 (1H, s), 9.24 (1H, d, J = 8.0 Hz), 9.80 (1H, d, J = 7.6 Hz), 11.77 (1H, brs). MS: 508 (M + H)+ |
| 117 | 1 | 1H-NMR (400 MHz, d6-DMSO) δ: 1.55-1.61 (2H, m), 1.71-1.75 (2H, m), 1.81-2.05 (10H, m), 4.16-4.21 (1H, m), 6.40-6.43 (1H, m), 6.81-7.06 (1H, br), 7.10-7.13 (1H, m), 7.53-7.91 (1H, br), 8.37 (1H, s), 10.17 (1H, d, J = 8.0 Hz), 11.44 (1H, brs). MS: 311 (M + H)+. |
| 118 | 1 | 1H-NMR (400 MHz, d6-DMSO) δ: 1.64-1.74 (6H, m), 2.02-2.15 (9H, m), 6.66-6.69 (1H, m), 6.96-7.13 (1H, br), 7.15-7.18 (1H, m), 7.66-7.93 (1H, br), 8.33 (1H, s), 9.70 (1H, brs), 11.45 (1H, brs). MS: 311 (M + H)+. |
| 119 | 1 | 1H-NMR (400 MHz, d6-DMSO) δ: 1.37-1.43 (2H, m), 1.91-2.10 (11H, m), 3.77-3.81 (1H, m), 4.68-4.70 (1H, m), 6.67-6.70 (1H, m), 6.92-7.14 (1H, br), 7.16-7.19 (1H, m), 7.66-7.91 (1H, br), 8.33 (1H, s), 9.68 (1H, brs), 11.45 (1H, brs). MS: 349 (M + Na)+. |
| 120 | 1 | 1H-NMR (400 MHz, d6-DMSO) δ: 1.45-1.66 (6H, m), 1.88-1.95 (6H, m), 2.21-2.26 (2H, m), 4.63 (1H, brs), 6.63-6.66 (1H, m), 6.93-7.15 (1H, br), 7.17-7.20 (1H, m), 7.70-7.91 (1H, br), 8.34 (1H, s), 9.70 (1H, brs), 11.46 (1H, brs). MS: 349 (M + Na)+. |
| 121 | 1 | 1H-NMR (400 MHz, d6-DMSO) δ: 1.38-1.44 (2H, m), 1.63-1.71 (4H, m), 1.80-1.87 (4H, m), 2.02-2.07 (1H, m), 2.12-2.16 (2H, m), 4.11-4.15 (1H, m), 4.50 (1H, brs), 6.39-6.41 (1H, m), 6.90-7.05 (1H, br), 7.11-7.14 (1H, m), 7.70-7.83 (1H, br), 8.37 (1H, s), 10.09 (1H, d, J = 8.0 Hz), 11.45 (1H, brs). MS: 327 (M + H)+ |
| 122 | 1 | 1H-NMR (400 MHz, d6-DMSO) δ: 1.44-1.50 (2H, m), 1.58-1.71 (4H, m), 1.76-1.86 (4H, m), 2.06-2.10 (1H, m), 2.21-2.25 (2H, m), 4.05-4.10 (1H, m), 4.54 (1H, brs), 6.51-6.53 (1H, m), 7.08-7.26 (2H, m), 7.88-8.03 (1H, br), 8.42 (1H, s), 10.43-10.51 (1H, m), 11.80 (1H, s). MS: 327 (M + H)+. |
| 123 | 1 | 1H-NMR (400 MHz, d6-DMSO) δ: 1.41-1.48 (0.8H, m), 1.49-1.56 (1.2H, m), 1.65-1.97 (8H, m), 2.08-2.16 (1H, m), 2.17-2.23 (0.8H, m), 2.23-2.28 (1.2H, m), 4.05-4.11 (0.6H, m), 4.15-4.20 (0.4H, m), 6.44-6.48 (1H, m), 6.87-7.11 (1H, br), 7.11-7.15 (1H, m), 7.66-7.91 (1H, br), 8.37 (0.4H, s), 8.38 (0.6H, s), 10.12 (0.4H, d, J = 8.4 Hz), 10.14 (0.6H, d, J = 8.4 Hz), 11.45 (1H, brs). MS: 341 (M + H)+. |
| 124 | 1 | 1H-NMR (400 MHz, d6-DMSO) δ: 1.43-1.51 (1H, m), 1.68-1.96 (8H, m), 2.01-2.31 (3H, m), 2.33-2.40 (1H, m), 4.06-4.12 (0.5H, m), 4.21-4.28 (0.5H, m), 6.45-6.53 (1H, m), 6.88-7.20 (2H, m), 7.65-7.95 (1H, br), 8.38 (0.5H, s), 8.39 (0.5H, s), 10.10 (0.5H, d, J = 8.4 Hz), 10.18 (0.5H, d, J = 8.4 Hz), 11.48 (1H, brs). MS: 329 (M + H)+. |
| 125 | 1 | 1H-NMR (400 MHz, d6-DMSO) δ: 1.41-1.48 (2H, m), 1.69-1.78 (4H, m), 1.82-1.98 (4H, m), 2.08-2.13 (1H, m), 2.17-2.23 (2H, m), 3.15 (3H, s), 4.15-4.20 (1H, m), 6.44-6.47 (1H, m), 6.86-7.10 (1H, br), 7.11-7.15 (1H, m), 7.62-7.91 (1H, br), 8.37 (1H, s), 10.12 (1H, d, J = 8.4 Hz), 11.45 (1H, brs). MS: 341 (M + H)+. |
| 126 | 1 | 1H-NMR (400 MHz, d6-DMSO) δ: 1.49-1.56 (2H, m), 1.64-1.75 (4H, m), 1.77-1.95 (4H, m), 2.10-2.15 (1H, m), 2.23-2.28 (2H, m), 3.12 (3H, s), 4.05-4.11 (1H, m), 6.44-6.48 (1H, m), 6.89-7.10 (1H, br), 7.11-7.15 (1H, m), 7.61-7.93 (1H, br), 8.38 (1H, s), 10.14 (1H, d), 11.45 (1H, brs). MS: 341 (M + H)+. |
| 127 | 1 | 1H-NMR (400 MHz, d6-DMSO) δ: 1.68-1.76 (4H, m), 1.79-1.89 (4H, m), 2.01-2.09 (2H, m), 2.19-2.25 (1H, m), 2.32-2.38 (2H, m), 4.06-4.12 (1H, m), 6.45-6.49 (1H, m), 6.91-7.18 (2H, m), 7.65-7.92 (1H, br), 8.39 (1H, s), 10.18 (1H, d, J = 8.4 Hz), 11.48 (1H, brs). MS: 351 (M + Na)+. |
| 128 | 1 | 1H-NMR (400 MHz, d6-DMSO) δ: 1.06 (3H, t, J = 8.0 Hz), 1.53-1.59 (2H, m), 1.68-1.75 (4H, m), 1.80-1.94 (4H, m), 2.10-2.14 (1H, m), 2.24-2.28 (2H, m), 3.42 (2H, q, J = 8.0 Hz), 4.08-4.13 (1H, m), 6.51-6.53 (1H, m), 7.12-7.31 (2H, m), 7.83-8.03 (1H, br), 8.42 (1H, s), 10.43 (1H, d, J = 8.0 Hz), 11.74 (1H, brs). MS: 355 (M + H)+. |
| 129 | 1 | 1H-NMR (400 MHz, d6-DMSO) δ: 1.53-2.20 (13H, m), 3.58-3.64 (3H, m), 4.19-4.29 (1H, m), 6.54-6.58 (1H, m), 7.19-7.47 (2H, m), 7.96-8.16 (1H, br), 8.46 (1H, s), 10.65-10.72 (1H, m), 11.98 (1H, brs). MS: 369 (M + H)+. |

TABLE 72-continued

| Ex | Ref-Ex | Data |
|---|---|---|
| 130 | 1 | 1H-NMR (400 MHz, d6-DMSO) δ: 1.44-1.49 (2H, m), 1.82-1.94 (6H, m), 2.12-2.29 (5H, m), 4.22-4.26 (1H, m), 6.47-6.50 (1H, m), 6.86-7.17 (2H, m), 7.66-7.93 (1H, br), 8.38 (1H, s), 10.10 (1H, d, J = 8.0 Hz), 11.47 (1H, brs). MS: 329 (M + H)+. |
| 131 | 1 | 1H-NMR (400 MHz, d6-DMSO) δ: 1.32-1.39 (1H, m), 1.63-1.90 (8H, m), 1.98-2.14 (2H, m), 2.30-2.37 (1H, m), 3.76-3.80 (1H, m), 4.18-4.23 (1H, m), 4.96-5.00 (1H, m), 6.34-.6.38 (1H, m), 6.61-7.09 (2H, m), 7.21-7.72 (1H, br), 8.23 (1H, s), 10.03 (1H, d, J = 8.0 Hz), 11.33 (1H, brs). MS: 327 (M + H)+. |
| 132 | 1 | 1H-NMR (400 MHz, d6-DMSO) δ: 1.45-1.83 (7H, m), 1.87-2.09 (4H, m), 2.19-2.25 (1H, m), 3.88-3.92 (1H, m), 4.53-4.58 (1H, m), 4.97-5.00 (1H, m), 6.75-6.78 (1H, m), 6.80-7.14 (2H, m), 7.59-7.89 (1H, br), 8.35 (1H, s), 10.17 (1H, d, J = 8.0 Hz), 11.39 (1H, brs). MS: 327 (M + H)+. |
| 133 | 1 | 1H-NMR (400 MHz, d6-DMSO) δ: 1.17-1.57 (7H, m), 1.87-1.91 (1H, m), 2.27-2.30 (2H, m), 3.90 (1H, m), 6.57-6.58 (1H, m), 6.88-7.15 (1H, brs), 7.11-7.13 (1H, m), 7.60-7.90 (1H, brs), 8.35 (1H, s), 9.57 (1H, d, J = 3.6 Hz), 11.45 (1H, s). MS: 271 (M + H)+ |
| 134 | 1 | 1H-NMR (400 MHz, d6-DMSO) δ: 0.12-0.15 (2H, m), 0.40-0.44 (2H, m), 0.89-0.92 (1H, m), 1.49-1.72 (8H, m), 1.81-1.91 (4H, m), 2.10 (1H, s), 2.30 (1H, s), 4.12 (1H, s), 4.21 (1H, d, J = 7.5 Hz), 4.54 (1H, s), 6.53-6.57 (2H, brs), 6.55 (1H, s), 7.24 (1H, m), 7.89 (1H, d, J = 7.7 Hz), 8.72 (1H, s), 11.63 (1H, s). MS: 435 (M + H)+ |
| 135 | 1 | 1H-NMR (400 MHz, d6-DMSO) δ: 1.44-1.91 (15H, m), 2.10 (1H, s), 2.30 (2H, s), 2.70 (2H, d, J = 5.7 Hz), 3.58-3.63 (1H, m), 3.72-3.77 (1H, m), 3.88-3.91 (1H, m), 4.12 (2H, s), 4.21 (1H, d, J = 7.6 Hz), 4.54 (1H, s), 6.54 (1H, d, J = 1.7 Hz), 7.23-7.24 (1H, m), 7.89 (1H, d, J = 7.6 Hz), 8.72 (1H, s), 11.62 (1H, s). MS: 465 (M + H)+, 487 (M + Na)+ |
| 136 | 1 | 1H-NMR (400 MHz, d6-DMSO) δ: 1.24-1.33 (2H, m), 1.48-1.51 (2H, m), 1.64-1.72 (4H, m), 1.79-1.91 (6H, m), 2.10 (1H, s), 2.30 (2H, s), 2.66 (1H, brs), 2.72-2.77 (1H, m), 3.26-3.33 (2H, m), 3.81-3.85 (2H, m), 4.13 (2H, s), 4.21 (1H, d, J = 7.5 Hz), 4.54 (1H, s), 6.54-6.55 (1H, m), 7.23-7.24 (1H, m), 7.90 (1H, d, J = 7.8 Hz), 8.71 (1H, s), 11.63 (1H, s). MS: 465 (M + H)+ |
| 137 | 1 | 1H-NMR (400 MHz, d6-DMSO) δ: 0.90 (1H, m), 1.48-1.51 (2H, m), 1.63 (2H, s), 1.69-1.72 (2H, m), 1.82-1.91 (4H, m), 2.10 (1H, s), 2.30 (2H, s), 2.79-2.82 (2H, m), 3.25 (3H, s), 3.41-3.44 (2H, m), 4.11 (2H, s), 4.20 (1H, d, J = 7.5 Hz), 4.54 (1H, s), 6.54 (1H, m), 7.23-7.24 (1H, m), 7.89 (1H, d, J = 7.8 Hz), 8.71 (1H, s), 11.63 (1H, s). MS: 439 (M + H)+, 461 (M + Na)+ |
| 138 | 1 | 1H-NMR (400 MHz, d6-DMSO) δ: 1.48-1.52 (2H, m), 1.63 (2H, s), 1.69-1.72 (2H, m), 1.82-1.92 (4H, m), 2.10 (1H, s), 2.30 (2H, s), 2.70-2.73 (2H, m), 3.49-3.50 (2H, m), 4.12 (2H, s), 4.22 (1H, d, J = 7.5 Hz), 4.55 (2H, s), 6.55 (1H, s), 7.24 (1H, s), 7.89 (2H, d, J = 7.8 Hz), 8.72 (1H, s), 11.63 (1H, s). MS: 425 (M + H)+, 447 (M + Na)+ |
| 139 | 2 | MS: 343 (M + H)+ |
| 140 | 2 | MS: 343 (M + H)+ |
| 141 | 2 | MS: 364 (M + H)+ |
| 142 | 2 | MS: 300 (M + H)+ |
| 143 | 2 | MS: 388 (M + H)+ |
| 144 | 3 | 1H-NMR (400 MHz, d6-DMSO) δ: 1.47-2.46 (11H, m), 2.64-2.82 (2H, m), 4.47-4.69 (1H, m), 6.33-6.39 (1H, m), 7.41-7.50 (1H, m), 7.89-7.94 (1H, m), 10.77-10.83 (1H, m), 11.59 (1H, s). MS: 421 (M + H)+ |
| 145 | 3 | 1H-NMR (400 MHz, d6-DMSO) δ: 1.40-1.46 (2H, m), 1.58-1.68 (4H, m), 1.72-1.78 (2H, m), 1.83-1.89 (2H, m), 2.04-2.09 (1H, m), 2.29-2.33 (2H, m), 3.99-4.03 (1H, m), 4.52 (1H, brs), 5.74-5.77 (1H, m), 6.26 (1H, d, J = 15.7 Hz), 6.43-6.45 (1H, m), 7.16-7.18 (1H, m), 7.87 (1H, d, J = 15.7 Hz), 8.16 (1H, s), 11.47 (1H, brs), 12.12 (1H, br). MS: 354 (M + H)+ |
| 146 | 3 | 1H-NMR (400 MHz, d6-DMSO) δ: 1.45-1.62 (4H, m), 1.69-1.78 (2H, m), 1.90-1.99 (2H, m), 2.09-2.14 (2H, m), 2.19-2.26 (2H, m), 2.77-2.88 (1H, m), 4.47-4.59 (1H, m), 6.43-6.47 (1H, m), 6.85-7.10 (1H, br), 7.20-7.23 (1H, m), 7.57-7.90 (1H, br), 8.34 (1H, s), 9.45 (1H, d, J = 8.0 Hz), 11.49 (1H, brs), 12.12 (1H, brs). MS: 343 (M + H)+. |
| 147 | 3 | MS: 328 (M + H)+ |

TABLE 72-continued

| Ex | Ref-Ex | Data |
|---|---|---|
| 148 | 3 | 1H-NMR (400 MHz, d6-DMSO) δ: 1.45-1.55 (2H, m), 1.58-1.75 (4H, m), 1.77-1.93 (4H, m), 2.05-2.13 (1H, m), 2.22-2.29 (2H, m), 4.09-4.16 (1H, m), 4.60 (1H, s), 6.61 (1H, d, J = 3.5 Hz), 7.27 (1H, d, J = 3.5 Hz), 8.63 (1H, s), 11.83-12.00 (1H, m), 12.08 (1H, brs), 13.43 (1H, br). MS: 396 (M + H)+ |
| 149 | 3 | 1H-NMR (400 MHz, d6-DMSO) δ: 1.45-1.50 (2H, m), 1.61-1.71 (4H, m), 1.77-1.86 (4H, m), 2.06-2.10 (1H, m), 2.23-2.27 (2H, m), 4.06-4.11 (1H, m), 4.54 (1H, brs), 6.46-6.50 (1H, m), 7.15-7.18 (1H, m), 8.52 (1H, s), 9.50 (1H, brs), 11.61 (1H, brs), 12.36 (1H, brs). MS: 350 (M + Na)+. |
| 150 | 3 | 1H-NMR (400 MHz, d6-DMSO) δ: 1.43-1.49 (2H, m), 1.65-1.73 (4H, m), 1.78-1.91 (4H, m), 2.05-2.10 (1H, m), 2.16-2.21 (2H, m), 4.18-4.24 (1H, m), 4.54 (1H, brs), 6.47-6.50 (1H, m), 7.20-7.22 (1H, m), 8.54 (1H, s), 9.65 (1H, d, J = 8.0 Hz), 11.76 (1H, brs), 12.69 (1H, brs). MS: 328 (M + H)+. |
| 151 | 3 | 1H-NMR (400 MHz, d6-DMSO) δ: 1.49-2.15 (13H, m), 4.12-4.20 (1H, m), 6.42-6.46 (1H, m), 6.87-7.15 (2H, m), 7.63-7.91 (1H, br), 8.37 (1H, s), 10.14-10.23 (1H, m), 11.45 (1H, brs), 12.13 (1H, brs). MS: 355 (M + H)+. |
| 152 | 4 | 1H-NMR (400 MHz, d6-DMSO) δ: 1.50-2.75 (15H, m), 3.21-3.72 (2H, m), 4.48-4.54 (1H, m), 6.33-6.39 (1H, m), 7.43-7.46 (1H, m), 7.75-8.01 (2H, m), 10.76-10.78 (1H, m), 11.58 (1H, s). MS: 405 (M + H)+ |
| 153 | 4 | 1H-NMR (400 MHz, d6-DMSO) δ: 1.69-1.77 (2H, m), 1.83-1.92 (4H, m), 2.03-2.12 (3H, m), 2.39-2.48 (2H, m), 2.70-2.75 (2H, m), 3.59 (2H, d, J = 5.6 Hz), 4.49 (1H, s), 6.34-6.36 (1H, m), 6.99 (1H, s), 7.12 (1H, s), 7.42-7.45 (2H, m), 7.90 (1H, s), 10.76 (1H, s), 11.57 (1H, s). MS: 409 (M + H)+ |
| 154 | 4 | 1H-NMR (400 MHz, d6-DMSO) δ: 1.50-1.57 (2H, m), 1.83-1.89 (2H, m), 1.95-2.03 (3H, m), 2.20-2.28 (2H, m), 2.38-2.46 (2H, m), 2.63-2.70 (2H, m), 3.63 (2H, d, J = 5.8 Hz), 4.54 (1H, s), 6.39-6.40 (1H, m), 6.95-7.25 (3H, m), 7.45 (1H, t, J = 3.0 Hz), 7.90 (1H, s), 10.77 (1H, br), 11.57 (1H, s). MS: 409 (M + H)+ |
| 155 | 4 | 1H-NMR (400 MHz, d6-DMSO) δ: 1.57-2.73 (13H, m), 3.20-3.28 (3H, m), 4.36-4.39 (2H, m), 4.51-4.59 (1H, m), 6.30-6.38 (1H, m), 7.41-7.46 (1H, m), 7.89-7.90 (1H, m), 10.72-10.87 (1H, m), 11.53-11.61 (1H, m). MS: 405 (M + H)+ |
| 156 | 4 | 1H-NMR (400 MHz, d6-DMSO) δ: 1.20-1.56 (2H, m), 1.80-2.16 (7H, m), 2.31-2.45 (2H, m), 2.65-2.78 (2H, m), 3.54-3.60 (2H, m), 4.45-4.54 (1H, m), 6.27-6.37 (1H, m), 7.43-7.46 (1H, m), 7.83-7.94 (2H, m), 10.78 (1H, s), 11.58 (1H, s). MS: 391 (M + H)+ |
| 157 | 4 | 1H-NMR (400 MHz, d6-DMSO) δ: 1.51-2.70 (17H, m), 3.71-3.84 (1H, m), 4.46-4.56 (1H, m), 6.29-6.39 (1H, m), 7.42-7.44 (1H, m), 7.89-7.91 (1H, m), 10.77-10.81 (1H, m), 11.55-11.59 (1H, m). MS: 417 (M + H)+ |
| 158 | 4 | 1H-NMR (400 MHz, d6-DMSO) δ: 1.40-2.87 (13H, m), 4.41-4.72 (1H, m), 6.28-6.42 (1H, m), 7.40-7.48 (1H, m), 7.86-7.93 (1H, m), 8.01-8.11 (1H, m), 8.20-8.32 (1H, m), 10.71-10.82 (1H, m), 11.54-11.63 (1H, m). MS: 420 (M + H)+ |
| 159 | 4 | 1H-NMR (400 MHz, d6-DMSO) δ: 1.49-2.22 (9H, m), 2.36-2.44 (2H, m), 2.63-2.74 (2H, m), 3.06-3.18 (2H, m), 3.36-3.44 (2H, m), 4.46-4.54 (1H, m), 4.61-4.68 (1H, m), 6.35-6.38 (1H, m), 7.24-7.55 (2H, m), 7.90 (1H, s), 10.74-10.76 (1H, m), 11.57 (1H, s). MS: 396 (M + H)+ |
| 160 | 4 | 1H-NMR (400 MHz, d6-DMSO) δ: 1.35-1.99 (9H, m), 1.50-2.45 (11H, m), 2.63-2.74 (2H, m), 2.92-3.14 (4H, m), 4.46-4.53 (1H, m), 6.32-6.39 (1H, m), 6.78-9.86 (1H, m), 7.32-7.60 (2H, m), 7.90 (1H, s), 10.73-10.79 (1H, m), 11.57 (1H, s). MS: 495 (M + H)+ |
| 161 | 4 | 1H-NMR (400 MHz, d6-DMSO) δ: 1.59-1.65 (2H, m), 1.85-1.95 (2H, m), 2.05-2.11 (1H, m), 2.13-2.21 (2H, m), 2.35-2.47 (6H, m), 5.16 (1H, d, J = 8.7 Hz), 7.13 (1H, br), 7.91 (1H, br), 8.08 (1H, s), 8.47 (1H, s), 9.98 (1H, d, J = 8.7 Hz), 12.81 (1H, br). MS: 390, 392 (M + H)+ |
| 162 | 4 | MS: 479 (M + H)+ |
| 163 | 4 | MS: 465 (M + H)+ |
| 164 | 4 | MS: 508 (M + H)+ |
| 165 | 4 | MS: 492 (M + H)+ |
| 166 | 4 | MS: 508 (M + H)+ |
| 167 | 4 | MS: 488 (M + H)+ |
| 168 | 4 | MS: 513 (M + H)+ |
| 169 | 4 | 1H-NMR (400 MHz, d6-DMSO) δ: 1.78-1.89 (4H, m), 2.04-2.11 (1H, m), 2.22-2.25 (4H, m), 2.30-2.35 (2H, m), 2.51-2.56 (2H, m), 5.05 (1H, d, J = 8.7 Hz), 7.20 (1H, br), 7.95 (1H, |

TABLE 72-continued

| Ex | Ref-Ex | Data |
|---|---|---|
| | | br), 8.07 (1H, s), 8.49 (1H, s), 10.17 (1H, d, J = 8.7 Hz), 12.81 (1H, br). MS: 390, 392 (M + H)+ |
| 170 | 4 | MS: 353 (M + H)+ |
| 171 | 4 | MS: 390 (M + H)+ |
| 172 | 4 | MS: 434 (M + H)+ |
| 173 | 4 | MS: 417 (M + H)+ |
| 174 | 4 | MS: 369 (M + H)+ |
| 175 | 4 | MS: 369 (M + H)+ |
| 176 | 4 | MS: 355 (M + H)+ |
| 177 | 4 | MS: 433 (M + H)+ |
| 178 | 4 | MS: 423 (M + H)+ |
| 179 | 4 | MS: 433 (M + H)+ |
| 180 | 4 | MS: 419 (M + H)+ |
| 181 | 4 | MS: 558 (M + Na)+ |
| 182 | 4 | 1H-NMR (400 MHz, d6-DMSO) δ: 1.39-2.34 (12H, m), 3.09 (3H, s), 4.08 (2H, s), 4.44 (1H, s), 4.50 (1H, m), 5.00 (1H, m), 8.04 (1H, s), 9.11 (1H, s), 10.18 (1H, m), 11.11 (1H, m), 12.80 (1H, s). MS: 424 (M + H)+ |
| 183 | 4 | MS: 434 (M + H)+. MS: 432 (M − H)− |
| 184 | 4 | 1H-NMR (400 MHz, d6-DMSO) δ: 1.43 (9H, s), 1.68-1.84 (2H, m), 1.84-2.13 (4H, m), 2.13-2.31 (2H, m), 4.04-4.17 (2H, m), 4.30-4.39 (1H, m), 6.44-6.49 (1H, m), 7.01 (1H, br), 7.06-7.12 (1H, m), 7.77 (1H, br), 8.37 (1H, s), 10.24 (1H, d, J = 7.6 Hz), 11.43 (1H, s). MS: 386 (M + H)+ |
| 185 | 4 | 1H-NMR (400 MHz, d6-DMSO) δ: 1.76-2.40 (8H, m), 3.95 (1H, d, J = 18.8 Hz), 4.05 (1H, d, J = 18.8 Hz), 4.13-4.24 (1H, m), 4.29-4.41 (1H, m), 4.44-4.55 (1H, m), 6.39-6.47 (1H, m), 7.04 (1H, br), 7.08-7.15 (1H, m), 7.80 (1H, br), 8.38 (1H, s), 10.28 (1H, d, J = 7.6 Hz), 11.46 (1H, s). MS: 353 (M + H)+ |
| 186 | 4 | 1H-NMR (400 MHz, d6-DMSO) δ: 1.72-2.52 (8H, m), 3.94-4.09 (1H, m), 4.37-4.48 (1H, m), 4.58-4.73 (1H, m), 6.45-6.51 (1H, m), 7.02 (1H, br), 7.07-7.14 (1H, m), 7.42-7.56 (5H, m), 7.79 (1H, br), 8.37 (1H, s), 10.29 (1H, d, J = 7.7 Hz), 11.45 (1H, s). MS: 390 (M + H)+ |
| 187 | 4 | 1H-NMR (400 MHz, d6-DMSO) δ: 1.30-1.50 (11H, m), 1.67-2.22 (6H, m), 4.12 (2H, brs), 5.40-5.55 (1H, m), 7.10 (1H, brs), 7.82 (1H, brs), 8.10 (1H, s), 8.43 (1H, s), 9.28 (1H, d, J = 8.6 Hz), 12.8 (1H, brs). MS: 387 (M + H)+ |
| 188 | 4 | 1H-NMR (400 MHz, d6-DMSO) δ: 0.96-2.19 (13H, m), 4.09-4.19 (1H, m), 6.42-6.43 (1H, m), 6.55-6.57 (1H, m), 7.11-7.14 (1H, m), 7.63-7.65 (1H, m), 7.86-7.89 (1H, m), 7.86-7.89 (1H, m), 8.20 (1H, s), 8.37 (1H, d, J = 2.8 Hz), 10.11-10.23 (1H, m), 11.47 (1H, s), 12.16 (1H, s).. MS: 393 (M + H)+ |
| 189 | 4 | 1H-NMR (400 MHz, d6-DMSO) δ: 1.42-1.60 (4H, m), 1.70-1.83 (4H, m), 2.05-2.11 (2H, m), 2.19-2.26 (2H, m), 2.76-2.87 (1H, m), 4.54-4.66 (1H, m), 6.53-6.56 (1H, m), 6.71 (1H, brs), 6.88-7.10 (1H, br), 7.19-7.22 (1H, m), 7.35 (1H, brs), 7.60-7.85 (1H, br), 8.34 (1H, s), 9.45 (1H, d, J = 8.0 Hz), 11.46 (1H, brs). MS: 364 (M + Na)+. |
| 190 | 4 | 1H-NMR (400 MHz, d6-DMSO) δ: 1.49-2.13 (13H, m), 4.10-4.21 (1H, m), 6.43-6.46 (1H, m), 6.73-6.78 (1H, m), 6.92-7.14 (3H, m), 7.61-7.95 (1H, br), 8.37-8.39 (1H, m), 10.11-10.18 (1H, m), 11.46 (1H, brs). MS: 354 (M + H)+ |
| 191 | 4 | 1H-NMR (400 MHz, d6-DMSO) δ: 1.47-1.53 (2H, m), 1.78-1.96 (7H, m), 2.00-2.10 (4H, m), 4.16-4.21 (1H, m), 6.44-6.46 (1H, m), 6.76 (1H, brs), 6.88-7.13 (3H, m), 7.62-7.90 (1H, br), 8.37 (1H, s), 10.17 (1H, d, J = 8.0 Hz), 11.45 (1H, brs). MS: 376 (M + Na)+. |
| 192 | 4 | 1H-NMR (400 MHz, d6-DMSO) δ: 1.69-1.98 (11H, m), 2.10-2.15 (2H, m), 4.10-4.15 (1H, m), 6.43-6.46 (1H, m), 6.75 (1H, brs), 6.90-7.09 (2H, m), 7.11-7.15 (1H, m), 7.66-7.93 (1H, br), 8.37 (1H, s), 10.13 (1H, d, J = 8.0 Hz), 11.46 (1H, brs). MS: 354.2 (M + H)+. |
| 193 | 4 | 1H-NMR (400 MHz, d6-DMSO) δ: 1.40-1.86 (10H, m), 2.05 (1H, brs), 2.19 (2H, brs), 4.48 (1H, s), 4.94 (1H, d, J = 8.7 Hz), 7.09 (1H, brs), 7.83 (1H, brs), 8.04 (1H, s), 8.45 (1H, s), 9.97 (1H, d, J = 8.7 Hz), 12.8 (1H, brs). MS: 328 (M + H)+ |
| 194 | 4 | 1H-NMR (400 MHz, d6-DMSO) δ: 1.40-1.89 (10H, m), 2.11 (1H, brs), 2.18 (2H, brs), 3.15 (3H, s), 5.04 (1H, d, J = 8.8 Hz), 7.10 (1H, brs), 7.82 (1H, brs), 8.06 (1H, s), 8.46 (1H, s), 9.98 (1H, d, J = 8.8 Hz), 12.7 (1H, brs). MS: 342 (M + H)+ |
| 195 | 4 | 1HNMR (400 MHz, d6-DMSO) δ: 1.40-1.65 (2H, m), 1.80-2.15 (6H, m), 3.90-4.10 (2H, m), 4.20 (1H, brs), 4.55 (1H, brs), 5.45-5.55 (1H, m), 7.18 (1H, brs), 7.81 (1H, brs), 8.11 (1H, s), 8.25 (1H, s), 9.25 (1H, d, J = 9.1 Hz), 12.8 (1H, brs). MS: 376 (M + Na)+ |

TABLE 72-continued

| Ex | Ref-Ex | Data |
|---|---|---|
| 196 | 4 | 1H-NMR (400 MHz, d6-DMSO) δ: 1.2-2.1 (14H, m), 2.73 (1H, s), 2.89 (1H, s), 3.7-4.6 (4H, m), 6.4-6.5 (1H, m), 7.1-7.5 (1H, m), 7.9-8.0 (1H, m), 8.3-8.4 (1H, m), 10.1-10.2 (1H, m), 11.46 (1H, s). MS: 497.2 (M + H)+. |
| 197 | 4 | MS: 385 (M + H)+ |
| 198 | 4 | 1H-NMR (400 MHz, d6-DMSO) δ: 1.52-2.23 (13H, m), 3.23-3.34 (3H, m), 4.12-4.47 (3H, m), 6.47-6.58 (1H, m), 6.94-7.14 (2H, m), 7.81 (1H, brs), 8.34-8.47 (1H, m), 10.12-10.27 (1H, m, J = 11.44 Hz), 11.44 (1H, s). MS: 393 (M + H)+. |
| 199 | 4 | 1H-NMR (400 MHz, d6-DMSO) δ: 1.56-2.31 (14H, m), 2.77 (3H, d, J = 4.4 Hz), 4.16-4.18 (1H, m), 6.43 (1H, s), 7.14-7.16 (1H, s), 8.31-8.40 (1H, m), 9.96-9.98 (1H, s), 11.48 (1H, s). MS: 350 (M + H)+ |
| 200 | 4 | 1H-NMR (400 MHz, d6-DMSO) δ: 1.51-2.34 (14H, m), 2.74 (3H, d, J = 4.0 Hz), 4.2-4.3 (1H, m), 6.50-6.52 (1H, m), 7.13-7.15 (1H, m), 8.25-8.26 (1H, m), 9.92-9.95 (1H, m), 11.46 (1H, s). MS: 350 (M + H)+ |
| 201 | 4 | 1H-NMR (400 MHz, d6-DMSO) δ: 1.47-1.54 (2H, m), 1.62-1.74 (4H, m), 1.81-1.92 (4H, m), 2.08-2.11 (1H, m), 2.28-2.31 (2H, m), 3.36-3.44 (2H, m), 3.48-3.76 (6H, m), 4.04, 4.12 (2H, s), 4.20-4.24 (1H, m), 4.40, 4.50 (1H, s), 6.58-6.61 (1H, m), 7.27-7.30 (1H, m), 8.65 (1H, s), 8.83-8.86 (1H, m), 11.90 (1H, brs). MS: 531 (M + H)+ |
| 202 | 4 | 1H-NMR (400 MHz, d6-DMSO) δ: 1.57-2.20 (8H, m), 2.42 (3H, s), 4.05-4.06 (2H, m), 4.26-4.27 (1H, m), 4.58 (2H, s), 6.66-6.67 (1H, m), 7.31-7.32 (1H, m), 8.43 (1H, d, J = 8.0 Hz), 8.57 (1H, s), 11.88 (1H, brs). MS: 392.2 (M + H)+ |
| 203 | 4 | 1H-NMR (400 MHz, d6-DMSO) δ: 1.31-1.50 (4H, m), 1.54-1.72 (8H, m), 1.72-1.89 (4H, m), 2.03-2.11 (1H, m), 2.16-2.25 (2H, m), 2.75-2.87 (4H, m), 3.98-4.06 (1H, m), 4.53 (1H, s), 6.41-6.47 (1H, m), 7.10-7.15 (1H, m), 8.27 (1H, s), 9.09 (1H, brs), 9.52 (1H, d, J = 6.8 Hz), 11.46 (1H, brs). MS: 410 (M + H)+ |
| 204 | 4 | 1H-NMR (400 MHz, d6-DMSO) δ: 1.38-1.81 (16H, m), 2.02-2.10 (1H, m), 2.14-2.22 (2H, m), 3.45-3.56 (4H, m), 3.93-4.01 (1H, m), 4.50 (1H, s), 6.44-6.48 (1H, m), 6.97 (1H, d, J = 8.4 Hz), 7.16-7.21 (1H, m), 7.80 (1H, s), 11.46 (1H, brs). MS: 395 (M + H)+ |
| 205 | 4 | 1H-NMR (400 MHz, d6-DMSO) δ: 0.93-1.88 (20H, m), 2.01-2.09 (1H, m), 2.12-2.22 (2H, m), 3.85-4.03 (2H, m), 4.48 (1H, s), 4.59 (2H, s), 6.42-6.47 (1H, m), 7.11 (1H, d, J = 8.0 Hz), 7.13-7.18 (1H, m), 7.94 (1H, s), 11.40 (1H, brs). MS: 424 (M + H)+ |
| 206 | 4 | 1H-NMR (400 MHz, d6-DMSO) δ: 1.04-1.92 (20H, m), 2.03-2.12 (1H, m), 2.15-2.27 (2H, m), 2.65-2.77 (1H, m), 3.98-4.08 (1H, m), 4.51 (1H, s), 4.90-5.01 (1H, m), 6.40-6.47 (1H, m), 7.10-7.16 (1H, m), 8.27 (1H, s), 9.47 (1H, d, J = 8.1 Hz), 9.66-9.74 (1H, m), 11.47 (1H, s). MS: 424 (M + H)+ |
| 207 | 4 | 1H-NMR (400 MHz, d6-DMSO) δ: 1.42-1.49 (2H, m), 1.58-1.72 (4H, m), 1.75-1.88 (4H, m), 1.92 (3H, s), 2.04-2.10 (1H, m), 2.18-2.25 (2H, m), 4.03-4.08 (1H, m), 4.52 (1H, s), 6.44-6.48 (1H, m), 7.14-7.17 (1H, m), 8.42 (1H, s), 9.65 (1H, d, J = 8.0 Hz), 9.76 (1H, s), 9.99 (1H, brs), 11.52 (1H, brs). MS: 384 (M + H)+ |
| 208 | 4 | 1H-NMR (400 MHz, d6-DMSO) δ: 1.88-2.47 (8H, m), 2.42 (3H, s), 3.98 (1H, d, J = 18.9 Hz), 4.08 (1H, d, J = 18.9 Hz), 4.20-4.26 (1H, m), 4.48-4.57 (2H, m), 6.56-6.61 (1H, m), 7.23-7.28 (1H, m), 8.58 (1H, s), 9.17 (1H, d, J = 7.6 Hz), 11.83 (1H, s). MS: 392 (M + H)+ |
| 209 | 4 | 1H-NMR (400 MHz, d6-DMSO) δ: 1.81-1.94 (4H, m), 2.11 (1H, m), 2.46-2.51 (3H, m), 4.13 (2H, s), 4.39 (1H, s), 4.71 (1H, s), 4.97 (1H, m), 6.26 (1H, s), 7.36-7.44 (1H, m), 7.94 (1H, s), 11.02 (1H, brs), 11.65 (1H, s). MS: 373 (M + Na)+ |
| 210 | 4 | MS: 439 (M + H)+ |
| 211 | 4 | MS: 493 (M + H)+ |
| 212 | 4 | MS: 404 (M + H)+ |
| 213 | 4 | MS: 404 (M + H)+ |
| 214 | 4 | MS: 415 (M + H)+ |
| 215 | 4 | MS: 415 (M + H)+ |
| 216 | 4 | MS: 415 (M + H)+ |
| 217 | 4 | MS: 408 (M + H)+ |
| 218 | 4 | MS: 420 (M + H)+ |
| 219 | 4 | MS: 420 (M + H)+ |
| 220 | 4 | MS: 432 (M + H)+ |
| 221 | 4 | MS: 448 (M + H)+ |

TABLE 72-continued

| Ex | Ref-Ex | Data |
|---|---|---|
| 222 | 4 | MS: 328 (M + H)+ |
| 223 | 4 | MS: 342 (M + H)+ |
| 224 | 4 | MS: 344 (M + H)+ |
| 225 | 4 | MS: 354 (M + H)+ |
| 226 | 4 | MS: 356 (M + H)+ |
| 227 | 4 | MS: 358 (M + H)+ |
| 228 | 4 | MS: 370 (M + H)+ |
| 229 | 4 | MS: 371 (M + H)+ |
| 230 | 4 | MS: 391 (M + H)+ |
| 231 | 4 | MS: 391 (M + H)+ |
| 232 | 4 | MS: 391 (M + H)+ |
| 233 | 4 | MS: 396 (M + H)+ |
| 234 | 4 | MS: 397 (M + H)+ |
| 235 | 4 | MS: 405 (M + H)+ |
| 236 | 4 | MS: 422 (M + H)+ |
| 237 | 4 | MS: 434 (M + H)+ |
| 238 | 4 | MS: 468 (M + H)+ |
| 239 | 4 | MS: 483 (M + H)+ |
| 240 | 4 | MS: 385 (M + H)+ |
| 241 | 4 | MS: 398 (M + H)+ |
| 242 | 4 | MS: 413 (M + H)+ |
| 243 | 4 | MS: 384 (M + H)+ |
| 244 | 4 | MS: 399 (M + H)+ |
| 245 | 4 | MS: 425 (M + H)+ |
| 246 | 4 | MS: 424 (M + H)+ |
| 247 | 4 | MS: 450 (M + H)+ |
| 248 | 4 | MS: 411 (M + H)+ |
| 249 | 4 | MS: 415 (M + H)+ |
| 250 | 4 | MS: 425 (M + H)+ |
| 251 | 4 | MS: 411 (M + H)+ |
| 252 | 4 | MS: 438 (M + H)+ |
| 253 | 4 | 1H-NMR (400 MHz, d6-DMSO) δ: 0.81 (3H, s), 0.91 (3H, s), 0.99 (3H, s), 0.87-1.31 (3H, m), 1.34-1.52 (3H, m), 2.33-2.49 (1H, m), 4.13-4.28 (1H, m), 6.42 (1H, d, J = 2.6 Hz), 6.72-7.94 (3H, m), 8.36 (1H, s), 10.09 (1H, d, J = 8.4 Hz), 11.46 (1H, brs). MS: 313 (M + H)+ |
| 254 | 4 | MS: 440 (M + H)+ |
| 255 | 4 | MS: 398 (M + H)+ |
| 256 | 4 | MS: 435 (M + H)+ |
| 257 | 4 | MS: 435 (M + H)+ |
| 258 | 4 | MS: 435 (M + H)+ |
| 259 | 4 | MS: 442 (M + H)+ |
| 260 | 4 | MS: 407 (M + H)+ |
| 261 | 4 | MS: 403 (M + H)+ |
| 262 | 4 | MS: 410 (M + H)+ |
| 263 | 4 | MS: 411 (M + H)+ |
| 264 | 4 | MS: 447 (M + H)+ |
| 265 | 4 | MS: 432 (M + H)+ |
| 266 | 4 | MS: 447 (M + H)+ |
| 267 | 4 | MS: 432 (M + H)+ |
| 268 | 7 | MS: 469 (M + H)+ |
| 269 | 7 | 1H-NMR (400 MHz, d6-DMSO) δ: 1.45-2.35 (10H, m), 3.39 (2H, m), 3.76-4.13 (5H, m), 4.23 (1H, m), 4.54 (1H, s), 6.56 (1H, m), 7.26 (1H, m), 7.74 (1H, m), 8.80 (1H, s), 9.41 (1H, m), 11.69 (1H, s). MS: 479 (M + H)+ |
| 270 | 7 | 1H-NMR (400 MHz, d6-DMSO) δ: 1.46-2.48 (14H, m), 3.41 (2H, m), 4.23 (1H, m), 4.55 (1H, s), 6.57 (1H, m), 7.26 (1H, m), 7.72 (1H, m), 8.78 (1H, s), 9.30 (1H, m), 11.69 (1H, s). MS: 466 (M + H)+ |
| 271 | 7 | 1H-NMR (400 MHz, d6-DMSO) δ: 1.39-2.32 (12H, m), 3.45 (2H, m), 3.85 (2H, m), 4.01 (1H, m), 4.23 (1H, m), 4.56 (1H, s), 4.87 (1H, m), 6.56 (1H, m), 7.26 (1H, m), 7.72 (1H, m), 8.71 (1H, s), 11.71 (1H, s). MS: 479 (M + H)+ |
| 272 | 7 | 1H-NMR (400 MHz, d6-DMSO) δ: 1.49-2.47 (14H, m), 3.67-3.78 (4H, m), 4.24 (1H, m), 4.56 (1H, s), 6.56 (1H, m), 7.25 (1H, m), 7.71 (1H, m), 8.71 (1H, s), 11.71 (1H, s). MS: 478 (M + H)+ |
| 273 | 7 | MS: 550 (M + H)+ |
| 274 | 7 | 1H-NMR (400 MHz, d6-DMSO) δ: 1.45-2.38 (13H, m), 3.55 (4H, m), 3.99 (1H, m), 4.23 (1H, m), 4.51 (1H, s), 4.82 (2H, m), 6.60 (1H, m), 7.27 (1H, m), 8.17 (1H, m), 8.65 (1H, m), 8.84 (1H, m), 11.88 (1H, s). MS: 469 (M + H)+ |
| 275 | 7 | MS: 469 (M + H)+ |
| 276 | 7 | MS: 556 (M + H)+ |
| 277 | 7 | MS: 505 (M + Na)+ |
| 278 | 7 | MS: 491 (M + Na)+ |

TABLE 72-continued

| Ex | Ref-Ex | Data |
|---|---|---|
| 279 | 7 | 1H-NMR (400 MHz, d6-DMSO) δ: 1.42 (9H, s), 1.44-2.38 (7H, m), 2.85 (2H, m), 3.89-4.05 (4H, m), 4.22 (1H, m), 4.38 (1H, s), 6.60 (1H, m), 7.27 (1H, m), 8.31 (1H, m), 8.73 (1H, m), 8.89 (1H, m), 11.87 (1H, s). MS: 600 (M + Na)+ |
| 280 | 7 | 1H-NMR (400 MHz, d6-DMSO) δ: 1.45-1.51 (2H, m), 1.61-1.64 (2H, m), 1.67-1.73 (2H, m), 1.81-1.87 (2H, m), 1.93-1.99 (2H, m), 2.08-2.12 (1H, m), 2.32-2.36 (2H, m), 4.19-4.23 (1H, m), 4.46 (1H, s), 6.60 (1H, d, J = 3.6 Hz), 7.28 (1H, d, J = 3.6 Hz), 8.17-8.21 (2H, m), 8.64 (1H, s), 8.88 (1H, d, J = 7.5 Hz), 11.88 (1H, brs). MS: 395 (M + H)+ |
| 281 | 7 | 1H-NMR (400 MHz, d6-DMSO) δ: 1.47-1.53 (2H, m), 1.62-1.65 (2H, m), 1.67-1.74 (2H, m), 1.81-1.92 (4H, m), 2.08-2.12 (1H, m), 2.28-2.32 (2H, m), 3.06 (3H, s), 3.11 (3H, s), 4.19-4.23 (1H, m), 4.50 (1H, s), 6.59 (1H, d, J = 3.6 Hz), 7.28 (1H, d, J = 3.6 Hz), 8.65 (1H, s), 8.88 (1H, d, J = 7.6 Hz), 11.89 (1H, brs). MS: 423 (M + H)+ |
| 282 | 7 | 1H-NMR (400 MHz, d6-DMSO) δ: 1.5-2.2 (14H, m), 2.98 (3H, s), 3.00 (3H, s), 4.11-4.18 (1H, m), 6.44-6.48 (1H, m), 7.11-7.12 (1H, m), 7.39-7.56 (1H, m), 7.70-7.73 (1H, m), 8.31 (1H, s), 8.37-8.38 (1H, m), 10.16-10.18 (1H, m), 11.46 (1H, brs). MS: 382.3 (M + H)+. |
| 283 | 7 | 1H-NMR (400 MHz, d6-DMSO) δ: 1.48-1.54 (2H, m), 1.61-1.65 (2H, m), 1.68-1.74 (2H, m), 1.82-1.93 (4H, m), 2.08-2.12 (1H, m), 2.29-2.33 (2H, m), 3.56-3.63 (4H, m), 3.68-3.70 (4H, m), 4.20-4.24 (1H, m), 4.52 (1H, s), 6.59 (1H, d, J = 3.6 Hz), 7.29 (1H, d, J = 3.6 Hz), 8.64 (1H, s), 8.84 (1H, d, J = 7.8 Hz), 11.89 (1H, brs). MS: 487 (M + Na)+ |
| 284 | 7 | 1H-NMR (400 MHz, d6-DMSO) δ: 1.47-1.53 (2H, m), 1.62-1.65 (2H, m), 1.68-1.73 (2H, m), 1.81-1.92 (4H, m), 2.08-2.12 (1H, m), 2.28-2.33 (2H, m), 2.68-2.72 (2H, m), 2.75-2.79 (2H, m), 3.40-3.43 (2H, m), 3.59-3.62 (2H, m), 4.19-4.22 (1H, m), 4.51 (1H, brs), 6.57-6.60 (1H, m), 7.27-7.29 (1H, m), 8.64 (1H, s), 8.83-8.86 (1H, m), 11.89 (1H, brs). MS: 464 (M + H)+ |
| 285 | 7 | 1H-NMR (400 MHz, d6-DMSO) δ: 1.48-1.54 (2H, m), 1.63-1.65 (2H, m), 1.69-1.74 (2H, m), 1.82-1.92 (4H, m), 2.09-2.12 (1H, m), 2.30-2.33 (2H, m), 2.86 (3H, s), 4.22-4.25 (1H, m), 4.55 (1H, brs), 6.57 (1H, d, J = 3.6 Hz), 7.27 (1H, d, J = 3.6 Hz), 7.71-7.74 (1H, m), 8.78 (1H, s), 9.38 (1H, brs), 11.68 (1H, brs). MS: 409 (M + H)+ |
| 286 | 7 | 1H-NMR (400 MHz, d6-DMSO) δ: 1.45-1.51 (2H, m), 1.61-1.64 (2H, m), 1.67-1.73 (2H, m), 1.81-1.87 (2H, m), 1.93-1.99 (2H, m), 2.08-2.12 (1H, m), 2.32-2.36 (2H, m), 4.19-4.23 (1H, m), 4.46 (1H, s), 6.60 (1H, d, J = 3.6 Hz), 7.28 (1H, d, J = 3.6 Hz), 8.17-8.21 (2H, m), 8.64 (1H, s), 8.88 (1H, d, J = 7.5 Hz), 11.88 (1H, brs). MS: 395 (M + H)+ |
| 287 | 7 | 1H-NMR (400 MHz, d6-DMSO) δ: 1.48-1.53 (2H, m), 1.63-1.80 (8H, m), 1.82-1.99 (6H, m), 2.09-2.12 (1H, m), 2.17 (3H, s), 2.30-2.33 (2H, m), 2.76-2.81 (2H, m), 3.73-3.79 (1H, m), 4.22-4.25 (1H, m), 4.53 (1H, s), 6.56-6.57 (1H, m), 7.25-7.27 (1H, m), 7.74-7.76 (1H, m), 8.80 (1H, s), 9.33-9.36 (1H, m), 11.68 (1H, brs). MS: 492 (M + H)+ |
| 288 | 7 | 1H-NMR (400 MHz, d6-DMSO) δ: 1.49-1.55 (2H, m), 1.63-1.66 (2H, m), 1.69-1.75 (2H, m), 1.82-1.93 (4H, m), 2.09-2.12 (1H, m), 2.30-2.33 (2H, m), 3.67-3.73 (6H, m), 3.83-3.86 (2H, m), 4.22-4.26 (1H, m), 4.52 (1H, s), 6.55-6.57 (1H, m), 7.24-7.26 (1H, m), 7.70-7.73 (1H, m), 8.72 (1H, s), 11.68 (1H, brs). MS: 465 (M + H)+ |
| 289 | 7 | 1H-NMR (400 MHz, d6-DMSO) δ: 1.49-1.54 (2H, m), 1.63-1.65 (2H, m), 1.69-1.75 (2H, m), 1.82-1.93 (4H, m), 2.09-2.12 (1H, m), 2.30-2.33 (2H, m), 3.10 (3H, s), 3.25 (3H, s), 4.22-4.26 (1H, m), 4.52 (1H, s), 6.55-6.57 (1H, m), 7.24-7.26 (1H, m), 7.71-7.73 (1H, m), 8.72 (1H, s), 11.67 (1H, brs). MS: 423 (M + H)+ |
| 290 | 7 | 1H-NMR (400 MHz, d6-DMSO) δ: 1.41-1.42 (9H, m), 1.48-1.57 (4H, m), 1.63-1.74 (4H, m), 1.78-1.92 (6H, m), 2.09-2.12 (1H, m), 2.30-2.32 (2H, m), 2.79-2.90 (1H, m), 3.33-3.39 (2H, m), 3.93-4.02 (2H, m), 4.22-4.26 (1H, m), 4.53 (1H, s), 6.56-6.58 (1H, m), 7.25-7.27 (1H, m), 7.73-7.76 (1H, m), 8.79 (1H, s), 9.37-9.40 (1H, m), 11.68 (1H, brs). MS: 578 (M + H)+ |
| 291 | 7 | 1H-NMR (400 MHz, d6-DMSO) δ: 1.48-1.54 (2H, m), 1.63-1.65 (2H, m), 1.69-1.74 (2H, m), 1.82-2.00 (6H, m), 2.09-2.12 (1H, m), 2.30-2.33 (2H, m), 3.33-3.62 (2H, m), 3.79-4.01 (2H, m), 4.22-4.25 (1H, m), 4.54, 4.55 (1H, m), 4.72-4.73 (1H, m), 5.00-5.01, 5.55-5.56 (1H, m), |

TABLE 72-continued

| Ex | Ref-Ex | Data |
|---|---|---|
| | | 6.55-6.57 (1H, m), 7.25-7.26 (1H, m), 7.71-7.74 (1H, m), 8.73, 8.74 (1H, s), 11.72 (1H, m). MS: 477 (M + H)+ |
| 292 | 7 | 1H-NMR (400 MHz, d6-DMSO) δ: 1.45-1.52 (2H, m), 1.67-1.75 (4H, m), 1.87-1.93 (4H, m), 2.08-2.12 (1H, m), 2.23-2.26 (2H, m), 2.85 (3H, d, J = 4.7 Hz), 3.17 (1H, s), 4.33-4.37 (1H, m), 6.53-6.55 (1H, m), 7.27-7.29 (1H, m), 7.74-7.77 (1H, m), 8.78 (1H, s), 9.37-9.41 (1H, m), 11.72 (1H, brs). MS: 409 (M + H)+ |
| 293 | 7 | 1H-NMR (400 MHz, d6-DMSO) δ: 1.49-2.31 (13H, m), 3.28 (3H, s), 3.47-3.52 (4H, m), 4.22-4.23 (1H, m), 4.52 (1H, brs), 6.55-6.57 (1H, m), 7.25-7.26 (1H, m), 7.71-7.73 (1H, m), 8.78 (1H, s), 9.42 (1H, brs), 11.66 (1H, brs). MS: 453 (M + H)+ |
| 294 | 7 | 1H-NMR (400 MHz, d6-DMSO) δ: 1.08 (3H, d, J = 6.0 Hz), 1.49-2.32 (13H, m), 3.16-3.27 (2H, m), 3.84-3.86 (1H, m), 4.23-4.24 (1H, m), 4.52 (1H, s), 4.82 (1H, d, J = 4.8 Hz), 6.55-6.57 (1H, m), 7.25-7.27 (1H, m), 7.72-7.74 (1H, m), 8.78 (1H, s), 9.26-9.27 (1H, m), 11.66 (1H, brs).. MS: 453 (M + H)+ |
| 295 | 7 | 1H-NMR (400 MHz, d6-DMSO) δ: 1.02-2.31 (18H, m), 3.20-3.24 (4H, m), 3.83-3.84 (2H, m), 4.23-4.24 (1H, m), 4.52 (1H, brs), 6.56-6.57 (1H, m), 7.24-7.26 (1H, m), 7.72-7.74 (1H, m), 8.78 (1H, s), 9.45-9.46 (1H, m), 11.66 (1H, brs). MS: 493 (M + H)+ |
| 296 | 8 | MS: 439 (M + H)+ |
| 297 | 8 | MS: 453 (M + H)+ |
| 298 | 8 | MS: 453 (M + H)+ |
| 299 | 8 | MS: 466 (M + H)+ |
| 300 | 8 | MS: 452 (M + H)+ |
| 301 | 8 | MS: 463 (M + H)+ |
| 302 | 8 | MS: 479 (M + H)+ |
| 303 | 8 | MS: 488 (M + H)+ |
| 304 | 8 | MS: 460 (M + H)+ |
| 305 | 8 | MS: 465 (M + H)+ |
| 306 | 8 | MS: 479 (M + H)+ |
| 307 | 8 | MS: 506 (M + H)+ |
| 308 | 8 | MS: 506 (M + H)+ |
| 309 | 8 | MS: 478 (M + H)+ |
| 310 | 8 | MS: 477 (M + H)+ |
| 311 | 8 | MS: 493 (M + H)+ |
| 312 | 8 | MS: 479 (M + H)+ |
| 313 | 8 | MS: 492 (M + H)+ |
| 314 | 8 | MS: 479 (M + H)+ |
| 315 | 8 | MS: 493 (M + H)+ |
| 316 | 8 | MS: 506 (M + H)+ |
| 317 | 8 | MS: 508 (M + H)+ |
| 318 | 8 | MS: 541 (M + H)+ |
| 319 | 8 | MS: 546 (M + H)+ |
| 320 | 8 | MS: 434 (M + H)+ |
| 321 | 8 | MS: 499 (M + H)+ |
| 322 | 8 | MS: 423 (M + H)+ |
| 323 | 8 | MS: 352 (M + H)+ |
| 324 | 8 | MS: 452 (M + H)+ |
| 325 | 8 | MS: 467 (M + H)+ |
| 326 | 8 | MS: 483 (M + H)+ |
| 327 | 8 | MS: 475 (M + H)+ |
| 328 | 8 | MS: 486 (M + H)+ |
| 329 | 8 | MS: 486 (M + H)+ |
| 330 | 8 | MS: 486 (M + H)+ |
| 331 | 8 | MS: 492 (M + H)+ |
| 332 | 8 | MS: 493 (M + H)+ |
| 333 | 8 | MS: 506 (M + H)+ |
| 334 | 8 | MS: 509 (M + H)+ |
| 335 | 8 | MS: 477 (M + H)+ |
| 336 | 8 | MS: 556 (M + H)+ |
| 337 | 8 | MS: 513 (M + H)+ |
| 338 | 8 | MS: 527 (M + H)+ |
| 339 | 8 | MS: 508 (M + H)+ |
| 340 | 8 | MS: 479 (M + H)+ |
| 341 | 8 | MS: 504 (M + H)+ |
| 342 | 8 | MS: 449 (M + H)+ |
| 343 | 8 | 1H-NMR (400 MHz, d6-DMSO) δ: 1.92-2.32 (8H, m), 2.49 (3H, s), 3.58-4.57 (5H, m), 6.76-6.77 (1H, m), 7.39-7.40 (1H, m), 8.69 (1H, s), 8.79-9.05 (3H, m), 12.20 (1H, brs). MS: 325 (M + H)+ |
| 344 | 10 | MS: 542 (M + H)+ |

TABLE 72-continued

| Ex | Ref-Ex | Data |
|---|---|---|
| 345 | 10 | 1H-NMR (400 MHz, d6-DMSO) δ: 1.43-2.39 (9H, m), 2.79 (6H, s), 2.81 (2H, m), 3.57 (2H, m), 3.99 (1H, m), 4.21 (1H, m), 4.40 (1H, s), 6.59 (1H, m), 7.27 (1H, m), 8.64 (1H, s), 8.76 (1H, m), 8.90 (1H, m), 11.89 (1H, s). MS: 571 (M + Na)+ |
| 346 | 10 | MS: 585 (M + H)+ |
| 347 | 10 | MS: 535 (M + H)+ |
| 348 | 13 | 1H-NMR (400 MHz, d6-DMSO) δ: 1.30 (3H, t, J = 7.1 Hz), 1.45-1.54 (2H, m), 1.58-1.75 (4H, m), 1.77-1.89 (4H, m), 2.06-2.12 (1H, m), 2.23-2.29 (2H, m), 4.09-4.15 (1H, m), 4.30 (2H, q, J = 7.1 Hz), 4.58 (1H, s), 6.49-9.53 (1H, m), 7.10 (2H, brs), 7.17-7.21 (1H, m), 8.90 (1H, s), 9.33 (1H, d, J = 7.8 Hz), 11.72 (1H, brs). MS: 442 (M + H)+ |
| 349 | 13 | 1H-NMR (400 MHz, d6-DMSO) δ: 1.43 (9H, s), 1.71-1.85 (2H, m), 1.80 (3H, s), 1.90-2.09 (4H, m), 2.17-2.32 (2H, m), 4.08-4.17 (2H, m), 4.38-4.46 (1H, m), 6.45 (2H, brs), 6.50-6.56 (1H, m), 7.12-7.17 (1H, m), 8.77 (1H, s), 9.51 (1H, d, J = 7.6 Hz), 11.64 (1H, s). MS: 443 (M + H)+ |
| 350 | 14 | 1H-NMR (400 MHz, d6-DMSO) δ: 1.47-1.55 (2H, m), 1.79-1.82 (2H, m), 1.86-1.99 (5H, m), 2.02-3.15 (4H, m), 4.09 (2H, d, J = 5.5 Hz), 4.17-4.23 (1H, m), 6.44-6.47 (1H, m), 7.00 (1H, br), 7.11-7.14 (1H, m), 7.78 (1H, br), 8.28 (1H, t, J = 5.4 Hz), 8.38 (1H, s), 10.18 (1H, d, J = 8.2 Hz), 11.46 (1H, s). MS: 393 (M + H)+ |
| 351 | 14 | 1H-NMR (400 MHz, d6-DMSO) δ: 1.71-2.03 (11H, m), 2.13-2.17 (2H, m), 4.06 (2H, d, J = 5.5 Hz), 4.12-4.16 (1H, m), 6.43-6.46 (1H, m), 6.99 (1H, br), 7.11-7.15 (1H, m), 7.77 (1H, br), 8.21 (1H, d, J = 5.5 Hz), 8.37 (1H, s), 10.18 (1H, d), 11.46 (1H, s). MS: 393 (M + H)+ |
| 352 | 14 | 1H-NMR (400 MHz, d6-DMSO) δ: 1.37-1.39 (9H, m), 1.43-1.48 (2H, m), 1.68-2.03 (8H, m), 2.05-2.19 (3H, m), 4.04-4.17 (1H, m), 6.36-6.56 (2H, m), 6.87-7.16 (2H, m), 7.76 (1H, br), 8.36-8.38 (1H, m), 10.11-10.15 (1H, m), 11.44 (1H, m). MS: 426 (M + H)+ |
| 353 | 14 | 1H-NMR (400 MHz, d6-DMSO) δ: 1.14-2.21 (13H, m), 4.02-4.04 (1H, m), 4.36 (2H, brs), 4.48 (1H, s), 6.43-6.33 (1H, m), 7.12-7.13 (1H, m), 8.28 (1H, s), 9.48 (1H, s), 9.67 (1H, d, J = 8.0 Hz), 11.42 (1H, brs). MS: 342 (M + H)+ |
| 354 | 14 | MS: 366 (M + H)+ |
| 355 | 14 | MS: 418 (M + H)+ |
| 356 | 14 | MS: 418 (M + H)+ |
| 357 | 14 | MS: 418 (M + H)+ |
| 358 | 14 | 1H-NMR (400 MHz, d6-DMSO) δ: 1.45-2.22 (8H, m), 3.70 (3H, s), 4.04 (1H, m), 4.53 (1H, s), 6.45 (1H, m), 7.15 (1H, m), 8.16 (1H, s), 9.41 (1H, s), 11.41 (1H, s), 11.51 (1H, s). MS: 357 (M + H)+ |
| 359 | 14 | MS: 355 (M + H)+, 353 (M − H)− |
| 360 | 14 | 1H-NMR (400 MHz, d6-DMSO) δ: 1.09-2.23 (16H, m), 3.28 (2H, m), 4.48 (1H, s), 4.96 (1H, m), 8.05 (1H, s), 8.31 (1H, m), 8.40 (1H, s), 9.73 (1H, m), 12.73 (1H, s). MS: 356 (M + H)+ |
| 361 | 14 | 1H-NMR (400 MHz, d6-DMSO) δ: 1.22-2.34 (13H, m), 4.29 (2H, m), 4.51 (1H, s), 5.01 (1H, m), 8.08 (1H, s), 8.43 (1H, s), 8.99 (1H, m), 9.65 (1H, m), 12.86 (1H, s). MS: 367 (M + H)+ |
| 362 | 14 | MS: 377 (M − H)− |
| 363 | 15 | MS: 408 (M + Na)+, 384 (M − H)− |
| 364 | 16 | 1H-NMR (400 MHz, d6-DMSO) δ: 0.80-2.84 (13H, m), 4.60-4.69 (1H, m), 7.43-7.47 (1H, m), 7.90-7.92 (1H, m), 8.91-8.94 (1H, m), 10.78-10.85 (1H, m), 11.55-11.65 (1H, m). MS: 402 (M + H)+ |
| 365 | 16 | 1H-NMR (400 MHz, d6-DMSO) δ: 1.90-1.97 (4H, m), 2.03-2.12 (5H, m), 2.62-2.67 (2H, m), 2.74-2.79 (2H, m), 4.54 (1H, s), 6.34-6.35 (1H, m), 7.45 (1H, t, J = 3.1 Hz), 7.91 (1H, s), 10.86 (1H, s), 11.61 (1H, s). MS: 334 (M + H)+ |
| 366 | 17 | 1H-NMR (400 MHz, d6-DMSO) δ: 1.46-1.83 (10H, m), 2.07 (1H, brs), 2.29 (2H, brs), 4.57 (1H, s), 4.67-4.77 (1H, m), 5.95-6.02 (1H, m), 8.245 (1H, s), 8.249 (1H, s), 13.1 (1H, brs). MS: 332 (M + Na)+ |
| 367 | 18 | 1H-NMR (400 MHz, d6-DMSO) δ: 1.52-1.61 (2H, m), 1.72-1.92 (3H, m), 1.99-2.13 (4H, m), 2.22-2.41 (3H, m), 2.64-2.74 (2H, m), 2.80-2.93 (2H, m), 3.26-3.38 (2H, m), 4.57-4.64 (1H, m), 6.52-6.59 (1H, m), 7.58-7.63 (1H, m), 7.82-7.91 (2H, m), 7.96. MS: 395 (M + H)+ |
| 368 | 18 | 1H-NMR (400 MHz, d6-DMSO) δ: 1.50-1.59 (2H, m), 1.72-1.99 (6H, m), 2.05-2.17 (2H, m), 2.24-2.36 (2H, m), 4.21-4.30 (1H, m), 6.52-6.66 (1H, m), 7.31-7.39 (1H, m), 7.62 (1H, br), 7.70-7.71 (1H, m), 8.00-8.39 (4H, m), |

TABLE 72-continued

| Ex | Ref-Ex | Data |
|---|---|---|
| | | 8.53-8.56 (1H, m), 9.10 (1H, s), 11.08 (1H, br), 12.44 (1H, br), 14.38 (1H, br). MS: 326 (M + H)+ |
| 369 | 18 | MS: 340 (M + H)+ |
| 370 | 18 | MS: 478 (M + H)+ |
| 371 | 18 | 1H-NMR (400 MHz, d6-DMSO) δ: 1.51-1.57 (1H, m), 1.71-1.79 (2H, m), 1.83-1.90 (2H, m), 1.96-2.02 (2H, m), 2.06-2.20 (4H, m), 2.33-2.46 (2H, m), 4.38-4.42 (1H, m), 6.60-6.62, 6.73-6.75 (1H, m), 7.41-7.45 (1H, m), 8.11-8.29 (3H, m), 8.44, 8.56 (1H, brs), 8.80 (1H, s), 9.31-9.34, 9.45-9.50 (1H, m), 12.45 (1H, brs). MS: 394 (M − 3HCl + H)+ |
| 372 | 18 | 1H-NMR (400 MHz, d6-DMSO) δ: 1.52-1.57 (2H, m), 1.65-1.75 (4H, m), 1.84-1.92 (6H, m), 1.97-2.02 (2H, m), 2.10-2.14 (1H, m), 2.32-2.36 (2H, m), 2.99-3.09 (2H, m), 3.30-3.36 (2H, m), 4.09-4.16 (1H, m), 4.32-4.35 (1H, m), 6.72-6.75 (1H, m), 7.40-7.42 (1H, m), 8.29-8.41 (1H, m), 8.56-8.65 (1H, m), 8.74-8.79 (1H, m), 8.82 (1H, s), 9.66-9.68 (1H, m), 12.37 (1H, brs). MS: 478 (M − 2HCl + H)+ |
| 373 | 18 | 1H-NMR (400 MHz, d6-DMSO) δ: 1.93-2.24 (6H, m), 2.46-2.61 (2H, m), 3.95-4.09 (2H, m), 4.42-4.54 (1H, m), 6.68-6.76 (1H, m), 7.34-7.41 (1H, m), 7.78 (1H, brs), 8.51 (1H, brs), 8.63 (1H, s), 9.11-9.51 (2H, m), 11.25 (1H, d, J = 7.3 Hz), 12.69 (1H, s), 14.76 (1H, br). MS: 286 (M + H − 2HCl)+ |
| 374 | 18 | 1H-NMR (400 MHz, d6-DMSO) δ: 2.02-2.20 (4H, m), 2.24-2.36 (2H, m), 2.43-2.61 (2H, m), 2.47 (3H, s), 4.01-4.11 (2H, m), 4.53-4.62 (1H, m), 6.67-6.73 (1H, m), 7.37-7.42 (1H, m), 8.74 (1H, s), 9.00-9.10 (1H, m), 9.18-9.29 (1H, m), 9.45 (1H, d, J = 7.6 Hz), 12.34 (1H, brs). MS: 325 (M + H − 2HCl)+ |
| 375 | 18 | 1H-NMR (400 MHz, d6-DMSO) δ: 1.34-2.15 (15H, m), 4.02-4.11 (1H, m), 6.43 (1H, d, J = 2.9 Hz), 6.56 (1H, d, J = 2.9 Hz), 7.11-7.12 (1H, m), 7.63-7.65 (1H, m), 8.37 (1H, s), 10.11 (1H, d, J = 8.0 Hz), 11.43 (1H, brs). MS: 326 (M + H)+. |
| 376 | 18 | 1H-NMR (400 MHz, d6-DMSO) δ: 1.38-2.08 (15H, m), 4.09-4.11 (1H, m), 6.39 (1H, d, J = 3.5 Hz), 6.56 (1H, d, J = 3.5 Hz), 7.11-7.12 (1H, m), 7.64-7.65 (1H, m), 8.35 (1H, s), 10.09 (1H, d, J = 8.2 Hz), 11.44 (1H, brs). MS: 326 (M + H)+. |
| 377 | 18 | 1H-NMR (400 MHz, d6-DMSO) δ: 1.15-2.51 (15H, m), 4.28-4.33 (1H, m), 6.53-6.59 (1H, m), 6.75-6.79 (1H, m), 7.32-7.34 (1H, m), 8.06-8.12 (3H, m), 8.24-8.25 (1H, m), 12.09-12.14 (1H, m). MS: 308 (M + H)+ |
| 378 | 19 | MS: 286 (M + H)+ |
| 379 | 19 | 1H-NMR (400 MHz, d6-DMSO) δ: 1.48-1.51 (2H, m), 1.63 (1H, brs), 1.68-1.71 (2H, m), 1.80-1.89 (4H, m), 2.09 (1H, brs), 2.25 (1H, brs), 4.10-4.13 (1H, m), 4.56 (1H, m), 4.75 (2H, d, J = 5.6 Hz), 4.87 (1H, t, J = 5.6 Hz), 6.50-6.52 (1H, m), 7.11-7.18 (1H, m), 8.47 (1H, s), 10.50 (1H, d, J = 8.0 Hz), 11.77 (1H, brs). MS: 342 (M + H)+ |
| 380 | 19 | 1H-NMR (400 MHz, d6-DMSO) δ: 1.46-2.19 (13H, m), 4.21-4.23 (1H, m), 4.51 (1H, s), 4.74-4.76 (2H, d, J = 6.0 Hz), 4.83 (1H, t, J = 6.9 Hz), 6.46-6.48 (1H, m), 7.17-7.19 (1H, m), 8.47 (1H, s), 10.46 (1H, d, J = 8.0 Hz), 11.74 (1H, s). MS: 342 (M + H)+ |
| 381 | 19 | 1H-NMR (400 MHz, d6-DMSO) δ: 1.23-2.32 (13H, m), 3.00-3.07 (2H, m), 4.21 (1H, brs), 4.43 (1H, brs), 4.75 (2H, brs), 6.46-6.49 (1H, m), 6.55 (1H, s), 7.16-7.17 (1H, m), 8.46 (1H, s), 10.54 (1H, d, J = 8.0 Hz), 11.75 (1H, brs). MS: 356 (M + H)+ |
| 382 | 22 | MS: 391 (M + H)+ |
| 383 | 22 | 1H-NMR (400 MHz, d6-DMSO) δ: 1.77-1.87 (2H, m), 1.92-2.08 (6H, m), 2.10-2.15 (1H, m), 2.65-2.73 (4H, m), 3.21 (3H, s), 4.36 (2H, s), 4.51 (1H, s), 6.35-6.38 (1H, m), 7.45 (1H, t, J = 2.9 Hz), 7.91 (1H, s), 10.84 (1H, s), 11.60 (1H, s). MS: 405 (M + H)+ |
| 384 | 22 | 1H-NMR (400 MHz, d6-DMSO) δ: 1.59-1.67 (2H, m), 1.82-2.07 (3H, m), 2.16-2.30 (4H, m), 2.35-2.43 (2H, m), 2.69-2.73 (2H, m), 3.28 (3H, s), 4.39 (2H, s), 4.59 (1H, s), 6.31-6.35 (1H, m), 7.43 (1H, t, J = 3.0 Hz), 7.90 (1H, s), 10.77 (1H, br), 11.56 (1H, s). MS: 406 (M + H)+ |
| 385 | 22 | MS: 340 (M + H)+ |
| 386 | 22 | MS: 340 (M + H)+ |
| 387 | 22 | 1H-NMR (400 MHz, d6-DMSO) δ: 1.48-1.53 (4H, m), 1.58-1.64 (2H, m), 1.70-1.75 (2H, m), 1.93-1.96 (1H, m), 2.05-2.11 (2H, m), 2.16-2.20 (2H, m), 3.06-3.08 (2H, m), 4.27-4.30 (1H, m), 4.41-4.45 (1H, m), 6.52-6.54 (1H, m), 7.26-7.28 (1H, m), 8.11-8.12 (1H, m), 8.29-8.31 (1H, m), 8.63 (1H, s), 9.03-9.06 (1H, m), 11.86 (1H, brs). MS: 409 (M + H)+ |

TABLE 72-continued

| Ex | Ref-Ex | Data |
|---|---|---|
| 388 | 22 | 1H-NMR (400 MHz, d6-DMSO) δ: 1.31-1.35 (2H, m), 1.47-1.49 (2H, m), 1.75-1.80 (2H, m), 1.85-2.00 (5H, m), 2.16-2.19 (2H, m), 3.01-3.03 (2H, m), 4.33-4.41 (2H, m), 6.61-6.63 (1H, m), 7.27-7.28 (1H, m), 8.14-8.16 (1H, m), 8.19-8.20 (1H, m), 8.63 (1H, s), 8.92-8.95 (1H, m), 11.87 (1H, brs). MS: 409 (M + H)+ |
| 389 | 22 | 1H-NMR (400 MHz, d6-DMSO) δ: 1.41-1.46 (2H, m), 1.69-1.79 (4H, m), 1.96-2.08 (3H, m), 2.31-2.37 (2H, m), 2.67-2.70 (2H, m), 4.48 (1H, s), 4.57 (1H, s), 6.3 (1H, d, J = 3.4 Hz), 7.45-7.45 (1H, m), 7.89 (1H, s), 10.75 (1H, s), 11.57 (1H, s). MS: 325 (M + H)+ |
| 390 | 22 | 1H-NMR (400 MHz, d6-DMSO) δ: 1.44-1.49 (2H, m), 1.63-1.79 (4H, m), 1.92-1.98 (2H, m), 2.14-2.34 (3H, m), 2.78-2.81 (2H, m), 4.37 (1H, s), 4.39 (1H, s), 6.33-6.35 (1H, m), 6.55 (1H, s), 7.43 (1H, t, J = 2.9 Hz), 7.89 (1H, s), 10.75 (1H, s), 11.56 (1H, s). MS: 325 (M + H)+ |
| 391 | 23 | 1H-NMR (400 MHz, d6-DMSO) δ: 1.57-1.63 (2H, m), 1.75-2.11 (8H, m), 2.44-2.59 (4H, m), 4.55 (1H, s), 6.34 (1H, dd, J = 1.4 Hz, 3.3 Hz), 7.43 (1H, t, J = 2.9 Hz), 7.89 (1H, s), 10.74 (1H, s), 11.56 (1H, s). MS: 309 (M + H)+ |
| 392 | 23 | 1H-NMR (400 MHz, d6-DMSO) δ: 1.42-3.57 (13H, m), 4.37-4.61 (2H, m), 3.29-3.36 (1H, m), 7.42-7.46 (1H, m), 7.90 (1H, s), 10.75-10.77 (1H, m), 11.56 (1H, s). MS: 325 (M + H)+ |
| 393 | 23 | 1H-NMR (400 MHz, d6-DMSO) δ: 1.54-1.68 (12H, m), 1.86-1.91 (3H, m), 3.71 (2H, s), 6.65 (1H, dd, J = 1.8 Hz, 3.5 Hz), 7.39 (1H, t, J = 3.1 Hz), 7.91 (1H, s), 10.86 (1H, s), 11.52 (1H, s). MS: 323 (M + H)+ |
| 394 | 23 | 1H-NMR (400 MHz, d6-DMSO) δ: 1.51-1.59 (2H, m), 2.03-2.14 (5H, m), 2.33-2.52 (4H, m), 2.63-2.68 (2H, m), 3.90 (1H, s), 4.76 (1H, d, J = 3.1 Hz), 6.64-6.65 (1H, m), 17.47 (1H, t, J = 3.1 Hz), 7.90 (1H, s), 10.78 (1H, s), 11.61 (1H, s. MS: 325 (M + H)+ |
| 395 | 23 | 1H-NMR (400 MHz, d6-DMSO) δ: 1.56-1.79 (5H, m), 2.31-2.55 (9H, m), 4.75 (1H, s), 6.61 (1H, s), 7.48 (1H, t, J = 3.1 Hz), 7.91 (1H, s), 10.78 (1H, s), 11.61 (1H, s). MS: 325 (M + H)+ |
| 396 | 23 | 1H-NMR (400 MHz, d6-DMSO) δ: 1.51-1.60 (2H, m), 1.71-1.84 (4H, m), 1.95-2.02 (2H, m), 2.20-2.25 (1H, m), 2.39-2.45 (2H, m), 2.79-2.84 (2H, m), 3.11 (3H, s), 4.42 (1H, s), 6.35-6.38 (1H, m), 7.44 (1H, t, J = 3.1 Hz), 7.90 (1H, s), 10.76 (1H, s), 11.57 (1H, s). MS: 338 (M + H)+ |
| 397 | 23 | 1H-NMR (400 MHz, d6-DMSO) δ: 1.43-1.50 (2H, m), 1.74-1.77 (2H, m), 1.83-1.88 (2H, m), 2.02-2.15 (3H, m), 2.72-2.37 (2H, m), 2.75-2.79 (2H, m), 3.19 (3H, s), 4.50 (1H, s), 6.34 (1H, dd, J = 1.7 Hz, 3.6 Hz), 7.44 (1H, t, J = 3.0 Hz), 7.90 (1H, s), 10.77 (1H, s), 11.56 (1H, s). MS: 339 (M + H)+ |
| 398 | 23 | 1H-NMR (400 MHz, d6-DMSO) δ: 1.53-1.60 (2H, m), 1.85-1.92 (2H, m), 1.97-2.09 (3H, m), 2.18-2.26 (2H, m), 2.38-2.45 (2H, m), 2.65-2.71 (2H, m), 3.64 (3H, s), 4.54 (1H, s), 6.30-6.31 (1H, m), 7.43 (1H, t, J = 3.0 Hz), 7.90 (1H, s), 10.78 (1H, s), 11.57 (1H, s). MS: 367 (M + H)+ |
| 399 | 23 | 1H-NMR (400 MHz, d6-DMSO) δ: 1.17 (3H, t, J = 7.1 Hz), 1.69-1.93 (6H, m), 2.03-2.11 (2H, m), 2.37-2.47 (2H, m), 2.71-2.75 (2H, m), 3.73 (2H, d, J = 5.8 Hz), 4.06 (2H, q, J = 7.1 Hz), 4.49 (1H, s), 6.34-6.36 (1H, m), 7.44 (1H, t, J = 3.0 Hz), 7.81 (1H, t, J = 5.8 Hz), 7.90 (1H, s), 10.75 (1H, s), 11.57 (1H, s). MS: 438 (M + H)+ |
| 400 | 23 | 1H-NMR (400 MHz, d6-DMSO) δ: 1.2 (3H, t, J = 7.1 Hz), 1.50-1.58 (2H, m), 1.84-1.88 (2H, m), 1.95-2.03 (3H, m), 2.18-2.26 (2H, m), 2.38-2.46 (2H, m), 2.63-2.70 (2H, m), 3.8 (2H, d, J = 5.8 Hz), 4.09 (2H, q, J = 7.1 Hz), 4.55 (1H, s), 6.36-6.38 (1H, m), 7.45 (1H, t, J = 3.0 Hz), 7.90 (1H, s), 8.07 (1H, t, J = 6.1 Hz), 10.78 (1H, s), 11.58 (1H, s). MS: 438 (M + H)+ |
| 401 | 23 | 1H-NMR (400 MHz, d6-DMSO) δ: 1.67-1.73 (2H, m), 1.78-1.82 (2H, m), 1.84-1.91 (2H, m), 2.00-2.10 (3H, m), 2.37-2.44 (2H, m), 2.68-2.72 (2H, m), 4.48 (1H, s), 6.34-6.35 (1H, m), 6.70 (1H, s), 6.91 (1H, s), 7.44 (1H, t, J = 3.0 Hz), 7.90 (1H, s), 10.75 (1H, s), 11.56 (1H, s). MS: 352 (M + H)+ |
| 402 | 23 | 1H-NMR (400 MHz, d6-DMSO) δ: 1.45-1.55 (2H, m), 1.81-1.85 (2H, m), 1.93-2.00 (3H, m), 2.16-2.21 (2H, m), 2.38-2.45 (2H, m), 2.61-2.66 (2H, m), 4.53 (1H, s), 6.38-6.39 (1H, m), 6.80 (1H, s), 7.15 (1H, s), 7.44 (1H, t, J = 3.0 Hz), 7.90 (1H, s), 10.76 (1H, s), 11.56 (1H, s). MS: 352 (M + H)+ |
| 403 | 23 | 1H-NMR (400 MHz, d6-DMSO) δ: 1.35-1.40 (9H, m), 1.45-2.13 (7H, m), 2.25-2.40 (4H, m), 2.64-2.77 (2H, m), 4.41-4.49 (1H, m), 6.27-6..34 (1H, m), 6.39-6.58 (1H, m), |

TABLE 72-continued

| Ex | Ref-Ex | Data |
|---|---|---|
| | | 7.42-7.47 (1H, m), 7.89 (1H, s), 10.75-10.76 (1H, m), 11.54-11.59 (1H, m). MS: 424 (M + H)+ |
| 404 | 23 | 1H-NMR (400 MHz, d6-DMSO) δ: 1.57-1.63 (2H, m), 1.74-1.85 (4H, m), 1.95-2.02 (2H, m), 2.21-2.26 (1H, m), 2.42-2.48 (2H, m), 2.65 (2H, t, J = 6.0 Hz), 2.79-2.83 (2H, m), 3.55 (2H, t, J = 6.0 Hz), 4.44 (1H, s), 6.38-6.40 (1H, m), 7.46 (1H, t, J = 3.0 Hz), 7.92 (1H, s), 10.83 (1H, s), 11.65 (1H, s). MS: 378 (M + H)+ |
| 405 | 23 | 1H-NMR (400 MHz, d6-DMSO) δ: 1.44-1.52 (2H, m), 1.75-1.81 (2H, m), 1.86-1.92 (2H, m), 2.08-2.17 (3H, m), 2.31-2.37 (2H, m), 2.71 (2H, t, J = 6.0 Hz), 2.75-2.79 (2H, m), 3.65 (2H, t, J = 6.0 Hz), 4.53 (1H, s), 6.38 (1H, s), 7.45 (1H, t, J = 3.0 Hz), 7.91 (1H, s), 10.82 (1H, s), 11.62 (1H, s). MS: 378 (M + H)+ |
| 406 | 23 | 1H-NMR (400 MHz, d6-DMSO) δ: 1.58-1.67 (2H, m), 2.06-2.11 (1H, m), 2.30-2.59 (6H, m), 2.66-2.78 (4H, m), 4.68 (1H, s), 6.34-6.36 (1H, m), 7.44 (1H, t, J = 3.1 Hz), 7.90 (1H, s), 10.79 (1H, s), 11.58 (1H, s). MS: 387, 389 (M + H)+ |
| 407 | 23 | 1H-NMR (400 MHz, d6-DMSO) δ: 1.59-1.69 (2H, m), 2.07-2.14 (1H, m), 2.36-2.47 (6H, m), 2.65-2.72 (2H, m), 2.86-2.92 (2H, m), 4.98 (1H, s), 7.99 (1H, s), 8.35 (1H, s), 10.98 (1H, s), 13.00 (1H, s). MS: 388, 390 (M + H)+ |
| 408 | 23 | 1H-NMR (400 MHz, d6-DMSO) δ: 1.17-2.47 (9H, m), 2.93-3.00 (1H, m), 4.36-4.42 (1H, m), 6.54-6.57 (1H, m), 7.42-7.44 (1H, m), 7.88 (1H, s), 10.77 (1H, brs), 11.58 (1H, brs). MS: 269 (M + H)+ |
| 409 | 23 | 1H-NMR (400 MHz, d6-DMSO) δ: 1.20-1.86 (7H, m), 2.32-2.42 (1H, m), 3.05-3.17 (1H, m), 4.71-4.84 (1H, m), 6.49-6.55 (1H, m), 6.91 (1H, s), 7.40-7.46 (1H, m), 7.90 (1H, s), 10.77 (1H, brs), 11.56 (1H, brs). MS: 269 (M + H)+ |
| 410 | 23 | 1H-NMR (400 MHz, d6-DMSO) δ: 1.01 (3H, d, J = 7.2 Hz), 1.24 (3H, s), 1.30 (3H, s), 1.88-2.09 (3H, m), 2.29-2.52 (4H, m), 4.81-4.92 (1H, m), 6.44-6.49 (1H, m), 7.43-7.47 (1H, m), 7.92 (1H, s), 10.92 (1H, brs), 11.64 (1H, brs). MS: 311 (M + H)+ |
| 411 | 23 | 1H-NMR (400 MHz, d6-DMSO) δ: 0.78 (3H, s), 0.91 (3H, s), 1.14 (3H, s), 1.21-1.31 (1H, m), 1.63-1.73 (1H, m), 1.80-1.88 (2H, m), 1.97-2.11 (2H, m), 2.75 (1H, dd, J = 5.3, 12.5 Hz), 4.80 (1H, ddd, J = 2.4, 5.3, 12.0 Hz), 6.45 (1H, dd, J = 1.7, 3.6 Hz), 7.40-7.43 (1H, m), 7.91 (1H, s), 10.89 (1H, brs), 11.58 (1H, brs). MS: 311 (M + H)+ |
| 412 | 23 | 1H-NMR (400 MHz, d6-DMSO) δ: 1.15-3.14 (13H, m), 4.41-4.60 (1H, m), 6.35-6.40 (1H, m), 7.43-7.47 (1H, m), 7.90-7.92 (1H, m), 10.80-10.87 (1H, m), 11.62 (1H, brs). MS: 327 (M + H)+ |
| 413 | 24 | MS: 330 (M + H)+ |
| 414 | 24 | 1H-NMR (400 MHz, d6-DMSO) δ: 1.46 (2H, d, J = 12.3 Hz), 1.63 (2H, s), 1.72 (2H, d, J = 12.1 Hz), 1.92 (2H, d, J = 12.1 Hz), 1.99 (1H, s), 2.39 (2H, d, J = 12.3 Hz), 2.96 (2H, s), 4.34 (1H, s), 4.67 (1H, s), 7.97 (1H, s), 8.31 (1H, s), 10.9 (1H, s), 13.0 (1H, s). MS: 348 (M + Na)+ |
| 415 | 24 | 1H-NMR (400 MHz, d6-DMSO) δ: 1.42 (2H, d, J = 12.5 Hz), 1.68 (2H, s), 1.72 (2H, d, J = 12.0 Hz), 2.00 (2H, d, J = 12.0 Hz), 2.08 (1H, s), 2.39 (2H, d, J = 12.5 Hz), 2.79 (2H, s), 4.49 (1H, s), 4.88 (1H, s), 7.97 (1H, s), 8.32 (1H, s), 10.9 (1H, brs), 13.0 (1H, brs). MS: 348 (M + Na)+ |
| 416 | 25 | 1HNMR (400 MHz, d6-DMSO) δ: 1.38-2.18 (11H, m), 3.33-3.40 (1H, m), 4.47 (1H, s), 4.92-5.05 (1H, m), 7.05 (1H, br), 7.82 (1H, br), 8.05 (1H, s), 8.45 (1H, s), 9.97 (1H, d, J = 9.2 Hz), 11.5 (1H, s), 12.8 (1H, br). MS: 328 (M + H)+ |
| 417 | 25 | 1HNMR (400 MHz, d6-DMSO) δ: 1.32 (3H, t, J = 7.1 Hz), 1.56 (2H, t, J = 10.7 Hz), 1.80-1.83 (2H, m), 1.92-2.08 (4H, m), 3.20 (2H, brs), 3.57 (2H, s), 4.28 (2H, q, J = 7.1 Hz), 5.30-5.45 (1H, brs), 7.20-7.24 (1H, m), 7.32 (2H, dd, J = 7.2, 7.8 Hz), 7.39 (2H, d, J = 7.2 Hz), 8.14 (1H, s), 8.48 (1H, d, J = 8.8 Hz), 8.60 (1H, s), 13.0 (1H, brs). MS: 406 (M + H)+ |
| 418 | 25 | 1HNMR (400 MHz, d6-DMSO) δ: 1.11 (6H, t, J = 6.8 Hz), 1.50-2.31 (13H, m), 3.46-3.68 (4H, m), 4.11-4.12 (1H, m), 4.57 (1H, s), 6.65-6.66 (1H, m), 6.74 (1H, s), 7.38-7.39 (1H, m), 8.54 (1H, s), 8.88 (1H, d, J = 8.0 Hz), 9.30 (1H, s). MS: 454 (M + H)+ |
| 419 | 26 | 1H-NMR (400 MHz, d6-DMSO) δ: 1.46-1.52 (2H, m), 1.64-1.66 (2H, m), 1.78-1.84 (2H, m), 2.01-2.06 (2H, m), 2.18-2.27 (3H, m), 3.10-3.12 (2H, m), 4.40 (1H, s), 4.76 (1H, br), 6.53-6.55 (1H, m), 7.61-7.63 (1H, m), 8.56-8.59 (1H, s), 12.09 (1H, brs), 13.14 (1H, brs). MS: 442 (M + Na)+ |

TABLE 72-continued

| Ex | Ref-Ex | Data |
|---|---|---|
| 420 | 26 | 1H-NMR (400 MHz, d6-DMSO) δ: 1.39 (3H, t, J = 7.1 Hz), 1.48-1.53 (2H, m), 1.62-1.65 (2H, m), 1.69-1.74 (2H, m), 1.81-1.93 (4H, m), 2.09-2.12 (1H, m), 2.29-2.33 (2H, m), 4.22-4.26 (1H, m), 4.47 (2H, q, J = 7.1 Hz), 4.54 (1H, brs), 6.56-6.58 (1H, m), 7.26-7.27 (1H, m), 7.80-7.83 (1H, m), 8.71 (1H, s), 11.71 (1H, brs). MS: 424 (M + H)+ |
| 421 | 26 | 1H-NMR (400 MHz, d6-DMSO) δ: 1.48-2.31 (13H, m), 4.24 (1H, m), 4.52 (1H, s), 6.55 (1H, m), 7.23 (1H, m), 7.86 (1H, m), 8.75 (1H, s), 9.67 (1H, s), 11.63 (1H, s). MS: 352 (M + H)+ |
| 422 | 26 | 1HNMR (400 MHz, d6-DMSO) δ: 1.34 (3H, t, J = 7.1 Hz), 1.45-1.84 (10H, m), 2.06 (1H, brs), 2.22 (2H, brs), 4.31 (2H, q, J = 7.1 Hz), 4.53 (1H, s), 5.04 (1H, d, J = 8.7 Hz), 8.12 (1H, s), 8.64 (1H, s), 9.16 (1H, d, J = 8.7 Hz), 12.8 (1H, brs). MS: 357 (M + H)+ |
| 423 | 26 | 1HNMR (400 MHz, d6-DMSO) δ: 1.32 (3H, t, J = 7.1 Hz), 1.42-1.90 (10H, m), 2.15 (1H, brs), 2.22 (2H, brs), 3.15 (3H, s), 4.31 (2H, q, J = 7.1 Hz), 5.12 (1H, d, J = 8.7 Hz), 8.14 (1H, s), 8.64 (1H, s), 9.14 (1H, d, J = 8.7 Hz), 13.0 (1H, brs). MS: 371 (M + H)+ |
| 424 | 26 | 1H-NMR (400 MHz, d6-DMSO) δ: 1.40-1.67 (10H, m), 1.88-1.94 (1H, m), 2.02 (2H, brs), 3..03 (2H, d, J = 5.5 Hz), 4.37 (1H, t, J = 5.5 Hz), 5.05 (1H, d, J = 8.9 Hz), 7.04 (1H, brs), 7.82 (1H, brs), 8.03 (1H, s), 8.45 (1H, s), 10.0 (1H, d, J = 8..9 Hz), 12.7 (1H, brs). MS: 342 (M + H)+ |
| 425 | 26 | 1H-NMR (400 MHz, d6-DMSO) δ: 1.22-1.84 (10H, m), 1.94 (1H, brs), 2.06 (2H, brs), 2.98 (2H, d, J = 5.7 Hz), 4.36 (1H, t, J = 5.7 Hz), 5.06 (1H, d, J = 8.7 Hz), 7.10 (1H, brs), 7.82 (1H, brs), 8.04 (1H, s), 8.45 (1H, s), 10.0 (1H, d, J = 8.7 Hz), 12.7 (1H, brs). MS: 342 (M + H)+ |
| 426 | 26 | MS: 337 (M + H)+ |
| 427 | 27 | 1H-NMR (400 MHz, d6-DMSO) δ: 1.36-1.41 (2H, m), 1.64-1.70 (4H, m), 1.80-1.93 (4H, m), 2.04-2.07 (1H, m), 2.11-2.14 (2H, m), 4.13-4.16 (1H, m), 4.44 (1H, s), 5.82 (2H, brs), 6.37-6.38 (1H, m), 7.09-7.11 (1H, m), 8.13 (1H, s), 8.97 (1H, d, J = 8.2 Hz), 9.54 (1H, s), 11.23 (1H, brs). MS: 342 (M + H)+ |
| 428 | 28 | 1H-NMR (400 MHz, d6-DMSO) δ: 1.39 (3H, t, J = 7.2 Hz), 1.46-1.54 (2H, m), 1.58-1.77 (4H, m), 1.80-1.90 (2H, m), 1.97-2.14 (3H, m), 2.28-2.35 (2H, m), 4.18-4.25 (1H, m), 4.42 (1H, s), 4.43 (2H, q, J = 7.2 Hz), 6.60 (1H, d, J = 3.5 Hz), 7.29 (1H, d, J = 3.5 Hz), 8.65 (1H, s), 9.04 (1H, d, J = 7.7 Hz), 11.91 (1H, brs). MS: 424 (M + H)+ |
| 429 | 28 | 1H-NMR (400 MHz, d6-DMSO) δ: 1.30-1.36 (3H, m), 1.63-1.72 (2H, m), 1.93-2.04 (2H, m), 2.07-2.49 (6H, m), 2.75-2.84 (3H, m), 4.37-4.45 (2H, m), 4.61-4.68 (1H, m), 6.36-6.41 (1H, m), 7.43-7.47 (1H, m), 7.91 (1H, s), 10.82 (1H, s), 11.58-11.61 (1H, m). MS: 449 (M + H)+ |
| 430 | 28 | 1H-NMR (400 MHz, d6-DMSO) δ: 1.45-2.29 (13H, m), 3.42 (3H, s), 4.21-4.22 (1H, m), 4.46 (1H, s), 4.65 (2H, s), 6.58-6.59 (1H, m), 7.26-7.27 (1H, m), 8.60 (1H, s), 9.04 (1H, d, J = 8.0 Hz), 11.84 (1H, s). MS: 396 (M + H)+ |
| 431 | 32 | 1H-NMR (400 MHz, d6-DMSO) δ: 1.45-2.39 (20H, m), 2.60 (1H, s), 2.69 (1H, m), 3.22 (3H, s), 3.69 (1H, m), 4.44 (1H, m), 4.77 (1H, s), 6.64 (1H, m), 7.45 (1H, m), 8.74 (1H, m), 8.78 (1H, m), 10.83 (1H, s), 12.05 (1H, s). MS: 507 (M + H)+ |
| 432 | 32 | 1H-NMR (400 MHz, d6-DMSO) δ: 1.45-2.67 (18H, m), 3.12 (2H, m), 4.02 (2H, m), 4.44 (1H, m), 4.77 (1H, s), 6.66 (1H, m), 7.46 (1H, m), 8.73 (1H, s), 9.21 (1H, m), 10.94 (1H, m), 12.07 (1H, m). MS: 549 (M + Na)+ |
| 433 | 32 | MS: 543 (M + Na)+ |
| 434 | 32 | MS: 505 (M − H)− |
| 435 | 32 | MS: 467 (M + H)+ |
| 436 | 32 | 1H-NMR (400 MHz, d6-DMSO) δ: 1.45-2.69 (21H, m), 3.89 (1H, m), 4.42 (1H, m), 4.76 (1H, s), 6.65 (1H, m), 7.45 (1H, m), 8.74 (1H, s), 9.02 (1H, m), 10.88 (1H, s), 12.05 (1H, s). MS: 513 (M + H)+ |
| 437 | 32 | 1H-NMR (400 MHz, d6-DMSO) δ: 0.85-2.61 (21H, m), 3.63-3.79 (2H, m), 4.35 (1H, m), 4.44 (1H, m), 4.76 (1H, s), 6.65 (1H, m), 7.46 (1H, m), 8.72 (1H, s), 8.74 (1H, s), 10.86 (1H, s), 12.07 (1H, s). MS: 493 (M + H)+ |
| 438 | 32 | MS: 464 (M + H)+ |
| 439 | 32 | 1H-NMR (400 MHz, d6-DMSO) δ: 1.45-1.50 (2H, m), 1.65-1.68 (2H, m), 1.77-2.04 (6H, m), 2.17-2.21 (1H, m), 2.33-2.40 (2H, m), 2.59-2.64 (2H, m), 3.35-3.48 (1H, m), 3.77-3.88 (3H, m), 4.46-4.48 (1H, m), 4.67-4.69 (1H, m), 4.75-4.77 (1H, m), 4.89, 5.18 (1H, m), 6.64-6.65 (1H, m), |

TABLE 72-continued

| Ex | Ref-Ex | Data |
|---|---|---|
|  |  | 7.44-7.46 (1H, m), 8.74, 8.78 (1H, m), 11.03-11.19 (1H, m), 12.10 (1H, brs). MS: 499 (M + N)+ |
| 440 | 32 | 1H-NMR (400 MHz, d6-DMSO) δ: 1.44-1.49 (2H, m), 1.65-1.68 (2H, m), 1.77-1.83 (2H, m), 1.99-2.05 (2H, m), 2.17-2.21 (1H, m), 2.35-2.40 (2H, m), 2.58-2.62 (2H, m), 4.45 (1H, s), 4.75-4.77 (1H, m), 6.65-6.67 (1H, m), 7.45-7.47 (1H, m), 8.03 (1H, brs), 8.39 (1H, brs), 8.74 (1H, s), 10.82 (1H, brs), 12.08 (1H, brs). MS: 417 (M + Na)+ |
| 441 | 32 | 1H-NMR (400 MHz, d6-DMSO) δ: 0.77-3.54 (22H, m), 4.84 (1H, brs), 6.82-6.86 (1H, m), 7.49-7.53 (1H, m), 8.64 (1H, s), 8.87-8.93 (1H, m), 12.12 (1H, brs). MS: 453 (M + H)+ |
| 442 | 32 | 1H-NMR (400 MHz, d6-DMSO) δ: 1.39-1.44 (2H, m), 1.71-1.73 (2H, m), 1.78-1.83 (2H, m), 2.04-2.09 (2H, m), 2.11-2.15 (1H, m), 2.38-2.44 (2H, m), 2.49-2.51 (2H, m), 4.56 (1H, s), 4.88-4.89 (1H, m), 6.60-6..62 (1H, m), 7.45-7.47 (1H, m), 8.01 (1H, brs), 8.36 (1H, brs), 8.74 (1H, s), 10.85-10.90 (1H, m), 12.07 (1H, brs). MS: 417 (M + Na)+ |
| 443 | 32 | 1H-NMR (400 MHz, d6-DMSO) δ: 1.45-2.39 (13H, m), 3.16 (2H, d, J = 5.2 Hz), 3.50 (2H, q, J = 5.6 Hz), 4.07 (1H, q, J = 5.6 Hz), 4.76 (1H, brs), 4.78 (1H, t, J = 5.2 Hz), 6.65-6.66 (1H, m), 7.45-7.47 (1H, m), 8.71 (1H, s), 8.88-8.90 (1H, m), 10.89 (1H, s), 12.07 (1H, brs). MS: 439 (M + H)+ |
| 444 | 32 | 1H-NMR (400 MHz, d6-DMSO) δ: 1.46-2.37 (13H, m), 2.94 (3H, s), 3.12 (3H, s), 4.46-4.47 (1H, m), 4.75 (1H, brs), 6.63-6.64 (1H, m), 7.45-7.46 (1H, m), 8.78 (1H, s), 11.36 (1H, s), 12.16 (1H, s). MS: 423.3 (M + H)+ |
| 445 | 32 | 1H-NMR (400 MHz, d6-DMSO) δ: 1.15-2.45 (13H, m), 2.49-2.51 (6H, m), 4.21 (4H, brs), 4.76 (1H, brs), 6.55-6.55 (1H, m), 7.45-7.46 (1H, m), 8.56 (1H, s), 8.72 (1H, s), 8.83-8.87 (1H, m), 11.44 (1H, s), 12.07 (1H, brs). MS: 466.3 (M + H)+ |
| 446 | 32 | 1H-NMR (400 MHz, d6-DMSO) δ: 1.45-2.39 (11H, m), 2.49-2.45 (m, 3H), 2.60 (2H, brs), 3.16-3.20 (2H, m), 3.81-3.82 (1H, m), 4.45 (1H, s), 4.76 (1H, brs), 4.85 (1H, d, J = 4.8 Hz), 6.65-6.67 (1H, m), 7.45-7.46 (1H, m), 8.72 (1H, s), 8.82-8.82 (1H, m), 10.90 (1H, s), 12.07 (1H, brs). MS: 453 (M + Na)+ |
| 447 | 32 | 1H-NMR (400 MHz, d6-DMSO) δ: 1.04-2.38 (17H, m), 3.46-3.70 (5H, m), 4.35-4.36 (1H, m), 4.45 (1H, q), 4.57-4.59 (1H, m), 4.76 (1H, brs), 6.65-6.66 (1H, m), 7.45-7.46 (1H, m), 8.72 (1H, s), 8.82 (1H, d, J = 8.0 Hz), 10.88 (1H, s), 12.06 (1H, brs). MS: 515 (M + H)+ |
| 448 | 32 | 1H-NMR (400 MHz, d6-DMSO) δ: 1.45-2.60 (17H, m), 3.45-4.00 (6H, m), 4.47 (1H, s), 4.76 (1H, brs), 6.56-6.57 (1H, m), 7.45-7.46 (1H, m), 8.71 (1H, s), 10.93 (1H, brs), 12.07 (1H, brs). MS477 (M − H)− |
| 449 | 32 | 1H-NMR (400 MHz, d6-DMSO) δ: 1.45-2.39 (17H, m), 3.43-3.99 (5H, m), 4.34-4.54 (1H, m), 4.76 (1H, brs), 6.65-6.66 (1H, m), 7.45-7.46 (1H, m), 8.73 (1H, s), 9.02 (1H, d, J = 8.0 Hz), 10.91 (1H, brs), 12.07 (1H, brs). MS: 477 (M − H)− |
| 450 | 32 | 1H-NMR (400 MHz, d6-DMSO) δ: 1.56-1.59 (2H, m), 2.03-2.08 (3H, m), 2.22-2.25 (2H, m), 2.46-2.57 (6H, m), 3.28 (3H, s), 3.39-3.40 (2H, m), 3.48-3.49 (2H, m), 5.04 (1H, s), 6.78 (1H, s), 7.46 (1H, s), 8.73 (1H, s), 8.95 (1H, m), 10.99 (1H, s), 12.05 (1H, s). MS: 462 (M + H)+, 484 (M + Na)+ |
| 451 | 32 | 1H-NMR (400 MHz, d6-DMSO) δ: 1.36-2.37 (17H, m), 3.43-3.60 (7H, m), 4.48 (1H, brs), 4.75 (1H, brs), 6.64 (1H, brs), 7.45 (1h, brs), 8.81-8.83 (1H, m), 11.45 (1H, brs), 12.11 (1H, brs). MS: 506 (M + H)+ |
| 452 | 32 | 1H-NMR (400 MHz, d6-DMSO) δ: 1.45-2.39 (18H, m), 3.42-4.01 (6H, m), 4.47 (1H, s), 4.76 (1H, brs), 6.56-6.57 (1H, m), 7.45-7.46 (1H, m), 8.71 (1H, s), 8.95-8.96 (1H, m), 10.93 (1H, brs), 12.07 (1H, brs). MS: 515 (M + Na)+ |
| 453 | 32 | 1H-NMR (400 MHz, d6-DMSO) δ: 1.56 (2H, m), 1.75-1.77 (1H, m), 1.88-1.95 (4H, m), 2.04-2.12 (4H, m), 2.29-2.33 (2H, m), 3.28 (3H, s), 3.38-3.42 (2H, m), 3.47-3.49 (2H, m), 3.59 and 3.65 (total 3H, each m), 4.90 and 4.96 (total 1H, each s), 6.66-6.77 (1H, m), 7.44-7.47 (1H, m), 8.71 and 8.72 (total 1H, each s), 8.97 (1H, m), 11.00 (1H, s), 12.07 (1H, s). MS: 517 (M + Na)+ |
| 454 | 32 | 1H-NMR (400 MHz, d6-DMSO) δ: 52-1.55 (3H, m), 1.74-1.84 (5H, m), 2.04-2.07 (2H, m), 2.25 (1H, s), 2.64 (2H, s), 3.13 (3H, s), 3.28 (3H, s), 3.39-3.42 (2H, m), 3.47-3.50 (2H, m), 4.81 (1H, s), 6.68 (1H, dd, J = 1.9, 3.3 Hz), 7.40 (1H, t, J = 3.0 Hz), 8.71 (1H, s), 8.94 (1H, t, J = 5.8 Hz), 11.02 (1H, s), 12.06 (1H, s). MS: 467 (M + H)+, 489 (M + Na)+ |

TABLE 72-continued

| Ex | Ref-Ex | Data |
|---|---|---|
| 455 | 32 | 1H-NMR (400 MHz, d6-DMSO) δ: 1.27-1.32 (2H, m), 1.45-1.55 (4H, m), 1.68-1.71 (2H, m), 1.84-1.91 (2H, m), 2.00 (1H, s), 2.09-2.17 (2H, m), 3.03 and 3.13 (total 2H, each d, J = 5.5 and 5.5 Hz), 3.28 (3H, s), 3.39-3.42 (2H, m), 3.47-3.50 (2H, m), 4.30 and 4.47 (total 1H, each t, J = 5.5 and 5.5 Hz), 4.85 and 4.87 (total 1H, each s), 6.60 and 6.65 (total 1H, each m), 7.46 (1H, t, J = 3.0 Hz), 8.71 and 8.72 (total 1H, s), 8.97 (1H, m), 10.96 and 10.97 (total 1H, s), 12.07 (1H, s). MS: 467 (M + H)+, 489 (M + Na)+ |
| 456 | 33 | MS: 646 (M + H)+ |
| 457 | 33 | MS: 506 (M + H)+ |
| 458 | 33 | 1H-NMR (400 MHz, d6-DMSO) δ: 1.01 (3H, d, J = 7.6 Hz), 1.24 (3H, s), 1.30 (3H, s), 1.88-2.83 (7H, m), 4.80-4.90 (1H, m), 6.45-6.48 (1H, m), 7.43-7.46 (1H, m), 7.92 (1H, s), 10.91 (1H, brs), 11.63 (1H, brs). MS: 311 (M + H)+ |
| 459 | 33 | MS: 465 (M + H)+ |
| 460 | 33 | MS: 497 (M + H)+ |
| 461 | 33 | MS: 509 (M + H)+ |
| 462 | 33 | MS: 509 (M + H)+ |
| 463 | 33 | MS: 478 (M + H)+ |
| 464 | 33 | MS: 465 (M + H)+ |
| 465 | 33 | MS: 463 (M + H)+ |
| 466 | 33 | MS: 434 (M + H)+ |
| 467 | 33 | MS: 499 (M + H)+ |
| 468 | 33 | MS: 541 (M + H)+ |
| 469 | 33 | MS: 477 (M + H)+ |
| 470 | 33 | MS: 449 (M + H)+ |
| 471 | 33 | MS: 546 (M + H)+ |
| 472 | 33 | MS: 506 (M + H)+ |
| 473 | 33 | MS: 453 (M + H)+ |
| 474 | 33 | MS: 504 (M + H)+ |
| 475 | 33 | MS: 453 (M + H)+ |
| 476 | 34 | 1H-NMR (400 MHz, d6-DMSO) δ: 1.75-1.90 (4H, m), 2.00-2.10 (2H, m), 2.14-2.28 (3H, m), 2.37-2.54 (4H, m), 4.21-4.27 (1H, m), 6.36 (1H, d, J = 6.8 Hz), 6.73-6.78 (1H, m), 7.27-7.31 (1H, m), 8.11 (1H, s), 11.86 (1H, brs). MS: 427 (M + Na)+ |
| 477 | 35 | MS: 314 (M + H)+ |
| 478 | 35 | MS: 393 (M + H)+ |
| 479 | 35 | MS: 382 (M + H)+ |
| 480 | 35 | 1H-NMR (400 MHz, d6-DMSO) δ: 1.39-1.46 (2H, m), 1.56-1.87 (8H, m), 2.07 (1H, m), 2.18 (3H, s), 2.25 (2H, m), 4.03 (1H, m), 4.47 (1H, s), 4.77 (1H, d, J = 7.2 Hz), 6.38 (1H, d, J = 3.6 Hz), 7.13 (1H, d, J = 3.6 Hz), 7.71 (1H, s), 8.32 (1H, s), 11.156 (1H, s). MS: 298 (M + H)+ |
| 481 | 35 | MS: 378 (M + Na)+ |
| 482 | 35 | MS: 420 (M + Na)+ |
| 483 | 35 | 1H-NMR (400 MHz, d6-DMSO) δ: 1.22-2.24 (13H, m), 3.20-3.40 (2H, m), 4.42-4.65 (2H, m), 6.44-6.48 (1H, m), 6.82-7.09 (1H, br), 7.16-7.19 (1H, m), 7.56-7.84 (1H, br), 8.34 (1H, s), 9.45 (1H, d, J = 8.0 Hz), 11.48 (1H, brs). MS: 329 (M + H)+. |
| 484 | 35 | 1H-NMR (400 MHz, d6-DMSO) δ: 1.47-1.51 (2H, m), 1.61-1.63 (2H, m), 1.68-1.73 (2H, m), 1.81-1.87 (2H, m), 1.91-1.96 (2H, m), 2.08-2.12 (1H, m), 2.28-2.31 (2H, m), 4.19-4.23 (1H, m), 4.46 (1H, brs), 4.66-4.68 (2H, m), 5.68-5.71 (1H, m), 6.58-6.60 (1H, m), 7.25-7.26 (1H, m), 8.60 (1H, s), 9.07 (1H, d, J = 7.8 Hz), 11.83 (1H, brs). MS: 382 (M + H)+ |
| 485 | 35 | 1H-NMR (400 MHz, d6-DMSO) δ: 1.31-1.35 (2H, m), 1.47-1.50 (2H, m), 1.61-1.98 (7H, m), 2.07-2.12 (2H, m), 2.96-2.99 (2H, m), 4.11-4.16 (1H, m), 4.35-4.39 (1H, m), 6.42-6.46 (1H, m), 6.80-7.09 (1H, br), 7.10-7.13 (1H, m), 7.52-7.88 (1H, br), 8.36 (1H, s), 10.13 (1H, d, J = 8.0 Hz), 11.43 (1H, brs). MS: (M + H)+. |
| 486 | 35 | 1H-NMR (400 MHz, d6-DMSO) δ: 1.43-1.70 (8H, m), 1.89-1.96 (3H, m), 2.05-2.10 (2H, m), 3.03-3.08 (2H, m), 4.08-4.15 (1H, m), 4.39-4.44 (1H, m), 6.40-6.44 (1H, m), 6.95-7.19 (2H, m), 7.68-7.96 (1H, br), 8.38 (1H, s), 10.27 (1H, d, J = 8.0 Hz), 11.55 (1H, brs). MS: 341 (M + H)+. |
| 487 | 35 | 1H-NMR (400 MHz, d6-DMSO) δ: 1.34-1.44 (2H, m), 1.58-1.72 (4H, m), 1.80-1.90 (2H, m), 2.00-2.11 (3H, m), 2.33-2.44 (2H, m), 4.18-4.28 (3H, m), 6.59-6.60, (1H, m), 6.90-6.98 (2H, m), 7.20 (1H, brs), 7.33 (1H, brs), 7.38-7.39 (1H, m), 7.46 (1H, brs), 8.19 (1H, s), 8.61 (3H, br), 12.63 (1H, brs). MS: 313 (M − 3HCl + H)+ |
| 488 | 39 | 1H-NMR (400 MHz, d6-DMSO) δ: 1.85-2.25 (8H, m), 2.37-2.41 (1H, m), 2.53-2.57 (2H, m), 2.91-2.96 (1H, m), |

TABLE 72-continued

| Ex | Ref-Ex | Data |
|---|---|---|
| | | 3.11-3.18 (1H, m), 4.74 (1H, s), 6.55-6.59 (1H, m), 7.37 (1H, t, J = 2.7 Hz), 8.51-8.52 (1H, m), 10.89 (1H, s), 11.94 (1H, s). MS: 387, 389 (M + H)+ |
| 489 | 39 | 1H-NMR (400 MHz, d6-DMSO) δ: 1.10-1.28 (2H, m), 1.36-2.38 (7H, m), 2.54 (1H, brs), 5.02-5.08 (1H, m), 6.72-6.74 (1H, m), 7.35-7.37 (1H, m), 8.47 (1H, s), 10.9 (1H, brs), 12.0 (1H, s). MS: 269 (M + H)+ |
| 490 | 39 | 1H-NMR (400 MHz, d6-DMSO) δ: 1.54-1.64 (2H, m), 2.10-2.63 (9H, m), 2.75-2.83 (2H, m), 4.91 (1H, s), 6.64-6.66 (1H, m), 7.37 (1H, t, J = 3.0 Hz), 8.50 (1H, s), 10.81 (1H, s), 11.93 (1H, s). MS: 387, 389 (M + H)+ |
| 491 | 39 | 1H-NMR (400 MHz, d6-DMSO) δ: 1.55-1.60 (2H, m), 1.77-1.80 (2H, m), 1.90-2.02 (4H, m), 2.06-2.13 (2H, m), 2.32-2.36 (2H, m), 2.52-2.57 (2H, m), 4.75-4.77 (1H, m), 6.53-6.56 (1H, m), 7.35-7.38 (1H, m), 8.50 (1H, s), 10.78 (1H, brs), 11.92 (1H, brs). MS: 309 (M + H)+. |
| 492 | 40 | 1H-NMR (400 MHz, d6-DMSO) δ: 1.38-1.48 (2H, m), 1.64-1.81 (4H, m), 1.93-2.05 (2H, m), 2.11-2.19 (1H, m), 2.37-2.57 (4H, m), 4.44 (0.34H, brs), 4.56-4.59 (1H, m), 4.70 (0.66H, brs), 6.50-6.52 (0.66H, m), 6.54-6.56 (0.34H, m), 7.36-7.38 (1H, m), 8.50 (0.66H, s), 8.51 (0.34H, s), 10.78 (1H, brs), 11.92 (1H, brs). MS: 325 (M + H)+. |
| 493 | 40 | MS: 325 (M + H)+. |
| 494 | 40 | 1HNMR (400 MHz, d6-DMSO) δ: 0.88 (3H, d, J = 6.9 Hz), 1.72-1.92 (2H, m), 2.15-2.26 (1H, m), 3.55-3.70 (4H, m), 5.30-5.40 (1H, m), 7.01 (1H, d, J = 9.2 Hz), 7.15 (1H, m), 7.76 (1H, d, J = 9.2 Hz), 7.90 (1H, brs), 8.09 (1H, s), 8.39 (1H, s), 8.48 (1H, s), 9.89 (1H, d, J = 9.0 Hz), 12.9 (1H, brs). MS: 420 (M + H)+ |
| 495 | 41 | 1H-NMR (400 MHz, d6-DMSO) δ: 1.43-1.52 (2H, m), 1.76-1.91 (6H, m), 2.10-2.16 (1H, m), 2.27-2.33 (3H, m), 2.68 (2H, t, J = 6 Hz), 3.59 (2H, t, J = 6 Hz), 4.76-4.85 (1H, m), 6.09 (1H, d, J = 7.3 Hz), 8.25-8.27 (3H, m), 13.21 (1H, br). MS: 363 (M + H)+ |
| 496 | 41 | 1H-NMR (400 MHz, d6-DMSO) δ: 1.00-1.59 (13H, m), 2.64-2.75 (2H, m), 3.54-3.69 (2H, m), 4.63-4.76 (1H, m), 6.55-6.64 (1H, m), 7.35-7.39 (1H, m), 8.50 (1H, s), 10.79-10.83 (1H, m), 11.91 (1H, s). MS: 378 (M + H)+ |
| 497 | 41 | 1H-NMR (400 MHz, d6-DMSO) δ: 1.54-1.62 (2H, m), 1.73-1.86 (4H, m), 1.96-2.27 (4H, m), 2.54-2.61 (3H, m), 2.67 (2H, t, J = 6.0 Hz), 3.57 (2H, t, J = 6.0 Hz), 4.63 (1H, s), 6.56-6.59 (1H, m), 7.36-7.39 (1H, m), 8.49-8.51 (1H, m), 10.83 (1H, s), 11.93 (1H, s). MS: 378 (M + H)+ |
| 498 | 41 | 1H-NMR (400 MHz, d6-DMSO) δ: 1.41-1.49 (2H, m), 1.77-1.82 (2H, m), 1.84-1.89 (2H, m), 2.15-2.22 (4H, m), 2.41-2.48 (3H, m), 2.71 (2H, t, J = 6.0 Hz), 3.66 (2H, t, J = 6.0 Hz), 4.76 (1H, m), 6.61-6.63 (1H, m), 7.36-7.37 (1H, m), 8.50 (1H, s), 10.79 (1H, s), 11.92 (1H, s). MS: 378 (M + H)+ |
| 499 | 41 | 1H-NMR (400 MHz, d6-DMSO) δ: 1.42-1.49 (2H, m), 1.73-1.80 (4H, m), 1.83-1.89 (2H, m), 1.97-2.03 (2H, m), 2.09-2.13 (1H, m), 2.18-2.23 (1H, m), 2.68 (2H, t, J = 6.0 Hz), 3.61 (2H, t, J = 6.0 Hz), 4.17-4.21 (1H, m), 6.48 (1H, dd, J = 1.9, 3.5 Hz), 6.99 (1H, br), 7.12 (1H, dd, J = 2.5, 3.5 Hz), 7.79 (1H, br), 8.37 (1H, s), 10.11 (1H, d, J = 8.3 Hz), 11.46 (1H, s). MS: 390 (M + H)+ |
| 500 | 41 | 1H-NMR (400 MHz, d6-DMSO) δ: 1.42-1.48 (2H, m), 1.71-1.90 (7H, m), 2.10-2.20 (4H, m), 2.68 (2H, t, J = 5.9 Hz), 3.59 (2H, t, J = 5.9 Hz), 5.07 (1H, d, J = 8.7 Hz), 7.12 (1H, br), 7.86 (1H, br), 8.05 (1H, s), 8.45 (1H, s), 9.97 (1H, d, J = 8.7 Hz), 12.78 (1H, br). MS: 381 (M + H)+ |
| 501 | 41 | 1H-NMR (400 MHz, d6-DMSO) δ: 1.53-1.60 (2H, m), 1.70-1.79 (6H, m), 1.87-1.95 (2H, m), 2.08-2.15 (1H, m), 2.21-2.27 (2H, m), 2.69 (2H, t, J = 6 Hz), 3.58 (2H, t, J = 6 Hz), 4.99 (1H, d, J = 8.6 Hz), 7.18 (1H, br), 7.89 (1H, br), 8.06 (1H, s), 8.46 (1H, s), 10.05 (1H, d, J = 8.6 Hz), 12.79 (1H, br). MS: 381 (M + H)+ |
| 502 | 41 | 1H-NMR (400 MHz, d6-DMSO) δ: 1.43-1.51 (2H, m), 1.77-1.80 (2H, m), 1.83-1.90 (2H, m), 2.03-2.09 (2H, m), 2.12-2.17 (1H, m), 2.33-2.40 (3H, m), 2.70 (2H, t, J = 6.0 Hz), 2.89-2.93 (2H, m), 3.61 (2H, t, J = 6.0 Hz), 4.87 (1H, s), 7.98 (1H, s), 10.94 (1H, s), 12.95 (1H, br). MS: 379 (M + H)+ |
| 503 | 41 | 1H-NMR (400 MHz, d6-DMSO) δ: 1.45-1.52 (2H, m), 1.79-1.84 (2H, m), 1.87-1.95 (2H, m), 2.06-2.10 (2H, m), 2.14-2.19 (1H, m), 2.28-2.38 (2H, m), 2.95-3.02 (2H, m), 4.48 (2H, s), 4.82 (1H, s), 7.98 (1H, s), 8.33 (1H, s), 10.95 (1H, s), 12.99 (1H, br). MS: 356 (M + H)+ |

TABLE 72-continued

| Ex | Ref-Ex | Data |
|---|---|---|
| 504 | 43 | 1H-NMR (400 MHz, d6-DMSO) δ: 1.83-1.90 (2H, m), 1.93-1.99 (2H, m), 2.08-2.13 (1H, m), 2.23-2.29 (5H, m), 2.32-2.36 (3H, m), 4.27 (1H, d, J = 7.8 Hz), 6.6 (1H, d, J = 1.9 Hz), 7.3 (1H, t, J = 2.3 Hz), 7.53 (1H, br), 8.16 (1H, br), 8.47 (1H, s), 10.94 (1H, s), 12.11 (1H, s). MS: 389, 391 (M + H)+ |
| 505 | 43 | 1H-NMR (400 MHz, d6-DMSO) δ: 1.22-2.33 (10H, m), 4.12 (1H, m), 6.44 (1H, m), 7.03 (1H, m), 7.14 (1H, m), 7.64 (1H, m), 8.39 (1H, s), 10.25 (1H, m), 11.48 (1H, s). MS: 345 (M + H)+ |
| 506 | 43 | 1H-NMR (400 MHz, d6-DMSO) δ: 1.68-2.38 (13H, m), 4.98-5.02 (1H, m), 7.08 (1H, brs), 7.90 (1H, brs), 8.06 (1H, s), 8.47 (1H, s), 10.4 (1H, d, J = 8.6 Hz), 12.7 (1H, brs). MS: 330 (M + H)+ |
| 507 | 45 | MS: 366 (M + H)+ |
| 508 | 46 | MS: 388 (M + H)+ |
| 509 | 46 | MS: 387 (M + H)+ |
| 510 | 46 | MS: 397 (M + H)+ |
| 511 | 46 | MS: 363 (M + H)+ |
| 512 | 46 | MS: 405 (M + H)+ |
| 513 | 46 | MS: 749 (M + H)+ |
| 514 | 46 | MS: 381 (M + H)+ |
| 515 | 46 | MS: 314 (M + H)+ |
| 516 | 46 | MS: 328 (M + H)+ |
| 517 | 46 | MS: 356 (M + H)+ |
| 518 | 46 | MS: 368 (M + H)+ |
| 519 | 46 | MS: 370 (M + H)+ |
| 520 | 46 | MS: 377 (M + H)+ |
| 521 | 46 | MS: 379 (M + H)+ |
| 522 | 46 | MS: 382 (M + H)+ |
| 523 | 46 | MS: 394 (M + H)+ |
| 524 | 46 | MS: 378 (M + H)+ |
| 525 | 46 | MS: 378 (M + H)+ |
| 526 | 46 | MS: 393 (M + H)+ |
| 527 | 46 | MS: 426 (M + H)+ |
| 528 | 46 | MS: 342 (M + H)+ |
| 529 | 46 | MS: 384 (M + H)+ |
| 530 | 47 | MS: 368 (M + H)+ |
| 531 | 47 | MS: 354 (M + H)+ |
| 532 | 47 | MS: 354 (M + H)+ |
| 533 | 47 | MS: 354 (M + H)+ |
| 534 | 47 | MS: 368 (M + H)+ |
| 535 | 47 | 1H-NMR (400 MHz, d6-DMSO) δ: 1.13-1.27 (1H, m), 1.43-1.52 (2H, m), 1.62-1.73 (4H, m), 1.78-1.91 (5H, m), 2.07-2.42 (6H, m), 3.54-3.67 (5H, m), 4.00-4.13 (1H, m), 4.53 (1H, brs), 6.35-6.43 (1H, m), 7.18-7.20 (1H, m), 7.70 (1H, s), 7.82 (1H, m), 11.64 (1H, brs). MS: 383 (M + H)+ |
| 536 | 49 | MS: 440 (M + H)+ |
| 537 | 47 | 1H-NMR (400 MHz, d6-DMSO) δ: 1.58-2.42 (8H, m), 3.04-3.66 (4H, m), 4.19-4.38 (1H, m), 6.37-6.54 (1H, m), 6.87-7.96 (8H, m), 8.36 (1H, s), 10.08-10.26 (1H, m), 11.42 (1H, brs). MS: 376 (M + H)+ |
| 538 | 49 | MS: 421 (M + H)+ |
| 539 | 49 | MS: 408 (M + H)+ |
| 540 | 49 | 1H-NMR (400 MHz, d6-DMSO) δ: 1.47-2.22 (9H, m), 4.59 (1H, m), 4.83 (2H, m), 6.59 (1H, m), 6.98 (1H, m), 7.20 (1H, m), 7.73 (1H, m), 8.33 (1H, m), 8.37 (1H, m), 9.34 (1H, m), 11.53 (1H, s). MS: 389 (M + H)+ |
| 541 | 49 | 1H-NMR (400 MHz, d6-DMSO) δ: 1.49-2.36 (7H, m), 4.63 (1H, m), 4.91 (2H, m), 6.61 (1H, m), 6.98 (1H, m), 7.21 (1H, m), 7.77 (1H, m), 8.32 (1H, m), 9.15 (2H, m), 9.39 (1H, m), 11.54 (1H, s). MS: 409 (M + H)+ |
| 542 | 49 | MS: 442, 444 |
| 543 | 49 | 1H-NMR (400 MHz, d6-DMSO) δ: 1.41-2.33 (8H, m), 4.61 (1H, m), 4.86 (2H, m), 6.60 (1H, m), 6.95 (1H, m), 7.21 (1H, m), 7.32 (1H, m), 7.74 (1H, m), 7.88 (1H, m), 8.32 (1H, m), 9.34 (1H, m), 11.53 (1H, s). MS: 389 (M + H)+ |
| 544 | 49 | MS: 394 (M + H)+ |
| 545 | 49 | MS: 389 (M + H)+ |
| 546 | 49 | 1H-NMR (400 MHz, d6-DMSO) δ: 1.45-1.51 (2H, m), 1.59-1.62 (2H, m), 1.66-1.71 (2H, m), 1.81-1.92 (4H, m), 2.07-2.10 (2H, m), 2.28-2.31 (2H, m), 3.69-3.87 (8H, m), 4.20-4.24 (1H, m), 4.47 (1H, s), 6.59-6.61 (1H, m), 6.96 (1H, d, J = 9.0 Hz), 7.28-7.29 (1H, m), 7.91 (1H, dd, J = 2.4, 9.1 Hz), 8.52-8.53 (1H, m), 8.66 (1H, s), 8.86-8.89 (1H, m), 11.90 (1H, brs). MS: 566 (M + H)+ |
| 547 | 49 | MS: 405 (M + H)+ |

TABLE 72-continued

| Ex | Ref-Ex | Data |
|---|---|---|
| 548 | 49 | 1H-NMR (400 MHz, d6-DMSO) δ: 1.75-1.87 (2H, m), 1.98-2.14 (2H, m), 2.14-2.33 (4H, m), 4.25-4.35 (1H, m), 4.50-4.83 (2H, m), 6.38-6.45 (1H, m), 6.85 (1H, d, J = 9.0 Hz), 7.03-7.10 (1H, m), 7.05 (1H, br), 7.83 (1H, br), 7.85 (1H, dd, J = 9.0, 2.2 Hz), 8.38 (1H, s), 8.51 (1H, d, J = 2.2 Hz), 10.36 (1H, d, J = 7.7 Hz), 11.43 (1H, s) MS: 388 (M + H)+ |
| 549 | 49 | 1H-NMR (400 MHz, d6-DMSO) δ: 1.75-1.87 (2H, m), 1.98-2.14 (2H, m), 2.14-2.33 (4H, m), 4.25-4.35 (1H, m), 4.50-4.83 (2H, m), 6.38-6.45 (1H, m), 6.85 (1H, d, J = 9.0 Hz), 7.03-7.10 (1H, m), 7.05 (1H, br), 7.83 (1H, br), 7.85 (1H, dd, J = 9.0, 2.2 Hz), 8.38 (1H, s), 8.51 (1H, d, J = 2.2 Hz), 10.36 (1H, d, J = 7.7 Hz), 11.43 (1H, s). MS: 388 (M + H)+ |
| 550 | 49 | 1H-NMR (400 MHz, d6-DMSO) δ: 1.83-1.94 (2H, m), 2.01-2.18 (2H, m), 2.18-2.36 (4H, m), 4.27-4.38 (1H, m), 4.46-5.09 (2H, m), 6.38-6.45 (1H, m), 6.87 (1H, d, J = 9.5 Hz), 7.04-7.11 (1H, m), 7.05 (1H, br), 7.83 (1H, br), 8.24 (1H, dd, J = 9.5, 2.8 Hz), 8.39 (1H, s), 9.01 (1H, d, J = 2.8 Hz), 10.38 (1H, d, J = 7.7 Hz), 11.45 (1H, s). MS: 408 (M + H)+ |
| 551 | 49 | 1H-NMR (400 MHz, d6-DMSO) δ: 1.69-1.84 (2H, m), 1.99-2.14 (2H, m), 2.14-2.36 (4H, m), 4.24-4.34 (1H, m), 4.54-4.75 (2H, m), 6.38-6.44 (1H, m), 6.88 (1H, d, J = 8.9 Hz), 7.02-7.07 (1H, m), 7.06 (1H, br), 7.79 (1H, dd, J = 8.9, 2.5 Hz), 7.80 (1H, br), 8.38 (1H, s), 8.42-8.45 (1H, m), 10.35 (1H, d, J = 7.7 Hz), 11.42 (1H, s). MS: 431 (M + H)+ |
| 552 | 49 | 1H-NMR (400 MHz, d6-DMSO) δ: 1.83-1.95 (2H, m), 2.05-2.21 (2H, m), 2.21-2.41 (4H, m), 2.45 (3H, s), 4.42-4.52 (1H, m), 4.58-4.85 (2H, m), 6.54-6.60 (1H, m), 6.89 (1H, d, J = 8.9 Hz), 7.17-7.22 (1H, m), 7.87 (1H, dd, J = 8.9, 2.4 Hz), 8.53 (1H, dd, J = 2.4, 0.4 Hz), 8.59 (1H, s), 9.26 (1H, d, J = 7.6 Hz), 11.79 (1H, s). MS: 427 (M + H)+ |
| 553 | 49 | 1H-NMR (400 MHz, d6-DMSO) δ: 1.80-2.00 (4H, m), 2.11-2.22 (2H, m), 2.29-2.42 (2H, m), 4.28-4.40 (3H, m), 6.42-6.48 (1H, m), 6.89 (1H, dd, J = 8.0, 4.6 Hz), 7.04 (1H, br), 7.05-7.10 (1H, m), 7.74 (1H, br), 8.21 (1H, dd, J = 8.0, 1.7 Hz), 8.37 (1H, s), 8.42 (1H, dd, J = 4.6, 1.7 Hz), 10.27 (1H, d, J = 7.7 Hz), 11.41 (1H, s). MS: 408 (M + H)+ |
| 554 | 49 | 1H-NMR (400 MHz, d6-DMSO) δ: 1.55-1.65 (2H, m), 2.02-2.25 (6H, m), 4.38-4.44 (2H, m), 5.55-5.65 (1H, m), 7.10 (1H, brs), 7.82 (1H, brs), 8.05 (1H, s), 8.11 (1H, s), 8.42 (1H, s), 9.18 (1H, d, J = 8.5 Hz), 12.9 (1H, brs). MS: 395 (M + H)+ |
| 555 | 49 | 1H-NMR (400 MHz, d6-DMSO) δ: 1.60-1.67 (2H, m), 1.96-2.06 (4H, m), 2.16-2.21 (2H, m), 4.50-4.60 (2H, m), 4.99 (1H, brs), 6.59 (1H, s), 7.00 (1H, brs), 7.20 (1H, s), 7.80 (1H, brs), 8.22 (1H, d, J = 1.9 Hz), 8.34 (1H, s), 8.55 (1H, d, J = 1.9 Hz), 9.43 (1H, d, J = 8.5 Hz), 11.5 (1H, s). MS: 422 (M + H)+ |
| 556 | 49 | 1H-NMR (400 MHz, d6-DMSO) δ: 1.22-2.03 (8H, m), 4.58-4.67 (5H, m), 5.38 (1H, brs), 6.58-6.59 (1H, m), 6.97 (1H, brs), 7.19-7.25 (2H, m), 7.44-7.46 (1H, m), 7.75 (1H, brs), 8.31 (1H, s), 9.30 (1H, d, J = 8.0 Hz), 11.54 (1H, s). MS: 394 (M + H)+ |
| 557 | 49 | 1H-NMR (400 MHz, d6-DMSO) δ: 1.30-2.15 (8H, m), 4.34 (2H, brs), 4.55-4.56 (1H, m), 6.57-6.58 (1H, m), 6.95 (1H, brs), 7.18-7.20 (1H, m), 7.86 (1H, brs), 8.00 (1H, s), 8.34 (1H, s), 9.39 (1H, d, J = 8.0 Hz), 11.55 (1H, brs). MS: 394 (M + H)+ |
| 558 | 49 | 1H-NMR (400 MHz, d6-DMSO) δ: 1.56-2.56 (8H, m), 3.69 (3H, s), 4.66-4.85 (3H, m), 6.66 (1H, s), 7.25-7.35 (2H, m), 7.85-7.94 (1H, m), 8.35-8.43 (1H, m), 9.33-9.45 (1H, m), 11.53 (1H, m). MS: 422 (M + H)+ |
| 559 | 49 | 1H-NMR (400 MHz, d6-DMSO) δ: 1.23-2.32 (8H, m), 4.60-4.80 (3H, m), 6.61 (1H, s), 7.24-7.36 (2H, m), 7.85-8.40 (6H, m), 9.27-9.37 (1H, m), 11.53 (1H, brs). MS: 405 (M − H)− |
| 560 | 49 | 1H-NMR (400 MHz, d6-DMSO) δ: 1.96-1.98 (2H, m), 2.15-2.20 (2H, m), 2.31-2.37 (2H, m), 2.51-2.58 (2H, m), 4.33 (1H, m), 5.00 (2H, s), 5.96 (1H, s), 6.94-6.97 (1H, m), 7.37 (1H, t, J = 3.0 Hz), 7.90 (1H, s), 8.14 (1H, dd, J = 1.8, 7.7 Hz), 8.47 (1H, dd, J = 2.0, 4.8 Hz), 10.95 (1H, s), 11.60 (1H, s). MS: 386 (M + H)+ |
| 561 | 49 | 1H-NMR (400 MHz, d6-DMSO) δ: 1.71-1.73 (2H, m), 1.98-1.99 (2H, m), 2.13 (2H, m), 2.43-2.54 (4H, m), 4.81 (2H, s), 5.10 (1H, brs), 7.07 (1H, d, J = 4.9 Hz), 7.44 (1H, s), 7.90 (1H, s), 8.41 (1H, d, J = 5.1 Hz), 10.97 (1H, s), 11.52 (1H, s). MS: 386 (M + H)+, 408 (M + Na)+ |

TABLE 72-continued

| Ex | Ref-Ex | Data |
|---|---|---|
| 562 | 49 | 1H-NMR (400 MHz, d6-DMSO) δ: 1.94-1.96 (2H, m), 2.15 (2H, m), 2.26-2.32 (2H, m), 2.47-2.54 (2H, m), 4.04 (1H, m), 4.77 (1H, s), 5.59 (1H, brs), 7.06 (1H, d, J = 5.2 Hz), 7.32 (1H, brs), 7.48 (1H, s), 7.88 (1H, s), 8.39 (1H, d, J = 5.0 Hz), 10.92 (1H, s), 11.58 (1H, s). MS: 386 (M + H)+ |
| 563 | 49 | 1H-NMR (400 MHz, d6-DMSO) δ: 1.97-1.99 (2H, m), 2.16 (2H, brs), 2.28-2.35 (2H, m), 2.46-2.54 (2H, m), 4.03 (1H, m), 4.83 (2H, s), 5.70 (1H, s), 7.70 (1H, d, J = 9.0 Hz), 7.33 (1H, s), 7.88 (1H, s), 7.98 (1H, dd, J = 2.4, 9.0 Hz), 8.60 (1H, d, J = 2.4 Hz), 10.94 (1H, s), 11.60 (1H, s). MS: 386 (M + H)+ |
| 564 | 50 | MS: 394 (M + H)− |
| 565 | 50 | 1H-NMR (400 MHz, d6-DMSO) δ: 1.46-2.22 (13H, m), 2.59 (3H, s), 4.09 (1H, m), 4.55 (1H, s), 6.49 (1H, m), 7.16 (1H, m), 8.58 (1H, s), 10.67 (1H, m), 11.71 (1H, s). MS: 326.2 (M + H)+ |
| 566 | 50 | MS: 4.10 (M + H)+ |
| 567 | 50 | 1H-NMR (400 MHz, d6-DMSO) δ: 1.43-1.50 (4H, m), 1.63 (6H, s), 1.65-1.74 (3H, m), 1.87-1.94 (3H, m), 2.03-2.11 (1H, m), 2.21-2.24 (2H, m), 4.30-4.34 (1H, m), 4.53 (1H, s), 6.06 (1H, s), 6.49-6.51 (1H, m), 7.23-7.25 (1H, m), 7.84-7.87 (1H, m), 8.71 (1H, s), 11.63 (1H, brs). MS: 410 (M + H)+ |
| 568 | 53 | 1H-NMR (400 MHz, d6-DMSO) δ: 1.45-2.33 (7H, m), 3.80 (3H, s), 4.07 (1H, m), 4.46 (1H, m), 6.07 (2H, s), 6.43 (1H, m), 7.11 (1H, m), 8.13 (1H, s), 8.84 (1H, m), 11.31 (1H, s). MS: 356 (M + H)+ |
| 569 | 53 | 1H-NMR (400 MHz, d6-DMSO) δ: 1.40-2.45 (13H, m), 4.11 (1H, m), 4.44 (1H, s), 6.45 (1H, m), 7.14 (1H, m), 7.86 (1H, s), 8.32 (1H, s), 8.60 (1H, m), 10.77 (1H, s), 11.41 (1H, s). MS: 327 (M + H)+ |
| 570 | 53 | 1H-NMR (400 MHz, d6-DMSO) δ: 1.47-2.25 (7H, m), 2.31 (3H, s), 3.96 (3H, s), 4.10 (1H, m), 4.50 (1H, s), 6.46 (1H, m), 7.13 (1H, m), 8.16 (1H, s), 9.12 (1H, m), 11.39 (1H, s). MS: 328 (M + H)+ |
| 571 | 53 | 1H-NMR (400 MHz, d6-DMSO) δ: 1.29-2.27 (12H, m), 2.31 (3H, s), 4.09 (1H, m), 4.32-4.37 (2H, m), 6.44 (1H, m), 7.12 (1H, m), 8.11 (1H, s), 9.33 (1H, m), 10.88 (1H, s), 11.32 (1H, s). MS: 341 (M + H)+ |
| 572 | 54 | MS: 398 (M + H)+ |
| 573 | 54 | MS: 366 (M + H)+ |
| 574 | 54 | MS: 439 (M − H)+ |
| 575 | 54 | MS: 384 (M + H)+ |
| 576 | 54 | MS: 440 (M − H)− |
| 577 | 54 | MS: 384 (M + H)+ |
| 578 | 55 | 1H-NMR (400 MHz, d6-DMSO) δ: 1.36-1.42 (2H, m), 1.57-1.69 (4H, m), 1.73-1.79 (2H, m), 1.93-1.99 (2H, m), 2.05-2.09 (1H, m), 2.27-2.31 (2H, m), 4.00-4.04 (1H, m), 4.48 (1H, s), 6.11 (1H, d, J = 16.1 Hz), 6.10-6.13 (1H, m), 6.42-6.44 (1H, m), 7.16-7.18 (1H, m), 7.91 (1H, d, J = 16.1 Hz), 8.21 (1H, s), 11.53 (1H, brs). MS: 335 (M + H)+ |
| 579 | 61 | 1H-NMR (400 MHz, d6-DMSO) δ: 1.45-2.69 (13H, m), 4.19 (1H, m), 4.53 (1H, s), 6.54 (1H, m), 7.25 (1H, m), 8.43 (1H, s), 8.75 (1H, m), 11.68 (1H, s), MS: 367 (M + H)+, 365 (M − H)− |

The invention claimed is:

1. A compound, a stereoisomer or a mixture of stereoisomers thereof, or a pharmaceutically acceptable salt thereof, of a compound selected from the group consisting of:

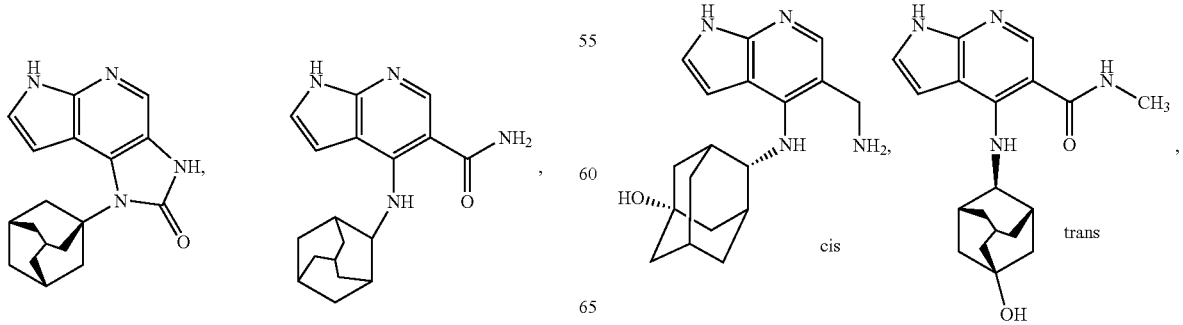

415
-continued
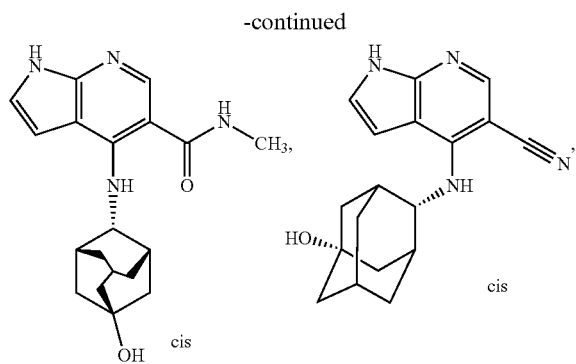
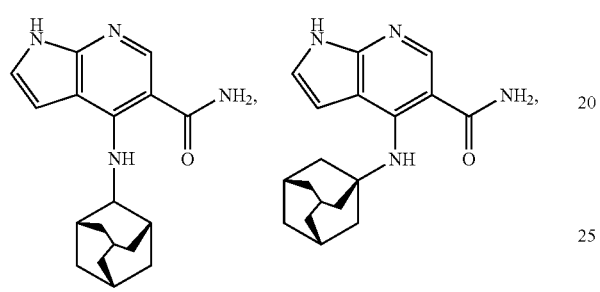
416
-continued
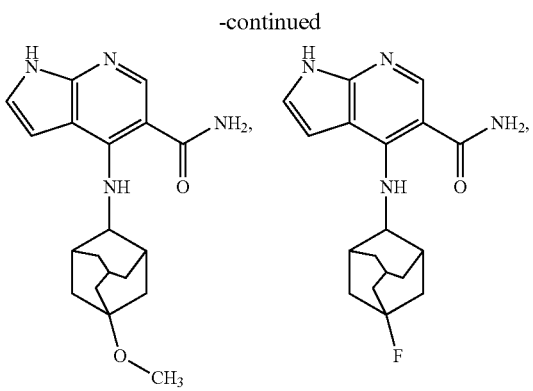
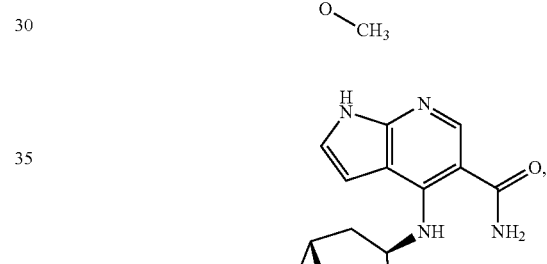
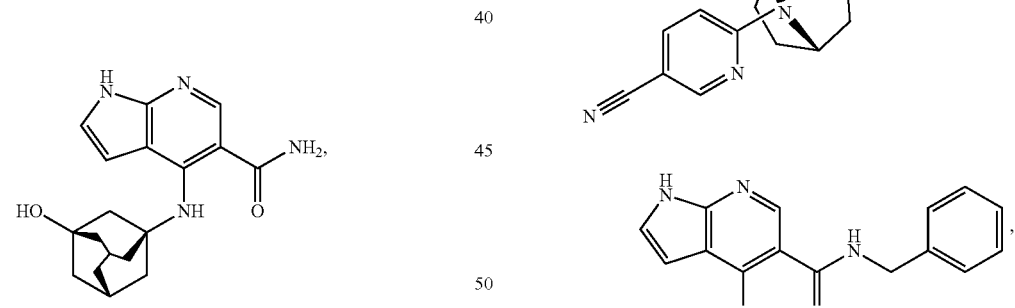
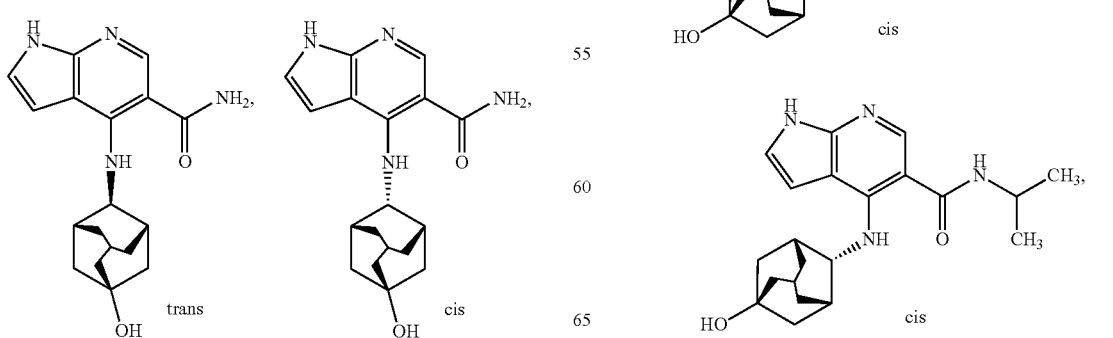

-continued

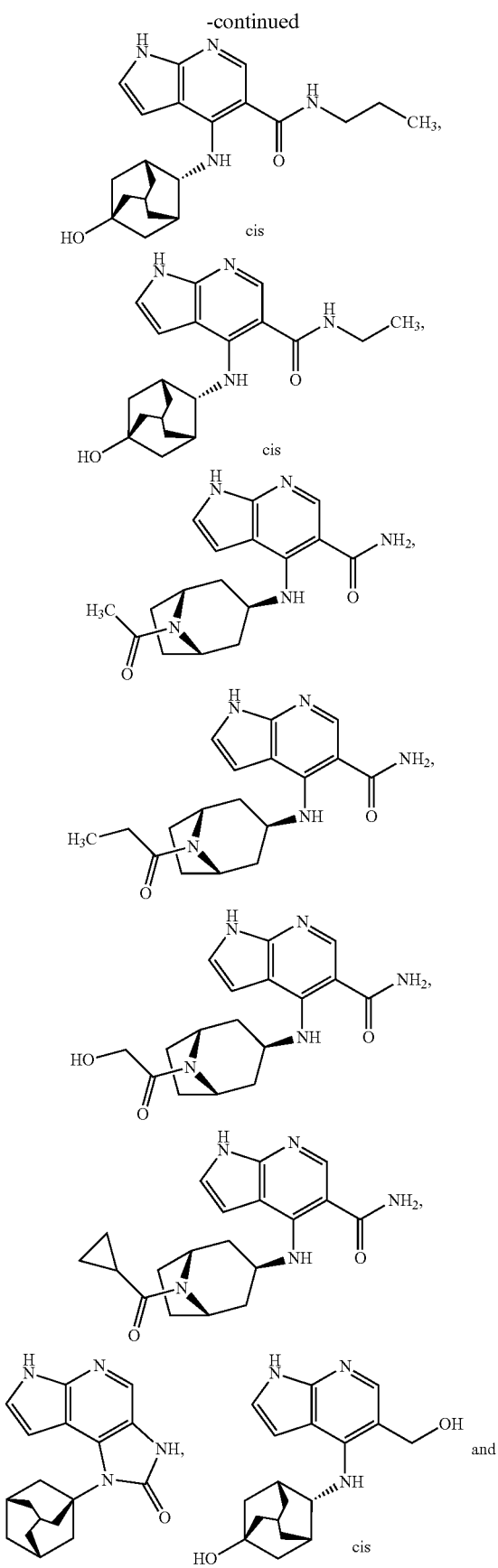

and

-continued

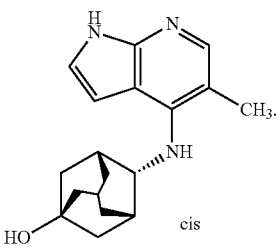

2. The compound according to claim 1, or a pharmaceutically acceptable salt thereof, wherein said compound is:

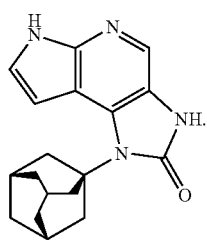

3. The compound according to claim 1, or a pharmaceutically acceptable salt thereof, wherein said compound is:

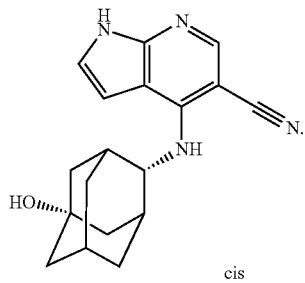

4. The compound according to claim 1, or a pharmaceutically acceptable salt thereof, wherein said compound is:

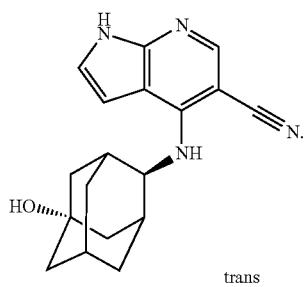

5. The compound according to claim 1, or a pharmaceutically acceptable salt thereof, wherein said compound is:

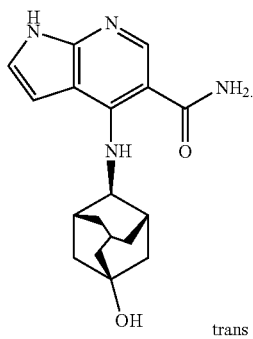
trans

6. The compound according to claim 1, or a pharmaceutically acceptable salt thereof, wherein said compound is:

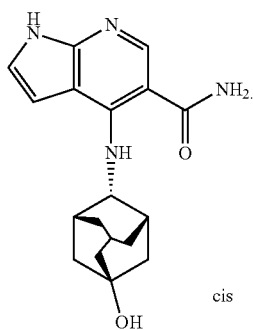
cis

7. The compound according to claim 1, or a pharmaceutically acceptable salt thereof, wherein said compound is:

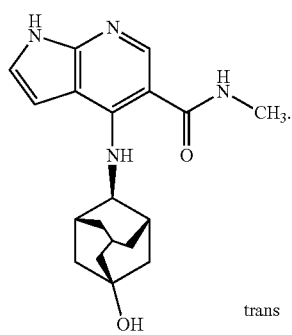
trans

8. The compound according to claim 1, or a pharmaceutically acceptable salt thereof, wherein said compound is:

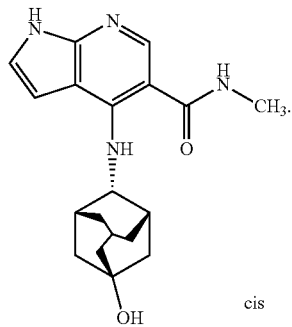
cis

9. The compound according to claim 1, or a pharmaceutically acceptable salt thereof, wherein said compound is:

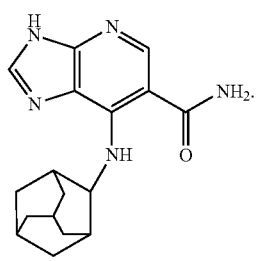

10. The compound according to claim 1, or a pharmaceutically acceptable salt thereof, wherein said compound is:

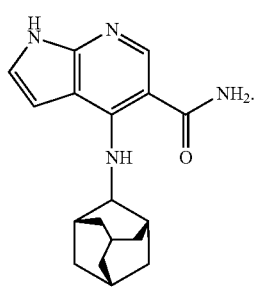

11. The compound according to claim 1, or a pharmaceutically acceptable salt thereof, wherein said compound is:

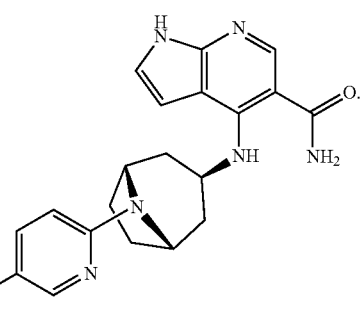

12. The compound according to claim 1, or a pharmaceutically acceptable salt thereof, wherein said compound is:

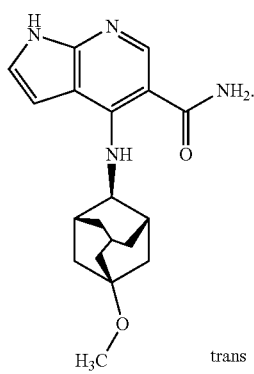
trans

13. The compound according to claim 1, or a pharmaceutically acceptable salt thereof, wherein said compound is:

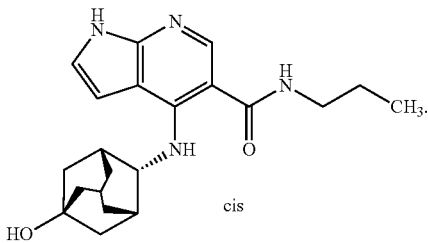

cis

14. The compound according to claim 1, or a pharmaceutically acceptable salt thereof, wherein said compound is:

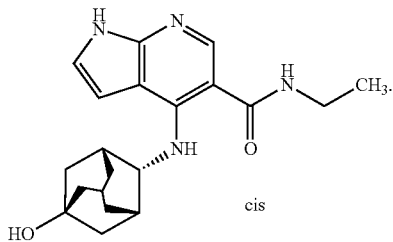

cis

15. A pharmaceutically acceptable salt form of a compound according to claim 1, wherein the pharmaceutically acceptable salt is selected from the group consisting of hydrochloric acid, hydrobromic acid, hydriodic acid, sulfuric acid, nitric acid, and phosphoric acid, formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid and glutamic acid.

16. A pharmaceutically acceptable salt form of a compound according to claim 1, wherein the pharmaceutically acceptable salt is hydrochloric acid.

17. A pharmaceutically acceptable salt form of a compound according to claim 1, wherein the pharmaceutically acceptable salt is hydrobromic acid.

18. A pharmaceutically acceptable salt form of a compound according to claim 1, wherein the pharmaceutically acceptable salt is succinic acid.

19. A pharmaceutical composition comprising a compound according to claim 1, or a pharmaceutical acceptable salt thereof, and a pharmaceutically acceptable carrier or excipient.

20. A pharmaceutically acceptable salt form of a compound according to claim 5, wherein the pharmaceutically acceptable salt is hydrobromic acid.

21. A pharmaceutical composition comprising pharmaceutically acceptable salt form according to claim 20, and a pharmaceutically acceptable carrier or excipient.

* * * * *

UNITED STATES PATENT AND TRADEMARK OFFICE
CERTIFICATE OF CORRECTION

PATENT NO.        : 7,879,844 B2
APPLICATION NO.   : 12/065234
DATED             : February 1, 2011
INVENTOR(S)       : Takayuki Inoue et al.

Page 1 of 2

It is certified that error appears in the above-identified patent and that said Letters Patent is hereby corrected as shown below:

Column 185, Structure 165,

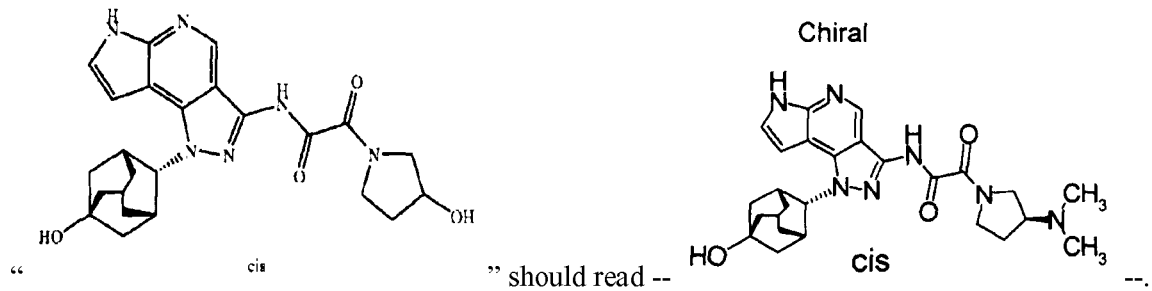

" should read --                                  --.

Column 209, Structure 225,

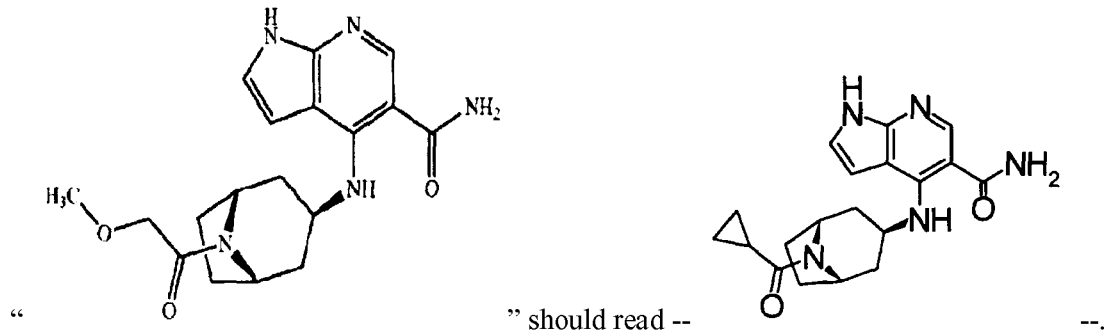

" should read --                                  --.

Column 259, Structure 339,

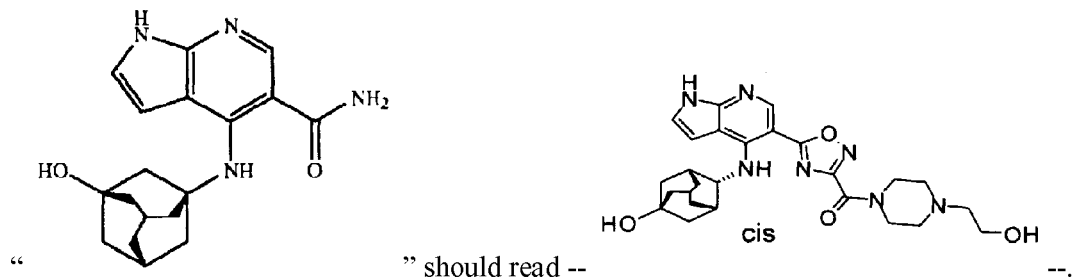

" should read --                                  --.

Signed and Sealed this
Sixth Day of December, 2011

David J. Kappos
*Director of the United States Patent and Trademark Office*

Column 301, Structure 429,
"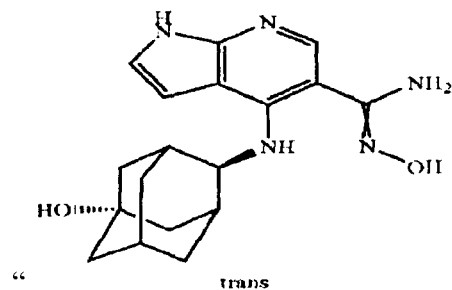" should read -- 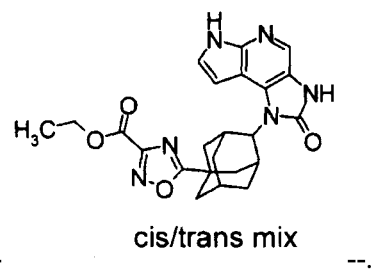 --.